United States Patent
Kojima et al.

(10) Patent No.: US 9,567,330 B2
(45) Date of Patent: Feb. 14, 2017

(54) AZABENZIMIDAZOLE DERIVATIVE HAVING AMPK-ACTIVATING ACTIVITY

(75) Inventors: Eiichi Kojima, Osaka (JP); Keisuke Tonogaki, Osaka (JP); Nobuyuki Tanaka, Osaka (JP); Manabu Katou, Osaka (JP); Akira Ino, Osaka (JP); Masafumi Iwatsu, Osaka (JP); Masahiko Fujioka, Osaka (JP); Yu Hinata, Osaka (JP); Naoki Ohyabu, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 279 days.

(21) Appl. No.: 14/233,058

(22) PCT Filed: Jul. 13, 2012

(86) PCT No.: PCT/JP2012/067889
§ 371 (c)(1),
(2), (4) Date: Jan. 15, 2014

(87) PCT Pub. No.: WO2013/011932
PCT Pub. Date: Jan. 24, 2013

(65) Prior Publication Data
US 2014/0194420 A1 Jul. 10, 2014

(30) Foreign Application Priority Data

Jul. 15, 2011 (JP) .................................. 2011-156297
Mar. 13, 2012 (JP) .................................. 2012-055785

(51) Int. Cl.
C07D 471/04 (2006.01)
C07D 519/00 (2006.01)
C07F 9/6561 (2006.01)
C07D 451/06 (2006.01)

(52) U.S. Cl.
CPC ........... *C07D 471/04* (2013.01); *C07D 451/06* (2013.01); *C07D 519/00* (2013.01); *C07F 9/6561* (2013.01)

(58) Field of Classification Search
None
See application file for complete search history.

(56) References Cited

U.S. PATENT DOCUMENTS

| 5,332,744 | A | 7/1994 | Chakravarty et al. |
| 5,849,753 | A | 12/1998 | Yoo et al. |
| 6,348,474 | B1 | 2/2002 | Kayakiri et al. |
| 6,969,712 | B2 * | 11/2005 | Okamoto ............ C07D 235/28 514/218 |
| 7,071,192 | B1 | 7/2006 | Janssens et al. |
| 2004/0044056 | A1 | 3/2004 | Okamoto et al. |
| 2004/0186127 | A1 | 9/2004 | Daun et al. |
| 2005/0101647 | A1 | 5/2005 | Oda et al. |
| 2005/0124649 | A1 | 6/2005 | Daun et al. |
| 2005/0171125 | A1 | 8/2005 | Ulrich |
| 2008/0103137 | A1 | 5/2008 | Daun et al. |
| 2008/0161326 | A1 | 7/2008 | Otake et al. |
| 2009/0176760 | A1 | 7/2009 | Yanagisawa et al. |
| 2010/0009992 | A1 | 1/2010 | Birnberg et al. |
| 2010/0305324 | A1 | 12/2010 | Kim et al. |
| 2011/0003809 | A1 | 1/2011 | Ahrendt |
| 2011/0105427 | A1 | 5/2011 | Daun et al. |
| 2012/0302576 | A1 | 11/2012 | Birnberg et al. |

(Continued)

FOREIGN PATENT DOCUMENTS

EP 1 460 067 A1 9/2004
GB 1186504 * 4/1970

(Continued)

OTHER PUBLICATIONS

Ito et al., A medium-term rat liver bioassay for rapid in vivo detection of carcinogenic potential of chemicals. Cancer Science, 2003, 94, 3-8.*
Chemical Abstract Registry No. 838881-30-4, indexed in the Registry File on STN CAS Online Feb. 28, 2005.*
Casimiro-Garcia, A., et al., "Discovery of a Series of Imidazo[4,5-b] pyridines with Dual Activity at Angiotensin II Type 1 Receptor and Peroxisome Proliferator-Activated Receptor-γ", Journal of Medicinal Chemistry, vol. 54, No. 12, pp. 4219-4233, (2011).
Zhang, B.B., et al., "AMPK: An Emerging Drug Target for Diabetes and the Metabolic Syndrome", Cell Metabolism Review, vol. 9, pp. 407-416, (May 6, 2009).

(Continued)

*Primary Examiner* — Rebecca Anderson
*Assistant Examiner* — Po-Chih Chen
(74) *Attorney, Agent, or Firm* — Oblon, McClelland, Maier & Neustadt, L.L.P.

(57) ABSTRACT

Disclosed is a compound which is useful as an AMPK activator.
A compound represented by formula:

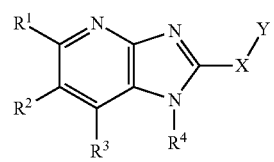

or a pharmaceutically acceptable salt thereof,
wherein $R^4$ is hydrogen, or substituted or unsubstituted alkyl,
$R^1$, $R^2$ and $R^3$ are each independently hydrogen, halogen, hydroxy, cyano, nitro, carboxy, substituted or unsubstituted alkyl or the like, with the proviso that $R^1$, $R^2$ and $R^3$ are not simultaneously hydrogen,
X is a single bond, —S—, —O—, —$NR^5$—, —C(=O)— or the like,
$R^5$ is hydrogen, or substituted or unsubstituted alkyl,
Y is substituted or unsubstituted cycloalkyl, substituted or unsubstituted cycloalkenyl, substituted or unsubstituted heterocyclyl or the like.

15 Claims, No Drawings

(56) References Cited

U.S. PATENT DOCUMENTS

| | | | |
|---|---|---|---|
| 2013/0184240 A1 | 7/2013 | Tonogaki et al. | |
| 2014/0147412 A1 | 5/2014 | Zhang et al. | |

FOREIGN PATENT DOCUMENTS

| | | |
|---|---|---|
| JP | 62 145084 | 6/1987 |
| JP | 63 146883 | 6/1988 |
| JP | 3 95181 | 4/1991 |
| JP | 4 120079 | 4/1992 |
| JP | 8 508268 | 9/1996 |
| JP | 9 507675 | 8/1997 |
| JP | 2003 503403 | 1/2003 |
| JP | 2005 524621 | 8/2005 |
| JP | 2005 525388 | 8/2005 |
| JP | 2010 280658 | 12/2010 |
| JP | 2011 513329 | 4/2011 |
| JP | 2011-088833 A | 5/2011 |
| JP | 2014-520822 A | 8/2014 |
| WO | 99 00372 | 1/1999 |
| WO | 02 40019 | 5/2002 |
| WO | 03 045929 | 6/2003 |
| WO | WO 03/057696 A1 | 7/2003 |
| WO | WO 03/080607 A1 | 10/2003 |
| WO | WO 2004/002986 A2 | 1/2004 |
| WO | 2005 082905 | 9/2005 |
| WO | WO 2005/080348 A1 | 9/2005 |
| WO | 2005 100353 | 10/2005 |
| WO | 2008 096829 | 8/2008 |
| WO | WO 2009/100130 A1 | 8/2009 |
| WO | 2010 036613 | 4/2010 |
| WO | 2010 047982 | 4/2010 |
| WO | WO 2010/045166 A1 | 4/2010 |
| WO | 2010 051176 | 5/2010 |
| WO | 2010 051206 | 5/2010 |
| WO | WO 2010/065674 A1 | 6/2010 |
| WO | WO 2010/099527 A1 | 9/2010 |
| WO | WO 2011/081918 A1 | 7/2011 |
| WO | 2011 106273 | 9/2011 |
| WO | WO 2011/109037 A1 | 9/2011 |
| WO | 2012 033149 | 3/2012 |
| WO | WO 2012/070114 A1 | 5/2012 |
| WO | 2012 116145 | 8/2012 |
| WO | WO 2013/007106 A1 | 1/2013 |

OTHER PUBLICATIONS

International Search Report Issued Aug. 21, 2012 in PCT/JP12/067889 Filed Jul. 13, 2012.

Julie Charton, et al., "Synthesis and biological evaluation of benzimidazole derivatives as potent AMP-activated protein kinase activators" Bioorganic & Medicinal Chemistry, vol. 14, No. 13, XP027992720, Jul. 1, 2006, pp. 4490-4518.

Supplementary European Search Report issued Jan. 14, 2015 in Patent Application No. 12 81 5211.

Heinz Berner, et al., "A biological comparison of benzene with pyridine in condensed ring systems. Imidazo [4,5-b] pyridines and [1,2,4]-Triazolo-[1,5-a] pyridines" Monatshefte Fur Chemie—Chemical Monthly, vol. 106, No. 5, XP055161236, Jan. 1, 1975, pp. 1059-1069.

Office Action issued May 24, 2016, in Japanese Patent Application No. 2013-524700 (with English-language Translation).

Perandones et al., "Synthesis of Imidazo[4,5-*b*]pyridines from Aminoimidazolecarbaldehydes" J. Heterocyclic Chem., v.34, 107, 1997, pp. 107-112.

* cited by examiner

AZABENZIMIDAZOLE DERIVATIVE HAVING AMPK-ACTIVATING ACTIVITY

FIELD OF THE INVENTION

The present invention relates to a compound which has the activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in liver and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 5 disclose a variety of compounds having an AMPK activating effect. However, an azabenzimidazole derivative like the compound of the present invention is not disclosed in any of the documents.

Patent Document 6 describes the following three compounds as compounds useful for an analgetic agent, an anti-obesity agent and the like. However, an azabenzimidazole derivative like the compound of the present invention is not disclosed, and also the AMPK activating effect is not described.

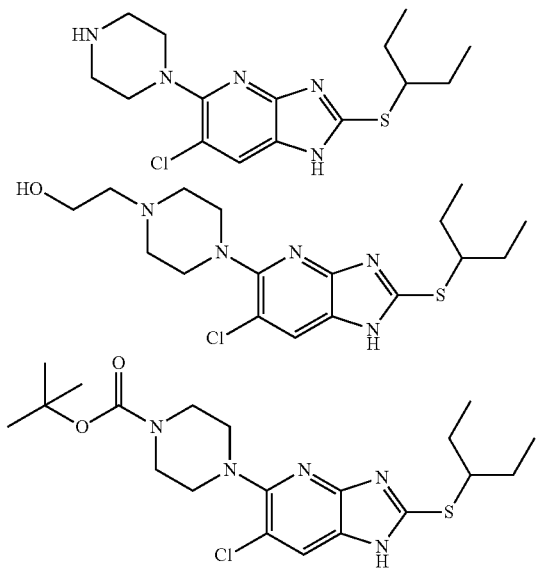

Patent Document 7 describes the following compound as a compound useful for hypertension, diabetes mellitus and the like. However, an azabenzimidazole derivative like the compound of the present invention is not disclosed, and also the AMPK activating effect is not described.

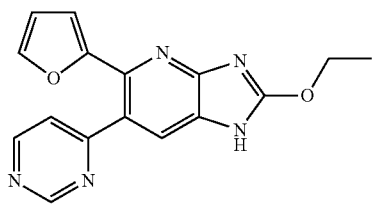

PRIOR ART DOCUMENT

Patent Document

Patent Document 1: WO 2010/036613
Patent Document 2: WO 2010/047982
Patent Document 3: WO 2010/051176
Patent Document 4: WO 2010/051206
Patent Document 5: WO 2011/106273
Patent Document 6: WO 2002/040019
Patent Document 7: WO 2005/100353

Non-Patent Document

Non-Patent Document 1: Cell Metabolism Vol. 9, Issue 5, 407-416, 2009

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.

The present invention relates to the following.

[1]

A compound represented by formula (I)

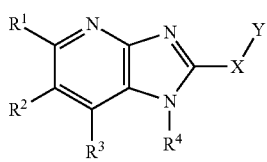

or a pharmaceutically acceptable salt thereof,
wherein $R^4$ is hydrogen, or substituted or unsubstituted alkyl,
$R^1$, $R^2$ and $R^3$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino, with the proviso that $R^1$, $R^2$ and $R^3$ are not simultaneously hydrogen, X is a single bond, —S—, —O—, —$NR^5$—, —C(=O)—, —$NR^5$C(=O)—, —C(=O)$NR^5$—, —$NR^5$—$SO_2$—, —$SO_2$—$NR^5$—, —C(=O)—O— or —O—C(=O)—, $R^5$ is hydrogen, or substituted or unsubstituted alkyl, Y is substituted or unsubstituted cycloalkyl, substituted or unsubstituted cycloalkenyl, substituted or unsubstituted heterocyclyl, or a group represented by formula: —($CR^6R^7$)m-Z, $R^6$ is each independently hydrogen, halogen, hydroxy, cyano, nitro, carboxy, substituted or unsubstituted alkyl, substituted or unsubstituted alkenyl, substituted or unsubstituted alkynyl, or substituted or unsubstituted alkyloxy, $R^7$ is each independently hydrogen, halogen, hydroxy, cyano, nitro, carboxy, substituted or unsubstituted alkyl, substituted or unsubstituted alkenyl, substituted or unsubstituted alkynyl, or substituted or unsubstituted alkyloxy, or $R^6$ and $R^7$ which are bound to the same carbon atom, together with the carbon atom, may form a substituted or unsubstituted ring, m is an integer from 1 to 3, Z is
(1) hydrogen,
(2) cyano,
(3) carboxy,
(4) substituted or unsubstituted alkenyl,
(5) substituted or unsubstituted alkynyl,
(6) substituted or unsubstituted aryl,
(7) substituted or unsubstituted heteroaryl,
(8) substituted or unsubstituted cycloalkyl,
(9) substituted or unsubstituted cycloalkenyl,
(10) substituted or unsubstituted heterocyclyl,
(11) —C(=O)—$NR^8R^9$,
(12) —$NR^{10}$—C(=O)—$R^{11}$
(13) —$SO_2$—$NR^{12}R^{13}$,
(14) —$NR^{14}$—$SO_2$—$R^{15}$,
(15) —$NR^{16}$—C(=O)—$NR^{17}R^{18}$,
(16) —C(=O)—O—$R^{19}$,
(17) —P(=O)(—OH)$_2$,
(18) —P(=O)H(—OH),
(19) —P(=O)(—$R^{20}$)$_2$,
(20) —P(=O)(—$OR^{20}$)$_2$,
(21) —P(=O)(—OH)(—$R^{20}$),
(22) —P(=O)(—OH)(—$OR^{20}$),
(23) —P(=O)(—$R^{20}$)(—$OR^{20}$),
(24) —P(=O)(—OH)(—O—($CR^{21}R^{22}$)$_{0-4}$—$R^{23}$),
(25) —(=O)(—$NR^{24}$—$CR^{21}R^{22}$—COOH)$_2$,
(26) —(=O)(—$NR^{24}$—$CR^{21}R^{22}$—$COOR^{20}$)$_2$,
(27) —(=O)(—OH)(—$NR^{24}$—$CR^{21}R^{22}$—COOH)$_2$,
(28) —(=O)(—OH)(—$NR^{24}$—$CR^{21}R^{22}$—$COOR^{20}$),
(29) —(=O)(—$NR^{24}$—$CR^{21}R^{22}$—$COOR^{20}$)(—O—$R^{20}$),
(30) —(=O)(—O—$CR^{21}R^{22}$—O—C(=O)—$R^{20}$)$_2$,
(31) —P(=O)(—OH)(—O—$CR^{21}R^{22}$—O—C(=O)—$R^{20}$),
(32) —P(=O)(—OH)(—O—($CR^{21}R^{22}$)$_{1-4}$—S(=O)—$R^{20}$),
(33) —P(=O)(—O—($CR^{21}R^{22}$)$_{1-4}$—S(=O)—$R^{20}$)$_2$,
(34) —P(=O)(—OH)(—O—($CR^{21}R^{22}$)$_{1-4}$—S—C(=O)—$R^{20}$),
(35) —P(=O)(—O—($CR^{21}R^{22}$)$_{1-4}$—S—C(=O)—$R^{20}$)$_2$
or
(36)

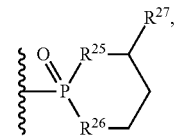

$R^8$ and $R^9$ are each independently hydrogen, hydroxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted alkyloxy, or $R^8$ and $R^9$ taken together with the adjacent nitrogen atom to which they are attached may form a substituted or unsubstituted ring, $R^{10}$, $R^{14}$ and $R^{16}$ are each independently hydrogen, or substituted or unsubstituted alkyl, $R^{21}$ is each independently hydrogen, or substituted or unsubstituted alkyl, $R^{22}$ is each independently hydrogen, or substituted or unsubstituted alkyl, $R^{24}$ is each independently hydrogen, or substituted or unsubstituted alkyl, $R^{11}$ and $R^{15}$ are each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^{12}$, $R^{13}$, $R^{17}$, $R^{18}$ and $R^{19}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^{20}$ is each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^{23}$ is substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^{25}$ and $R^{26}$ are each independently —O— or —NH—, $R^{27}$ is substituted or unsubstituted aryl, or substituted or unsubstituted heteroaryl, with the proviso that a compound wherein $R^2$ is halogen, X is —S—, Y is a group represented by formula: —(CR⁶R⁷)m-Z, m is 3, Z is hydrogen and $R^1$ is substituted or unsubstituted heterocyclyl, a compound wherein $R^1$ is substituted or unsubstituted heteroaryl, $R^2$ is substituted or unsubstituted heteroaryl, or substituted or unsubstituted heterocyclyl, X is —O— and Y is a group represented by formula: —(CR⁶R⁷)m-Z, and compounds shown below are excluded:

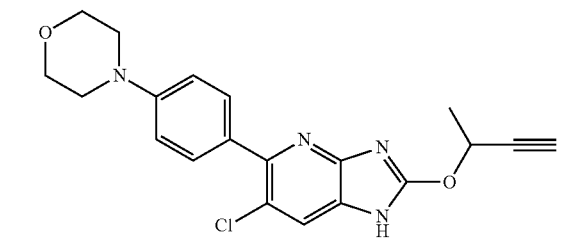

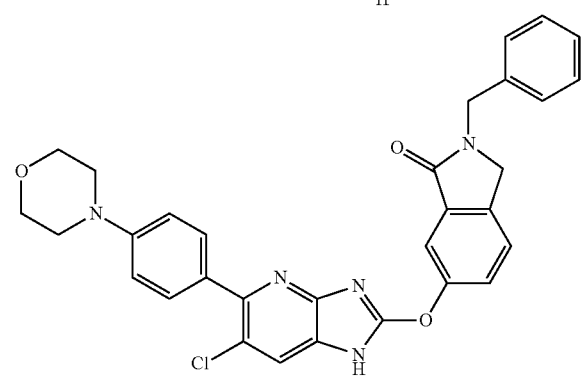

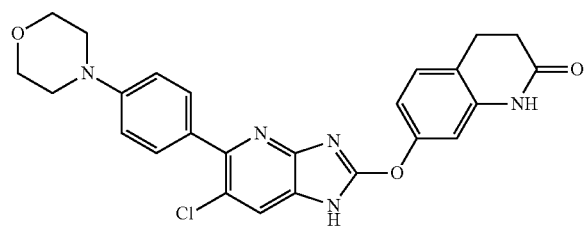

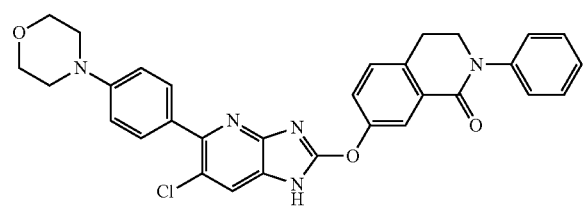

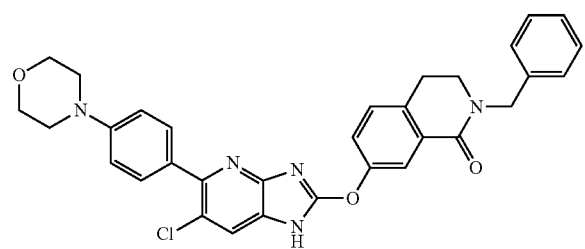

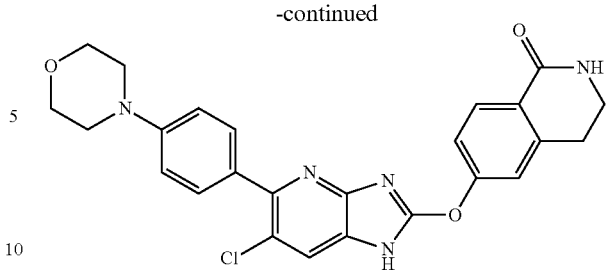

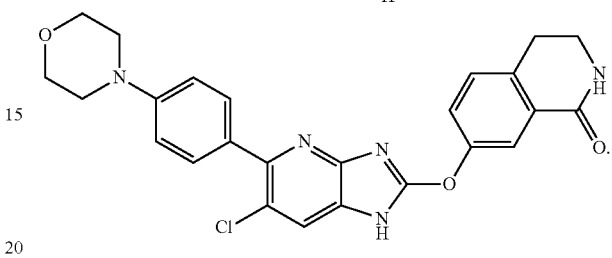

[2]
The compound according to the above [1] or a pharmaceutically acceptable salt thereof, wherein $R^2$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

[3]
The compound according to the above [2] or a pharmaceutically acceptable salt thereof, wherein $R^2$ is halogen.

[4]
The compound according to the above [1] or a pharmaceutically acceptable salt thereof, wherein $R^2$ is hydrogen.

[5]
The compound according to any one of the above [1] to [4] or a pharmaceutically acceptable salt thereof, wherein $R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

[6]

The compound according to the above [5] or a pharmaceutically acceptable salt thereof, wherein $R^1$ is substituted or unsubstituted aryl.

[7]

The compound according to any one of the above [1] to [6] or a pharmaceutically acceptable salt thereof, wherein X is —O—.

[8]

The compound according to any one of the above [1] to [6] or a pharmaceutically acceptable salt thereof, wherein X is —S—.

[9]

The compound according to any one of the above [1] to [8] or a pharmaceutically acceptable salt thereof, wherein Y is substituted or unsubstituted monocyclic heterocyclyl, or substituted or unsubstituted monocyclic cycloalkyl.

[10]

The compound according to the above [9] or a pharmaceutically acceptable salt thereof, wherein Y is

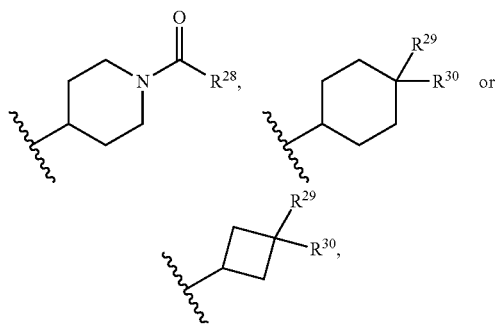

$R^{28}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, or substituted or unsubstituted amino, and $R^{29}$ and $R^{30}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted carbamoyl, or substituted or unsubstituted amino.

[11]

The compound according to any one of the above [1] to [8] or a pharmaceutically acceptable salt thereof, wherein Y is a group represented by formula: —(CR$^6$R$^7$)m-Z, wherein $R^6$, $R^7$, m and Z have the same meaning as in the above [1].

[12]

The compound according to the above [11] or a pharmaceutically acceptable salt thereof, wherein m is 1.

[13]

The compound according to the above [11] or [12] or a pharmaceutically acceptable salt thereof, wherein either one of $R^6$ and $R^7$ is substituted or unsubstituted alkyl, and another one of $R^6$ and $R^7$ is hydrogen.

[14]

The compound according to any one of the above [11] to [13] or a pharmaceutically acceptable salt thereof, wherein Z is carboxy, —C(=O)—NR$^8$R$^9$, or substituted or unsubstituted heteroaryl, and $R^8$ and $R^9$ have the same meaning as in the above [1].

[15]

The compound according to any one of the above [1] to [14] or a pharmaceutically acceptable salt thereof, wherein $R^4$ is hydrogen.

[16]

The compound according to any one of the above [1] to [15] or a pharmaceutically acceptable salt thereof, wherein $R^3$ is hydrogen.

[17]

A pharmaceutical composition comprising the compound according to any one of the above [1] to [16] or a pharmaceutically acceptable salt thereof.

[18]

A pharmaceutical composition having an activating effect on adenosine monophosphate-activated protein kinase, wherein the pharmaceutical composition comprises a compound according to any one of the above [1] to [16] or a pharmaceutically acceptable salt thereof.

Further, the present invention includes:

[19]

The pharmaceutical composition according to the above [17] for the treatment and/or prevention of diabetes,

[20]

A method for preventing or treating diabetes, comprising administering the compound according to any one of the above [1] to [16] or a pharmaceutically acceptable salt thereof, and

[21]

The compound according to any one of the above [1] to [16] or a pharmaceutically acceptable salt thereof for the treatment and/or prevention of diabetes.

Effect of the Invention

The compound of the present invention has an AMPK activating effect, and thus a pharmaceutical composition comprising a compound of the present invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral adsorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin $A_{1C}$ (HbA1c), the effect of improving fatty liver or the like.

MODE FOR CARRYING OUT THE INVENTION

Each term used in this description will be described below. In this description, even when each term is used individually or used with other terms, the term has the same meaning.

"Halogen" includes fluorine, chlorine, bromine and iodine.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl or 3-cyclopenten-1-yl), cyclohexenyl (e.g.: 1-cyclohexen-1-yl, 2-1-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group and a fused aromatic heterocyclic group.

The "monocyclic aromatic heterocyclic group" means a group which is induced from a 5 to 8-membered aromatic ring which has one or more, the same or different, hetero atoms optionally selected from oxygen, sulfur and nitrogen atoms in the ring, which group may have a bond at any substitutable position.

The "fused aromatic heterocyclic group" means a group in which a 5 to 8-membered aromatic ring which has one or more, the same or different, hetero atoms optionally selected from oxygen, sulfur and nitrogen atoms in the ring is fused with one to four 5 to 8-membered aromatic carbocyclic rings or another 5 to 8-membered aromatic hetero ring, which group may have a bond at any substitutable position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2, 4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocyclyl" means a non aromatic heterocyclic group, which may have a bond at any substitutable position of a ring which has at least one or more nitrogen, oxygen or sulfur atoms in the ring, or a ring in which such ring is fused with a cycloalkane (preferably 5 to 6-membered), a benzene ring and/or a ring which has at least one or more nitrogen, oxygen or sulfur atoms in the ring. "Nonaromatic heterocyclic group" can be saturated or unsaturated as long as it is non-aromatic. Preferable is a 5-to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl, 1,2,3,4-tetrahydroisoquinolinyl, 1,2,3,4-tetrahydroquinolinyl, 1,3-dihydro-2H-isoindol-5-yl or the like.

"Heterocyclyl" further contains a bridged group or a spiro ring forming group shown below.

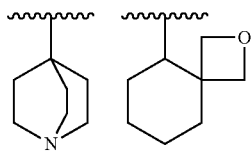

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

The alkyl part of "alkyloxy", "alkylthio" and "alkylsulfonyl" means the above "alkyl".

The aryl part of "aryloxy", "arylthio" and "arylsulfonyl" means the above "aryl".

The heteroaryl part of "heteroaryloxy", "heteroarylthio" and "heteroarylsulfonyl" means the above "heteroaryl".

The cycloalkyl part of "cycloalkyloxy", "cycloalkylthio" and "cycloalkylsulfonyl" means the above "cycloalkyl".

The cycloalkenyl part of "cycloalkenyloxy", "cycloalkenylthio" and "cycloalkenylsulfonyl" means the above "cycloalkenyl".

The heterocyclyl part of "heterocyclyloxy", "heterocyclylthio" and "heterocyclylsulfonyl" means the above "heterocyclyl".

Examples of substituents of "substituted alkyl", "substituted alkenyl", "substituted alkynyl", "substituted aryl", "substituted heteroaryl", "substituted cycloalkyl", "substituted cycloalkenyl", "substituted heterocyclyl", "substituted alkyloxy", "substituted aryloxy", "substituted heteroaryloxy", "substituted cycloalkyloxy", "substituted cycloalkenyloxy", "substituted heterocyclyloxy", "substituted alkylthio", "substituted arylthio", "substituted heteroarylthio", "substituted cycloalkylthio", "substituted cycloalkenylthio", "substituted heterocyclylthio", "substituted alkylsulfonyl", "substituted arylsulfonyl", "substituted heteroarylsulfonyl", "substituted cycloalkylsulfonyl", "substituted cycloalkenylsulfonyl", "substituted heterocyclylsulfonyl", "substituted acyl", "substituted carbamoyl", "substituted sulfamoyl", "a ring formed by $R^6$ and $R^7$ which are bound to the same carbon atom, together with the carbon atom", or "a ring formed by taking together $R^8$ and $R^9$ with the adjacent nitrogen atom to which they are attached" include groups selected from the group consisting of halogen; hydroxy; carboxy; nitro; cyano;

substituted or unsubstituted alkyl (an example of a substituent of substituted alkyl includes halogen, hydroxy, carboxy, nitro, cyano, alkyl, aryl, cycloalkyl, cycloalkenyl, heteroaryl, heterocyclyl, alkyloxycarbonyl, acylamino or substituted or unsubstituted carbamoyl (an example of a substituent of substituted carbamoyl includes alkyl. e.g. methylcarbamoyl, ethylcarbamoyl, dimethylcarbamoyl). e.g. methyl, ethyl, isopropyl, tert-butyl or $CF_3$);

substituted or unsubstituted alkenyl (an example of a substituent of substituted alkenyl includes halogen, hydroxy, carboxy, nitro, cyano, alkyl, aryl, cycloalkyl, cycloalkenyl, heteroaryl or heterocyclyl. e.g. vinyl);

substituted or unsubstituted alkynyl (an example of a substituent of substituted alkynyl includes halogen, hydroxy, carboxy, nitro, cyano, alkyl, aryl, cycloalkyl, cycloalkenyl, heteroaryl or heterocyclyl. e.g. ethynyl);

substituted or unsubstituted aryl (an example of a substituent of substituted aryl includes halogen, hydroxy, carboxy, nitro, cyano, alkyl, aryl, cycloalkyl, cycloalkenyl, heteroaryl, heterocyclyl, substituted or unsubstituted acyl (an example of a substituent of substituted acyl includes hydroxy), alkyloxy or substituted or unsubstituted carbamoyl (an example of a substituent of substituted carbamoyl includes heterocyclyl). e.g. phenyl or naphthyl);

substituted or unsubstituted cycloalkyl (an example of a substituent of substituted cycloalkyl includes halogen, hydroxy, carboxy, nitro, cyano, substituted or unsubstituted alkyl (an example of a substituent of substituted alkyl includes hydroxy), aryl, cycloalkyl, cycloalkenyl, heteroaryl, heterocyclyl or alkyloxycarbamoyl. e.g. cyclopropyl or cyclobutyl.);

substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl, heterocyclyl, substituted or unsubstituted acyl (an example of a substituent of substituted acyl includes hydroxy or alkyloxy), acylamino, alkyloxycarbonyl, substituted or unsubstituted carbamoyl (an example of a substituent of substituted carbamoyl includes substituted or unsubstituted alkyl (an example of a substituent of substituted alkyl includes hydroxy.).) or alkylsulfonyl. e.g. cyclopropenyl);

substituted or unsubstituted heteroaryl (an example of a substituent of substituted heteroaryl includes halogen, hydroxy, carboxy, nitro, cyano, alkyl, aryl, cycloalkyl, cycloalkenyl, heteroaryl or heterocyclyl.);

substituted or unsubstituted heterocyclyl (an example of a substituent of substituted heterocyclyl includes halogen, hydroxy, carboxy, nitro, cyano, substituted or unsubstituted alkyl (an example of a substituent of substituted alkyl includes hydroxy.), aryl, cycloalkyl, cycloalkenyl, heteroaryl, heterocyclyl, substituted or unsubstituted acyl (an example of a substituent of substituted acyl includes hydroxy or alkyloxy.), acylamino, oxo, substituted or unsubstituted carbamoyl (an example of a substituent of substituted carbamoyl includes substituted or unsubstituted alkyl (an example of a substituent of substituted alkyl includes hydroxy.).) or alkylsulfonyl. e.g. morpholinyl, piperidyl or pyrrolidinyl.);

substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl or heterocyclyl. e.g. methoxy or ethoxy.);

substituted or unsubstituted alkenyloxy (an example of a substituent of substituted alkenyloxy includes halogen, hydroxy, carboxy, nitro, cyano, alkyl, aryl, cycloalkyl, cycloalkenyl, heteroaryl or heterocyclyl. e.g. vinyloxy or allyloxy.);

substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl. e.g. phenyloxy);

substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl.);

substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl.);

substituted or unsubstituted heteroaryloxy (an example of a substituent of substituted heteroaryloxy includes halogen, hydroxy, carboxy, nitro, cyano, alkyl, aryl, cycloalkyl, cycloalkenyl, heteroaryl or heterocyclyl.);

substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl.);

substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl. e.g. benzyl);

substituted or unsubstituted arylalkyloxy (an example of a substituent of substituted arylalkyloxy includes halogen, hydroxy, carboxy, nitro, cyano, alkyl, aryl, cycloalkyl, cycloalkenyl, heteroaryl or heterocyclyl. e.g. benzyloxy);

substituted or unsubstituted cycloalkylalkyloxy (an example of a substituent of substituted cycloalkylalkyloxy includes halogen, hydroxy, carboxy, nitro, cyano, alkyl, aryl, cycloalkyl, cycloalkenyl, heteroaryl or heterocyclyl.);

substituted or unsubstituted silyloxy;

substituted or unsubstituted amino (e.g. alkylamino (e.g. methylamino, ethylamino or dimethylamino), acylamino (e.g. acetylamino or benzoylamino), arylamino, substituted or unsubstituted cycloalkylamino (an example of a substituent of substituted cycloalkylamino includes carboxy.), arylalkylamino (e.g. benzylamino or tritylamino), hydroxyamino, alkyloxycarbonylamino, carbamoylamino, alkylsulfonylamino, arylsulfonylamino, cycloalkylsulfonylamino, cycloalkenylsulfonylamino, heteroarylsulfonylamino or heterocyclylsulfonylamino.);

substituted or unsubstituted carbamoyl (an example of a substituent of substituted carbamoyl includes halogen, hydroxy, carboxy, nitro, cyano, substituted or unsubstituted alkyl (an example of a substituent of substituted alkyl includes hydroxy or carboxy.), aryl, cycloalkyl, cycloalkenyl, heteroaryl or heterocyclyl. e.g. alkylcarbamoyl (e.g. methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or alkyloxycarbamoyl);

substituted or unsubstituted carbamoyloxy (an example of a substituent of substituted carbamoyloxy includes halogen, alkyl, aryl, cycloalkyl, cycloalkenyl, heteroaryl or heterocyclyl.);

substituted or unsubstituted acyl (an example of a substituent of substituted acyl includes halogen, hydroxy, carboxy, nitro, cyano, substituted or unsubstituted alkyl (an example of a substituent of substituted alkyl hydroxy.), aryl, cycloalkyl, cycloalkenyl, heteroaryl or heterocyclyl, amino, acylamino or carbamoyl. e.g. alkylcarbonyl, arylcarbonyl, cycloalkylcarbonyl, cycloalkenylcarbonyl, heteroarylcarbonyl, heterocyclylcarbonyl, formyl, acetyl or isopropylcarbonyl.);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl. e.g. methanesulfonyl or ethanesulfonyl);

substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl.);

substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl.);

substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, heteroaryl or heterocyclyl.);

substituted or unsubstituted sulfamoyl (an example of a substituent of substituted sulfamoyl includes halogen, alkyl, aryl, cycloalkyl, cycloalkenyl, heteroaryl or heterocyclyl.);

substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl. e.g. methoxycarbonyl, ethoxycarbonyl or tert-butoxycarbonyl);

aryloxycarbonyl; cycloalkyloxycarbonyl; cycloalkenyloxycarbonyl; heteroaryloxycarbonyl; heterocyclyloxycarbonyl; alkylsulfinyl; arylsulfinyl; cycloalkylsulfinyl; cycloalkenylsulfinyl; heteroarylsulfinyl; heterocyclylsulfinyl; nitroso;

substituted or unsubstituted alkylidene (an example of a substituent of substituted alkylidene includes halogen, hydroxy, carboxy, nitro, cyano, alkyl, aryl, cycloalkyl, cycloalkenyl, heteroaryl or heterocyclyl.);

azido;

isocyano; isocyanato; thiocyanato; isothiocyanato; mercapto;

alkylthio (e.g. methylthio);

$P(=O)(OH)_2$, $P(=O)(OCH_2CH_3)_2$, $C(=O)C(=O)OH$, $C(CH_3)=N-O-CH_3$, $C(CH_3)=N-OH$, formyloxy; haloformyl; oxalo; thioformyl; thiocarboxy; dithiocarboxy; thiocarbamoyl; sulfino; sulfo; sulfoamino; hydrazine; ureido; amidino; guanidine; phthalimido; oxo and the like.

The above substituted groups can be substituted with one to four substituents.

Preferred examples of substituents of "substituted carbamoyl", "substituted sulfamoyl" or "substituted amino" include substituted or unsubstituted alkyl (an example of a substituent of substituted alkyl includes halogen, hydroxy, carboxy, nitro, cyano, alkyl, aryl, cycloalkyl, cycloalkenyl, heteroaryl or heterocyclyl. e.g. methyl, ethyl, isopropyl, tert-butyl or $CF_3$.);

substituted or unsubstituted alkenyl (an example of a substituent of substituted alkenyl includes halogen, hydroxy, carboxy, nitro, cyano, alkyl, aryl, cycloalkyl, cycloalkenyl, heteroaryl or heterocyclyl. e.g. vinyl.);

substituted or unsubstituted aryl (an example of a substituent of substituted aryl includes halogen, hydroxy, carboxy, nitro, cyano, alkyl, aryl, cycloalkyl, cycloalkenyl, heteroaryl or heterocyclyl. e.g. phenyl or naphthyl.);

substituted or unsubstituted cycloalkyl (an example of a substituent of substituted cycloalkyl includes halogen, hydroxy, carboxy, nitro, cyano, alkyl, aryl, cycloalkyl, cycloalkenyl, heteroaryl or heterocyclyl. e.g. cyclopropyl or cyclobutyl.);

substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl or heterocyclyl. e.g. cyclopropenyl.);

substituted or unsubstituted heteroaryl (an example of a substituent of substituted heteroaryl includes halogen, hydroxy, carboxy, nitro, cyano, alkyl, aryl, cycloalkyl, cycloalkenyl, heteroaryl or heterocyclyl.);

substituted or unsubstituted heterocyclyl (an example of a substituent of substituted heterocyclyl includes halogen, hydroxy, carboxy, nitro, cyano, alkyl, aryl, cycloalkyl, cycloalkenyl, heteroaryl or heterocyclyl.);

substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl.);

substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl or heterocyclyl. e.g. methoxy or ethoxy.);

substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl. e.g. phenyloxy.);

substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl.);

substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl.);

substituted or unsubstituted heteroaryloxy (an example of a substituent of substituted heteroaryloxy includes halogen, hydroxy, carboxy, nitro, cyano, alkyl, aryl, cycloalkyl, cycloalkenyl, heteroaryl or heterocyclyl.);

substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl.);

substituted or unsubstituted acyl (an example of a substituent of substituted acyl includes halogen, hydroxy, carboxy, nitro, cyano, alkyl, aryl, cycloalkyl, cycloalkenyl, heteroaryl or heterocyclyl.);

substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl. e.g. methoxycarbonyl, ethoxycarbonyl or tert-butoxycarbonyl.);

aryloxycarbonyl; cycloalkyloxycarbonyl; cycloalkenyloxycarbonyl; heteroaryloxycarbonyl; heterocyclyloxycarbonyl;

substituted or unsubstituted sulfamoyl (an example of a substituent of substituted sulfamoyl includes halogen, hydroxy, carboxy, nitro, cyano, alkyl, aryl, cycloalkyl, cycloalkenyl, heteroaryl or heterocyclyl.);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl. e.g. methanesulfonyl or ethanesulfonyl.);

substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroaryl or heterocyclyl.);

substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl.);

substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, heteroaryl or heterocyclyl.);

substituted or unsubstituted carbamoyl (an example of a substituent of substituted carbamoyl includes halogen, hydroxy, carboxy, nitro, cyano, alkyl, aryl, cycloalkyl, cycloalkenyl, heteroaryl or heterocyclyl.);

halogen; hydroxy; carboxy; nitro; cyano; alkylsulfinyl; cycloalkylsulfinyl; cycloalkenylsulfinyl; arylsulfinyl; heteroarylsulfinyl; heterocyclylsulfinyl; amino and the like.

The alkyl part of "alkyloxycarbonyl", "arylalkyl", "arylalkyloxy", "cycloalkylalkyloxy", "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "alkyloxycarbonyl" and "alkylsulfinyl" means the above-described "alkyl".

The alkenyl part of "alkenyloxy" means the above-described "alkenyl".

The aryl part of "arylalkyl", "arylalkyloxy", "arylamino", "arylalkylamino", "arylsulfonylamino", "aryloxycarbonyl" and "arylsulfinyl" means the above-described "aryl".

The heteroaryl part of "heteroarylsulfonylamino", "heteroarylalkylcarbamoyl", "heteroaryloxycarbonyl" and "heteroarylsulfinyl" means the above-described "heteroaryl".

The cycloalkyl part of "cycloalkylalkyloxy", "cycloalkylsulfonylamino", "cycloalkyloxycarbonyl", "cycloalkylsulfinyl" and "cycloalkylamino" means the above-described "cycloalkyl".

The cycloalkenyl part of "cycloalkenylsulfonylamino", "cycloalkenyloxycarbonyl" and "cycloalkenylsulfinyl" means the above-described "cycloalkenyl".

The heterocyclyl part of "heterocyclylsulfonylamino", "heterocyclyloxycarbonyl" and "heterocyclylsulfinyl" means the above-described "heterocyclyl".

Among the compounds of the present invention, the compounds in the following embodiment are preferred.

$R^4$ is hydrogen, or substituted or unsubstituted alkyl. Preferably, $R^4$ is hydrogen.

$R^1$, $R^2$ and $R^3$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino, with the proviso that $R^1$, $R^2$ and $R^3$ are not simultaneously hydrogen.

$R^1$ is preferably substituted or unsubstituted alkynyl, substituted or unsubstituted aryl, substituted or unsubstituted heteroaryl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted acyl, substituted or unsubstituted carbamoyl, substituted or unsubstituted sulfamoyl, or substituted or unsubstituted amino.

$R^1$ is further preferably substituted or unsubstituted aryl, or substituted or unsubstituted heterocyclyl.

$R^1$ is particularly preferably substituted or unsubstituted aryl.

$R^2$ is preferably hydrogen, halogen, cyano, substituted or unsubstituted alkyl, substituted or unsubstituted alkyloxy, or substituted or unsubstituted amino.

$R^2$ is further preferably hydrogen or halogen, and particularly preferably halogen.

$R^3$ is preferably hydrogen, halogen, or substituted or unsubstituted alkyl.

$R^3$ is particularly preferably hydrogen.

X is a single bond, —S—, —O—, —NR$^5$—, —C(=O)—, —NR$^5$C(=O)—, —C(=O)NR$^5$—, —NR$^5$—SO$_2$—, —SO$_2$—NR$^5$—, —C(=O)—O— or —O—C(=O)—.

X is preferably a single bond, —S— or —O—. X is particularly preferably —O—.

$R^5$ is hydrogen, or substituted or unsubstituted alkyl.

Y is substituted or unsubstituted cycloalkyl, substituted or unsubstituted cycloalkenyl, substituted or unsubstituted heterocyclyl, or a group represented by formula: —(CR$^6$R$^7$)m-Z.

Y is preferably substituted or unsubstituted cycloalkyl, substituted or unsubstituted heterocyclyl, or a group represented by formula: —(CR$^6$R$^7$)m-Z.

Y is further preferably substituted or unsubstituted monocyclic cycloalkyl, or substituted or unsubstituted monocyclic heterocyclyl.

Y is particularly preferably

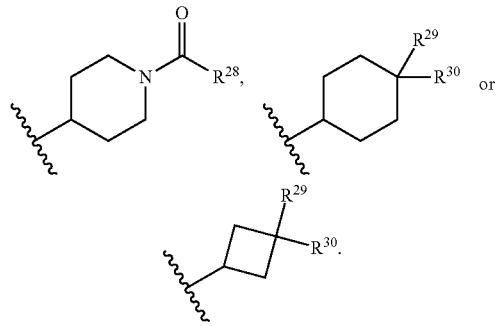

$R^{28}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, or substituted or unsubstituted amino.

$R^{28}$ is preferably substituted or unsubstituted alkyl.

$R^{29}$ and $R^{30}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted carbamoyl, or substituted or unsubstituted amino.

$R^{29}$ is preferably carboxy, substituted or unsubstituted alkyl, substituted or unsubstituted carbamoyl, or substituted or unsubstituted amino.

$R^{29}$ is particularly preferably carboxy, or substituted or unsubstituted alkyl.

$R^{30}$ is preferably hydrogen, halogen or hydroxy.

$R^6$ is each independently hydrogen, halogen, hydroxy, cyano, nitro, carboxy, substituted or unsubstituted alkyl, substituted or unsubstituted alkenyl, substituted or unsubstituted alkynyl, or substituted or unsubstituted alkyloxy, $R^7$ is each independently hydrogen, halogen, hydroxy, cyano, nitro, carboxy, substituted or unsubstituted alkyl, substituted or unsubstituted alkenyl, substituted or unsubstituted alkynyl, or substituted or unsubstituted alkyloxy, or $R^6$ and $R^7$ which are bound to the same carbon atom, together with the carbon atom, may form a substituted or unsubstituted ring.

$R^6$ is preferably hydrogen, or substituted or unsubstituted alkyl. $R^7$ is preferably hydrogen, or substituted or unsubstituted alkyl.

Particularly preferably, either one of $R^6$ and $R^7$ is substituted or unsubstituted alkyl, and another one of $R^6$ and $R^7$ is hydrogen.

m is an integer from 1 to 3. Preferably, m is 1 or 2, and further preferably m is 1.

The ring, which is formed by $R^6$ and $R^7$ which are bound to the same carbon atom, together with the carbon atom, means a 3 to 15-membered saturated or unsaturated hydrocarbon ring, and a saturated or unsaturated hetero ring containing one to four oxygen, sulfur and/or nitrogen atom(s) in the hydrocarbon ring. Preferred is a non aromatic ring, and examples of such ring are cyclopropane, cyclobutane, cyclopentane, cyclohexane, cycloheptane, cyclooctane, cyclopropene, cyclobutene, cyclopentene, cyclohexene, cycloheptene, and saturated or unsaturated hetero rings containing one to four oxygen, sulfur and/or nitrogen atom(s) in the above hydrocarbon ring.

Examples thereof include as follows.

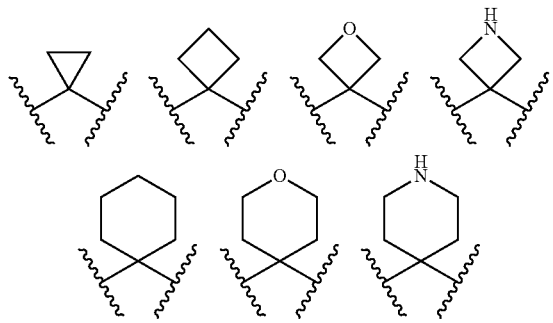

Z is
(1) hydrogen,
(2) cyano,
(3) carboxy,
(4) substituted or unsubstituted alkenyl,
(5) substituted or unsubstituted alkynyl,
(6) substituted or unsubstituted aryl,
(7) substituted or unsubstituted heteroaryl,
(8) substituted or unsubstituted cycloalkyl,
(9) substituted or unsubstituted cycloalkenyl,
(10) substituted or unsubstituted heterocyclyl,
(11) —C(=O)—NR$^8$R$^9$,
(12) —NR$^{10}$—C(=O)—R$^{11}$,
(13) —SO$_2$—NR$^{12}$R$^{13}$,
(14) —NR$^{14}$—SO$_2$—R$^{15}$,
(15) —NR$^{16}$—C(=O)—NR$^{17}$R$^{18}$,
(16) —C(=O)—O—R$^{19}$,
(17) —P(=O)(—OH)$_2$,
(18) —P(=O)H(—OH),
(19) —P(=O)(—R$^{20}$)$_2$,
(20) —P(=O)(—OR$^{20}$)$_2$,
(21) —P(=O)(—OH)(—R$^{20}$),
(22) —P(=O)(—OH)(—OR$^{20}$),
(23) —P(=O)(—R$^{20}$)(—OR$^{20}$),
(24) —P(=O)(—OH)(—O—(CR$^{21}$R$^{22}$)$_{0-4}$—R$^{23}$),
(25) —P(=O)(—NR$^{24}$—CR$^{21}$R$^{22}$—COOH)$_2$,
(26) —P(=O)(—NR$^{24}$—CR$^{21}$R$^{22}$—COOR$^{20}$)$_2$,
(27) —P(=O)(—OH)(—NR$^{24}$—CR$^{21}$R$^{22}$—COOR$^{20}$)$_2$,
(28) —P(=O)(—OH)(—NR$^{24}$—CR$^{21}$R$^{22}$—COOR$^{20}$),
(29) —P(=O)(—NR$^{24}$—CR$^{21}$R$^{22}$—COOR$^{20}$)(—O—R$^{20}$),
(30) —P(=O)(—O—CR$^{21}$R$^{22}$—O—C(=O)—R$^{20}$)$_2$,
(31) —P(=O)(—OH)(—O—CR$^{21}$R$^{22}$—O—C(=O)—R$^{20}$),
(32) —P(=O)(—OH)(—O—(CR$^{21}$R$^{22}$)$_{1-4}$—S(=O)—R$^{20}$),
(33) —P(=O)(—O—(CR$^{21}$R$^{22}$)$_{1-4}$—S(=O)—R$^{20}$)$_2$,
(34) —P(=O)(—OH)(—O—(CR$^{21}$R$^{22}$)$_{1-4}$—S—C(=O)—R$^{20}$),
(35) —P(=O)(—O—(CR$^{21}$R$^{22}$)$_{1-4}$—S—C(=O)—R$^{20}$)$_2$,
or (36)

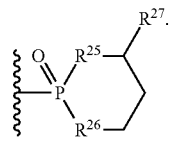

Z is preferably carboxy, a group represented by formula: —C(=O)—NR$^8$R$^9$, or substituted or unsubstituted heteroaryl.

R$^8$ and R$^9$ are each independently hydrogen, hydroxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted alkyloxy, or R$^8$ and R$^9$ taken together with the adjacent nitrogen atom to which they are attached may form a substituted or unsubstituted ring.

"The ring formed by taking together R$^8$ and R$^9$ with the adjacent nitrogen atom to which they are attached" means a 3 to 15-membered saturated or unsaturated hetero ring which may contain, other than the nitrogen atom, one to four oxygen, sulfur and/or nitrogen atom(s) in the ring. Preferred is a non aromatic ring, and such non aromatic ring may be further cross-linked by a C1 to C4 alkyl chain, and may be fused with cycloalkane (preferably 5 to 6-membered) and a benzene ring. Examples thereof include as follows.

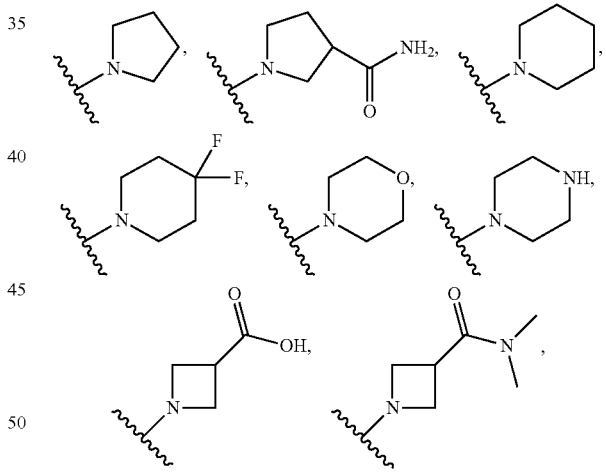

R$^{10}$, R$^{14}$ and R$^{16}$ are each independently hydrogen, or substituted or unsubstituted alkyl.

R$^{21}$ is each independently hydrogen, or substituted or unsubstituted alkyl.

R$^{22}$ is each independently hydrogen, or substituted or unsubstituted alkyl.

R$^{24}$ is each independently hydrogen, or substituted or unsubstituted alkyl.

R$^{11}$ and R$^{15}$ are each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^{12}$, $R^{13}$, $R^{17}$, $R^{18}$ and $R^{19}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^{20}$ is each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^{23}$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^{25}$ and $R^{26}$ are each independently —O— or —NH—.

$R^{27}$ is substituted or unsubstituted aryl, or substituted or unsubstituted heteroaryl.

Preferred combinations of substituents of a compound represented by formula (I) include the following 1) to 10):

1) a compound wherein X is —O—, Y is substituted or unsubstituted monocyclic heterocyclyl, $R^1$ is substituted or unsubstituted aryl, $R^2$ is halogen, $R^3$ is hydrogen and $R^4$ is hydrogen, 2) a compound wherein X is —O—, Y is substituted or unsubstituted monocyclic heterocyclyl, $R^1$ is aryl which is substituted with at least one or more halogen, $R^2$ is hydrogen, $R^3$ is hydrogen and $R^4$ is hydrogen, 3) a compound wherein X is —O—, Y is substituted or unsubstituted monocyclic cycloalkyl, $R^1$ is substituted or unsubstituted aryl, $R^2$ is halogen, $R^3$ is hydrogen and $R^4$ is hydrogen, 4) a compound wherein X is —O—, Y is substituted or unsubstituted monocyclic cycloalkyl, $R^1$ is aryl which is substituted with at least one or more halogen, $R^2$ is hydrogen, $R^3$ is hydrogen and $R^4$ is hydrogen, 5) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is carboxy, $R^1$ is substituted or unsubstituted aryl, $R^2$ is halogen, $R^3$ is hydrogen and $R^4$ is hydrogen, 6) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is carboxy, $R^1$ is aryl which is substituted with at least one or more halogen, $R^2$ is hydrogen, $R^3$ is hydrogen and $R^4$ is hydrogen, 7) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is a group represented by formula: —C(=O)—$NR^8R^9$, $R^1$ is substituted or unsubstituted aryl, $R^2$ is halogen, $R^3$ is hydrogen and $R^4$ is hydrogen, 8) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is a group represented by formula: —C(=O)—$NR^8R^9$, $R^1$ is aryl which is substituted with at least one or more halogen, $R^2$ is hydrogen, $R^3$ is hydrogen and $R^4$ is hydrogen, 9) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is substituted or unsubstituted heteroaryl, $R^1$ is substituted or unsubstituted aryl, $R^2$ is halogen, $R^3$ is hydrogen and $R^4$ is hydrogen, and 10) a compound wherein X is —O—, Y is a group represented by formula: —($CR^6R^7$)m-Z, m is 1, either one of $R^6$ and $R^7$ is substituted or unsubstituted alkyl, another one of $R^6$ and $R^7$ is hydrogen, Z is substituted or unsubstituted heteroaryl, $R^1$ is aryl which is substituted with at least one or more halogen, $R^2$ is hydrogen, $R^3$ is hydrogen and $R^4$ is hydrogen.

Among the compounds of the present invention, when $R^4$ is hydrogen, a compound represented by formula (I) is a compound represented by formula (I') or a compound represented by formula (I")

One or more hydrogen, carbon or other atoms of the compound of formula (I) of the present invention can be replaced by an isotope of the hydrogen, carbon or other atoms.

For example, compounds of formula (I) include all radiolabeled forms of compounds of formula (I). The "radioactive labeling," "radiolabeled form" and the like of the compound of formula (I) are encompassed by the present invention and useful as a research and/or diagnostic tool in metabolism pharmacokinetic studies and in binding assays.

Examples of isotopes that can be incorporated into the compound of formula (I) of the present invention include isotopes of hydrogen, carbon, nitrogen, oxygen, phosphorous, sulfur, fluorine and chlorine, such as 2H, 3H, 13C, 14C, 15N, 18O, 17O, 31P, 32P, 35S, 18F and 36Cl, respectively. Radiolabeled compounds of the present invention can be prepared by methods known in the art. For example, tritium-labeled compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). 14C-labeled compounds can be prepared by employing starting materials having a 14C carbon.

As a pharmaceutically acceptable salt of the present compound, the following salts can be included.

As a basic salt, example includes alkali metal salt such as sodium salt or potassium salt; alkaline earth metal salt such as calcium salt or strontium salt; metal salt such as beryllium salt, magnesium salt, zinc salt or transition metal salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

A compound represented by formula (I) in the present invention or a pharmaceutically acceptable salt thereof can form a solvate (e.g. hydrate etc.) and/or a crystal polymorph, and the present invention also contains such various types of solvate and crystal polymorph. In the "solvate", any number of solvent molecules (e.g. water molecule etc.) may be coordinated with a compound represented by formula (I). When left in the atmosphere, a compound represented by formula (I) or a pharmaceutically acceptable salt thereof may absorb water, and a case where adsorbed water is attached thereto or a case where hydrate is formed may arise. In addition, by recrystallization of a compound represented by formula (I) or a pharmaceutically acceptable salt thereof, a crystal polymorph thereof can be formed.

A compound represented by formula (I) in the present invention or a pharmaceutically acceptable salt thereof can form a prodrug, and the present invention also contains such various types of prodrug. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I) by enzymatic oxidation, reduction, hydrolysis and the like in living organisms under physiological conditions; a compound which is converted into a compound represented by formula (I) by hydrolysis by e.g. gastric acid; and the like. A method for selecting and a method for producing a proper prodrug derivative are described in e.g. Design of Prodrugs, Elsevier, Amsterdam 1985. Prodrugs can have activity in themselves.

When a compound represented by formula (I) or a pharmaceutically acceptable salt thereof has a hydroxyl group, prodrugs such as an acyloxy derivative and a sulfonyloxy derivative are exemplified, which derivatives are produced, for example, by a reaction of a compound having a hydroxy group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, tert-BuCOO—, $C_{15}H_{31}COO-$, PhCOO—, (m-NaOOCPh) COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3-$.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatment which is carried out in common experiments in organic chemistry may be carried out.

A compound represented by formula (I-1) can be synthesized as follows.

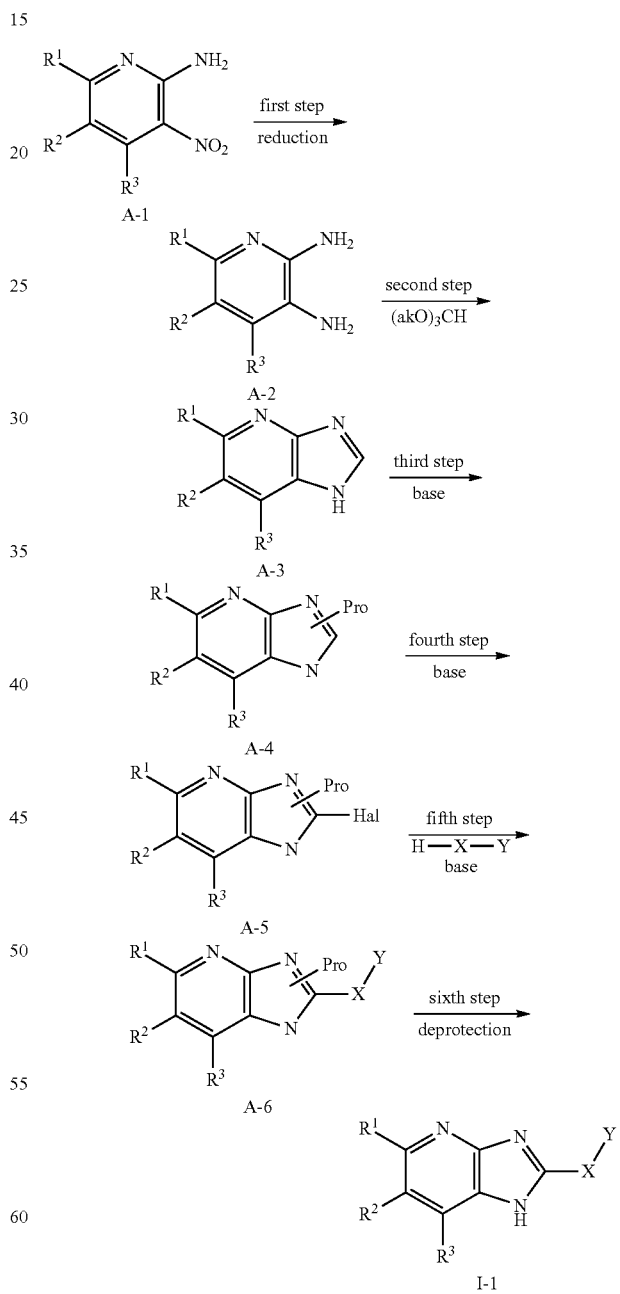

wherein each symbol has the same meaning as above, and as a compound represented by formula (A-1), a known compound can be used or a compound which is derived from a known compound by a conventional method can be used. "ak" means C1 to C3 alkyl, "Hal" means halogen, and Pro means a protecting group. Pro includes a benzyl group, a benzoyl group, SEM (trimethylsilylethoxymethyl) and the like.

First Step

The first step is the step of producing a compound represented by formula (A-2) by reduction of a compound represented by formula (A-1).

Reaction solvents include N,N-dimethylformamide, dimethylsulfoxide, aromatic hydrocarbons (e.g. toluene, benzene, xylene etc.), saturated hydrocarbons (e.g. cyclohexane, hexane etc.), halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), ketones (e.g. acetone, methylethylketone etc.), nitriles (e.g. acetonitrile etc.), alcohols (e.g. methanol, ethanol, t-butanol etc.), water, mixed solvents thereof and the like.

Preferably, halogenated hydrocarbons (e.g. dichloromethane, chloroform, 1,2-dichloroethane etc.), ethers (e.g. tetrahydrofuran, diethylether, dioxane, 1,2-dimethoxyethane etc.), esters (e.g. methyl acetate, ethyl acetate etc.), nitriles (e.g. acetonitrile etc.), alcohols (e.g. methanol, ethanol, t-butanol etc.) or water can be used.

The reaction can be carried out in the presence of Fe, Pd/C, Sn or the like at room temperature to 100° C. for 0.5 to 12 hours.

Although an acid can be used, there is no need to use it. Preferably, acids include hydrochloric acid, ammonium chloride and the like.

This step can be carried out using conditions for a reaction which is known as a hydrogenation reaction. The reduction, for example, can be carried out in the presence of Pd/C.

This step can be also carried out using an organic chemical reaction, which is known as a reduction method of a nitro group.

This step can be carried out in a state in which substituents $R^1$ to $R^3$ on the pyridine ring are suitably protected.

Second Step

The second step is the step of producing a compound represented by formula (A-3) by reacting a compound represented by formula (A-2) and a compound represented by formula: $(akO)_3CH$.

As a reaction solvent, the solvents described in the first step can be used. Preferred reaction solvents include halogenated hydrocarbons (e.g. dichloromethane, chloroform, 1,2-dichloroethane etc.), alcohols (e.g. methanol, ethanol, t-butanol etc.) or the like.

Although an acid can be used, there is no need to use it. Preferably, acids include hydrochloric acid, $NH_3SO_3$ and the like.

The reaction can be carried out at room temperature to 150° C. for 0.5 to 12 hours.

Examples of a compound represented by formula: $(akO)_3CH$ include $(MeO)_3CH$, $(EtO)_3CH$ and the like.

Third Step

The third step is the step of producing a compound represented by formula (A-4) from a compound represented by formula (A-3).

As a reaction solvent, the solvents described in the first step can be used. Preferred reaction solvents include N,N-dimethylformamide, ethers (e.g. tetrahydrofuran, diethyl ether, dioxane, 1,2-dimethoxyethane etc.), halogenated hydrocarbons (e.g. dichloromethane, chloroform, 1,2-dichloroethane etc.), nitriles (e.g. acetonitrile etc.) or the like.

Examples of bases include metal hydrides (e.g. sodium hydride etc.), metal hydroxides (e.g. sodium hydroxide, potassium hydroxide, lithium hydroxide, barium hydroxide etc.), metal carbonates (e.g. sodium carbonate, calcium carbonate, cesium carbonate etc.), metal alkoxides (e.g. sodium methoxide, sodium ethoxide, potassium t-butoxide etc.), sodium hydrogen carbonate, metallic sodium, metal amides, organic amines (e.g. triethylamine, diisopropylethylamine, DBU, 2,6-lutidine etc.), pyridine, alkyllithiums (n-BuLi, sec-BuLi, tert-BuLi), and the like.

Preferably, metallic sodium, organic amines (e.g. triethylamine, diisopropylethylamine, DBU, 2,6-lutidine etc.), pyridine or the like can be used.

The reaction can be carried out at 0 to 100° C. for 0.5 to 12 hours.

Fourth Step

The fourth step is the step of producing a compound represented by formula (A-5) by halogenation of a compound represented by formula (A-4).

As a reaction solvent, the solvents described in the first step can be used. Preferred reaction solvents include N-dimethylformamide, halogenated hydrocarbons (e.g. dichloromethane, chloroform, 1,2-dichloroethane etc.), ethers (e.g. tetrahydrofuran, diethylether, dioxane, 1,2-dimethoxyethane etc.), nitriles (e.g. acetonitrile etc.) or the like. Further preferably, alcohols (e.g. methanol, ethanol, t-butanol etc.) can be used.

As a base, the bases described in the third step can be used. Preferred examples of bases include metal hydrides (e.g. sodium hydride etc.), metal amides (e.g. lithium hexamethyldisilazide etc.), alkyllithiums (n-BuLi, sec-BuLi, tert-BuLi) or the like.

The reaction can be carried out at −78 to 50° C. for 0.5 to 24 hours.

As a halogenating agent, $I_2$, $Br_2$, NIS (N-iodosuccinimide), NBS (N-bromosuccinimide) or NCS (N-chlorosuccinimide) can be used.

Among compounds represented by formula (A-6), a compound, wherein X is —S—, —O— or —$NR^5$—, can be synthesized as follows.

Fifth Step

The fifth step is the step of producing a compound represented by formula (A-6) by reacting a compound represented by formula (A-5) and a compound represented by formula: H—X—Y.

When X is —O—, examples of a compound represented by formula: H—O—Y include methanol, ethanol and the like.

When X is —S—, examples of a compound represented by formula: H—S—Y include methanethiol, ethanethiol and the like.

When X is —$NR^5$—, examples of a compound represented by formula: H—$NR^5$—Y include methylamine, ethylamine and the like.

As a reaction solvent, the solvents described in the first step can be used. Preferred reaction solvents include N-dimethylformamide, dimethylsulfoxide, ethers (e.g. tetrahydrofuran, diethyl ether, dioxane, 1,2-dimethoxyethane etc.), nitriles (e.g. acetonitrile etc.) or the like.

As a base, the bases described in the third step can be used. Preferred examples of bases include metal hydrides (e.g. sodium hydride etc.), metal carbonates (e.g. sodium carbonate, calcium carbonate, cesium carbonate etc.), metal amides, organic amines (e.g. triethylamine, diisopropylethylamine, DBU, 2,6-lutidine etc.), pyridine, alkyllithiums (n-BuLi, sec-BuLi, tert-BuLi) or the like.

Further preferably, metal hydrides (e.g. sodium hydride etc.) or metal carbonates (e.g. sodium carbonate, calcium carbonate, cesium carbonate etc.) can be used.

The reaction can be carried out at 0 to 100° C. for 0.5 to 12 hours.

(When Hal is Bromine or Iodine)

The reaction can be carried out using conditions for a reaction which is known as the Ullmann reaction.

As a reaction solvent, the solvents described in the first step can be used. Preferred reaction solvents include N-dimethylformamide, dimethylsulfoxide, ethers (e.g. tetrahydrofuran, diethyl ether, dioxane, 1,2-dimethoxyethane etc.), nitriles (e.g. acetonitrile etc.) or the like.

As a base, the bases described in the third step can be used. Preferred examples of bases include metal hydrides (e.g. sodium hydride etc.), metal carbonates (e.g. sodium carbonate, calcium carbonate, cesium carbonate etc.), metal amides, organic amines (e.g. triethylamine, diisopropylethylamine, DBU, 2,6-lutidine etc.), pyridine, alkyllithiums (n-BuLi, sec-BuLi, tert-BuLi) or the like.

Further preferably, metal carbonates (e.g. sodium carbonate, calcium carbonate, cesium carbonate etc.) can be used.

As a catalyst, copper iodide can be used.

The reaction can be carried out at room temperature to 100° C. for 0.5 to 12 hours.

Sixth Step

The sixth step is the step of producing a compound represented by formula (I-1) by deprotection of a compound represented by formula (A-6).

As a reaction solvent, the solvents described in the first step can be used. Preferred reaction solvents include N-dimethylformamide, halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), nitriles (e.g. acetonitrile etc.), alcohols (e.g. methanol, ethanol, t-butanol etc.) or the like.

The reaction can be carried out in the presence of hydrochloric acid, TFA (trifluoroacetic acid), TBAF (tetrabutylammoniumfluoride) or the like at 0 to 100° C. for 0.5 to 24 hours.

The substituents $R^1$, $R^2$ and $R^3$ can be introduced in any step of the above-described first to sixth steps.

For example, the substituent $R^1$ can be introduced as follows.

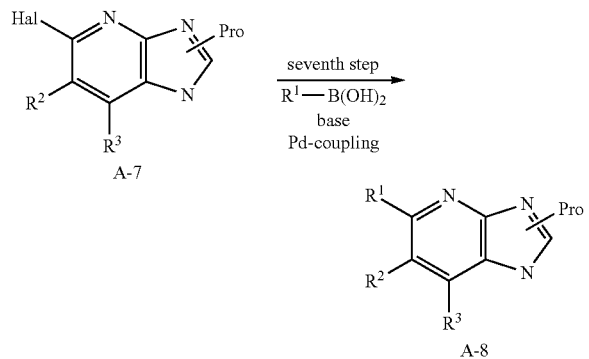

wherein each symbol has the same meaning as above, and as a compound represented by formula (A-7), a known compound can be used or a compound which is derived from a known compound by a conventional method can be used. "Hal" means halogen, and Pro means a protecting group. Pro includes a benzyl group, a benzoyl group, SEM (trimethylsilylethoxymethyl) and the like.

Seventh Step

The seventh step is the step of producing a compound represented by formula (A-8) by reacting a compound represented by formula (A-7) and a compound represented by formula: $R^1$—$B(OH)_2$ in the presence of a palladium catalyst. As a compound represented by formula: $R^1$—$B(OH)_2$, boronic acid ester can be used.

As a solvent, the solvents described in the first step can be used. Preferably, N-dimethylformamide, aromatic hydrocarbons (e.g. toluene, benzene, xylene etc.), ethers (e.g. tetrahydrofuran, diethyl ether, dioxane, 1,2-dimethoxyethane etc.) or alcohols (e.g. methanol, ethanol, t-butanol etc.) can be used.

As a base, the bases described in the third step can be used. Preferably, metal carbonates (e.g. sodium carbonate, calcium carbonate, cesium carbonate etc.) or organic amines (e.g. triethylamine, diisopropylethylamine, DBU, 2,6-lutidine etc.) can be used.

The reaction can be carried out in the presence of a palladium catalyst (e.g. $Pd(PPh_3)_4$, $PdCl_2$, $Pd(OAc)_2$, $Pd(dba)_2$ etc.) and a phosphine ligand (e.g. $PPh_3$, BINAP etc.) at a temperature, at which a solvent to be used is refluxed, for 0.5 to 12 hours.

When using microwave, the reaction can be carried out at 80 to 200° C. for 5 minutes to one hour.

Examples of a compound represented by formula: $R^1$—$B(OH)_2$ include phenylboronic acid and the like.

A compound represented by formula (I-2) can be synthesized as follows.

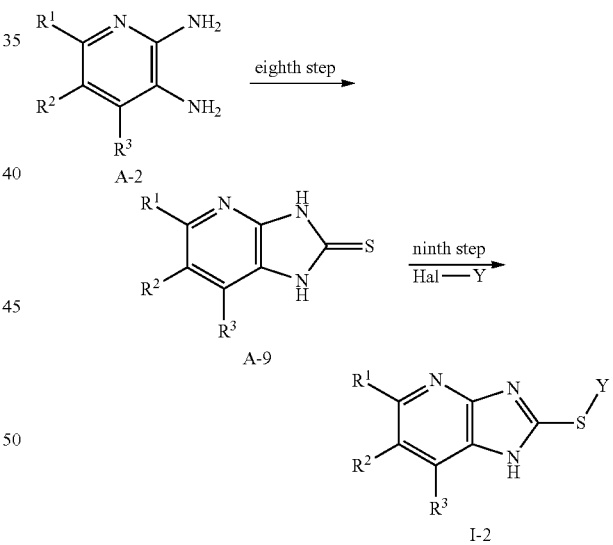

wherein each symbol has the same meaning as above, and as a compound represented by formula (A-2), a known compound can be used or a compound which is derived from a known compound by a conventional method can be used. "Hal" means halogen.

Eighth Step

The eighth step is the step of producing a compound represented by formula (A-9) by reacting a compound represented by formula (A-2) and thiocarbonyldiimidazole or carbon disulfide ($CS_2$).

As a reaction solvent, the solvents described in the first step can be used. Preferred reaction solvents include N,N- dimethylformamide, halogenated hydrocarbons (e.g. dichloromethane, chloroform, 1,2-dichloroethane etc.), nitriles (e.g. acetonitrile etc.), water or the like.

When carbon disulfide ($CS_2$) is used, it is preferred that a base be used.

As a base, the bases described in the third step can be used. Preferred examples of bases include metal hydrides (e.g. sodium hydride etc.), metal hydroxides (e.g. sodium hydroxide, potassium hydroxide, lithium hydroxide, barium hydroxide etc.) or the like.

The reaction can be carried out at room temperature to 150° C. for 0.5 to 12 hours.

When using microwave, the reaction can be carried out at 80 to 200° C. for 5 minutes to one hour.

Ninth Step

The ninth step is the step of producing a compound represented by formula (I-2) by reacting a compound represented by formula (A-9) and a compound represented by formula: Hal-Y.

As a reaction solvent, the solvents described in the first step can be used. Preferred reaction solvents include N-dimethylformamide, dimethylsulfoxide, ethers (e.g. tetrahydrofuran, diethyl ether, dioxane, 1,2-dimethoxyethane etc.), nitriles (e.g. acetonitrile etc.), alcohols (e.g. methanol, ethanol, t-butanol etc.) or the like.

As a base, the bases described in the third step can be used. Preferred examples of bases include metal hydrides (e.g. sodium hydride etc.), metal hydroxides (e.g. sodium hydroxide, potassium hydroxide, lithium hydroxide, barium hydroxide etc.), metal carbonates (e.g. sodium carbonate, calcium carbonate, cesium carbonate etc.) or the like.

The reaction can be carried out at 0 to 150° C. for 0.5 to 12 hours.

When using microwave, the reaction can be carried out at 80 to 200° C. for 5 minutes to one hour.

A compound represented by formula (I-3) can be synthesized as follows.

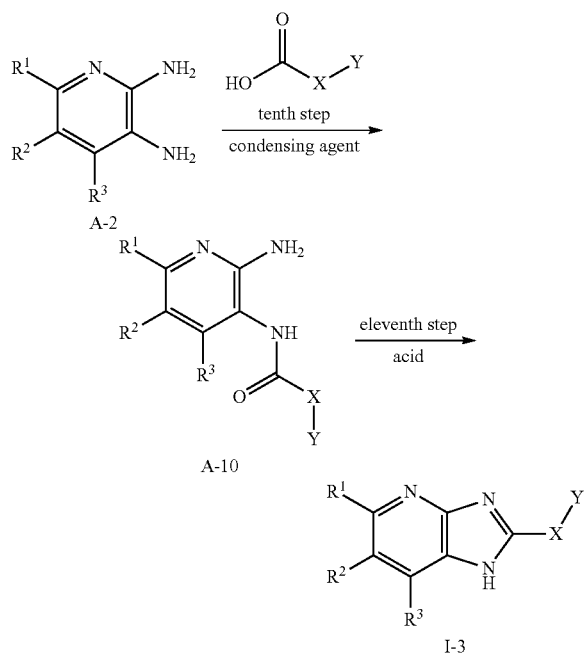

wherein X is a single bond, and Y is a group represented by formula: —($CR^6R^7$)m-Z. Each of the other symbols has the same meaning as above, and as a compound represented by formula (A-2), a known compound can be used or a compound which is derived from a known compound by a conventional method can be used.

Tenth Step

The tenth step is the step of producing a compound represented by formula (A-10) by reacting a compound represented by formula (A-2) and a compound represented by formula: Y—X—COOH.

As a reaction solvent, the solvents described in the first step can be used. Preferred reaction solvents include N,N-dimethylformamide, ethers (e.g. tetrahydrofuran, diethyl ether, dioxane, 1,2-dimethoxyethane etc.), nitriles (e.g. acetonitrile etc.) or the like.

As a base, the bases described in the third step can be used. Preferred examples of bases include organic amines (e.g. triethylamine, diisopropylethylamine, DBU, 2,6-lutidine etc.), pyridine or the like.

The condensing agents include dicyclohexylcarbodiimide, dicyclohexylcarbodiimide-N-hydroxybenzotriazole, EDC, HATU and the like.

The reaction can be carried out at −20 to 100° C. for 0.1 to 24 hours.

Eleventh Step

The eleventh step is the step of producing a compound represented by formula (I-3) from a compound represented by formula (A-10).

Although the solvents described in the first step can be used as a reaction solvent, any solvent is not required to be used. The acid includes acetic acid, hydrochloric acid, sulfuric acid or the like.

The reaction can be carried out at −20 to 100° C. for 0.1 to 24 hours.

When using microwave, the reaction can be carried out at 80 to 200° C. for 5 minutes to 5 hours.

Various types of substituent of the compound of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS and the like.

The compound of the present invention has an excellent AMPK activating effect. Therefore, the compound can be used for the treatment or prevention of a disease concerning AMPK, particularly disease such as type II diabetes, hyperglycemia, metabolic syndrome, obesity, hypercholesterolemia and/or hypertension. Particularly, the compound is useful in the treatment or prevention of type II diabetes, hyperglycemia, metabolic syndrome or obesity.

A compound used in the present invention can be orally or parenterally administered. For oral administration, a compound used in the present invention can be used in any dosage form of normal formulations, for example, solid formulations such as a tablet, powder, granule, capsule or the like; aqueous formulations; oleaginous suspensions; or liquid formulations such as syrup or elixir. For parenteral administration, a compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of a compound used in the present invention can be produced by combining (e.g. mixing) a compound used in the present invention in a therapeutically effective amount with a pharmaceutically acceptable carrier or diluent. A formulation of a compound used in the present invention can be produced using a well-known and easily-available ingredient by a known method.

A dose of a compound used in the present invention is different depending on an administration method, a patient's age, a body weight, the condition of a patient and a kind of a disease, and commonly for oral administration, usually about 0.05 mg to 3000 mg, preferably about 0.1 mg to 1000 mg per a day for adult person may be administered, if necessary, in divided doses. For parenteral administration, about 0.01 mg to 1000 mg, preferably about 0.05 mg to 500 mg per a day for adult person may be administered. When a compound used in the present invention is administered, it can be used together with other therapeutic agents.

A compound of the present invention can be used in combination with an insulin secretagogue (e.g. a sulfonylurea (SU) drug), a fast-acting insulin secretagogue (e.g. a phenylalanine derivative), a glucose uptake inhibitor (e.g. an α-glucosidase inhibitor (α-GI drug)), an insulin resistance improving drug (e.g. a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT 2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulation comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is further explained by the following Examples, which are not intended to limit the scope of the present invention.

NMR spectrum data of the compounds of the present invention and intermediates thereof were shown. NMR analysis obtained in each example was measured by 400 MHz, and measured using CDCl$_3$ or dimethylsulfoxide (d6-DMSO).

The measurement by LC/MS was carried out under the following conditions.
(Method A)
Column: ACQUITY UPLC BEH C18 (1.7 μm i.d. 2.1×50 mm) (made by Waters)
Flow rate: 0.8 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3.5 minutes and the solvent [B] at 100% was maintained for 0.5 minutes.

(Method B)
Column: Shim-pack XR-ODS (2.2 μm, i.d. 50×3.0 mm) (made by Shimadzu)
Flow rate: 1.6 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3 minutes and the solvent [B] at 100% was maintained for 1 minute.

The meaning of each term in examples is as follows.
DMF: N,N-dimethylformamide
DIPEA: diisopropylethylamine
SEMCl: trimethylsilyl ethoxymethyl chloride
THF: tetrahydrofuran
TMEDA: tetramethylethylenediamine
LiHMDS: lithium hexamethyldisilazide
PdCl$_2$(PPh$_3$)$_2$: dichloro bistriphenylphosphine palladium
TFA: trifluoroacetic acid
DCM: methylene chloride
NCS: N-chlorosuccinimide
TCDI: thiocarbonyldiimidazole
HATU: 2-(7-azabenzotriazol-1-yl)-N,N,N',N' tetramethyluronium hexafluorophosphate
PdCl$_2$(dtbpf): 1,1'-bis(di-t-butylphosphino)ferrocene palladium dichloride
PPTS: para-toluenesulfonic acid pyridinium
DAST: N,N-diethylaminosulfur trifluoride
DMAP: dimethylaminopyridine
NFSI: N-fluorobenzenesulfonimide
TBSCl: t-butyldimethylsilyl chloride

EXAMPLE 1

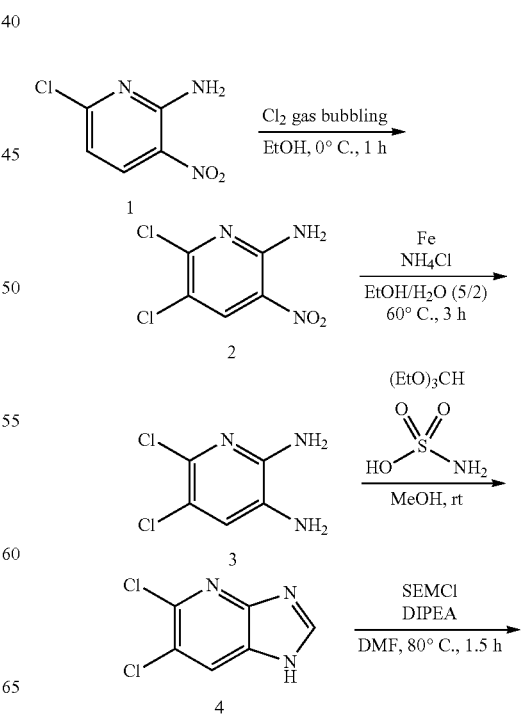

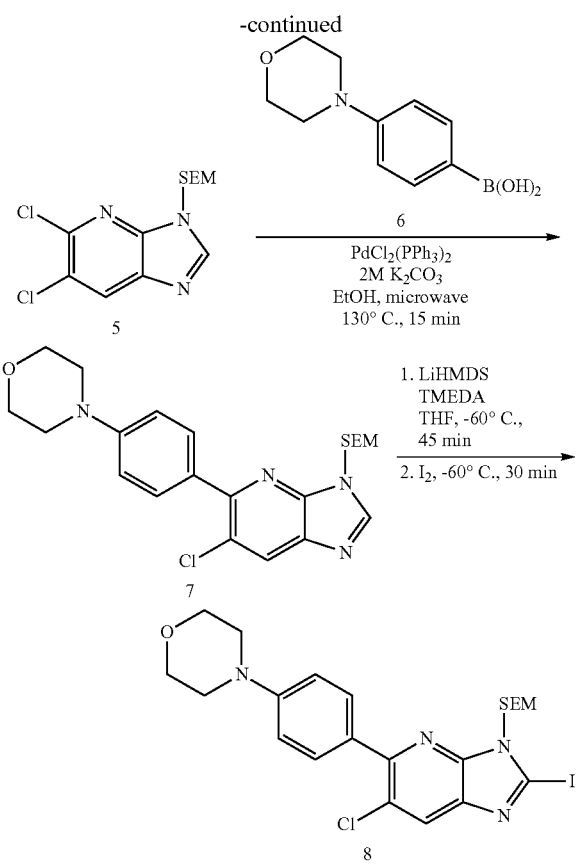

A suspension of Compound 1 (20 g, 115 mmol) in anhydrous ethanol (970 mL) was subjected to bubbling with chlorine gas with stirring at 0° C. over one hour. Thereafter, the reaction liquid was subjected to bubbling with nitrogen gas with stirring at room temperature over one hour, and then stirred at 0° C. for 30 minutes. The reaction suspension was filtered, and the obtained residue was washed with diisopropyl ether to obtain a solid. The solvent of the resulting filtrate was removed by distillation under reduced pressure, and the precipitated solid was filtered and the obtained solid was then washed with diisopropyl ether to further obtain a solid. The above-described two collected solids were combined to obtain Compound 2 (18.1 g, 76%) as a yellow solid.

Compound 2; $^1$H-NMR (DMSO-$d_6$) δ: 8.33 (brs, 2H), 8.59 (s, 1H).

To a solution of Compound 2 (36.2 g, 174 mmol) in ethanol (775 mL) and water (310 mL) were added iron (48.6 g, 870 mmol) and ammonium chloride (46.5 g, 870 mmol), and the obtained reaction mixture was stirred at 60° C. for 3 hours. The reaction suspension was filtered with Celite, followed by washing with ethanol, and ethanol of the filtrate was removed by distillation under reduced pressure. The reaction solution was extracted with ethyl acetate. The organic layer was then washed with water and brine and dried with magnesium sulfate. The solvent was removed by distillation under reduced pressure, and to the residue, hexane was then added, followed by filtration. The obtained residue was washed with hexane to obtain Compound 3 (28.46 g, 92%) as a brown solid.

Compound 3; $^1$H-NMR (DMSO-$d_6$) δ: 5.10 (s, 2H), 6.02 (s, 2H), 6.82 (s, 1H).

To a solution of Compound 3 (28.1 g, 158 mmol) in methanol (840 mL) were successively added sulfamic acid (765 mg, 7.88 mmol) and ortho formic acid triethyl (39.3 mL, 236 mmol), and the obtained reaction mixture was stirred at room temperature for 7.5 hours. The reaction suspension was filtered, followed by washing with methanol, and the solvent of the filtrate was removed by distillation under reduced pressure. To the residue, hexane was added, followed by filtration. The obtained residue was washed with hexane to obtain Compound 4 (24.3 g, 82%) as a gray solid.

Compound 4; $^1$H-NMR (DMSO-$d_6$) δ: 8.40 (s, 1H), 8.58 (s, 1H).

To a solution of Compound 4 (15 g, 80 mmol) in N,N-dimethylformamide (150 ml) were successively added diisopropylethylamine (20.9 mL, 120 mmol) and SEMCl (17.0 mL, 96 mmol), and the obtained reaction mixture was stirred at 80° C. for 2 hours. The reaction solution was extracted with water and ethyl acetate. The organic layer was then washed with water and brine and dried with magnesium sulfate. The solvent was removed by distillation under reduced pressure, and the residue was purified by silica gel column chromatography to obtain Compound 5 (11.6 g, 46%).

Compound 5; $^1$H-NMR (DMSO-$d_6$) δ: 0.00 (s, 9H), 0.94 (t, J=8.0 Hz, 2H), 3.68 (t, J=8.0 Hz, 2H), 5.71 (s, 2H), 8.64 (s, 1H), 8.83 (s, 1H).

To a solution of Compound 5 (4.23 g, 13.29 mmol) in ethanol (43 mL) were added Compound 6 (2.75 g, 13.29 mmol), PdCl$_2$(PPh$_3$)$_2$ (467 mg, 0.67 mmol) and an aqueous solution of potassium carbonate (2 M, 16.6 ml, 33.23 mmol), and the obtained reaction mixture was stirred under microwave irradiation at 130° C. for 15 minutes. The reaction suspension was extracted with water and ethyl acetate. The organic layer was then washed with water and brine and dried with magnesium sulfate. The solvent was removed by distillation under reduced pressure, and the residue was purified by silica gel column chromatography to obtain Compound 7 (5.51 g, 93%) as a yellow solid.

Compound 7; $^1$H-NMR (DMSO-$d_6$) δ: 0.00 (s, 9H), 0.97 (t, J=8.0 Hz, 2H), 3.32 (t, J=4.8 Hz, 4H), 3.74 (t, J=8.0 Hz, 2H), 3.88 (t, J=4.8 Hz, 4H), 5.75 (s, 2H), 7.15 (d, J=8.4 Hz, 2H), 7.73 (d, J=8.4 Hz, 2H), 8.45 (s, 1H), 8.78 (s, 1H).

To a solution of Compound 7 (4.7 g, 10.56 mmol) in anhydrous THF (47 mL) was added TMEDA (4.8 ml, 31.70 mmol). To the reaction mixture was added dropwise a solution of LiHMDS in THF (1M, 22.2 mL, 22.2 mmol) under nitrogen atmosphere at −60° C. over 15 minutes. Thereafter, the obtained reaction mixture was stirred at −60° C. for 45 minutes, and iodine (13.4 g, 52.8 mmol) was then added thereto. The obtained reaction mixture was stirred at −60° C. for 30 minutes. The reaction solution was extracted with a saturated aqueous solution of ammonium chloride and ethyl acetate. The organic layer was then washed with a 10% aqueous solution of sodium thiosulfate, water and brine and dried with magnesium sulfate. The solvent was removed by distillation under reduced pressure, and the residue was purified by silica gel column chromatography. The solvent was removed by distillation under reduced pressure, and to the residue, hexane was added, followed by filtration. The obtained residue was washed with hexane to obtain Compound 8 (4.69 g, 78%) as a yellow solid.

Compound 8; $^1$H-NMR (DMSO-$d_6$) δ: 0.00 (s, 9H), 0.98 (t, J=8.0 Hz, 2H), 3.32 (t, J=4.8 Hz, 4H), 3.75 (t, J=8.0 Hz, 2H), 3.88 (t, J=4.8 Hz, 4H), 5.68 (s, 2H), 7.15 (d, J=8.4 Hz, 2H), 7.74 (d, J=8.4 Hz, 2H), 8.40 (s, 1H).

EXAMPLE 2

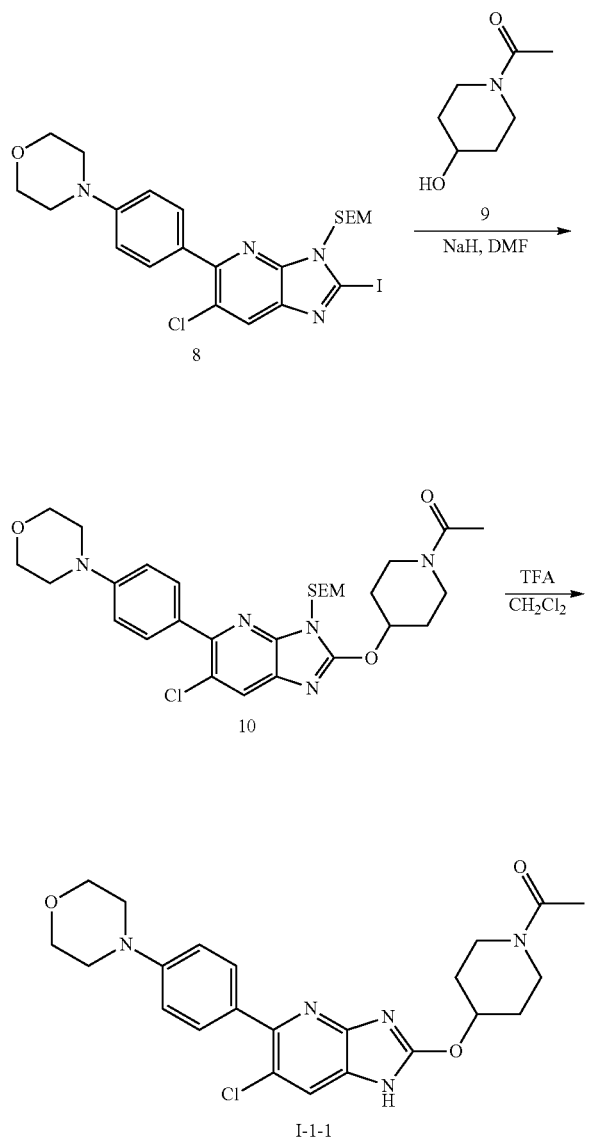

To a suspension of sodium hydride (18.5 mg, 0.46 mmol) in N,N-dimethylformamide (2 mL) was added a solution of Compound 9 (66.2 mg, 0.46 mmol) in N,N-dimethylformamide (1 mL) at 0° C., and the obtained reaction mixture was stirred at room temperature for 30 minutes. Thereafter, to the reaction suspension was added Compound 8 (120 mg, 0.21 mmol) at 0° C., and the obtained reaction mixture was stirred at room temperature for one hour. Further, to the reaction suspension were successively added Compound 9 (66.2 mg, 0.46 mmol) and sodium hydride (18.5 mg, 0.46 mmol) at 0° C., and the obtained reaction mixture was stirred at room temperature for 30 minutes. The reaction liquid was extracted with a saturated aqueous solution of ammonium chloride and ethyl acetate, and the organic layer was then washed with water and brine and dried with magnesium sulfate. The solvent was removed by distillation under reduced pressure, and the residue was purified by silica gel column chromatography to obtain Compound 10 (91.9 mg, 0.16 mmol, 75%) as a colorless solid (amorphous).

Compound 10; $^1$H-NMR (DMSO-d6) δ: −0.11 (s, 9H), 0.86 (t, J=8.0 Hz, 2H), 1.73-1.76 (m, 1H), 1.83-1.86 (m, 1H), 2.00-2.04 (m, 4H), 2.08-2.10 (m, 1H), 3.19 (dd, J=5.2, 4.4 Hz, 4H), 3.45-3.47 (m, 2H), 3.63-3.78 (m, 8H), 5.36-5.40 (m, 1H), 5.42 (s, 2H), 7.02 (d, J=8.6 Hz, 2H), 7.58 (d, J=8.6 Hz, 2H), 8.00 (s, 1H).

To a solution of Compound 10 (86.9 mg, 0.15 mmol) in methylene chloride (1 mL) was added trifluoroacetic acid (1 ml), and the obtained reaction mixture was stirred at room temperature overnight. Thereafter, to the reaction solution was added methanol (0.5 ml), and the obtained reaction mixture was stirred at room temperature for one hour. The reaction solution was neutralized with a saturated aqueous solution of sodium hydrogen carbonate, and extracted with ethyl acetate. The organic layer was washed with water and brine, and dried with magnesium sulfate. The solvent was removed by distillation under reduced pressure, and the residue was purified by reverse-phase preparative liquid chromatography (a 0.3% formic acid-containing aqueous solution/acetonitrile; gradient 20-40%, 10 min) to obtain Compound (I1-1) (26.7 mg, 0.059 mmol, 40%) as a white solid.

Compound (I-1-1); $^1$H-NMR (DMSO-d6) δ: 1.63-1.68 (m, 1H), 1.76-1.80 (m, 1H), 2.04-2.13 (m, 5H), 3.17-3.40 (m, 6H), 3.70-3.77 (m, 5H), 3.92-3.95 (m, 1H), 5.24-5.29 (m, 1H), 7.01 (d, J=8.6 Hz, 2H), 7.55 (d, J=8.6 Hz, 2H), 7.89 (brs, 1H).

EXAMPLE 3

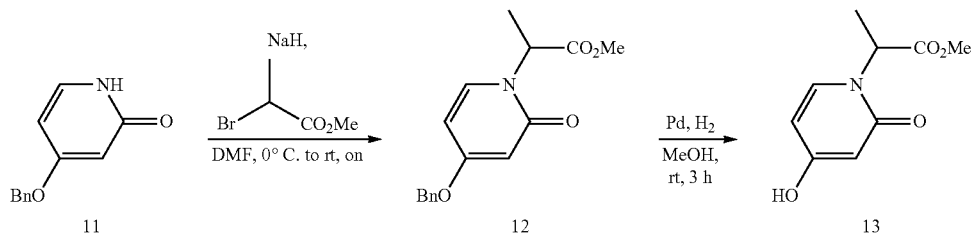

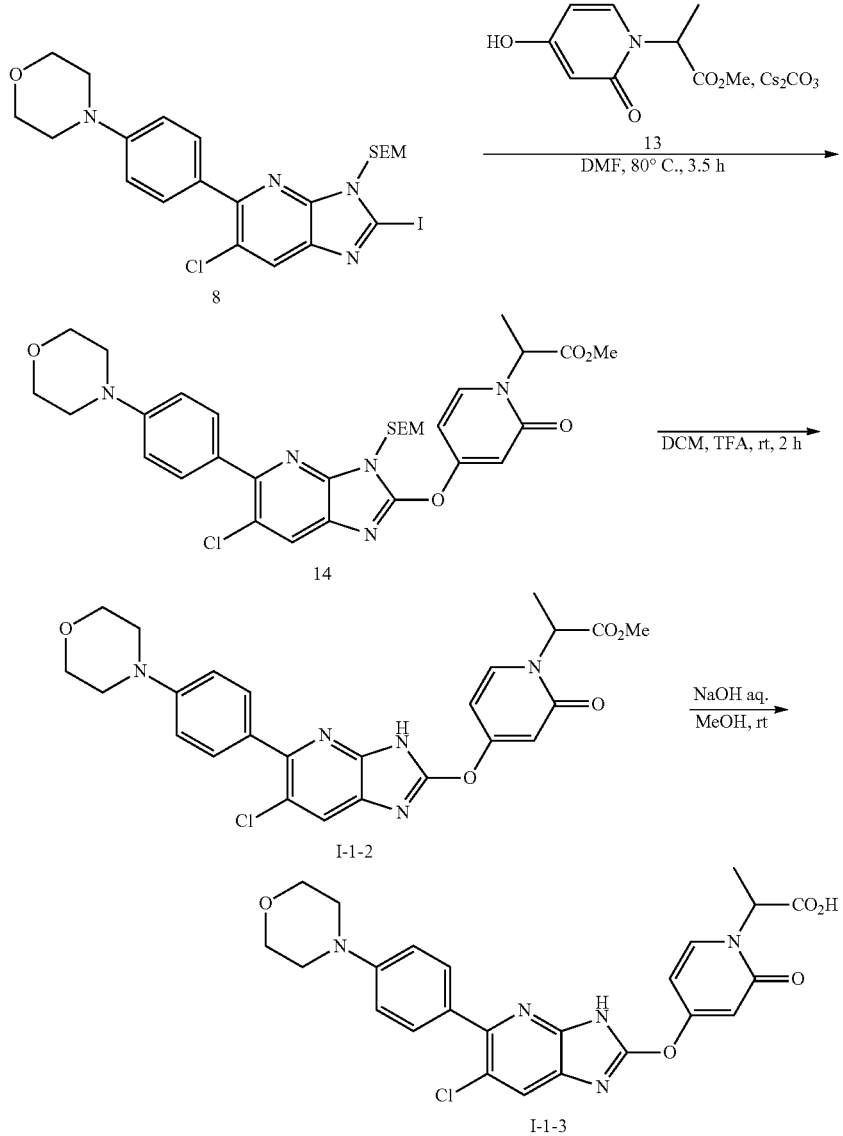

To a solution of Compound 11 (1 g, 4.97 mmol) in DMF (10 mL) was slowly added sodium hydride (219 mg, 5.47 mmol) under ice-cooling, and the obtained reaction mixture was stirred under ice-cooling for 45 minutes. Methyl 2-bromopropionate was added dropwise thereto, and the obtained reaction mixture was warmed up to room temperature and then stirred overnight. To the reaction liquid was added water, followed by extraction with ethyl acetate. The organic layer was washed twice with water and then dried with magnesium sulfate, and the solvent was removed by distillation under reduced pressure. The concentrated residue was purified by silica gel column chromatography (hexane/ethyl acetate=1:1 to 1:4) to obtain Compound 12 (1.03 g, 72%) as a yellow solid.

Compound 12; $^1$H-NMR (CDCl$_3$) δ: 1.62 (3H, d, J=7.60 Hz), 3.75 (3H, s), 4.99 (2H, s), 5.54 (1H, q, J=7.44 Hz), 5.99 (1H, d, J=2.53 Hz), 6.04 (1H, dd, J=7.60, 2.53 Hz), 7.19 (1H, d, J=7.60 Hz), 7.35-7.40 (5H, m).

To a solution of Compound 12 (500 mg, 1.74 mmol) in methanol (5 mL) was added Pd/C (50 mg), and the obtained reaction mixture was stirred under a hydrogen atmosphere at room temperature for 3 hours. The reaction solution was filtered with Celite, and the solvent was then removed by distillation under reduced pressure to obtain Compound 13 (350 mg, 100%) as a white solid.

Compound 13; $^1$H-NMR (DMSO-d$_6$) δ: 1.48 (3H, d, J=7.60 Hz), 3.61 (3H, s), 5.08 (1H, q, J=7.27 Hz), 5.56 (1H, d, J=2.53 Hz), 5.90 (1H, dd, J=7.60, 2.53 Hz), 7.52 (1H, d, J=7.60 Hz), 10.65 (1H, brs).

To a solution of Compound 8 (100 mg, 0.175 mmol) in DMF (1 mL) were added Compound 13 (69 mg, 0.35 mmol) and cesium carbonate (114.2 mg, 0.35 mmol), and the obtained reaction mixture was stirred at 80° C. for 3.5 hours. After cooling, to the reaction liquid was added water, followed by extraction with ethyl acetate. The organic layer was washed with water and then dried with magnesium sulfate, and the solvent was removed by distillation under reduced pressure. The concentrated residue was purified by silica gel column chromatography (hexane/ethyl acetate=1:1 to 1:3) to obtain Compound 14 (59.8 mg, 53%) as a pale yellow solid (amorphous).

Compound 14; $^1$H-NMR (DMSO-$d_6$) δ: −0.11 (9H, s), 0.89 (2H, t, J=8.11 Hz), 1.58 (3H, d, J=7.10 Hz), 3.21 (4H, t, J=4.82 Hz), 3.67-3.70 (5H, m), 3.77 (4H, t, J=4.82 Hz), 5.23 (1H, q, J=7.27 Hz), 5.56 (2H, s), 6.52 (1H, dd, J=7.60, 2.53 Hz), 6.60 (1H, d, J=2.53 Hz), 7.04 (2H, d, J=9.12 Hz), 7.62 (2H, d, J=8.62 Hz), 7.90 (1H, d, J=8.11 Hz), 8.19 (1H, s)

To a solution of Compound 14 (59.8 mg, 0.093 mmol) in methylene chloride (1 mL) was added trifluoroacetic acid (1 ml), and the obtained reaction mixture was stirred at room temperature for 2 hours. The reaction mixture was alkalified with a saturated aqueous solution of sodium hydrogen carbonate, and extracted with methylene chloride. The organic layer was dried with magnesium sulfate, and the solvent was then removed by distillation under reduced pressure to obtain Compound (I-1-2) (48.5 mg, 100%) as a pale yellow solid.

Compound (I-1-2); $^1$H-NMR (CDCl3) δ: 1.66 (3H, d, J=7.60 Hz), 3.20 (4H, t, J=4.82 Hz), 3.78 (3H, s), 3.86 (4H, t, J=4.82 Hz), 5.60 (1H, q, J=7.60 Hz), 6.53 (1H, s), 6.97 (2H, d, J=9.12 Hz), 7.39 (1H, d, J=7.60 Hz), 7.68 (2H, d, J=8.62 Hz), 7.94 (1H, br s).

To a suspension of Compound (I-1-2) (33.5 mg, 0.066 mmol) in methanol (1 mL) was added a 2M aqueous solution of sodium hydroxide (72.2 μl, 0.144 mmol), and the obtained reaction mixture was stirred at room temperature for 7 hours. The solvent was removed by distillation under reduced pressure, and water was added thereto. The obtained liquid was adjusted to pH 4 using a 1 N aqueous solution of hydrochloric acid. The precipitated solid was filtered, followed by washing with water and drying under reduced pressure to obtain Compound (I-1-3) (2.3 mg, 7%) as a pale yellow solid.

Compound (I-1-3);
MS (ESI) m/z=495.95 (M+).
LC/MS retension time=1.54 min.
Method B

EXAMPLE 4

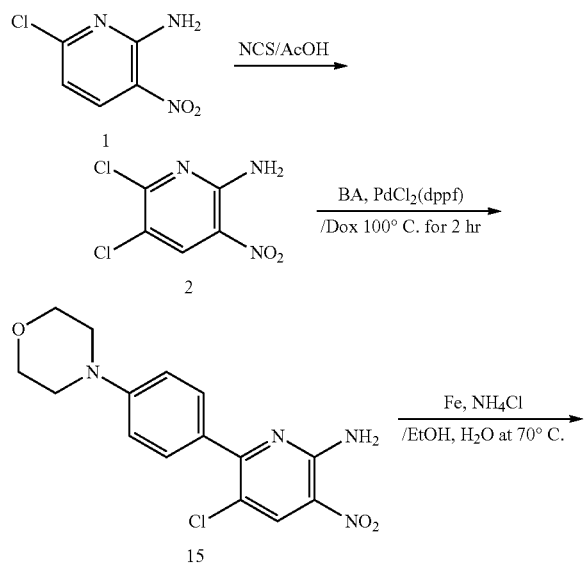

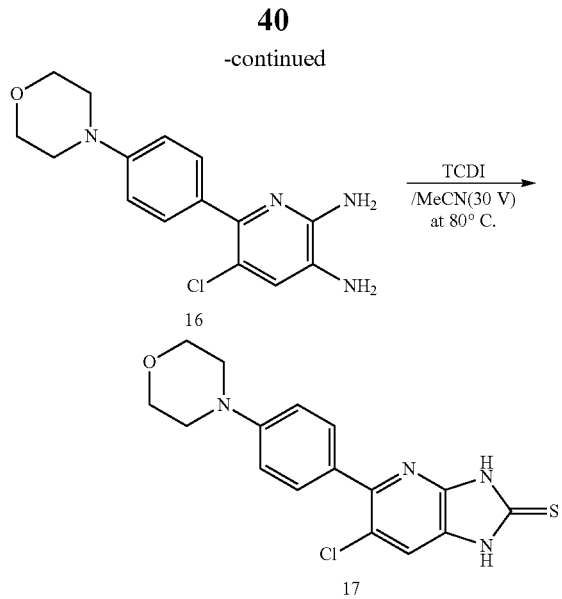

To a suspension of Compound 1 (5 g, 28.8 mmol) in acetic acid (50 mL) was added NCS (4.04 g, 30.2 mmol), and the obtained reaction mixture was stirred at 100° C. for one hour. The reaction mixture was allowed to cool to room temperature, and NCS (0.385 g, 2.88 mmol) was added thereto. The obtained reaction mixture was stirred at 100° C. for one hour again. The obtained reaction mixture was allowed to cool to room temperature, and the solvent was then removed by distillation under reduced pressure. The residue was suspended in distilled water (50 ml), and the obtained liquid was stirred and adjusted to pH=8 using a saturated sodium bicarbonate solution at 0° C.

The solid residue was filtered, and the obtained residue was washed twice with distilled water, followed by vacuum drying to obtain Compound 2 (5.5 g, 92%) as a yellow solid
Compound 2; $^1$H-NMR (DMSO-$d_6$) δ: 8.33 (brs, 2H), 8.59 (s, 1H).

To a suspension of Compound 2 (5.5 g, 26.4 mmol) in 1,4-dioxane (50 mL) were added 4-morpholinophenylboronic acid (6.57 g, 31.7 mmol), PdCl$_2$(dppf)CH$_2$Cl$_2$ (1.51 g, 1.85 mmol) and a 2 M aqueous solution of Na$_2$CO$_3$ (26.4 ml, 52.9 mmol), and the obtained reaction mixture was stirred under a nitrogen atmosphere at 100° C. for one hour. The reaction mixture was allowed to cool to room temperature, and ethyl acetate (50 ml) was added thereto. The obtained liquid was stirred for 10 minutes, and the reaction suspension was then filtered with Celite. The organic layer of the filtrate was washed with water and brine and dried with magnesium sulfate. The solvent was removed by distillation under reduced pressure, and the residue was then purified by silica gel column chromatography (hexane/EtOAc=1:1) to obtain Compound 15 (6.27 g, 71%) as a yellow solid.
Compound 15; $^1$H-NMR (DMSO-$d_6$) δ: 3.25 (t, J=4.82 Hz, 4H), 3.75 (t, J=4.82 Hz, 4H), 7.04 (d, J=9.12 Hz, 2H), 7.74 (d, J=9.12 Hz, 2H), 8.03 (s, 2H), 8.45 (s, 1H).

To a suspension of Compound 15 (5.7 g, 17.0 mmol) in ethanol (100 mL) and distilled water (40 ml) were successively added ammonium chloride (3.64 g, 68.1 mmol) and reduced iron (3.8 g, 68.1 mmol), and the obtained reaction mixture was stirred vigorously at 70° C. for 2 hours. The reaction suspension was filtered with Celite, and the solvent was then removed by distillation under reduced pressure. To the residue was added ethyl acetate (100 ml), and the organic layer was washed three times with brine and then dried with sodium sulfate. The solvent was removed by distillation under reduced pressure, followed by crystallization with chloroform to obtain Compound 16 (4.73 g, 91%) as a brown solid.

Compound 16; $^1$H-NMR (DMSO-$d_6$) δ: 3.13 (t, J=4.82 Hz, 4H), 3.75 (t, J=4.82 Hz, 4H), 4.99 (s, 2H), 5.61 (s, 2H), 6.77 (s, 1H), 6.92 (d, J=9.12 Hz, 2H), 7.49 (d, J=9.12 Hz, 2H).

To a suspension of Compound 16 (3 g, 9.84 mmol) in acetonitrile (90 ml) was added thiocarbonyldiimidazole (2.63 g, 14.8 mmol), and the obtained reaction mixture was stirred at 80° C. for 4 hours. The obtained reaction mixture was allowed to cool to room temperature, and then stirred for one hour, and the resulting solid was filtered. The obtained solid was washed with ethyl acetate, followed by vacuum drying to obtain Compound 17 (3.4 g, 100%) as a brown solid.

Compound 17; $^1$H-NMR (DMSO-$d_6$) δ: 3.19 (t, J=4.82 Hz, 4H), 3.76 (t, J=4.82 Hz, 4H), 7.02 (d, J=9.12 Hz, 2H), 7.54 (d, J=9.12 Hz, 2H), 7.59 (s, 1H), 12.81 (s, 1H), 13.24 (s, 1H).

EXAMPLE 5

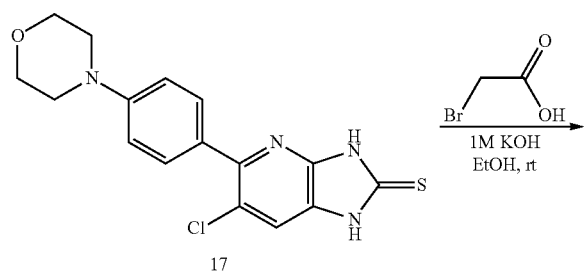

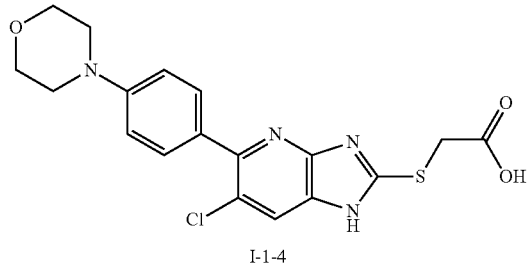

To a solution of Compound 17 (200 mg, 0.58 mmol) in ethanol (5 mL) were added a 1 M aqueous solution of sodium hydroxide (2.9 mL) and 2-bromoacetic acid (160 mg, 0.083 mmol), and the obtained reaction mixture was stirred at room temperature for 2 hours. The reaction liquid was adjusted to pH=5 using 2 N hydrochloric acid, and the precipitated solid was filtered, and the obtained residue was washed with water and dried. The residue was washed with ethyl acetate to obtain Compound (I-1-4) (184 mg, 0.45 mmol) as a yellow solid.

Compound (I-1-4); $^1$H-NMR (DMSO-$d_6$) δ: 2.50 (s, 6H), 3.20 (s, 4H), 3.76 (s, 4H), 4.15 (s, 2H), 7.02 (d, J=8.6 Hz, 2H), 7.57 (d, J=8.1 Hz, 2H), 8.02 (s, 1H), 13.22 (br s, 1H).

EXAMPLE 6

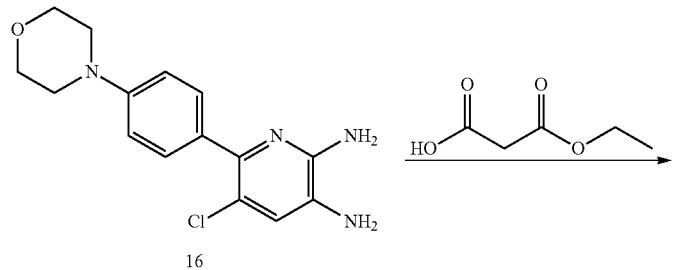

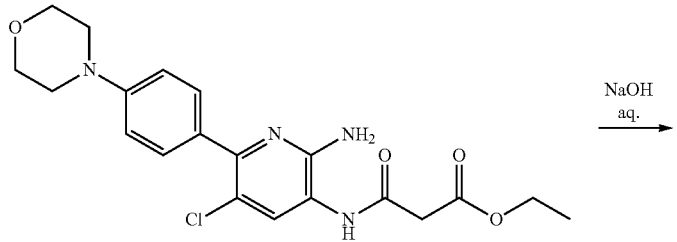

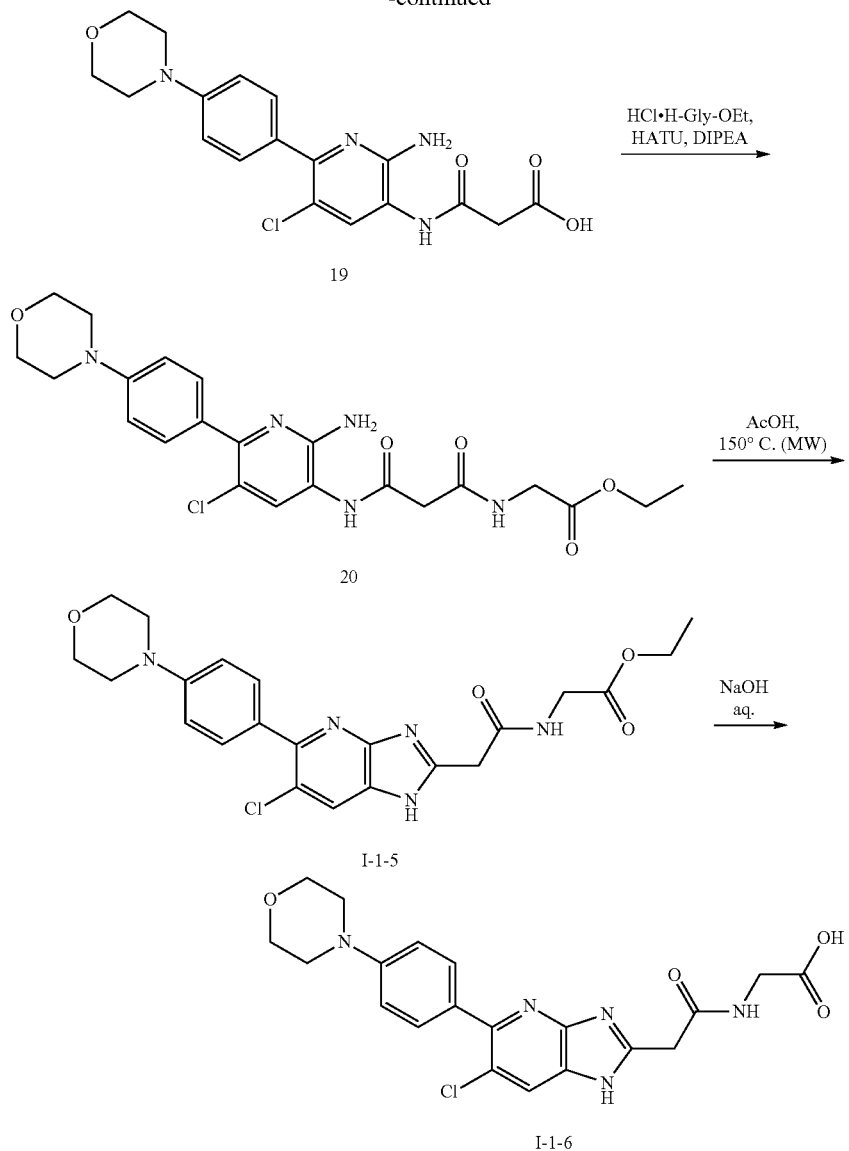

To a solution of Compound 16 (300 mg, 0.984 mmol) in DMF (3 ml) were successively added malonic acid monoethyl ester (173 mg, 1.181 mmol), DIPEA (344 μl, 1.969 mmol), HATU (449 mg, 1.181 mmol), and the obtained reaction mixture was stirred at room temperature for one hour. To the reaction solution, distilled water was added, followed by extraction with ethyl acetate. The organic layer was washed with a saturated sodium bicarbonate solution and brine and then dried with sodium sulfate, and the solvent was removed by distillation under reduced pressure. The concentrated residue was purified by silica gel column chromatography (hexane/ethyl acetate=1:4) to obtain Compound 18 (270 mg, 66%) as a pink solid.

Compound 18; $^1$H-NMR (DMSO-$d_6$) δ: 1.22 (t, J=7.10 Hz, 3H), 3.18 (t, J=4.82 Hz, 4H), 3.75 (t, J=4.82 Hz, 4H), 4.14 (q, J=7.10 Hz, 2H), 6.06 (s, 2H), 6.98 (d, J=8.62 Hz, 2H), 7.57 (d, J=8.62 Hz, 2H), 7.81 (s, 1H), 9.47 (s, 1H).

To a suspension of Compound 18 (214 mg, 0.511 mmol) in ethanol (2 ml) was added dropwise a 2 N NaOH aqueous solution (0.766 ml, 1.533 mmol) under ice-cooling, and the obtained reaction mixture was warmed up to room temperature and then stirred for 2 hours. To the reaction liquid, 2 ml of distilled water was added, and the aqueous layer was washed three times with chloroform. To the aqueous layer, a 2 N HCl aqueous solution (0.74 ml) was added, followed by extraction three times with ethyl acetate and drying with sodium sulfate, and the solvent was then removed by distillation under reduced pressure. The solid residue of the resulting Compound 19 was used for the following reaction without further purification.

To a solution of Compound 19 (180 mg, 0.461 mmol) in DMF (2 ml) were added glycine ethyl ester hydrochloride (77 mg, 0.553 mmol), DIPEA (161 μl, 0.921 mmol), HATU (210 mg, 0.553 mmol), and the obtained reaction mixture was stirred at room temperature for 3 hours. To the reaction liquid, a saturated sodium bicarbonate solution was added, followed by extraction with ethyl acetate, washing with a saturated sodium bicarbonate solution and brine and drying with sodium sulfate. The solvent was then removed by distillation under reduced pressure. The resulting solid residue was suspended in ether, and the suspension was filtered to obtain Compound 20 (200 mg, 91%) as a white solid.

Compound 20; $^1$H-NMR (DMSO-d$_6$) δ: 1.20 (t, J=7.10 Hz, 3H), 3.17 (t, J=4.82 Hz, 4H), 3.36 (s, 2H), 3.75 (t, J=4.82 Hz, 4H), 3.90 (d, J=5.58 Hz, 2H), 4.11 (q, J=7.10 Hz, 2H), 6.10 (s, 2H), 6.98 (d, J=8.62 Hz, 2H), 7.57 (d, J=8.62 Hz, 2H), 7.77 (s, 1H), 8.54 (t, J=5.58 Hz, 1H), 9.43 (s, 1H).

A solution of Compound 20 (195 mg, 0.410 mmol) in acetic acid (3 ml) was stirred under microwave irradiation at 150° C. for 20 minutes. Acetic acid was removed by distillation under reduced pressure, followed by dilution with ethyl acetate (10 ml), and then washing with a saturated sodium bicarbonate solution and brine. After drying with sodium sulfate, the solvent was removed by distillation under reduced pressure, followed by purification by silica gel column chromatography (chloroform: methanol=10:1) to obtain Compound (I-1-5) (160 mg, 85%) as a white solid.

Compound (I-1-5); $^1$H-NMR (DMSO-d$_6$) δ: 1.18 (t, J=7.10 Hz, 3H), 3.20 (t, J=4.56 Hz, 4H), 3.77 (t, J=4.82 Hz, 4H), 3.84 (s, 2H), 3.91 (d, J=5.58 Hz, 2H), 4.10 (q, J=7.10 Hz, 2H), 7.03 (d, J=8.62 Hz, 2H), 7.57 (d, J=8.62 Hz, 2H), 8.13 (s, 1H), 8.62 (t, J=5.58 Hz, 1H), 13.06 (s, 1H).

To a solution of Compound (I-1-5) (138 mg, 0.301 mmol) in ethanol (2.5 ml) was added a 2 N NaOH aqueous solution (377 μl, 0.753 mmol), and the obtained reaction mixture was stirred at room temperature for 2 hours. The solvent was removed by distillation under reduced pressure, followed by dilution with distilled water (3 ml), and then washing three times with chloroform. The aqueous layer was adjusted to pH=4 using a 2 N HCl aqueous solution, and the resulting solid was filtered to obtain Compound (I-1-6) (40 mg, 31%) as a brown solid.

Compound (I-1-6); $^1$H-NMR (DMSO-d$_6$) δ: δ: 3.20 (t, J=4.82 Hz, 4H), 3.77 (t, J=4.82 Hz, 4H), 3.83 (d, J=5.58 Hz, 2H), 3.87 (s, 2H), 7.03 (d, J=9.12 Hz, 2H), 7.57 (d, J=9.12 Hz, 2H), 8.10 (s, 1H), 8.58 (t, J=5.58 Hz, 1H), 12.62 (s, 1H).

EXAMPLE 7

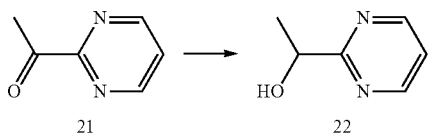

To a solution of Compound 21 (390 mg, 3.19 mmol) in MeOH (4 ml) was added sodium borohydride (60 mg, 1.60 mmol), and the obtained reaction mixture was stirred at room temperature for one hour. The solvent was removed by distillation under reduced pressure, followed by dilution with a saturated aqueous solution of ammonium chloride, and extraction with ethyl acetate. The organic layer was washed with a saturated aqueous solution of ammonium chloride and brine and dried with sodium sulfate. The solvent was then removed by distillation under reduced pressure to obtain Compound 22 (350 mg, 88%) as a colorless oil.

Compound 22; $^1$H-NMR (CDCl$_3$) δ: 1.58 (d, J=6.65 Hz, 3H), 4.18 (s, 1H), 4.97 (q, J=6.65 Hz, 1H), 7.24 (t, J=4.89 Hz, 1H), 8.75 (d, J=4.89 Hz, 2H).

EXAMPLE 8

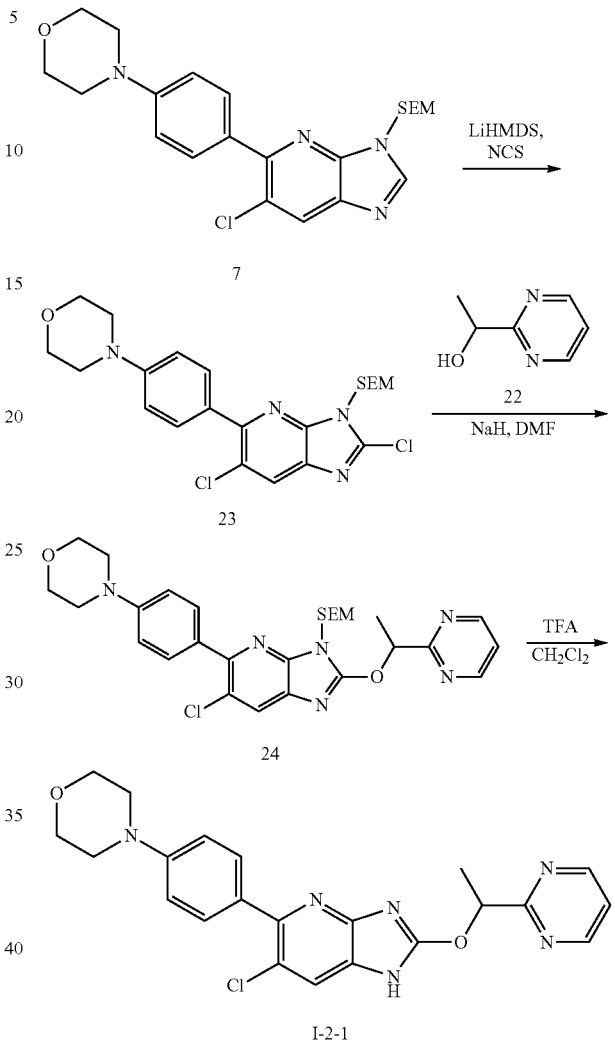

To a solution of Compound 7 (2.15 g, 4.83 mmol) in THF (25 ml) were added dropwise TMEDA (2.19 ml, 14.5 mmol) and 1M LiHMDS/THF (10.15 ml, 10.15 mmol) at −60° C., and the obtained reaction mixture was stirred for one hour. NCS (1.94 g, 14.5 mmol) was added thereto at −60° C., and the obtained reaction mixture was stirred for another 2.5 hours. The reaction liquid was quenched with a saturated aqueous solution of ammonium chloride, followed by extraction with ethyl acetate and washing with brine. The organic layer was dried with sodium sulfate, and the solvent was removed by distillation under reduced pressure. The concentrated residue was purified by silica gel column chromatography (hexane/ethyl acetate=31) to obtain Compound 23 (1.6 g, 69%) as a yellow solid.

Compound 23; $^1$H-NMR (CDCl$_3$) δ: −0.06 (s, 9H), 0.95 (t, J=8.36 Hz, 2H), 3.26 (t, J=4.82 Hz, 4H), 3.70 (t, J=8.36 Hz, 2H), 3.89 (t, J=4.82 Hz, 4H), 5.68 (s, 2H), 6.98 (d, J=8.62 Hz, 2H), 7.72 (d, J=8.62 Hz, 2H), 8.04 (s, 1H).

To a solution of Compound 23 (52 mg, 0.417 mmol) in DMF (1 ml) was added sodium hydride (17 mg, 0.417 mmol) under ice-cooling, and the obtained reaction mixture was stirred for 10 minutes. Compound 23 (100 mg, 0.209 mmol) was added thereto, and the obtained reaction mixture was stirred at room temperature for another 30 minutes. To the reaction liquid, a saturated aqueous solution of ammonium chloride was added, followed by extraction with ethyl acetate, washing with a saturated aqueous solution of ammonium chloride and brine and drying with sodium sulfate. The solvent was then removed by distillation under reduced pressure. The concentrated residue was purified by silica gel column chromatography (hexane/ethyl acetate=1:2) to obtain Compound 24 (113 mg, 96%) as a colorless oil.

Compound 24; $^1$H-NMR (CDCl$_3$) δ: −0.04 (s, 9H), 0.98 (t, J=9.04 Hz, 2H), 1.88 (d, J=6.78 Hz, 3H), 3.24 (t, J=4.83 Hz, 4H), 3.79 (t, J=9.04 Hz, 2H), 3.89 (t, J=4.83 Hz, 4H), 5.60 (dd, J=13.24, 11.23 Hz, 2H), 6.32 (q, J=6.78 Hz, 1H), 6.96 (d, J=8.91 Hz, 2H), 7.22 (t, J=4.89 Hz, 1H), 7.70 (d, J=8.91 Hz, 2H), 7.73 (s, 1H), 8.72 (d, J=4.89 Hz, 2H).

To a solution of Compound 24 (113 mg, 0.199 mmol) in DCM (0.5 ml) was added TFA (0.5 ml, 6.49 mmol), and the obtained reaction mixture was stirred at room temperature for 5 hours. MeOH (0.5 ml) was added thereto, and the obtained reaction mixture was stirred for another 3 hours, and then adjusted to around pH 8 with 2 ml of 2 N NaOH aq. and a saturated sodium bicarbonate solution, followed by extraction three times with chloroform. After drying with sodium sulfate, the solvent was removed by distillation under reduced pressure, followed by purification by silica gel column chromatography (chloroform:methanol=10:1), and the resulting concentrated residue was crystallized with ethyl acetate and hexane to obtain Compound (I-2-1) (63 mg, 72%) as a white solid.

Compound (I-2-1); $^1$H-NMR (DMSO-d$_6$) δ: 1.74 (d, J=6.53 Hz, 3H), 3.18 (t, J=4.64 Hz, 4H), 3.76 (t, J=4.64 Hz, 4H), 6.16 (q, J=6.53 Hz, 1H), 7.00 (d, J=8.53 Hz, 2H), 7.45 (t, J=4.77 Hz, 1H), 7.53 (d, J=8.53 Hz, 2H), 7.81 (s, 1H), 8.81 (d, J=4.77 Hz, 2H), 12.88 (s, 1H).

EXAMPLE 9

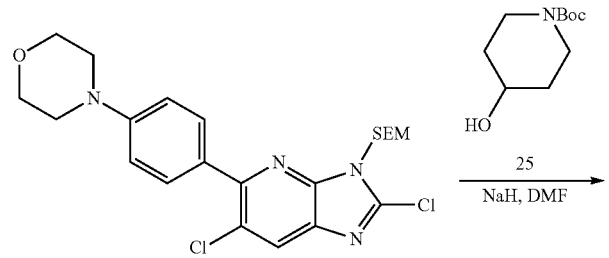

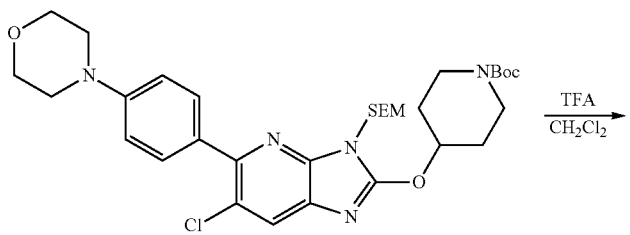

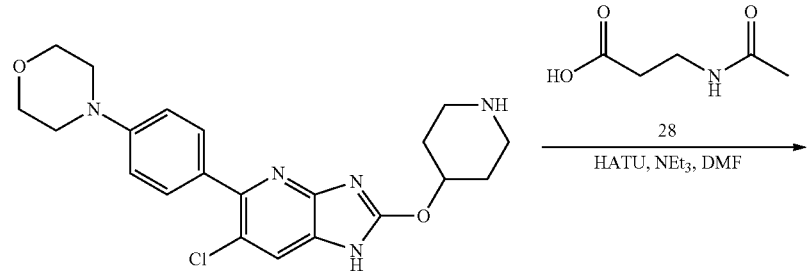

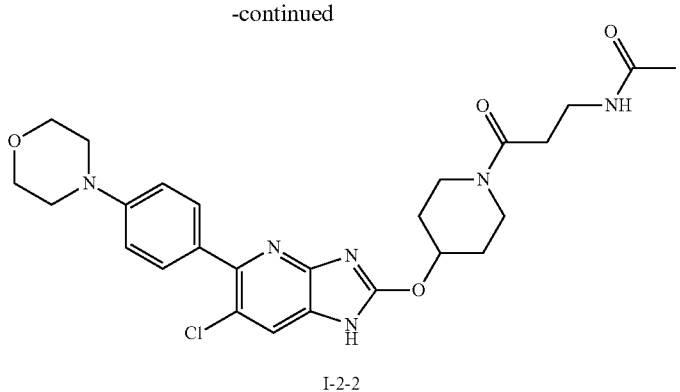

I-2-2

To a solution of Compound 25 (504 mg, 2.50 mmol) in N,N-dimethylformamide (5 ml) was added sodium hydride (100 mg, 2.50 mmol) at 0° C., and the obtained reaction mixture was stirred for 30 minutes. Thereafter, to the reaction suspension, a solution of Compound 23 (800 mg, 1.67 mmol) in N,N-dimethylformamide (5 ml) was added at 0° C., and the obtained liquid was stirred at room temperature for 3 hours. The reaction liquid was extracted with water and ethyl acetate, and the organic layer was then washed with brine and dried with sodium sulfate. The solvent was removed by distillation under reduced pressure to obtain a colorless oily compound 26. The following reaction was carried out without further purification.

To a solution of Compound 26 obtained above in methylene chloride (2 ml) was added trifluoroacetic acid (2 ml), and the obtained reaction mixture was stirred at room temperature overnight. Thereafter, to the reaction solution, a 2 N aqueous solution of sodium hydroxide was added, followed by extraction with ethyl acetate. The organic layer was washed with water and brine and dried with sodium sulfate. The solvent was removed by distillation under reduced pressure, and to the residue, hexane was added, followed by filtration. The obtained residue was washed with hexane to obtain Compound 27 (617.6 mg, 1.49 mmol, 89%) as a white solid.

Compound 27: $^1$H-NMR (DMSO-d$_6$) δ: 1.51-1.60 (m, 2H), 2.03-2.05 (m, 2H), 2.57-2.62 (m, 2H), 2.97-3.00 (m, 2H), 3.16-3.18 (m, 4H), 3.75-3.77 (m, 4H), 5.00-5.04 (m, 1H), 6.99 (d, J=8.78 Hz, 2H), 7.54 (d, J=8.78 Hz, 2H), 7.64 (s, 1H).

To a solution of Compound 27 (70 mg, 0.17 mmol) in N,N-dimethylformamide (1 ml) were added Compound 28 (24 mg, 0.18 mmol), HATU (77 mg, 0.20 mmol) and triethylamine (0.047 ml, 0.20 mmol), and the obtained reaction mixture was stirred at room temperature for 2 hours. Thereafter, butylamine (0.5 ml) was added thereto, and the obtained reaction mixture was stirred overnight. Thereafter, to the reaction liquid, a saturated solution of sodium hydrogen carbonate was added, followed by extraction with ethyl acetate. The organic layer was washed with water and brine and dried with sodium sulfate. The solvent was removed under reduced pressure, and the residue was purified by silica gel chromatography to obtain Compound (I-2-2) (20 mg, 0.038 mmol, 22%) as a white solid.

Compound (I-2-2):

MS(ESI) m/z=527.25 (M+H)

LC/MS retension time=1.47 min

Method B

EXAMPLE 10

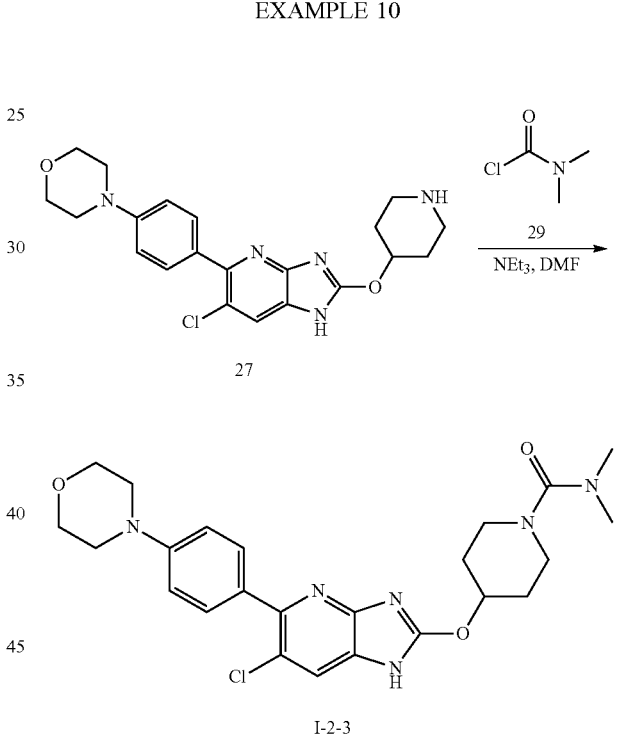

To a solution of Compound 27 (80 mg, 0.19 mmol) in N,N-dimethylformamide (1 ml) were added triethylamine (0.054 ml, 0.38 mmol) and Compound 29 (23 mg, 0.21 mmol), and the obtained reaction mixture was stirred at room temperature for 2 hours. Thereafter, the reaction liquid was extracted with water and ethyl acetate, and the organic layer was then washed with water and brine and dried with sodium sulfate. The solvent was removed under reduced pressure, and the residue was purified by silica gel chromatography to obtain Compound (I-2-3) (34.3 mg, 0.071 mmol, 37%) as a white solid.

Compound (I-2-3): $^1$H-NMR (DMSO-d$_6$) δ: 1.70-1.76 (m, 2H), 2.07-2.14 (m, 2H), 2.75 (s, 6H), 3.00-3.06 (m, 2H), 3.17-3.20 (m, 4H), 3.40-3.48 (m, 2H), 3.75-3.77 (m, 4H), 5.19-5.23 (m, 1H), 7.01 (d, J=8.62 Hz, 2H), 7.55 (d, J=8.62 Hz, 2H), 7.85 (s, 1H).

EXAMPLE 11

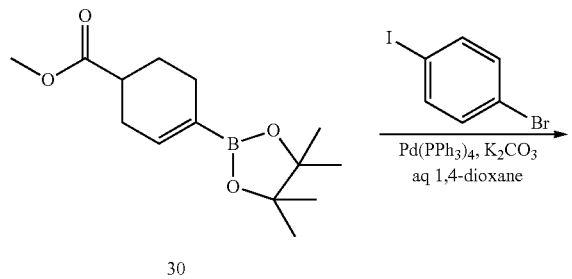

To a solution of iodobromobenzene (1.1 g, 3.8 mmol) in 1,4-dioxane (10 mL) were successively added Compound 30 (1 g, 3.8 mmol), Pd(PPh$_3$)$_4$ (0.22 g, 0.19 mmol) and a 2 N aqueous solution of potassium carbonate (4.1 mL, 8.3 mmol), and the obtained reaction mixture was stirred at 80° C. for 2 hours. Thereafter, the reaction liquid was extracted with ethyl acetate and then drying with magnesium sulfate. The solvent was removed by distillation under reduced pressure, and the residue was purified by silica gel column chromatography to obtain Compound 31 (0.83 g, 2.8 mmol, 75%) as a white solid.

Compound 31; $^1$H-NMR (DMSO-d$_6$) δ: 1.66-1.76 (m, 1H), 2.06-2.09 (m, 1H), 2.28-2.36 (m, 1H), 2.41-2.44 (m, 3H), 2.59-2.66 (m, 1H), 3.63 (s, 3H), 6.18-6.21 (m, 1H), 7.35-7.38 (m, 2H), 7.49-7.51 (m, 2H).

To a solution of Compound 31 (0.83 g, 2.8 mmol) in 1,4-dioxane (4 mL) were successively added a borane reagent (0.79 g, 3.1 mmol), PdCl$_2$(dppf) dichloromethane complex (0.23 g, 0.28 mmol) and potassium acetate (0.36 g, 3.7 mmol), and the obtained reaction mixture was stirred under microwave irradiation at 130° C. for 20 minutes. Thereafter, the reaction solution was filtered. The solvent was removed by distillation under reduced pressure, and the residue was purified by silica gel column chromatography to obtain Compound 32 (0.76 g, 2.2 mmol, 78%) as a white solid.

Compound 32; $^1$H-NMR (DMSO-d$_6$) δ: 1.29 (s, 12H), 1.69-1.73 (m, 1H), 2.08-2.09 (m, 1H), 2.35-2.38 (m, 1H), 2.44-2.46 (m, 3H), 2.63-2.65 (m, 1H), 3.62 (s, 3H), 6.22-6.25 (m, 1H), 7.42 (d, J=8.2 Hz, 2H), 7.62 (d, J=8.2 Hz, 2H).

EXAMPLE 12

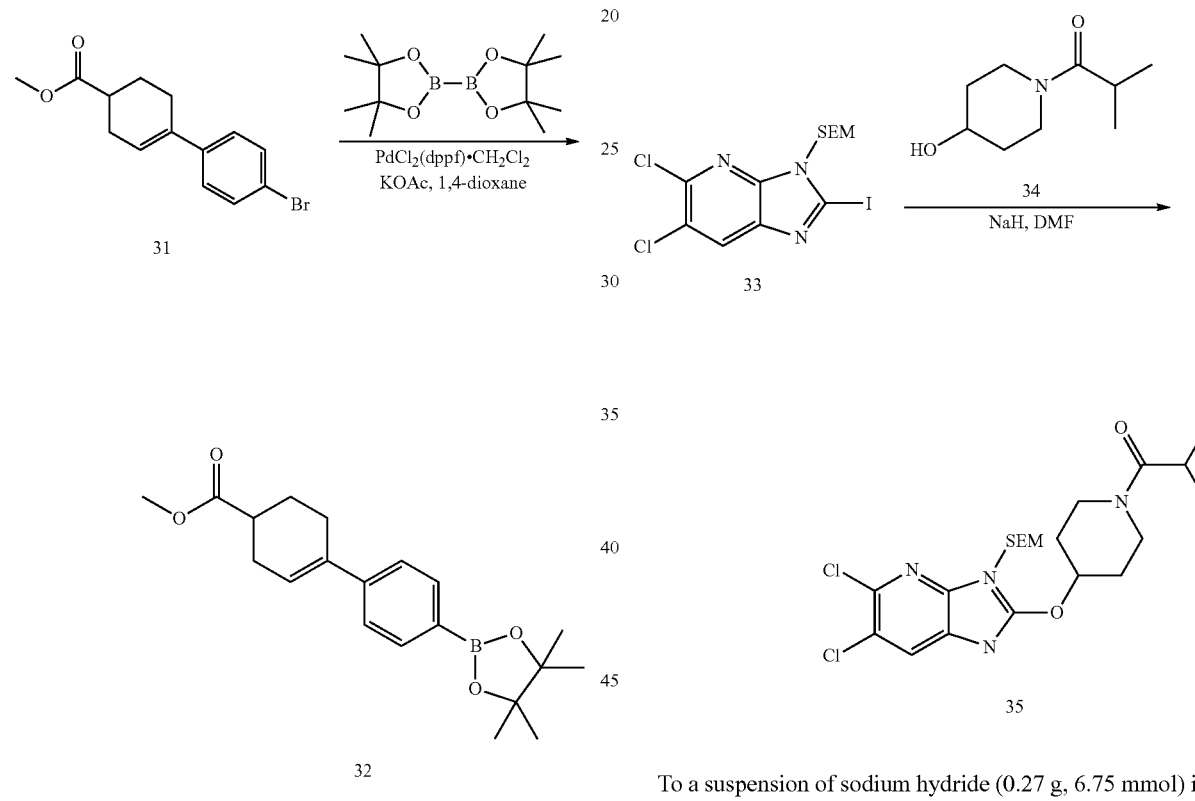

To a suspension of sodium hydride (0.27 g, 6.75 mmol) in N,N-dimethylformamide (15 mL) was added Compound 34 (1.16 g, 6.75 mmol) at room temperature, and the obtained reaction mixture was stirred for 10 minutes. Thereafter, to the reaction suspension, Compound 33 (2.00 g, 4.50 mmol) was added, and the reaction mixture was stirred at room temperature for 2 hours. The reaction liquid was extracted with water and ethyl acetate, and the organic layer was then washed with water and brine and dried with magnesium sulfate. The solvent was removed by distillation under reduced pressure, and the residue was purified by silica gel column chromatography to obtain Compound 35 (1.49 g, 3.06 mmol, 68%) as a colorless liquid.

Compound 35: $^1$H-NMR (DMSO-d$_6$) δ: −0.06 (s, 9H), 0.86 (t, J=7.9 Hz, 2H), 1.01 (d, J=6.6 Hz, 6H), 1.75-1.83 (m, 2H), 1.99-2.09 (m, 2H), 2.87-2.94 (m, 1H), 3.45-3.56 (m, 2H), 3.62 (t, J=7.9 Hz, 2H), 3.73-3.77 (m, 2H), 5.37-5.39 (m, 3H), 8.19 (s, 1H).

EXAMPLE 13

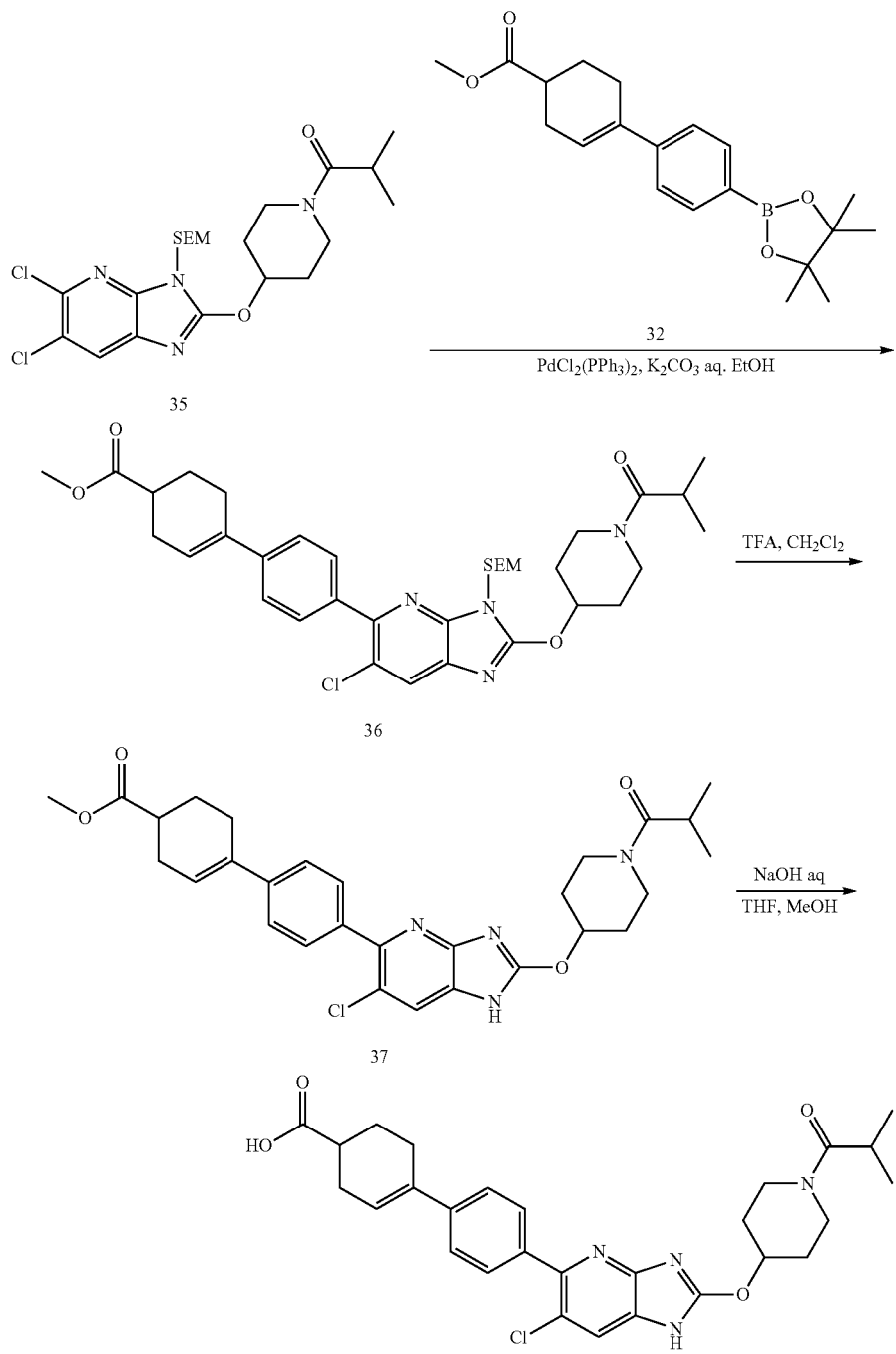

To a solution of Compound 35 (90 mg, 0.18 mmol) in ethanol (0.9 mL) were successively added boronic acid ester 32 (67 mg, 0.19 mmol), $PdCl_2(PPh_3)_2$ (12 mg, 0.018 mmol), and a 2 M aqueous solution of potassium carbonate (0.21 mL, 0.42 mmol), and the obtained reaction mixture was stirred under microwave irradiation at 130° C. for 8 minutes. Thereafter, boronic acid ester (6.7 mg, 0.019 mmol) and $PdCl_2(PPh_3)^2$ (12 mg, 0.018 mmol) were successively added thereto, and the obtained reaction mixture was stirred under microwave irradiation at 130° C. for 8 minutes. To the reaction liquid, water and ethyl acetate were added, followed by extraction, and the organic layer was dried with magnesium sulfate. The solvent was removed by distillation under reduced pressure to obtain a crude product 36.

To a solution of the resulting crude product 36 in dichloromethane (0.3 mL) was added trifluoroacetic acid (0.3 mL, 3.9 mmol), and the obtained reaction mixture was stirred at room temperature for 2 hours. Thereafter, to the reaction liquid, a saturated sodium bicarbonate solution was added under ice-cooling, and chloroform was then added thereto, followed by extraction. The organic layer was dried with magnesium sulfate, and the solvent was then removed by distillation under reduced pressure to obtain a crude product 37.

The crude product 37 was dissolved in 1,4-dioxane (0.6 mL), and methanol (0.3 mL) and a 2 M aqueous solution of sodium hydroxide (0.27 mL, 0.53 mmol) were successively added thereto, and the obtained reaction mixture was stirred at room temperature for 1.5 hours. Thereafter, the reaction liquid was washed with ethyl acetate, and the aqueous layer was neutralized with 2 N hydrochloric acid. The resulting white solid was filtered, and the obtained solid was dissolved in chloroform and methanol. Ethyl acetate was added thereto, followed by recrystallization to obtain Compound (I-2-4) (45 mg, 0.083 mmol, 47%) as a white solid.

Compound (I-2-4); $^1$H-NMR (DMSO-$d_6$) δ: 1.01 (d, J=6.5 Hz, 6H), 1.67-1.74 (m, 3H), 2.08-2.12 (m, 3H), 2.36-2.41 (m, 5H), 2.90-2.94 (m, 1H), 3.35-3.50 (m, 2H), 3.77-3.81 (m, 1H), 3.90-3.93 (m, 1H), 5.27-5.29 (m, 1H), 6.25-6.27 (m, 1H), 7.50 (d, J=8.4 Hz, 2H), 7.60 (d, J=8.4 Hz, 2H), 7.89 (s, 1H).

EXAMPLE 14

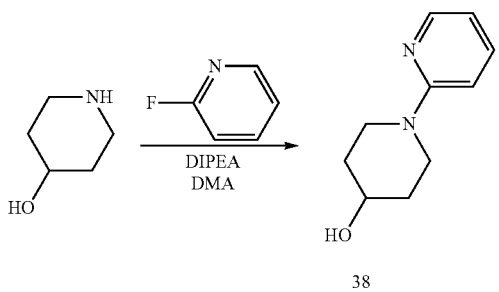

To a solution of 4-hydroxypiperidine (375 mg, 3.71 mmol) in N,N-dimethylacetamide (3 mL) was added 2-fluoropyridine (300 mg, 3.09 mmol), and the obtained reaction mixture was stirred under microwave irradiation at 160° C. for 50 minutes. Thereafter, to the reaction liquid, water and chloroform were added, followed by extraction, and the organic layer was then washed with water and brine and dried with magnesium sulfate. The solvent was removed by dilution under reduced pressure, and the residue was purified by silica gel column chromatography to obtain Compound 38 (463.3 mg, 2.60 mmol) as a brown oil.

Compound 38; $^1$H-NMR (DMSO-$d_6$) δ: 1.27-1.39 (m, 2H), 1.72-1.80 (m, 2H), 3.00-3.09 (m, 2H), 3.65-3.72 (m, 2H), 3.96-4.03 (m, 2H), 4.67 (d, J=4.2 Hz, 1H), 6.55-6.59 (m, 1H), 6.81 (d, J=8.7 Hz, 1H), 7.45-7.51 (m, 1H), 8.07-8.09 (m, 1H).

EXAMPLE 15

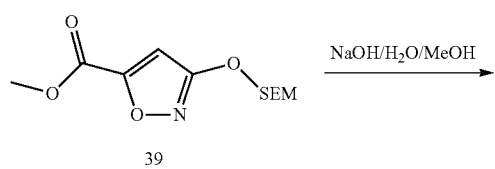

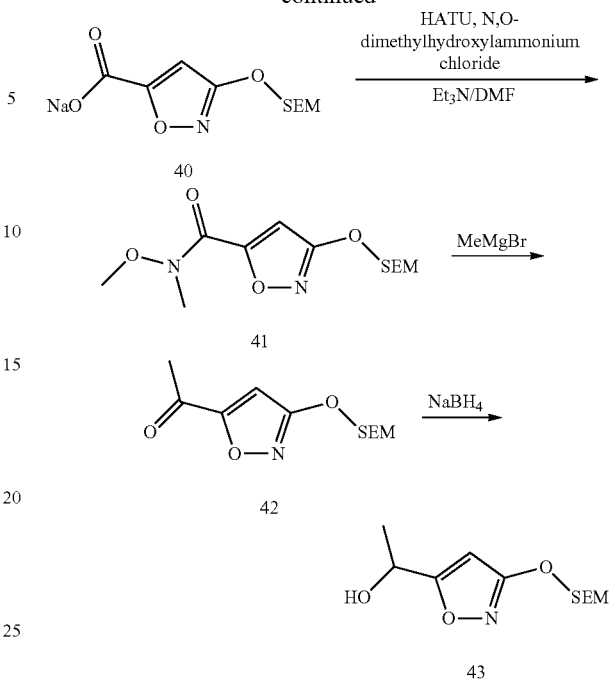

To a solution of Compound 39 (1 g, 3.66 mmol) in methanol (10 mL) was added a 5 N NaOH aqueous solution (0.805 ml, 4.02 mmol), and the obtained reaction mixture was stirred at room temperature for one hour. The solvent was removed by distillation under reduced pressure, and the residue was subjected to vacuum drying to obtain Compound 40 (1 g, 97%) as a white solid.

To a solution of Compound 40 (1 g, 3.55 mmol) in DMF (10 mL) were added Et$_3$N (1.08 ml, 7.82 mmol), N,O-dimethyl hydroxylammonium chloride (416 mg, 4.27 mmol) and HATU (1.62 g, 4.27 mmol), and the obtained reaction mixture was stirred under a nitrogen atmosphere at room temperature for 0.5 hours. Ethyl acetate (30 ml) was added thereto, and the obtained liquid was washed three times with a saturated sodium bicarbonate solution and three times with brine and dried with sodium sulfate. The solvent was removed by distillation under reduced pressure, and the residue was subjected to vacuum drying to obtain Compound 41 (1.07 g, 100%) as a colorless oil.

Compound 41; $^1$H-NMR (CDCl$_3$) δ: 0.02 (s, 9H), 1.00 (t, J=8.47 Hz, 2H), 3.37 (s, 3H), 3.81 (s, 3H), 3.82 (t, J=8.47 Hz, 2H), 5.41 (s, 2H), 6.56 (s, 1H).

To a solution of a 0.99 M methylmagnesium bromide solution in ether (5.31 ml, 5.26 mmol) in THF (5 ml) was slowly added dropwise a solution of Compound 41 (1.06 g, 3.51 mmol) in THF (5 ml) at 0° C., and the obtained reaction mixture was stirred at 0° C. for one hour. The reaction was stopped by a saturated aqueous solution of ammonium chloride, followed by extraction with ethyl acetate, and the organic layer was washed with water and brine and dried with sodium sulfate. The solvent was removed by distillation under reduced pressure, and the concentrated residue was purified by silica gel column chromatography (hexane/ethyl acetate=21) to obtain Compound 42 (873 mg, 97%) as a colorless oil.

Compound 42; $^1$H-NMR (CDCl$_3$) δ: 0.02 (s, 9H), 1.00 (t, J=8.53 Hz, 2H), 2.57 (s, 3H), 3.81 (t, J=8.53 Hz, 2H), 5.41 (s, 2H), 6.59 (s, 1H).

To a solution of Compound 42 (334 mg, 1.30 mmol) in methanol (5 ml) was added sodium borohydride (25 mg, 0.650 mmol), and the obtained reaction mixture was stirred at room temperature for one hour. The solvent was removed by distillation under reduced pressure, followed by dilution with a saturated aqueous solution of ammonium chloride, and extraction with ethyl acetate. The organic layer was washed with a saturated aqueous solution of ammonium chloride and brine and dried with sodium sulfate. The solvent was then removed by distillation under reduced pressure to obtain Compound 43 (340 mg, 101%) as a colorless oil.

Compound 43; $^1$H-NMR (CDCl$_3$) δ: 0.02 (s, 9H), 1.00 (t, J=8.28 Hz, 2H), 1.56 (d, J=6.78 Hz, 3H), 2.18 (d, J=5.27 Hz, 1H), 3.80 (t, J=8.28 Hz, 2H), 4.90 (dq, J=5.27, 6.78 Hz, 1H), 5.35 (s, 2H), 5.92 (s, 1H).

EXAMPLE 16

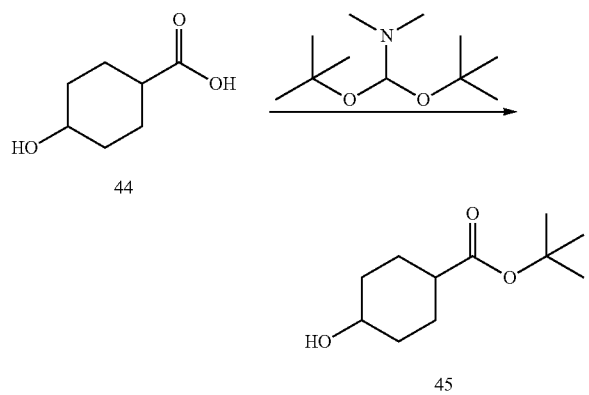

A suspension of Compound 44 (4.52 g, 31.4 mmol) in 1,1-di-tert-butoxy-N,N-dimethylmethanamine (75 ml, 314 mmol) was stirred at 80° C. for 3 hours, and a saturated aqueous solution of ammonium chloride was then added thereto, followed by extraction with ethyl acetate. The organic layer was washed with a saturated aqueous solution of ammonium chloride, a saturated sodium bicarbonate solution and brine and then dried with anhydrous magnesium sulfate. The solvent was then removed by distillation under reduced pressure. The obtained solid residue was suspended in cold hexane, and then filtered to obtain Compound 45 (5.22 g, 83%) as a white solid.

Compound 45; $^1$H-NMR (DMSO-d$_6$) δ: 1.06-1.47 (m, 13H), 1.76-1.85 (m, 4H), 2.06 (tt, J=11.80, 3.22 Hz, 1H), 3.28-3.40 (m, 1H), 4.55 (d, J=4.27 Hz, 1H).

EXAMPLE 17

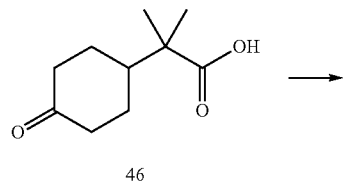

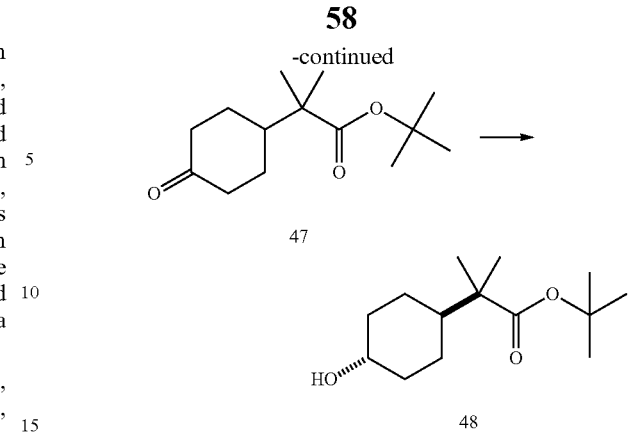

Commercially available Compound 46 (1 g, 5.43 mmol) and 1,1-di-tert-butoxy-N,N-dimethylmethaneamine (11 g, 54.3 mmol) were stirred with heating at 80° C. for 3 hours. To the reaction liquid, water and ethyl acetate were added, followed by separation and extraction with ethyl acetate. The organic layer was dried with anhydrous magnesium sulfate, and then concentrated under reduced pressure. The obtained residue was purified by silica gel column chromatography (hexane/ethyl acetate) to obtain Compound 47 (300 mg, 1.25 mmol, 23%) as a colorless liquid.

Compound 47; $^1$H-NMR (CDCl$_3$) δ: 1.04 (s, 6H), 1.33-1.45 (m, 11H), 1.83 (d$_q$, J=13.0, 3.0 Hz, 2H), 2.01 (tt, J=12.0, 3.0 Hz, 1H), 2.20 (dt, J=14.6, 2.1 Hz, 2H), 2.40 (td, J=14.2, 5.9 Hz, 2H).

To a solution of Compound 47 (300 mg, 1.25 mmol) in methanol (5 mL) was added sodium borohydride (70.8 mg, 1.87 mmol), and the obtained reaction mixture was stirred at room temperature for 2 hours. To the reaction liquid, water and ethyl acetate were added, followed by separation and extraction with ethyl acetate. The organic layer was dried with anhydrous magnesium sulfate, and concentrated under reduced pressure. The obtained residue was purified by silica gel column chromatography (hexane/ethyl acetate) to obtain Compound 48 (60 mg, 0.248 mmol, 20%) as a colorless liquid.

Compound 48; $^1$H-NMR (DMSO-d$_6$) δ: 0.97 (s, 6H), 1.04 (t, J=9.3 Hz, 3H), 1.38 (s, 9H), 1.41 (tt, J=12.0, 3.0 Hz, 2H), 1.51 (d, J=12.4 Hz, 2H), 1.84 (dd, J=9.1, 3.6 Hz, 2H), 3.26 (dt, J=14.8, 5.2 Hz, 1H), 4.49 (d, J=4.4 Hz, 1H).

EXAMPLE 18

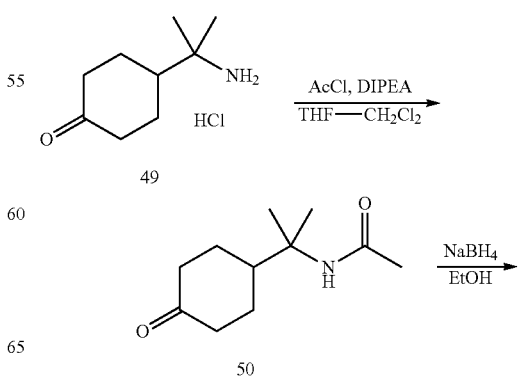

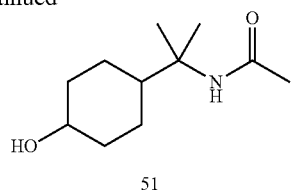

51

To a solution of Compound 49 (208 mg, 1.09 mmol) described in WO2009/156100 in THF (2 mL) and methylene chloride (1 mL) were successively added DIPEA (0.474 mL, 2.71 mmol) and acetyl chloride (0.93 mL, 1.30 mmol), and the obtained reaction mixture was stirred at room temperature overnight. Thereafter, to the reaction liquid, water and ethyl acetate were added, followed by extraction, and the organic layer was dried with magnesium sulfate. The solvent was removed by distillation under reduced pressure, and the residue was purified by silica gel column chromatography to obtain Compound 50 (137 mg, 0.69 mmol, 64%) as a colorless solid (amorphous).

Compound 50; $^1$H-NMR (CDCl$_3$) δ: 1.28 (s, 6H), 1.43-1.49 (m, 2H), 1.95 (s, 3H), 2.02-2.05 (m, 2H), 2.39-2.40 (m, 4H), 2.75-2.79 (m, 1H), 5.20 (s, 1H).

To a solution of Compound 50 (127 mg, 0.69 mmol) in ethanol (2.7 mL) was added sodium borohydride (28.9 mg, 0.76 mmol) under ice-cooling, and the obtained reaction mixture was heated and then stirred at room temperature for 3.5 hours. Thereafter, to the reaction liquid, ethyl acetate was added, and the solvent was removed by distillation under reduced pressure. The residue was purified by silica gel column chromatography to obtain Compound 51 (trans/cis=10/1, 120 mg, 0.60 mmol, 88%) as a colorless solid (amorphous).

Compound 51 (trans); $^1$H-NMR (CDCl$_3$) δ: 1.04-1.11 (m, 2H), 1.24-1.55 (m, 9H), 1.73-1.77 (m, 2H), 1.93 (s, 3H), 2.02-2.08 (m, 3H), 3.51-3.53 (m, 1H), 5.14 (s, 1H).

EXAMPLE 19

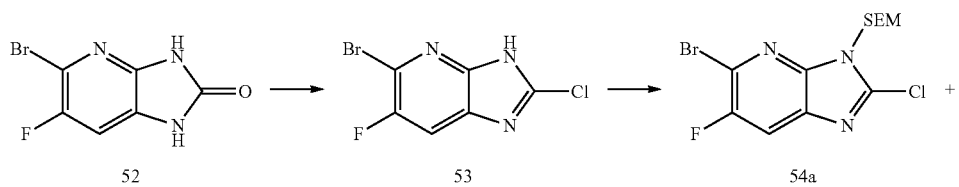

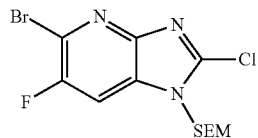

54b

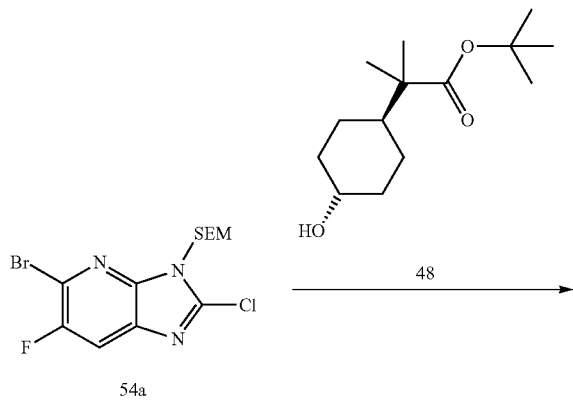

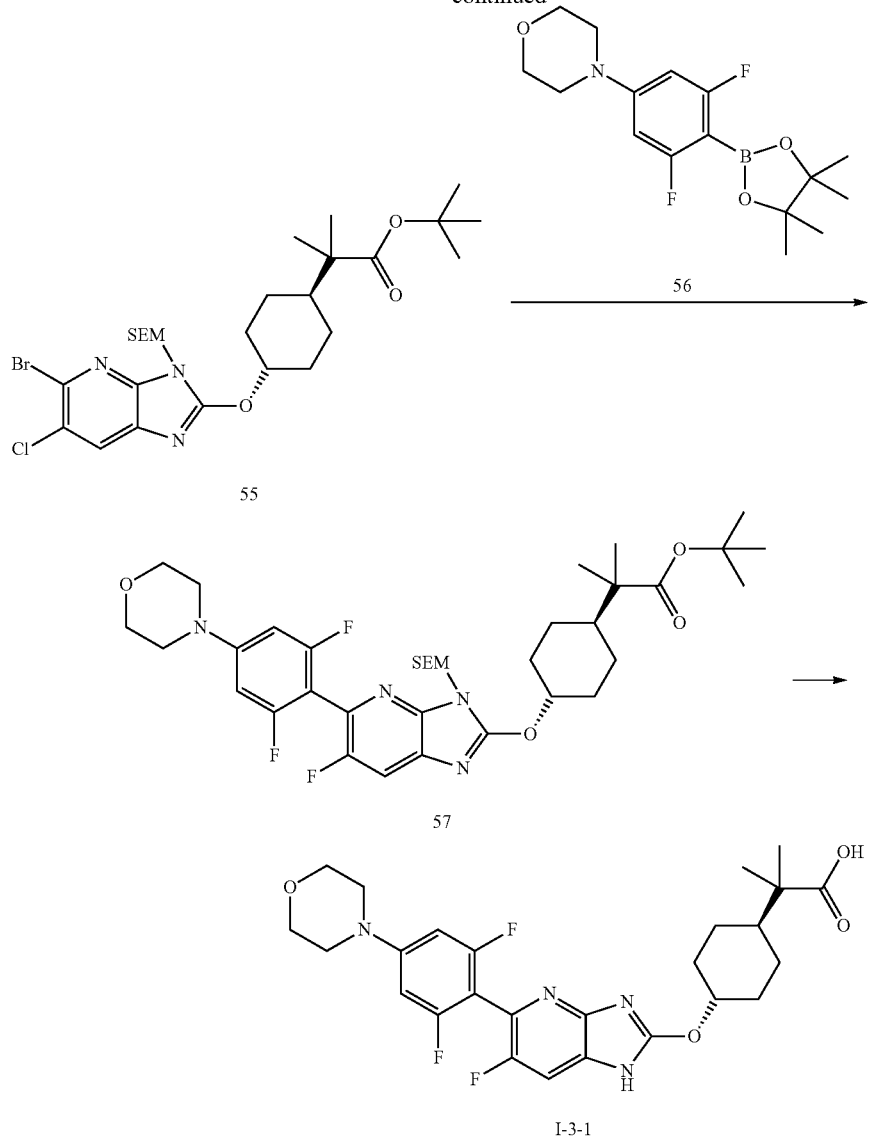

Compound 52 is described as Compound 41 in Example 13 in WO2012/033149.

To Compound 52 (200 mg, 0.86 mmol) were added phosphorus oxychloride (0.8 mL, 8.6 mmol) and 2,6-lutidine (0.20 mL, 1.7 mmol), and water (0.024 mL, 1.3 mmol) was added dropwise thereto under ice-cooling. The obtained reaction mixture was stirred at 95° C. for 4 hours. Thereafter, the reaction liquid was added dropwise to ice water under ice-cooling, and the resulting solid was filtered. The solid was washed with a sodium bicarbonate solution, followed by drying to obtain Compound 53 (0.14 g, 0.54 mmol, 63%) as a brown solid.

To a solution of Compound 53 (0.14 g, 0.54 mmol) in DMF (1 mL) were successively added diisopropylethylamine (0.14 mL, 0.82 mmol) and SEMCl (0.11 mL, 0.60 mmol), and the obtained reaction mixture was stirred at 70° C. for one hour. Thereafter, ethyl acetate (10 mL) and a saturated aqueous solution of ammonium chloride (10 mL) were added thereto, followed by extraction, and the aqueous layer was washed with ethyl acetate (10 mL). Thereafter, the organic layer was washed with water (10 mL), dried with magnesium sulfate, and then filtered. The solvent was removed by distillation under reduced pressure, and the residue was purified by silica gel column chromatography to obtain Compound 54a (86 mg, 0.23 mmol, 42%) as a yellow solid, and Compound 54b (32 mg, 0.084 mmol, 16%) as a yellow solid.

To a solution of Compound 54a (96 mg, 0.25 mmol) and Compound 48 (86 mg, 0.35 mmol) in THF (0.8 mL) was added potassium tert-butoxide (34 mg, 0.30 mmol) under ice-cooling, and the obtained reaction mixture was stirred at 0° C. for 3 hours. Thereafter, potassium tert-butoxide was added thereto until the disappearance of the starting material. The reaction liquid was added to a saturated aqueous solution of ammonium chloride (10 mL), followed by extraction with chloroform (2 mL), and the aqueous layer was washed with chloroform (2 mL). The solvent was removed by distillation under reduced pressure, and the residue was purified by silica gel column chromatography to obtain Compound 55 (143 mg, 0.24 mmol, 97%) as a colorless oil.

Compound 55; $^1$H-NMR (CDCl$_3$) δ: −0.04 (9H, s), 0.93 (2H, J=8.2 Hz, t), 1.09 (6H, s), 1.24-1.36 (3H, m), 1.57-1.69 (2H, m), 1.75-1.78 (2H, m), 2.32-2.36 (2H, m), 3.65 (2H, J=8.2 Hz, t), 5.00-5.08 (1H, m), 5.41 (2H, s), 7.51-7.55 (1H, m).

To a solution of Compound 55 (110 mg, 0.188 mmol) in 1,4-dioxane (0.9 mL) were successively added boronic acid ester 56 (134 mg, 0.27 mmol), PdCl$_2$(dtbpf) (12 mg, 0.019 mmol) and a 2 M aqueous solution of potassium carbonate (0.28 mL, 0.56 mmol), and the obtained reaction mixture was stirred under microwave irradiation at 130° C. for 15 minutes. To the reaction liquid, water (1 mL) and chloroform (2 mL) were added, followed by extraction, and the aqueous layer was washed with chloroform (2 mL). The collected organic layer was dried with magnesium sulfate. After filtration, the solvent was removed by distillation under reduced pressure, and the residue was purified by silica gel column chromatography to obtain Compound 57 (96 mg, 0.11 mmol, 59%) as a yellow solid.

Compound 57; $^1$H-NMR (DMSO-D$_6$) δ: −0.12 (9H, s), 0.08 (6H, s), 0.83-0.87 (13H, m), 1.04 (6H, s), 1.18-1.29 (3H, m), 1.41 (9H, s), 1.49-1.72 (4H, m), 2.27-2.34 (2H, m), 3.58-3.64 (4H, m), 4.11-4.19 (2H, m), 4.33-4.40 (2H, m), 5.00-5.07 (1H, m), 5.36 (2H, s), 6.47 (1H, s), 7.33-7.37 (2H, m), 7.97 (1H, J=9.8 Hz, d).

To a solution of Compound 57 in dichloromethane (0.4 mL) was added trifluoroacetic acid (0.4 mL, 5.2 mmol), and the obtained reaction mixture was stirred at room temperature for one hour. Thereafter, to the reaction liquid, a 2 N aqueous solution of sodium hydroxide (2.8 mL, 5.7 mmol) was added under ice-cooling, and ethyl acetate (5 mL) and water (5 mL) were then added thereto, followed by extraction. The organic layer was washed with water (5 mL), and the aqueous layer was adjusted to pH=5 using 5 N HCl. Next, chloroform/methanol (10:1, 5 mL) was added thereto, followed by extraction, and chloroform/methanol (10:1, 5 mL) was added to the aqueous layer, followed by extraction. The obtained organic layer was dried with magnesium sulfate, and then filtered, and the solvent was removed by distillation under reduced pressure. The residue was then purified by silica gel column chromatography, followed by recrystallization with chloroform and ethyl acetate to obtain Compound (I-3-1) (32 mg, 0.056 mmol, 51%) as a colorless solid.

Compound (I-3-1); $^1$H-NMR (DMSO-D$_6$) δ: 1.05 (6H, s), 1.16-1.30 (2H, m), 1.42-1.52 (2H, m), 1.58-1.72 (3H, m), 2.26-2.33 (2H, m), 2.56-2.63 (2H, m), 3.57-3.64 (1H, m), 3.68-3.72 (1H, m), 4.09-4.21 (4H, m), 4.58-4.67 (1H, m), 4.88-4.93 (1H, m), 6.44-6.48 (1H, m), 7.34-7.39 (2H, m), 7.83 (1H, br s).

EXAMPLE 20

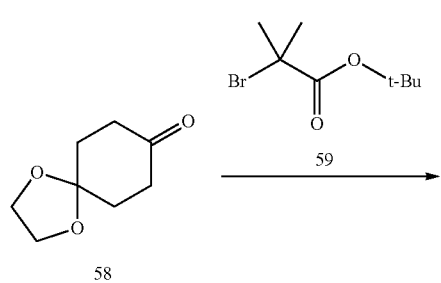

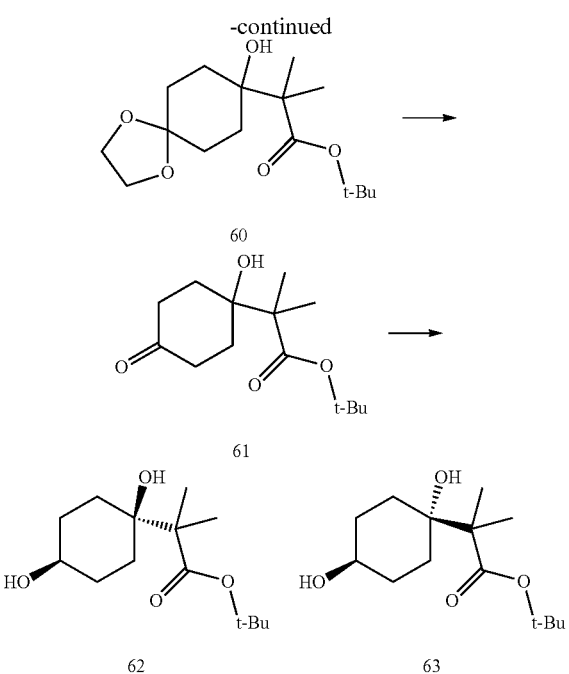

To a solution of Compound 58 (5 g, 32 mmol) in THF (50 mL) were added tert-butyl 2-bromo-2-methylpropanoate 59 (9.24 ml, 48 mmol), Zn powder (3.14 g, 48 mmol) and iodine (813 mg, 3.2 mmol), and the obtained reaction mixture was stirred under a nitrogen atmosphere at room temperature for 3.5 hours, and stirred at 50° C. for 4 hours. After confirmation of the disappearance of the starting materials, the reaction suspension was filtered with Celite, and 150 ml of ethyl acetate was added to the filtrate. The obtained liquid was washed separately with 100 ml of a saturated aqueous solution of ammonium chloride and 100 ml of brine and then dried with sodium sulfate. The solvent was removed by distillation under reduced pressure, and the residue was subjected to vacuum drying to obtain Compound 60 (1 g, 97%) as a white solid.

Compound 60; $^1$H-NMR (DMSO-D$_6$) δ: 1.06 (s, 6H), 1.39 (s, 9H), 1.40-1.48 (m, 2H), 1.54-1.69 (m, 4H), 1.76 (td, J=12.49, 4.73 Hz, 2H), 3.82 (s, 4H), 4.19 (s, 1H).

To a solution of Compound 60 (512 mg, 1.7 mmol) in acetone (5 mL) and distilled water (1 ml) was added PPTS (86 mg, 0.34 mmol), and the obtained reaction mixture was stirred under a nitrogen atmosphere at 90° C. for 2 hours. Ethyl acetate (20 ml) was added thereto, and the obtained liquid was washed three times with a saturated sodium bicarbonate solution and with brine and dried with sodium sulfate. The solvent was removed by distillation under reduced pressure to obtain Compound 61 (436 mg, 99%) as a colorless oil.

Compound 61; $^1$H-NMR (DMSO-D$_6$) δ: 1.12 (s, 6H), 1.39 (s, 9H), 1.82 (td, J=13.30, 4.77 Hz, 2H), 1.91-2.08 (m, 4H), 2.59 (td, J=14.05, 6.27 Hz, 2H), 4.69 (s, 1H).

To a solution of Compound 61 (430 mg, 1.677 mmol) in MeOH (5 mL) was added sodium borohydride (32 mg, 0.84 mmol) at 0° C., and the obtained reaction mixture was stirred for 2 hours. The reaction was stopped by 5 ml of a saturated aqueous solution of ammonium chloride, followed by extraction with 20 ml of ethyl acetate, and the organic layer was washed with water and brine and dried with sodium sulfate. The solvent was removed by distillation under reduced pressure, and the concentrated residue was purified by silica gel column chromatography (hexane/ethyl acetate=2:1) to separately obtain Compound 62 (356 mg, 82%) and Compound 63 (35 mg, 8%) as white solids.
Compound 62; $^1$H-NMR (DMSO-D$_6$) δ: 1.05 (s, 6H), 1.33-1.61 (m, 8H), 1.38 (s, 9H), 3.22 (m, 1H), 4.03 (s, 1H), 4.41 (d, J=4.52 Hz, 1H).
Compound 63; $^1$H-NMR (DMSO-D$_6$) δ: 1.05 (s, 6H), 1.29 (d, J=11.80 Hz, 2H), 1.37-1.45 (m, 2H), 1.39 (s, 9H), 1.64-1.84 (m, 4H), 3.76 (m, 1H), 3.91 (s, 1H), 4.08 (d, J=2.26 Hz, 1H).

EXAMPLE 21

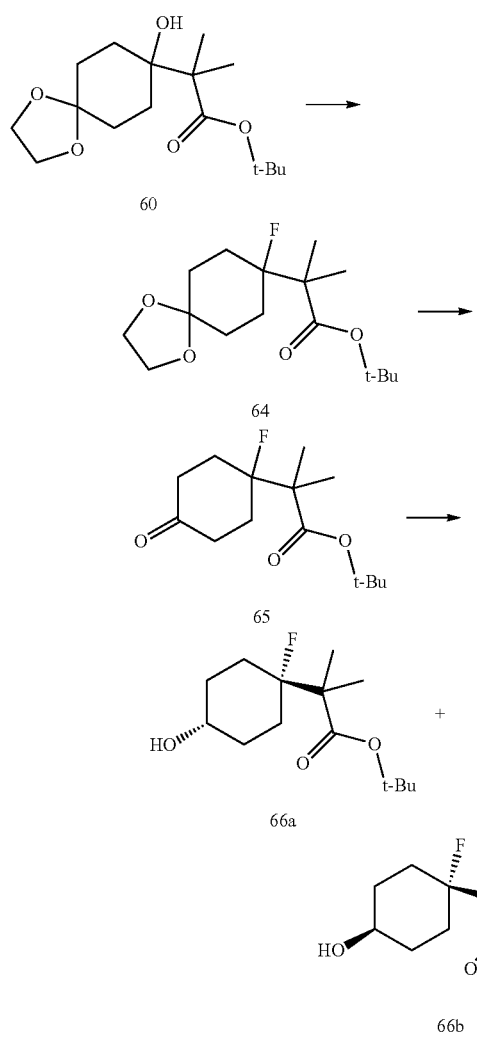

To a solution of Compound 60 (5.0 g, 16.64 mmol) in toluene (50 mL) was added DAST (5.37 g, 33.3 mmol) at 0° C., and the obtained reaction mixture was stirred at room temperature overnight. Thereafter, to the reaction liquid, water was added, followed by extraction with ethyl acetate. The organic layer was washed with water, a saturated sodium bicarbonate solution and brine and then dried with sodium sulfate. The solvent was removed by distillation under reduced pressure, and the residue was purified by silica gel column chromatography to obtain Compound 64 (0.60 g, 1.97 mmol, 11%) as a white solid.

Compound 64; $^1$H-NMR (CDCl3) δ: 1.21 (s, 6H), 1.45 (s, 9H), 1.61-1.64 (m, 2H), 1.80-2.01 (m, 8H), 3.95 (m, 4H).

To a solution of Compound 64 (0.60 g, 2.0 mmol) in acetone (10 mL) and water (2 ml) was added p-toluenesulfonic acid pyridine salt (0.025 g, 0.10 mmol), and the obtained liquid was refluxed overnight by heating. Thereafter, the solvent was removed by distillation under reduced pressure. The residue was extracted with ethyl acetate, and the organic layer was washed with water and brine and then dried with sodium sulfate. The solvent was removed by distillation under reduced pressure to obtain Compound 65 as a mixture. To a solution of Compound 65 in methanol (6 ml) was added NaBH$_4$ (0.038 g, 1.00 mmol) at 0° C., and the obtained reaction mixture was stirred for 30 minutes. The reaction solvent was concentrated under reduced pressure, and to the reaction liquid, a saturated aqueous solution of ammonium chloride was then added, followed by extraction with ethyl acetate. The organic layer was washed with water and brine and then dried with sodium sulfate. The solvent was removed by distillation under reduced pressure, and the residue was purified by silica gel column chromatography to obtain Compound 66a (0.41 g, 1.58 mmol, 79%) as an oily substance. Simultaneously, Compound 66b (0.008 g, 0.031 mmol, 2%), isomers of the hydroxy group, and Compound 64 (0.112 g, 0.37 mmol, 19%) were obtained.

Compound 66a; $^1$H-NMR (CDCl3) δ: 1.20 (s, 6H), 1.44 (s, 9H), 1.51-1.69 (m, 4H), 1.86 (br. d, 2H), 2.05 (br.t, 2H), 3.57 (m, 1H).
Compound 66b; $^1$H-NMR (CDCl3) δ: 1.21 (s, 6H), 1.45 (s, 9H), 1.67-1.69 (m, 2H), 1.77-2.01 (m, 4H), 4.09 (s, 1H).

EXAMPLE 22

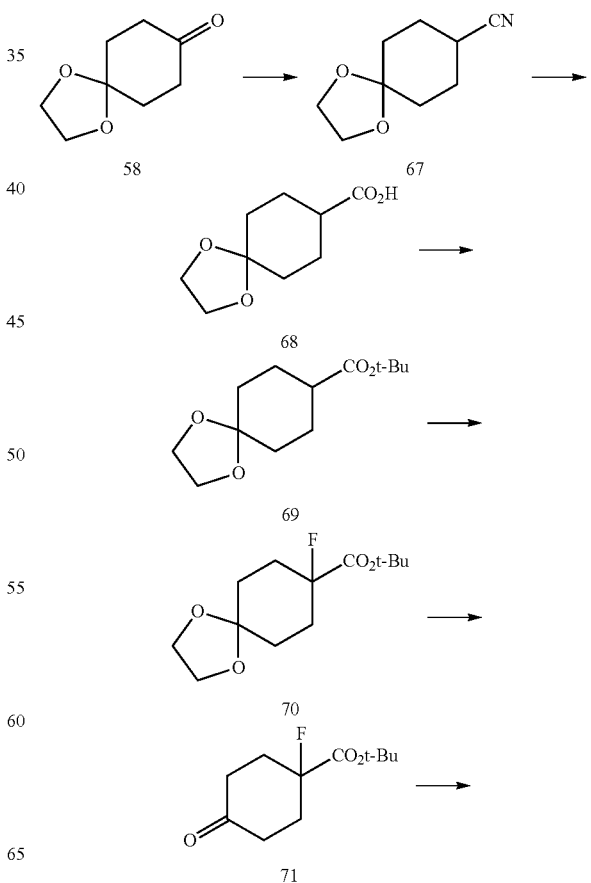

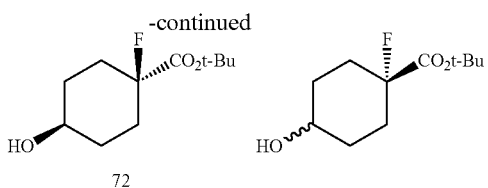

72

To a solution of Compound 58 (10.0 g, 64.0 mmol) in a mixture of 1,2-dimethoxyethane (218 ml)-ethanol (6.5 mL) was added p-toluenesulfonyl methyl isocyanide (16.3 g, 83.0 mmol), and the obtained reaction mixture was cooled to −13° C. Potassium t-butoxide (17.2 g, 154 mmol) was added thereto at 5° C. or less over 40 minutes. The reaction liquid was stirred under ice-cooling for one hour, and further stirred at room temperature for one hour, and the solvent was removed by distillation under reduced pressure. The residue was diluted with ethyl acetate, and then washed with water, and the solvent was removed by distillation under reduced pressure, followed by purification by silica gel chromatography to obtain Compound 67 (7.63 g, 45.6 mmol, 71%) as a colorless oily substance.

Compound 67: $^1$H-NMR (CDCl$_3$) δ: 1.57-1.67 (2H, m), 1.79-2.03 (5H, m), 2.66 (1H, s), 3.95 (4H, s).

To a solution of Compound 67 (7.63 g, 45.6 mmol) in a mixture of ethanol (57 ml)-water (14 mL) was added caustic potash (9.04 g, 137 mmol), and the obtained reaction mixture was refluxed for 1.5 hours by heating. Then, caustic potash (4.52 g, 68.4 mmol) was added thereto, and the obtained reaction mixture was refluxed for another 6 hours by heating. After cooling to room temperature, the solvent was removed by distillation under reduced pressure, followed by dilution with water (25 mL). The aqueous layer was then washed with diethyl ether (30 mL), and concentrated hydrochloric acid was added thereto under ice-cooling to obtain pH 4. After extraction with ethyl acetate, the solvent was removed by distillation under reduced pressure to obtain Compound 68 (8.36 g, 44.9 mmol, 98.4%) as a brown oily substance. The substance was used for the following step without purification.

To a solution of Compound 68 (8.36 g, 44.9 mmol) in t-butanol (84 mL) was added di-tert-butyl dicarbonate (18.8 g, 86.0 mmol) at room temperature, and further DMAP (1.65 g, 13.5 mmol) was added, and the obtained reaction mixture was stirred at room temperature for 30 minutes. The solvent was removed by distillation under reduced pressure, and the residue was purified by silica gel chromatography to obtain Compound 69 (9.63 g, 39.7 mmol, 89%) as a colorless oily substance.

Compound 69: $^1$H-NMR (CDCl$_3$) δ: 1.43 (9H, s), 1.49-1.59 (2H, m), 1.71-1.81 (4H, m), 1.86-1.94 (2H, m), 2.19-2.28 (1H, m), 3.94 (4H, s).

To a solution of diisopropylamine (1.35 mL, 9.49 mmol) in THF (10 mL) was added dropwise n-butyllithium (a 1.59 M hexane solution, 5.7 mL, 9.1 mmol) at −78° C., and the obtained reaction mixture was stirred at the same temperature for 30 minutes. Thereafter, a solution of Compound 69 (1.00 g, 4.13 mmol) in THF (10 mL) was added dropwise thereto, and the obtained reaction mixture was stirred under ice-cooling for one hour. A solution of NFSI (1.95 g, 6.19 mmol) in THF (14 mL) was then added dropwise thereto, and the obtained reaction mixture was stirred for 2 hours. To the reaction liquid, a saturated aqueous solution of ammonium chloride was added to stop the reaction, followed by extraction with ethyl acetate. The solvent was removed by distillation under reduced pressure, and the residue was then purified by silica gel chromatography to obtain Compound 70 (852 mg, 3.27 mmol, 79%) as a colorless oily substance.

Compound 70: $^1$H-NMR (CDCl$_3$) δ: 1.49 (9H, s), 1.69 (2H, d, J=13.2 Hz), 1.89 (2H, td, J=13.1, 4.5 Hz), 1.98-2.07 (3H, m), 2.09-2.21 (1H, m), 3.97 (4H, t, J=9.7 Hz).

To a solution of Compound 70 (852 mg, 3.27 mmol) in acetone (8.5 mL) was added 2 N hydrochloric acid (24.6 mL, 49.2 mmol) at room temperature, and the obtained reaction mixture was stirred for 3.5 hours. The solvent was then removed by distillation under reduced pressure. To the residue, sodium bicarbonate powder (5.07 g, 60.4 mmol) was added, followed by dilution with ethyl acetate and water, and then separation. The organic layer was washed with brine, and the solvent was then removed by distillation under reduced pressure. The residue was purified by silica gel chromatography to obtain Compound 71 (645 mg, 2.89 mmol, purity 97%, 88%) as a white powder.

Compound 71: $^1$H-NMR (CDCl$_3$) δ: 1.51 (9H, s), 2.10-2.45 (6H, m), 2.68 (2H, td, J=14.2, 6.3 Hz).

To a solution of Compound 71 (640.0 mg, 2.96 mmol) in ethanol (14 mL) was added NaBH$_4$ (56.0 mg, 1.48 mmol) under ice-cooling, and the obtained reaction mixture was stirred for 20 minutes. Acetone was then added thereto to stop the reaction. After dilution with ethyl acetate, the obtained liquid was washed with brine and dried with anhydrous sodium sulfate, and the solvent was removed by distillation under reduced pressure. To the residue, hexane (10 mL) was added, followed by crystallization to obtain Compound 72 (348 mg, 1.57 mmol, purity 98.3%, 53%) as a white crystal. In addition, a mother liquid was concentrated to retrieve 347.9 mg of a mixture of Compound 72 and an isomer, 1.65:1.

Compound 72: $^1$H-NMR (CDCl$_3$) δ: 1.49 (9H, s), 1.60-1.69 (2H, m), 1.75-1.95 (4H, m), 2.06 (2H, t, J=10.7 Hz), 3.70 (1H, s).

EXAMPLE 23

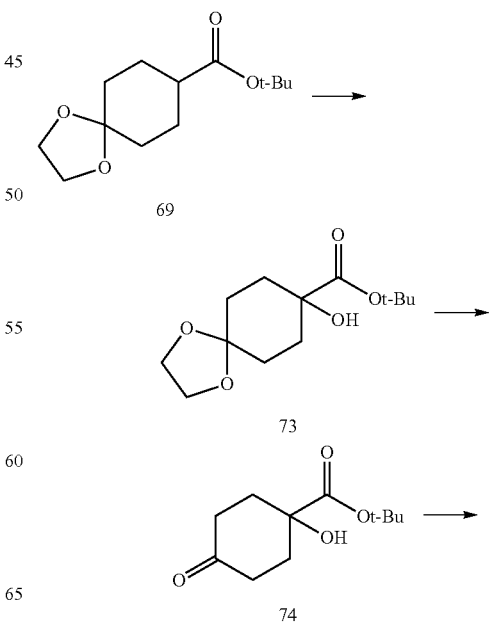

-continued

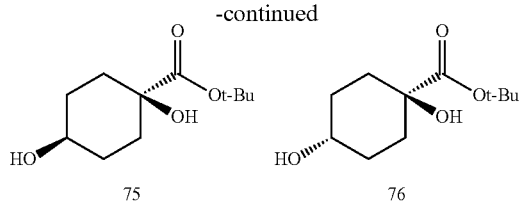

To a solution of diisopropylamine (1.43 mL, 10.0 mmol) in THF (15 mL) was added dropwise n-butyllithium (a 1.59 M hexane solution, 5.8 mL, 9.3 mmol) at −78° C., and the obtained reaction mixture was stirred at the same temperature for 30 minutes. Thereafter, a solution of Compound 69 (1.00 g, 4.13 mmol) in THF (15 mL) was added dropwise thereto, and the obtained reaction mixture was stirred at the same temperature for 40 minutes. Triethyl phosphite (2.5 mL, 14.3 mmol) was then added thereto, and oxygen gas dried by concentrated sulfuric acid was passed through the obtained liquid at −78° C. for 1.5 hours and at room temperature for 30 minutes. To the reaction liquid, acetic acid (1.8 mL) and water (20 mL) were added to stop the reaction, followed by extraction with ethyl acetate. The organic layer was washed with a saturated sodium bicarbonate solution and water, and the solvent was then removed by distillation under reduced pressure. The residue was purified by silica gel chromatography to obtain Compound 73 (1.34 g, 5.18 mmol, 73%) as a colorless oily substance.

Compound 73: $^1$H-NMR (CDCl$_3$) δ: 1.48 (9H, s), 1.63-1.71 (4H, m), 1.90-2.10 (4H, m), 3.05 (1H, s), 3.97 (4H, s).

To a solution of Compound 73 (600 mg, 2.32 mmol) in acetone (3 mL) was added 2N hydrochloric acid (4.65 mL, 9.29 mmol) at room temperature, and the obtained reaction mixture was stirred for one hour. The solvent was then removed by distillation under reduced pressure. To the residue, sodium bicarbonate powder (5.07 g, 60.4 mmol) was added, followed by dilution with ethyl acetate and water, and then separation. The organic layer was washed with brine, and the solvent was then removed by distillation under reduced pressure. The residue was purified by silica gel chromatography to obtain Compound 74 (472 mg, 2.20 mmol, 95%) as a white powder.

Compound 74: $^1$H-NMR (CDCl$_3$) δ: 1.50 (9H, s), 2.04-1.96 (2H, m), 2.19 (2H, td, J=13.5, 4.9 Hz), 2.30-2.38 (2H, m), 2.76 (2H, td, J=14.2, 6.3 Hz), 3.39 (1H, s).

To a solution of Compound 74 (450 mg, 2.10 mmol) in ethanol (5 mL) was added NaBH$_4$ (23.8 mg, 0.630 mmol) at room temperature, and the obtained reaction mixture was stirred for 15 minutes. Acetone (2 mL) was then added thereto to stop the reaction, and the solvent was removed by distillation under reduced pressure. After dilution with dichloromethane, the obtained liquid was washed with brine and dried with anhydrous sodium sulfate, and the solvent was then removed by distillation under reduced pressure. The residue was purified by silica gel chromatography to obtain Compound 75 (256 mg, 1.18 mmol, 56%) as a white powder. In addition, Compound 76, an isomer, (80.3 mg, 0.371 mmol, 18%) was obtained as a white powder.

Compound 75: $^1$H-NMR (CDCl3) δ: 1.48 (9H, s), 1.64-1.89 (8H, m), 3.05 (1H, s), 3.71-3.61 (1H, m). Compound 11: $^1$H-NMR (CDCl$_3$) δ: 1.33-1.52 (11H, m), 1.65-1.69 (2H, m), 1.90-2.00 (2H, m), 2.15 (2H, td, J=12.8, 3.9 Hz), 3.06 (1H, s), 4.06 (1H, s).

EXAMPLE 24

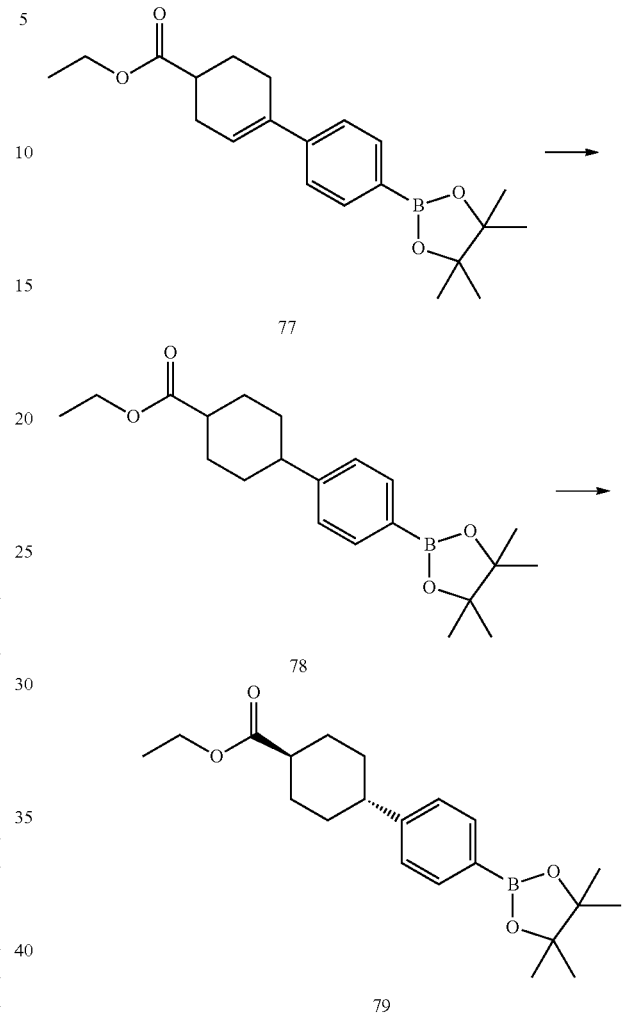

To a solution of Compound 77 (1.0 g, 2.8 mmol) in methanol/ethyl acetate (30 mL, 5:1) was added palladium hydroxide (70 mg, 20 wt % on C, 50% wet), and the obtained reaction mixture was stirred under a hydrogen atmosphere for 4 hours. The reaction solution was filtered with Celite, and the solvent was removed by distillation under reduced pressure to obtain a crude product 78 (1.0 g, 2.8 mmol) as a cis/trans mixture.

To a solution of Compound 78 (1.0 g, 2.8 mmol) in tert-butanol (25 mL) was added potassium tert-butoxide (0.38 g, 3.4 mmol), and the obtained reaction mixture was stirred at 40° C. for 21 hours. The reaction liquid was poured into a mixed liquid of a saturated aqueous solution of ammonium chloride (50 mL) and dichloromethane (50 mL) under ice-cooling, followed by extraction, and the aqueous layer was washed with dichloromethane (30 mL). Thereafter, the organic layer was dried with magnesium sulfate, and then filtered. The solvent was removed by distillation under reduced pressure, and the residue was purified by silica gel column chromatography to obtain Compound 79 (0.60 g, 1.7 mmol, 60% (2 steps)) as a colorless solid.

Compound 79: $^1$H-NMR (CDCl$_3$) δ: 1.27 (3H, J=6.9 Hz, t), 1.35 (12H, s), 1.48-1.60 (4H, m), 1.97 (2H, m), 2.08-2.12

(2H, m), 2.34 (1H, J=11.8, 3.8 Hz, tt), 2.53 (1H, J=11.7, 3.1 Hz, tt), 4.14 (2H, J=6.9 Hz, q), 7.22 (2H, J=7.4 Hz, d), 7.75 (2H, J=7.4 Hz, d).

Compound 84; $^1$H-NMR (CDCl$_3$) δ: 1.34 (s, 13H), 1.49 (s, 9H), 2.54 (s, 2H), 3.64 (t, J=5.5 Hz, 2H), 4.10 (br s, 2H), 6.09 (s, 1H), 7.38 (d, J=8.3 Hz, 2H), 7.77 (d, J=8.3 Hz, 2H).

EXAMPLE 25

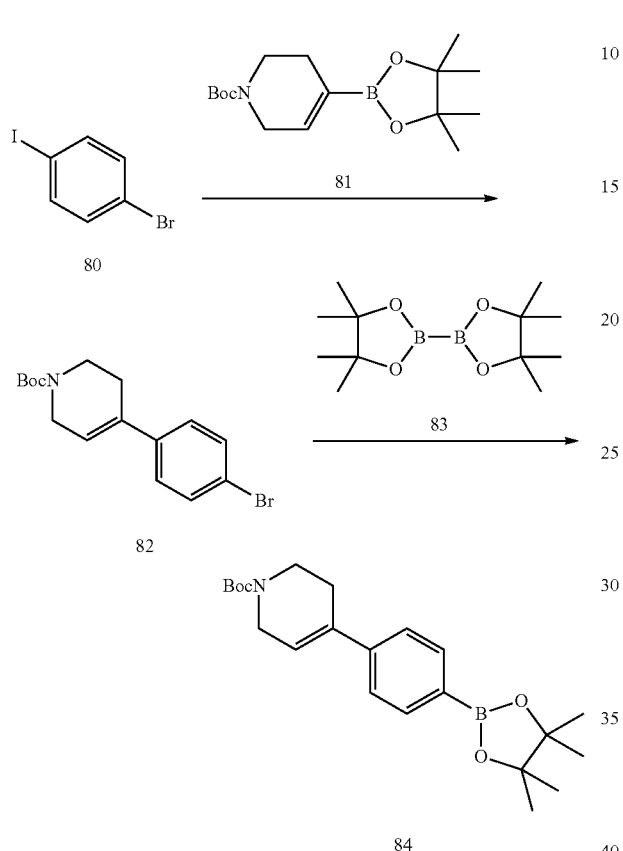

EXAMPLE 26

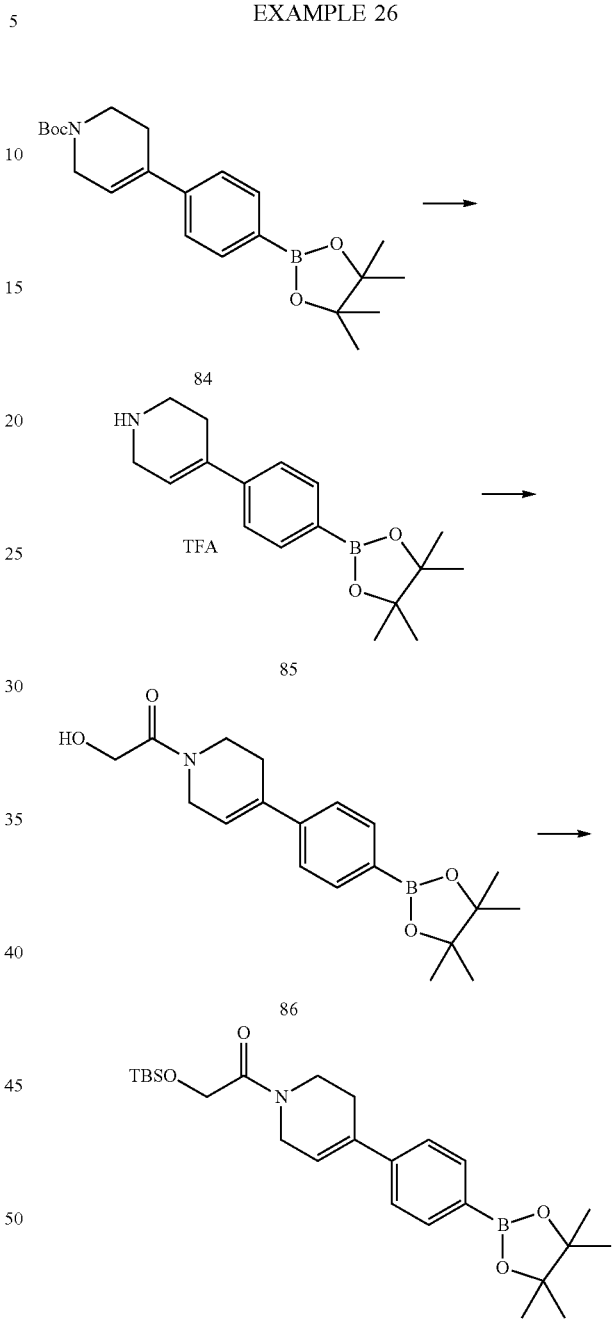

To a solution of Compound 80 (10.0 g, 35.3 mmol) in 1,4-dioxane (100 mL) were added Compound 81 (13.12 g, 42.4 mmol) and Pd(PPh$_3$)$_4$ (2.04 g, 1.77 mmol), and the obtained reaction mixture was stirred under a nitrogen current at 80° C. for 2 hours. To the reaction liquid, 300 mL of water was added, followed by extraction with 300 mL of ethyl acetate. The organic layer was dried with magnesium sulfate, and the solvent was then removed by distillation under reduced pressure. The residue was purified by silica gel column chromatography to obtain Compound 82 (10.6 g, 31.1 mmol, 89%) as a yellow oil.

Compound 82; $^1$H-NMR (CDCl$_3$) δ: 1.48 (s, 9H), 2.49 (br s, 2H), 3.63 (t, J=5.5 Hz, 2H), 4.06 (br s, 2H), 6.03 (br s, 1H), 7.24 (d, J=8.5 Hz, 2H), 7.45 (d, J=8.4 Hz, 2H).

To a solution of Compound 82 (1.0 g, 2.96 mmol) in 1,4-dioxane (10 mL) were added Compound 83 (1.13 g, 4.43 mmol) and PdCl$_2$(dppf) CH$_2$Cl$_2$, and the obtained reaction mixture was stirred under a nitrogen current at 100° C. for 2 hours. The reaction liquid was filtered with Celite, and the residue was washed with chloroform. The filtrate was then removed by distillation under reduced pressure. The residue was purified by silica gel column chromatography to obtain Compound 84 (905.1 mg, 2.35 mmol, 80%) as a pale yellow solid.

To a solution of Compound 84 (12.7 g, 32.5 mmol) in methylene chloride (51 mL) was added TFA (51 mL, 657 mmol) under ice-cooling, and the obtained reaction mixture was stirred at room temperature for one hour. The solvent was removed by distillation under reduced pressure, and the residue was recrystallized with hexane-ethyl acetate to obtain Compound 85 (9.60 g, 24.0 mmol, 74%) as a white powder.

Compound 85; $^1$H-NMR (DMSO-D$_6$) δ: 1.29 (s, 12H), 2.68 (s, 2H), 3.33 (s, 2H), 3.78 (s, 2H), 6.28 (s, 1H), 7.49 (d, J=7.3 Hz, 2H), 7.69 (d, J=7.3 Hz, 2H), 8.83 (s, 2H).

To a solution of Compound 85 (4.50 g, 11.2 mmol) in DMF (45 mL) were successively added glycolic acid (1.11 g, 14.7 mmol), HATU (5.57 g, 14.7 mmol) and triethylamine (4.69 ml, 33.8 mmol) under ice-cooling, and the obtained reaction mixture was heated to room temperature and then stirred for 1.5 hours. To the reaction liquid, a saturated aqueous solution of ammonium chloride was added, followed by extraction with ethyl acetate, and the organic layer was then washed with brine and dried with magnesium sulfate. The resulting crude product 86 (3.84 g) was used for the following reaction.

To a solution of the crude product 86 (3.84 g) in DMF (19 mL) were added TBSCl (2.53 g, 16.8 mmol) and imidazole (1.14 g, 16.8 mmol) under ice-cooling, and the obtained reaction mixture was stirred at room temperature for 3 hours. To the reaction liquid, water was added, and the resulting white solid was filtered. The obtained solid was purified by silica gel column chromatography to obtain Compound 87 (2.45 g, 5.36 mmol, 48% in 2 steps) as a white solid.

Compound 87; $^1$H-NMR (CDCl$_3$) δ: 0.11-0.12 (m, 6H), 0.91-0.93 (m, 9H), 1.35 (s, 12H), 2.56-2.60 (m, 2H), 3.76-3.81 (m, 2H), 4.20-4.23 (m, 2H), 4.34-4.36 (m, 2H), 6.08-6.15 (m, 1H), 7.37 (d, J=7.8 Hz, 2H), 7.78 (d, J=7.8 Hz, 2H).

Compounds shown below were synthesized in the same manner. The measurement results of NMR or LC/MS of each compound were shown.

TABLE 1

| No. | Structure | NMR(δ) |
|---|---|---|
| I-1-7 | 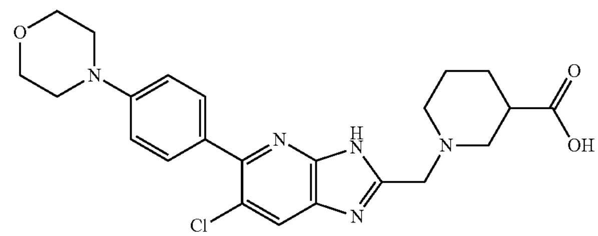 [SMILES: O=C(O)C1CCCN(Cc2nc3cc(Cl)c(-c4ccc(N5CCOCC5)cc4)nc3[nH]2)C1] | 1H-NMR (DMSO-d6) δ: 1.22-1.90 (m, 4H), 2.09-2.24 (m, 2H), 2.46 (d, J = 10.65 Hz, 1H), 2.75 (d, J = 10.65 Hz, 1H), 2.93 (d, J = 8.62 Hz, 1H), 3.20 (t, J = 4.82 Hz, 4H), 3.73-3.81 (m, 6H), 7.03 (d, J = 9.12 Hz, 2H), 7.58 (d, J = 8.62 Hz, 2H), 8.10 (s, 1H). |
| I-1-8 | 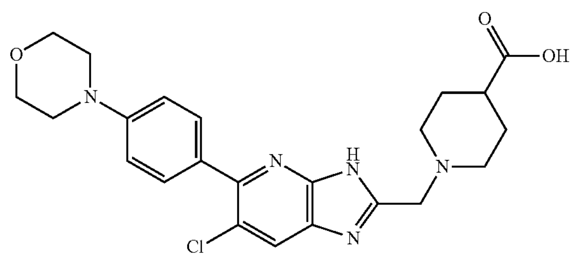 [SMILES: O=C(O)C1CCN(Cc2nc3cc(Cl)c(-c4ccc(N5CCOCC5)cc4)nc3[nH]2)CC1] | 1H-NMR (DMSO-d6) δ: 1.55-1.84 (m, 4H), 2.10-2.22 (m, 3H), 2.82 (d, J = 11.15 Hz, 2H), 3.20 (t, J = 4.82 Hz, 4H), 3.73 (s, 2H), 3.77 (t, J = 4.82 Hz, 4H), 7.03 (d, J = 8.62 Hz, 2H), 7.57 (d, J = 8.62 Hz, 2H), 8.14 (br s, 1H). |
| I-1-9 | 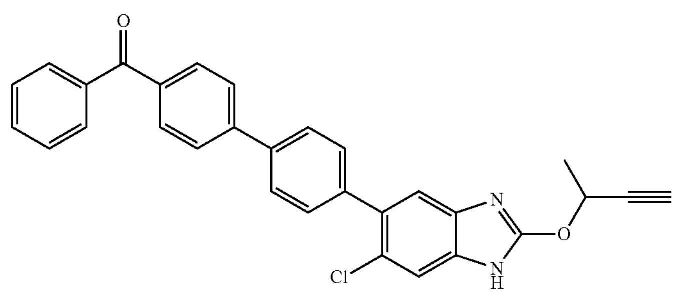 [SMILES: C#CC(C)Oc1nc2cc(-c3ccc(-c4ccc(C(=O)c5ccccc5)cc4)cc3)c(Cl)cc2[nH]1] | (DMSO-d6) δ: 1.63 (d, J = 6.8 Hz, 3H), 3.64 (d, J = 2.0 Hz, 1H), 5.76 (qd, J = 6.8, 2.0 Hz, 1H), 7.36 (s, 1H), 7.53 (s, 1H), 7.58-7.62 (m, 4H), 7.71 (ddd, J = 6.6, 1.5, 1.5 Hz, 1H), 7.78-7.81 (m, 2H), 7.85-7.88 (m, 4H), 7.95 (d, J = 8.6 Hz, 2H). |
| I-1-10 | 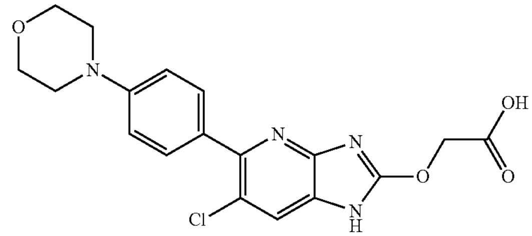 [SMILES: O=C(O)COc1nc2nc(-c3ccc(N4CCOCC4)cc3)c(Cl)cc2[nH]1] | (DMSO-d6) δ: 3.19 (dd, J = 5.2, 4.4 Hz, 4H), 3.76 (dd, J = 5.2, 4.4 Hz, 4H), 4.89 (s, 2H), 7.01 (d, J = 8.6 Hz, 2H), 7.55 (d, J = 8.8 Hz, 2H), 7.84 (s, 1H). |

TABLE 1-continued

| No. | Structure | NMR(δ) |
|---|---|---|
| I-1-11 | 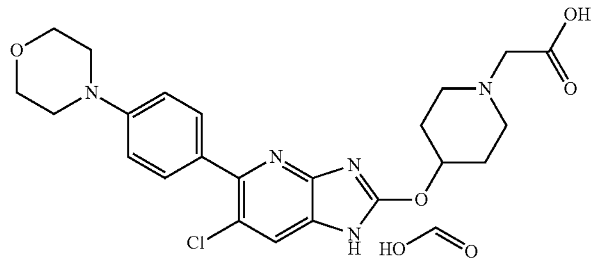 | (DMSO-d6) δ: 1.84-1.91 (m, 2H), 2.14-2.17 (m, 2H), 2.63-2.68 (m, 2H), 2.94-2.97 (m, 2H), 3.18-3.23 (m, 6H), 3.73-3.81 (m, 4H), 5.09-5.11 (m, 1H), 7.01 (d, J = 8.6 Hz, 2H), 7.55 (d, J = 8.6 Hz, 2H), 7.85 (s, 1H), 8.18 (s, 1H). |

TABLE 2

| No. | Structure | NMR(δ) |
|---|---|---|
| I-1-12 | 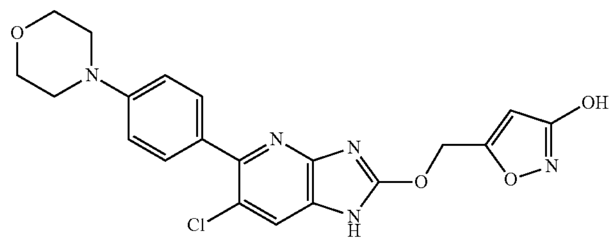 [SMILES: Oc1cc(COc2nc3nc(-c4ccc(N5CCOCC5)cc4)c(Cl)cc3[nH]2)on1] | 1H-NMR (DMSO-d6) δ: 3.19 (t, J = 4.82 Hz, 4H), 3.76 (t, J = 4.82 Hz, 4H), 5.56 (s, 2H), 6.24 (s, 1H), 7.02 (d, J = 8.62 Hz, 2H), 7.56 (d, J = 8.62 Hz, 2H), 7.95 (s, 1H), 11.42 (br s, 1H), 12.96 (br s, 1H). |
| I-1-13 | 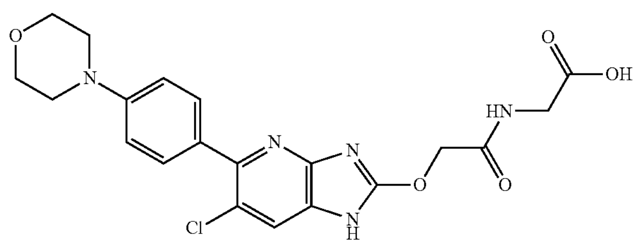 [SMILES: O=C(O)CNC(=O)COc1nc2nc(-c3ccc(N4CCOCC4)cc3)c(Cl)cc2[nH]1] | 1H-NMR (DMSO-d6) δ: 3.19 (t, J = 4.56 Hz, 4H), 3.74-3.80 (m, 6H), 5.00 (s, 2H), 7.01 (d, J = 8.62 Hz, 2H), 7.55 (d, J = 8.62 Hz, 2H), 7.88 (s, 1H), 8.43 (t, J = 5.58 Hz, 1H). |
| I-1-14 | 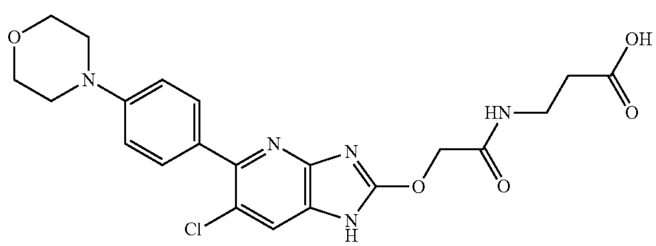 [SMILES: O=C(O)CCNC(=O)COc1nc2nc(-c3ccc(N4CCOCC4)cc3)c(Cl)cc2[nH]1] | 1H-NMR (DMSO-d6) δ: 2.41 (t, J = 6.84 Hz, 2H), 3.19 (t, J = 4.82 Hz, 4H), 3.29-3.33 (m, 2H), 3.76 (t, J = 4.82 Hz, 4H), 4.91 (s, 2H), 7.01 (d, J = 8.62 Hz, 2H), 7.55 (d, J = 8.62 Hz, 2H), 7.87 (s, 1H), 8.25 (t, J = 5.32 Hz, 1H). |
| I-1-15 | 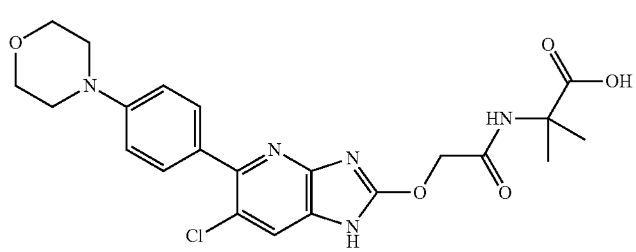 [SMILES: CC(C)(NC(=O)COc1nc2nc(-c3ccc(N4CCOCC4)cc3)c(Cl)cc2[nH]1)C(=O)O] | 1H-NMR (DMSO-d6) δ: 1.38 (s, 6H), 3.19 (t, J = 4.82 Hz, 4H), 3.76 (t, J = 4.82 Hz, 4H), 4.93 (s, 2H), 7.01 (d, J = 8.62 Hz, 2H), 7.55 (d, J = 8.62 Hz, 2H), 7.89 (br s, 1H), 8.36 (s, 1H), 12.34 (s, 1H), 12.89 (s, 1H). |

TABLE 2-continued

| No. | Structure | NMR(δ) |
|---|---|---|
| I-1-16 | 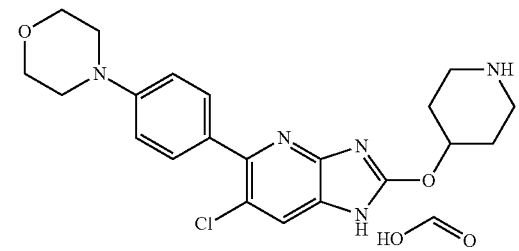 | (DMSO-d6) δ: 1.76-1.80 (m, 2H), 2.14-2.17 (m, 2H), 2.82-2.87 (m, 2H), 3.10-3.13 (m, 2H), 3.18 (dd, J = 5.2, 4.4 Hz, 4H), 3.76 (dd, J = 5.2, 4.4 Hz, 4H), 5.17-5.19 (m, 1H), 7.01 (d, J = 8.6 Hz, 2H), 7.55 (d, J = 8.6 Hz, 2H), 7.84 (s, 1H), 8.30 (s, 1H). |

TABLE 3

| No. | Structure | NMR(δ) | retention time | Mass (M + H) | method |
|---|---|---|---|---|---|
| I-1-17 | 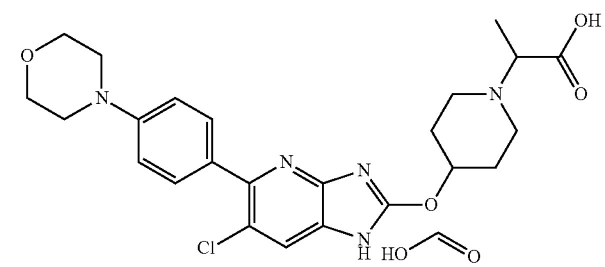 | (DMSO-d6) δ: 1.21 (d, J = 7.2 Hz, 3H), 1.81-1.86 (m, 2H), 2.13-2.15 (m, 2H), 2.60-2.70 (m, 2H), 2.89-2.96 (m, 2H), 3.18 (dd, J = 5.2, 4.4 Hz, 4H), 3.30 (q, J = 7.2 Hz, 1H), 3.76 (dd, J = 5.2, 4.4 Hz, 4H), 5.07-5.10 (m, 1H), 7.01 (d, J = 9.1 Hz, 2H), 7.55 (d, J = 9.1 Hz, 2H), 7.84 (s, 1H), 8.18 (s, 1H). | | | |
| I-1-18 | 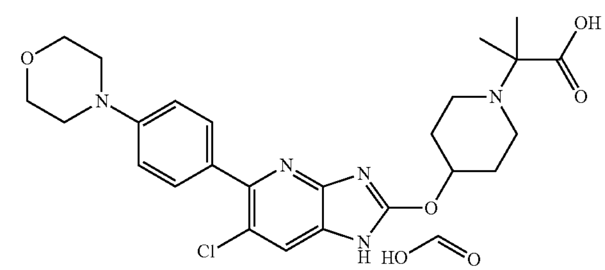 | | 1.30 | 500.3 | B |
| I-1-19 | 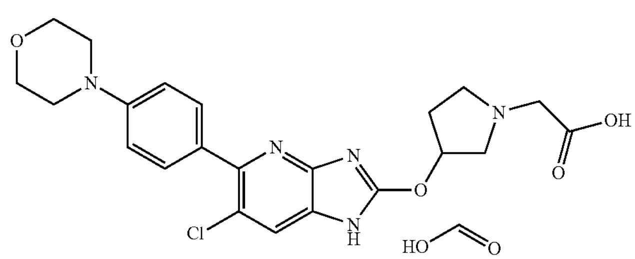 | (DMSO-d6) δ: 1.96-2.01 (m, 1H), 2.32-2.39 (m, 1H), 2.59-2.65 (m, 1H), 2.99-3.07 (m, 4H), 3.19 (dd, J = 5.2, 4.4 Hz, 4H), 3.76 (dd, J = 5.2, 4.4 Hz, 4H), 5.47-5.49 (m, 1H), 7.01 (d, J = 9.1 Hz, 2H), 7.55 (d, J = 9.1 Hz, 2H), 7.86 (s, 1H), 8.16 (s, 1H). | | | |
| I-1-20 | 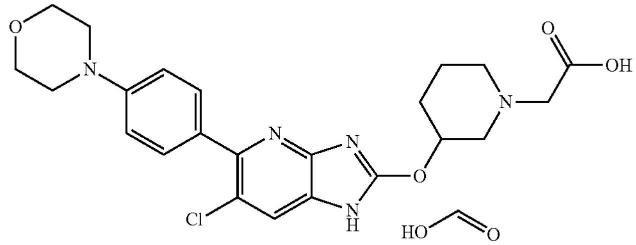 | | 1.27 | 472.3 | B |

TABLE 3-continued

| No. | Structure | NMR(δ) | retention time | Mass (M + H) | method |
|---|---|---|---|---|---|
| I-1-21 | 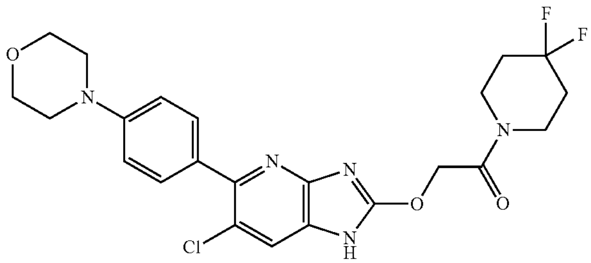 [SMILES: O=C(COc1nc2nc(-c3ccc(N4CCOCC4)cc3)c(Cl)cc2[nH]1)N1CCC(F)(F)CC1] | 1H-NMR (DMSO-d6) δ: 1.95 (br s, 2H), 2.12 (br s, 2H), 3.19 (t, J = 4.82 Hz, 4H), 3.56 (br s, 4H), 3.76 (t, J = 4.82 Hz, 4H), 5.35 (s, 2H), 7.01 (d, J = 8.62 Hz, 2H), 7.55 (d, J = 8.62 Hz, 2H), 7.85 (s, 1H), 12.92 (br s, 1H). | | | |

TABLE 4

| No. | Structure | NMR(δ) |
|---|---|---|
| I-1-22 | 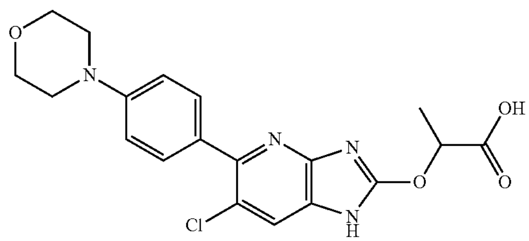 [SMILES: CC(Oc1nc2nc(-c3ccc(N4CCOCC4)cc3)c(Cl)cc2[nH]1)C(=O)O] | 1H-NMR (DMSO-d6) δ: 1.59 (d, J = 7.10 Hz, 3H), 3.19 (t, J = 4.82 Hz, 4H), 3.76 (t, J = 4.82 Hz, 4H), 5.36 (q, J = 7.10 Hz, 1H), 7.01 (d, J = 8.62 Hz, 2H), 7.55 (d, J = 8.62 Hz, 2H), 7.88 (s, 1H). |
| I-1-23 | 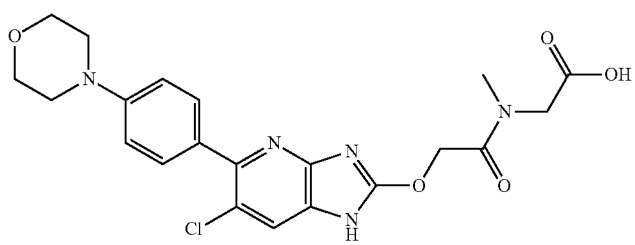 [SMILES: CN(CC(=O)O)C(=O)COc1nc2nc(-c3ccc(N4CCOCC4)cc3)c(Cl)cc2[nH]1] | 1H-NMR (DMSO-d6) δ: 3.05 (s, 3H), 3.19 (t, J = 4.56 Hz, 4H), 3.76 (t, J = 4.56 Hz, 4H), 4.03 (s, 2H), 5.34 (s, 2H), 7.01 (d, J = 8.62 Hz, 2H), 7.55 (d, J = 8.62 Hz, 2H), 7.87 (br s, 1H). |
| I-1-24 | 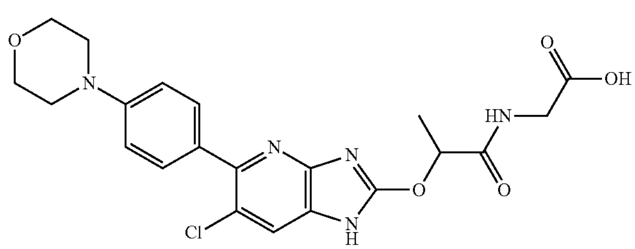 [SMILES: CC(Oc1nc2nc(-c3ccc(N4CCOCC4)cc3)c(Cl)cc2[nH]1)C(=O)NCC(=O)O] | 1H-NMR (DMSO-d6) δ: 1.55 (d, J = 6.93 Hz, 3H), 3.19 (t, J = 4.82 Hz, 4H), 3.76 (t, J = 4.82 Hz, 4H), 3.79 (d, J = 6.08 Hz, 2H), 5.47 (q, J = 6.93 Hz, 1H), 7.01 (d, J = 8.62 Hz, 2H), 7.55 (d, J = 8.62 Hz, 2H), 7.90 (s, 1H), 8.51 (br s, 1H), 12.51 (br s, 1H), 12.84 (br s, 1H). |
| I-1-25 | 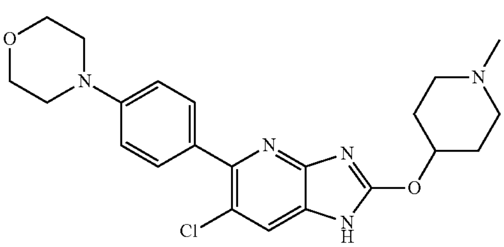 [SMILES: CN1CCC(Oc2nc3nc(-c4ccc(N5CCOCC5)cc4)c(Cl)cc3[nH]2)CC1] | (DMSO-d6) δ: 1.70-1.75 (m, 2H), 2.04-2.06 (m, 2H), 2.15-2.19 (m, 5H), 2.63-2.65 (m, 2H), 3.17 (brs, 4H), 3.76 (brs, 4H), 4.97 (brs, 1H), 6.99 (d, J = 8.6 Hz, 2H), 7.54 (d, J = 8.6 Hz, 2H), 7.65 (s, 1H). |

TABLE 4-continued

| No. | Structure | NMR(δ) |
|---|---|---|
| I-1-26 | 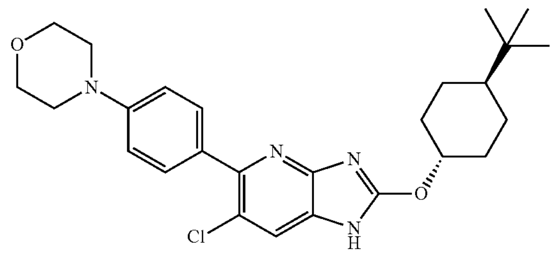 [SMILES: CC(C)(C)[C@H]1CC[C@H](Oc2nc3nc(-c4ccc(N5CCOCC5)cc4)c(Cl)cc3[nH]2)CC1] | (CDCl3) δ: 0.88 (s, 9H), 1.04-1.10 (m, 1H), 1.17-1.27 (m, 2H), 1.36-1.46 (m, 2H), 1.86-1.89 (m, 2H), 2.26-2.29 (m, 2H), 3.25 (dd, J = 4.6, 4.6 Hz, 4H), 3.89 (dd, J = 4.6, 4.6 Hz, 4H), 4.96-5.02 (m, 1H), 6.98 (d, J = 8.6 Hz, 2H), 7.65 (d, J = 8.6 Hz, 2H), 7.81 (s, 1H), 9.53 (brs, 1H). |

TABLE 5

| No. | Structure | NMR(δ) |
|---|---|---|
| I-1-27 | 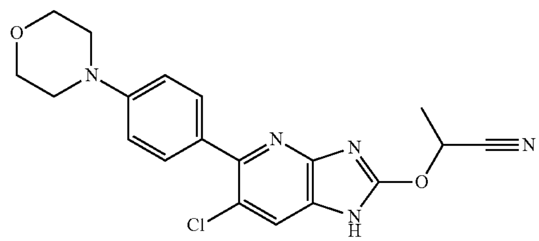 [SMILES: CC(C#N)Oc1nc2nc(-c3ccc(N4CCOCC4)cc3)c(Cl)cc2[nH]1] | 1H-NMR (DMSO-d6) δ: 1.79 (d, J = 7.10 Hz, 3H), 3.19 (t, J = 4.82 Hz, 4H), 3.76 (t, J = 4.82 Hz, 4H), 5.92 (q, J = 7.10 Hz, 1H), 7.02 (d, J = 8.62 Hz, 2H), 7.57 (d, J = 8.62 Hz, 2H), 8.02 (br s, 1H), 13.13 (br s, 1H). |
| I-1-28 | 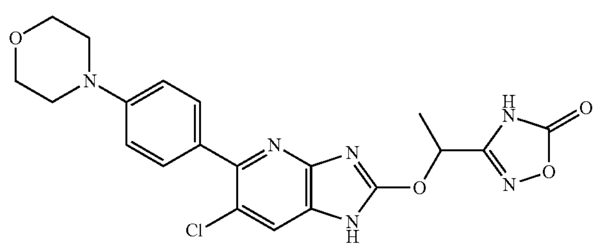 [SMILES: CC(Oc1nc2nc(-c3ccc(N4CCOCC4)cc3)c(Cl)cc2[nH]1)c1noc(=O)[nH]1] | 1H-NMR (DMSO-d6) δ: 1.71 (d, J = 6.59 Hz, 3H), 3.19 (t, J = 4.82 Hz, 4H), 3.76 (t, J = 4.82 Hz, 4H), 6.08 (q, J = 6.59 Hz, 1H), 7.01 (d, J = 8.62 Hz, 2H), 7.56 (d, J = 8.62 Hz, 2H), 7.92 (s, 1H). |
| I-1-29 | 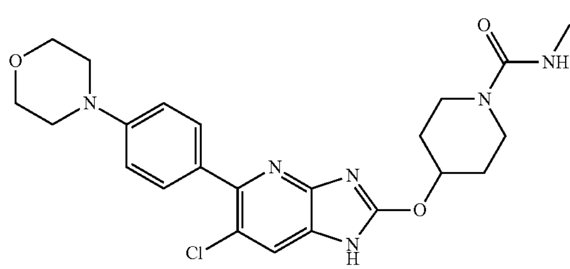 | (DMSO-d6) δ: 1.02 (t, J = 7.2 Hz, 3H), 1.62-1.64 (m, 2H), 2.05-2.07 (m, 2H), 3.04-3.19 (m, 8H), 3.72-3.76 (m, 6H), 5.18-5.21 (m, 1H), 6.55 (brs, 1H), 7.01 (d, J = 8.6 Hz, 2H), 7.55 (d, J = 8.6 Hz, 2H), 7.85 (s, 1H). |
| I-1-30 | 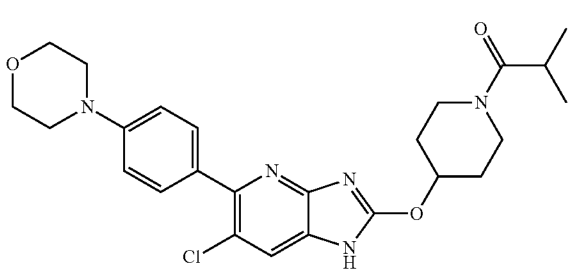 [SMILES: CC(C)C(=O)N1CCC(Oc2nc3nc(-c4ccc(N5CCOCC5)cc4)c(Cl)cc3[nH]2)CC1] | (DMSO-d6) δ: 1.01 (d, J = 6.6 Hz, 6H), 1.63-1.75 (m, 2H), 2.07-2.14 (m, 2H), 2.88-2.95 (m, 1H), 3.17-3.44 (m, 6H), 3.75-3.83 (m, 5H), 3.94-3.98 (m, 1H), 5.25-5.30 (m, 1H), 7.01 (d, J = 9.1 Hz, 2H), 7.55 (d, J = 9.1 Hz, 2H), 7.88 (brs, 1H). |

TABLE 5-continued

| No. | Structure | NMR(δ) |
|---|---|---|
| I-1-31 | 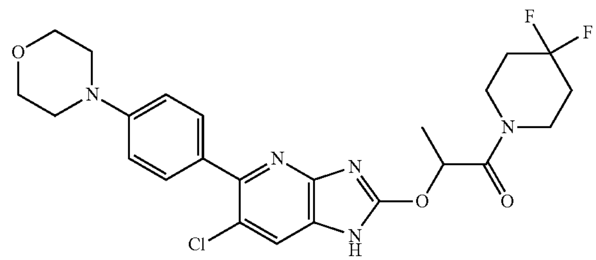 [SMILES: CC(Oc1nc2nc(-c3ccc(N4CCOCC4)cc3)c(Cl)cc2[nH]1)C(=O)N1CCC(F)(F)CC1] | 1H-NMR (DMSO-d6) δ: 1.52 (d, J = 6.59 Hz, 3H), 1.80-2.40 (m, 4H), 3.18 (t, J = 4.82 Hz, 4H), 3.40-3.82 (m, 8H), 5.93 (q, J = 6.59 Hz, 1H), 7.01 (d, J = 8.62 Hz, 2H), 7.54 (d, J = 8.62 Hz, 2H), 7.78 (s, 1H), 12.90 (br s, 1H). |

TABLE 6

| No. | Structure | NMR(δ) | retention time | Mass (M + H) | method |
|---|---|---|---|---|---|
| I-1-32 | 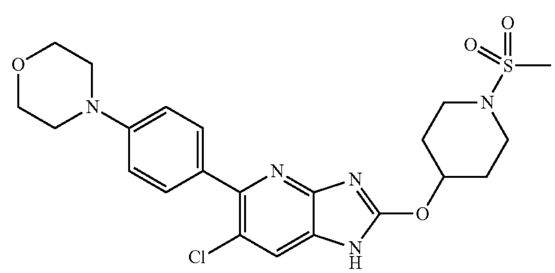 [SMILES: CS(=O)(=O)N1CCC(Oc2nc3nc(-c4ccc(N5CCOCC5)cc4)c(Cl)cc3[nH]2)CC1] | (DMSO-d6) δ: 1.86-1.92 (m, 2H), 2.18-2.21 (m, 2H), 2.93 (s, 3H), 3.14-3.20 (m, 6H), 3.40-3.43 (m, 2H), 3.76 (dd, J = 5.2, 4.4 Hz, 4H), 5.18-5.22 (m, 1H), 7.01 (d, J = 8.6 Hz, 2H), 7.55 (d, J = 8.6 Hz, 2H), 7.87 (brs, 1H). | | | |
| I-1-33 | 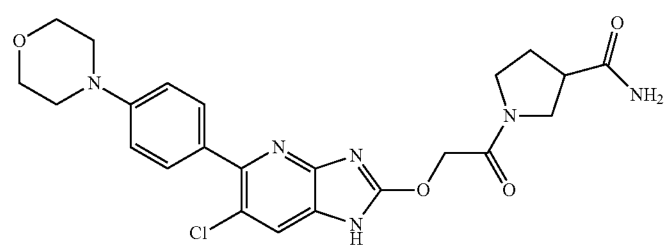 [SMILES: NC(=O)C1CCN(C(=O)COc2nc3nc(-c4ccc(N5CCOCC5)cc4)c(Cl)cc3[nH]2)C1] | | 1.31 | 485.2 | B |
| I-1-34 | 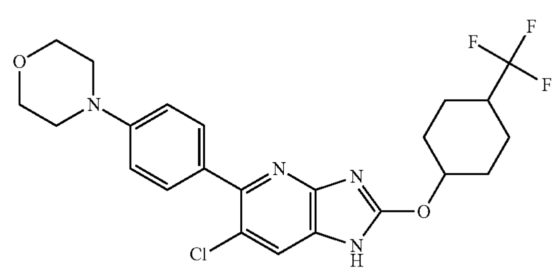 [SMILES: FC(F)(F)C1CCC(Oc2nc3nc(-c4ccc(N5CCOCC5)cc4)c(Cl)cc3[nH]2)CC1] | | 2.37 | 481.1 | A |
| I-1-35 | 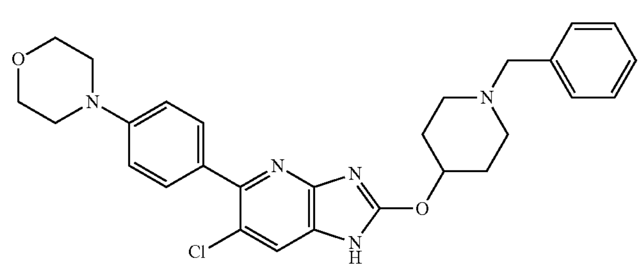 [SMILES: Clc1cc2[nH]c(OC3CCN(Cc4ccccc4)CC3)nc2nc1-c1ccc(N2CCOCC2)cc1] | | 1.43 | 504.2 | A |

TABLE 6-continued

| No. | Structure | NMR(δ) | retention time | Mass (M + H) | method |
|---|---|---|---|---|---|
| I-1-36 | 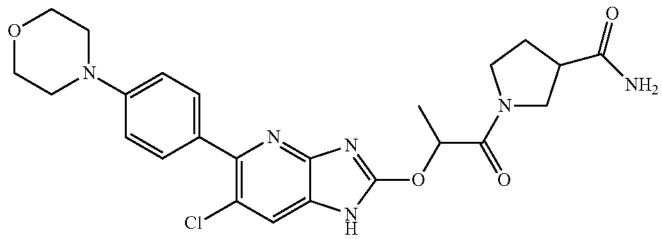 [SMILES: CC(Oc1nc2nc(-c3ccc(N4CCOCC4)cc3)c(Cl)cc2[nH]1)C(=O)N1CCC(C(N)=O)C1] | | 1.37 | 499.2 | B |

TABLE 7

| No. | Structure | NMR(δ) | retention time | Mass (M + H) | method |
|---|---|---|---|---|---|
| I-1-37 | 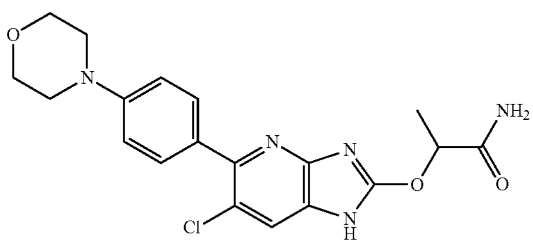 [SMILES: CC(Oc1nc2nc(-c3ccc(N4CCOCC4)cc3)c(Cl)cc2[nH]1)C(N)=O] | 1H-NMR (DMSO-d6) δ: 1.53 (d, J = 6.76 Hz, 3H), 3.19 (t, J = 4.82 Hz, 4H), 3.76 (t, J = 4.82 Hz, 4H), 5.31 (q, J = 6.76 Hz, 1H), 7.01 (d, J = 9.12 Hz, 2H), 7.25 (s, 1H), 7.55 (d, J = 9.12 Hz, 2H), 7.62 (s, 1H), 7.85 (s, 1H). | | | |
| I-1-38 | 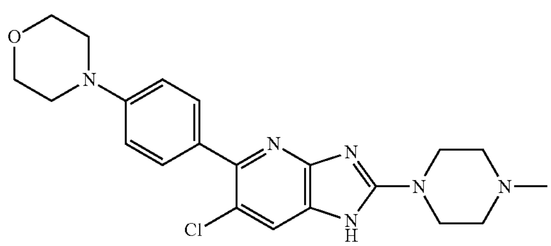 [SMILES: CN1CCN(c2nc3nc(-c4ccc(N5CCOCC5)cc4)c(Cl)cc3[nH]2)CC1] | | 0.92 | 413.0 | B |
| I-1-39 | 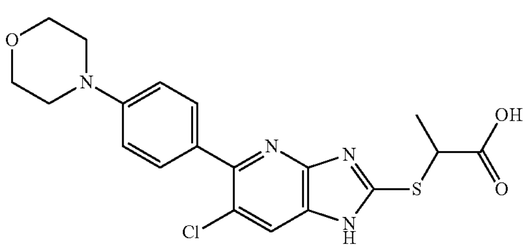 [SMILES: CC(Sc1nc2nc(-c3ccc(N4CCOCC4)cc3)c(Cl)cc2[nH]1)C(=O)O] | 1H-NMR (DMSO-d6) δ: 1.62 (d, J = 7.27 Hz, 3H), 3.20 (t, J = 4.82 Hz, 4H), 3.76 (t, J = 4.82 Hz, 4H), 4.63 (q, J = 7.27 Hz, 1H), 7.02 (d, J = 9.12 Hz, 2H), 7.57 (d, J = 9.12 Hz, 2H), 8.06 (s, 1H), 13.11 (br s, 2H). | | | |
| I-1-40 | 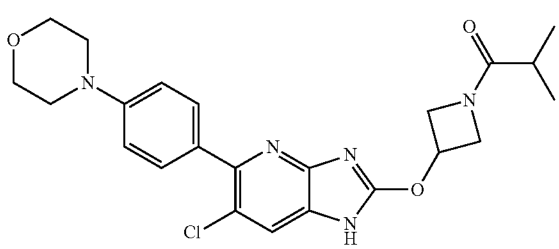 [SMILES: CC(C)C(=O)N1CC(Oc2nc3nc(-c4ccc(N5CCOCC5)cc4)c(Cl)cc3[nH]2)C1] | (DMSO-d6) δ: 0.98-1.00 (m, 6H), 2.47-2.53 (m, 1H), 3.19 (dd, J = 5.2, 4.4 Hz, 4H), 3.76 (dd, J = 5.2, 4.4 Hz, 4H), 3.92-3.94 (m, 1H), 4.26-4.33 (m, 2H), 4.63-4.67 (m, 1H), 5.50-5.53 (m, 1H), 7.01 (d, J = 8.6 Hz, 2H), 7.56 (d, J = 8.6 Hz, 2H), 7.94 (s, 1H). | | | |

TABLE 7-continued

| No. | Structure | NMR(δ) | retention time | Mass (M + H) | method |
|---|---|---|---|---|---|
| I-1-41 | 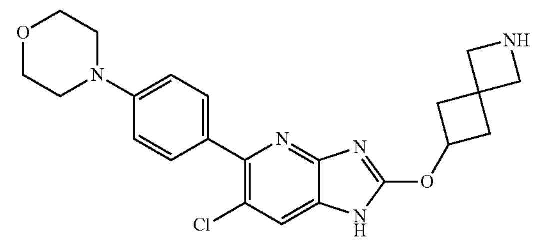 [SMILES: Clc1cc2[nH]c(OC3CC4(CNC4)C3)nc2nc1-c1ccc(N2CCOCC2)cc1] | (DMSO-d6) δ: 2.21-2.30 (m, 2H), 2.70-2.74 (m, 2H), 3.17 (dd, J = 5.2, 4.4 Hz, 4H), 3.64-3.70 (m, 4H), 3.76 (dd, J = 5.2, 4.4 Hz, 4H), 5.10-5.16 (m, 1H), 6.99 (d, J = 8.6 Hz, 2H), 7.54 (d, J = 8.6 Hz, 2H), 7.72 (s, 0.7H), 7.76 (s, 0.3H). | | | 15 |

TABLE 8

| No. | Structure | NMR(δ) |
|---|---|---|
| I-1-42 | 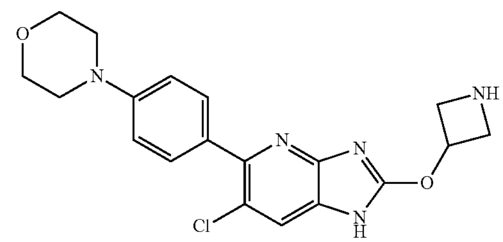 [SMILES: Clc1cc2[nH]c(OC3CNC3)nc2nc1-c1ccc(N2CCOCC2)cc1] | (DMSO-d6) δ: 3.17-3.34 (m, 7H), 3.72-3.77 (m, 4H), 3.90-3.94 (m, 1H), 5.33-5.36 (m, 1H), 7.01 (d, J = 8.6 Hz, 2H), 7.55 (d, J = 8.6 Hz, 2H), 7.87 (s, 1H). |
| I-1-43 | 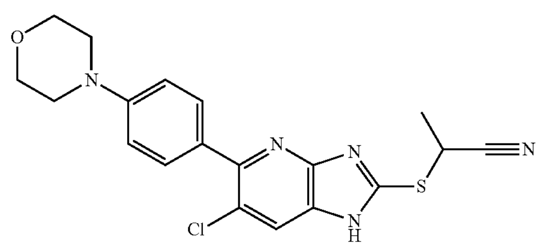 | 1H-NMR (DMSO-d6) δ: 1.77 (d, J = 7.27 Hz, 3H), 3.20 (t, J = 4.56 Hz, 4H), 3.77 (t, J = 4.82 Hz, 4H), 5.02 (q, J = 7.27 Hz, 1H), 7.03 (d, J = 8.62 Hz, 2H), 7.59 (d, J = 8.62 Hz, 2H), 8.17 (s, 1H). |
| I-1-44 | 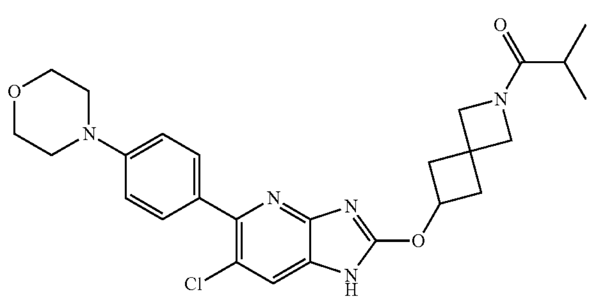 [SMILES: CC(C)C(=O)N1CC2(CC(Oc3nc4nc(-c5ccc(N6CCOCC6)cc5)c(Cl)cc4[nH]3)C2)C1] | (DMSO-d6) δ: 0.94-0.97 (m, 6H), 2.39-2.42 (m, 3H), 2.77-2.79 (m, 2H), 3.18 (dd, J = 5.2, 4.4 Hz, 4H), 3.76 (dd, J = 5.2, 4.4 Hz, 4H), 3.89 (d, J = 23.8 Hz, 2H), 4.20 (d, J = 23.8 Hz, 2H), 5.19-5.22 (m, 1H), 7.01 (d, J = 8.6 Hz, 2H), 7.55 (d, J = 8.6 Hz, 2H), 7.76 (s, 0.3H), 7.89 (s, 0.7H). |
| I-1-45 | 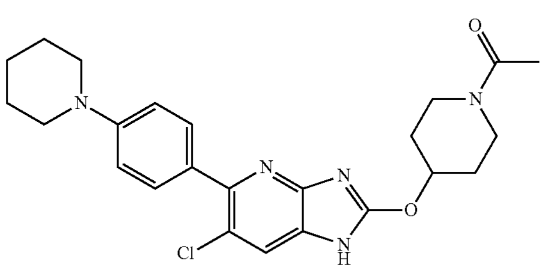 [SMILES: CC(=O)N1CCC(Oc2nc3nc(-c4ccc(N5CCCCC5)cc4)c(Cl)cc3[nH]2)CC1] | 1H-NMR (DMSO-d6) δ: 1.56-1.68 (m, 6H), 1.75-1.79 (m, 1H), 2.04-2.15 (m, 5H), 3.19-3.24 (m, 3H), 3.70-3.74 (m, 1H), 3.92-3.953 (m, 1H), 5.23-5.29 (m, 1H), 6.98 (d, J = 8.6 Hz, 2H), 7.52 (d, J = 8.6 Hz, 2H), 7.85 (brs, 1H). |

TABLE 8-continued

| No. | Structure | NMR(δ) |
|---|---|---|
| I-1-46 | 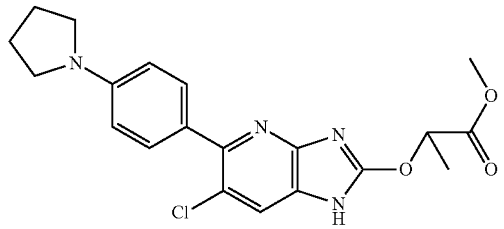 [SMILES: COC(=O)C(C)Oc1nc2nc(-c3ccc(N4CCCC4)cc3)c(Cl)cc2[nH]1] | 1H-NMR (DMSO-d6) δ: 1.60 (d, J = 7.10 Hz, 3H), 1.98 (t, J = 6.59 Hz, 4H), 3.28 (t, J = 6.59 Hz, 4H), 3.71 (s, 3H), 5.47 (q, J = 7.10 Hz, 1H), 6.59 (d, J = 8.62 Hz, 2H), 7.51 (d, J = 8.62 Hz, 2H), 7.88 (br s, 1H), 12.91 (br s, 1H). |

TABLE 9

| No. | Structure | NMR (δ) |
|---|---|---|
| I-1-47 | 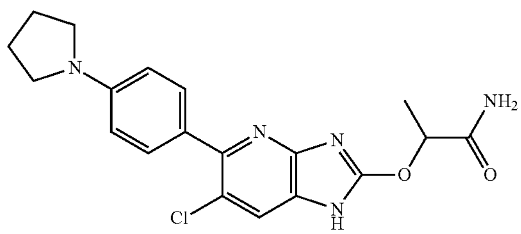 [SMILES: CC(Oc1nc2nc(-c3ccc(N4CCCC4)cc3)c(Cl)cc2[nH]1)C(N)=O] | 1H-NMR (DMSO-d6) δ: 1.52 (d, J = 7.10 Hz, 3H), 1.98 (t, J = 6.59 Hz, 4H), 3.28 (t, J = 6.59 Hz, 4H), 5.30 (q, J = 7.10 Hz, 1H), 6.59 (d, J = 8.62 Hz, 2H), 7.24 (s, 1H), 7.51 (d, J = 8.62 Hz, 2H), 7.61 (s, 1H), 7.85 (s, 1H), 12.73 (br s, 1H). |
| I-1-48 | 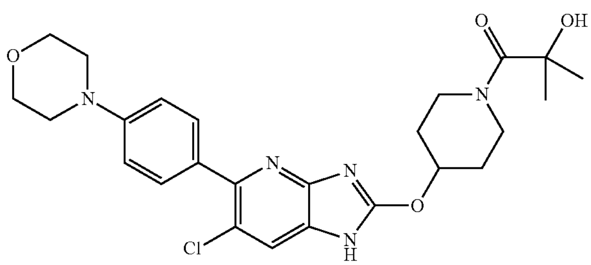 [SMILES: CC(C)(O)C(=O)N1CCC(Oc2nc3nc(-c4ccc(N5CCOCC5)cc4)c(Cl)cc3[nH]2)CC1] | 1H-NMR (DMSO-d6) δ: 1.24 (s, 6H) 1.71 (brs, 2H), 2.11-2.12 m, 2H), 3.18 (dd, J = 5.2, 4.4 Hz, 4H), 3.37 (brs, 1H), 3.58 (brs, 1H), 3.76 (dd, J = 5.2, 4.4 Hz, 4H), 4.01 (brs, 1H), 4.38 (brs, 1H), 5.27-5.31 (m, 1H), 5.45 (s, 1H), 7.01 (d, J = 8.6 Hz, 2H), 7.55 (d, J = 8.6 Hz, 2H), 7.75 (s, 0.3H), 7.90 (s, 0.7H), 12.34 (s, 0.3H), 12.74 (s, 0.7H). |
| I-1-49 | 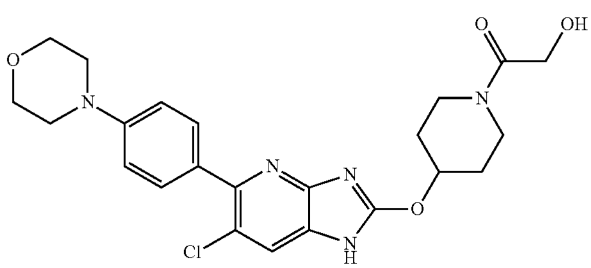 [SMILES: O=C(CO)N1CCC(Oc2nc3nc(-c4ccc(N5CCOCC5)cc4)c(Cl)cc3[nH]2)CC1] | 1H-NMR (DMSO-d6) δ: 1.67-1.78 (m, 2H), 2.11-2.12 (m, 2H), 3.20 (dd, J = 5.2, 4.4 Hz, 4H), 3.23-3.43 (m, 2H), 3.60-3.64 (m, 1H), 3.76 (dd, J = 5.2, 4.4 Hz, 4H), 3.93-3.96 (m, 1H), 4.12-4.13 (m, 2H), 4.56-4.59 (m, 1H), 5.25-5.31 (m, 1H), 7.01 (d, J = 8.6 Hz, 2H), 7.55 (d, J = 8.6 Hz, 2H), 7.85 (s, 1H). |
| I-1-50 | 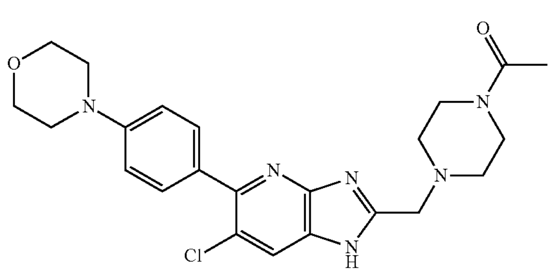 | 1H-NMR (CDCl3) δ: 2.09 (s, 3H), 2.46-2.54 (m, 4H), 3.26 (t, J = 4.82 Hz, 4H), 3.48 (t, J = 4.82 Hz, 2H), 3.61-3.68 (m, 4H), 3.89 (t, J = 4.82 Hz, 4H), 7.00 (d, J = 8.62 Hz, 2H), 7.70 (d, J = 8.62 Hz, 2H), 8.08 (s, 1H), 10.66 (br s, 1H). |

TABLE 9-continued

| No. | Structure | NMR (δ) | | |
|---|---|---|---|---|
| I-1-51 | 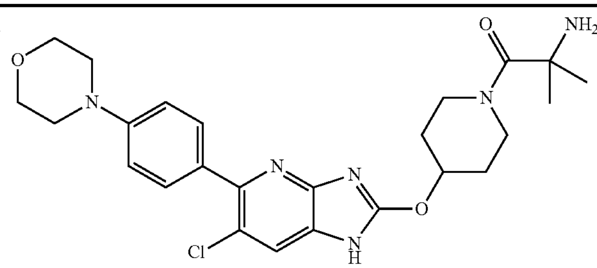 | 1H-NMR (DMSO-d6) δ: 1.30 (s, 6H), 1.66-1.73 (m, 2H), 2.09-2.12 (m, 2H), 3.18 (dd, J = 5.2, 4.4 Hz, 4H), 3.41-3.51 (m, 2H), 3.76 (dd, J = 5.2, 4.4 Hz, 4H), 4.30 (brs, 2H), 5.24-5.30 (m, 1H), 7.01 (d, J = 8.6 Hz, 2H), 7.55 (d, J = 8.6 Hz, 2H), 7.82 (s, 1H). | | |

TABLE 10

| No. | Structure | NMR (δ) | retention time | Mass (M + H) | method |
|---|---|---|---|---|---|
| I-1-52 | 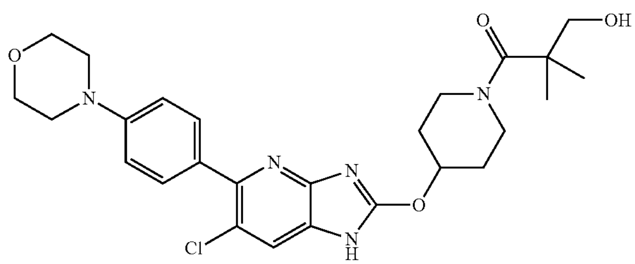 [SMILES: CC(C)(CO)C(=O)N1CCC(Oc2nc3nc(-c4ccc(N5CCOCC5)cc4)c(Cl)cc3[nH]2)CC1] | (DMSO-d6) δ: 1.18 (s, 6H), 1.68-1.73 (m, 2H), 2.11-2.13 (m, 2H), 3.19 (dd, J = 5.2, 4.4 Hz, 4H), 3.34-3.38 (m, 2H), 3.44 (d, J = 5.6 Hz, 2H), 3.76 (dd, J = 5.2, 4.4 Hz, 4H), 3.95-3.99 (m, 2H), 4.57 (t, J = 5.6 Hz, 1H), 5.25-5.31 (m, 1H), 7.01 (d, J = 8.6 Hz, 2H), 7.55 (d, J = 8.6 Hz, 2H), 7.90 (brs, 1H). | | | |
| I-1-53 | 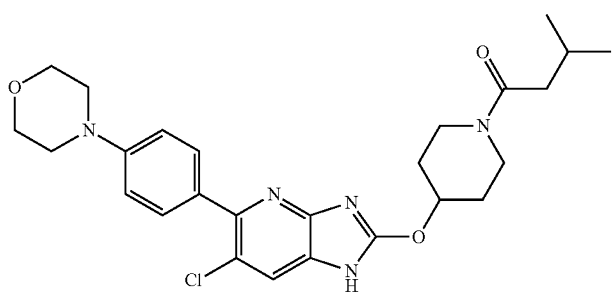 [SMILES: CC(C)CC(=O)N1CCC(Oc2nc3nc(-c4ccc(N5CCOCC5)cc4)c(Cl)cc3[nH]2)CC1] | 1H-NMR (DMSO-d6) δ: 0.91 (d, J = 6.6 Hz, 6H), 1.62-1.74 (m, 2H), 1.98-2.12 (m, 3H), 2.23 (d, J = 6.6 Hz, 2H), 3.17-3.28 (m, 5H), 3.37-3.40 (m, 1H), 3.75-3.77 (m, 5H), 3.95-3.98 (m, 1H), 5.24-5.30 (m, 1H), 7.01 (d, J = 8.6 Hz, 2H), 7.55 (d, J = 8.6 Hz, 2H), 7.86 (s, 1H). | | | |
| I-1-54 | 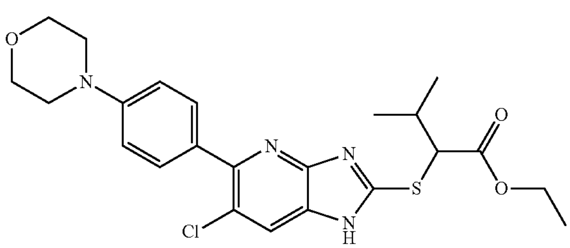 [SMILES: CCOC(=O)C(Sc1nc2nc(-c3ccc(N4CCOCC4)cc3)c(Cl)cc2[nH]1)C(C)C] | 1H-NMR (DMSO-d6) δ: 1.06 (dd, J = 6.6, 5.1 Hz, 6H), 1.18 (t, J = 7.1 Hz, 3H), 2.27-2.33 (m, 1H), 3.20 (t, J = 4.8 Hz, 5H), 3.76 (t, J = 4.8 Hz, 4H), 4.15 (q, J = 6.9 Hz, 2H), 4.62 (d, J = 6.6 Hz, 1H), 7.02 (d, J = 8.6 Hz, 2H), 7.57 (d, J = 8.6 Hz, 2H), 8.04 (s, 1H), 13.36 (br s, 1H). | 2.36 | 475.2 | B |
| I-1-55 | 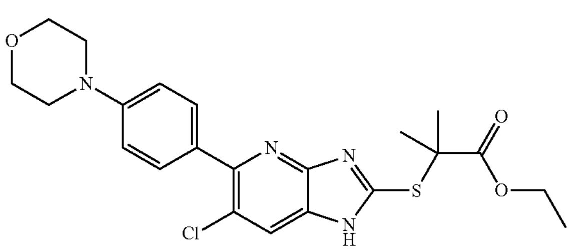 [SMILES: CCOC(=O)C(C)(C)Sc1nc2nc(-c3ccc(N4CCOCC4)cc3)c(Cl)cc2[nH]1] | 1H-NMR (DMSO-d6) δ: 1.07 (t, J = 7.1 Hz, 3H), 1.69 (s, 6H), 3.20 (t, J = 4.8 Hz, 4H), 3.76 (t, J = 4.8 Hz, 4H), 4.08 (q, J = 7.1 Hz, 2H), 7.02 (d, J = 9.1 Hz, 2H), 7.58 (d, J = 9.1 Hz, 2H), 8.12 (s, 1H), 13.45 (s, 1H). | 2.15 | 461.1 | B |

TABLE 10-continued

| No. | Structure | NMR (δ) | retention time | Mass (M + H) | method |
|---|---|---|---|---|---|
| I-1-56 | 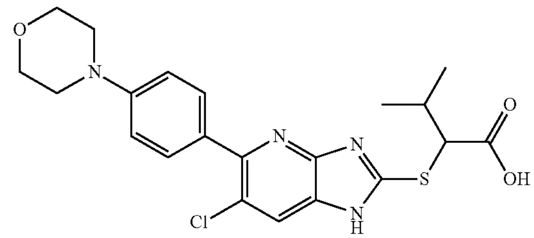 [SMILES: CC(C)C(Sc1nc2nc(-c3ccc(N4CCOCC4)cc3)c(Cl)cc2[nH]1)C(=O)O] | 1H-NMR (DMSO-d6) δ: 1.06 (dd, J = 6.8, 1.8 Hz, 6H), 2.32 (td, J = 13.2, 6.6 Hz, 1H), 3.20 (t, J = 4.8 Hz, 4H), 3.76 (t, J = 4.8 Hz, 4H), 4.55 (d, J = 6.1 Hz, 1H), 7.02 (d, J = 9.1 Hz, 2H), 7.57 (d, J = 9.1 Hz, 2H), 8.04 (s, 1H), 13.09 (s, 2H). | 1.90 | 447.0 | B |

TABLE 11

| No. | Structure | NMR (δ) | retention time | Mass (M + H) | method |
|---|---|---|---|---|---|
| I-1-57 | 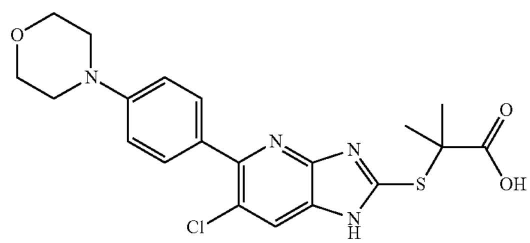 [SMILES: CC(C)(Sc1nc2nc(-c3ccc(N4CCOCC4)cc3)c(Cl)cc2[nH]1)C(=O)O] | 1H-NMR (DMSO-d6) δ: 1.69 (s, 6H), 3.20 (t, J = 4.8 Hz, 4H), 3.76 (t, J = 4.8 Hz, 4H), 7.02 (d, J = 9.1 Hz, 2H), 7.58 (d, J = 8.6 Hz, 2H), 8.09 (s, 1H), 12.97 (s, 1H), 13.45 (s, 1H). | 1.75 | 433.2 | B |
| I-1-58 | 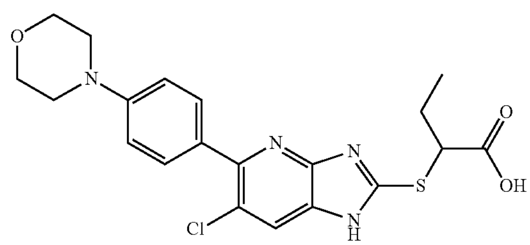 [SMILES: CCC(Sc1nc2nc(-c3ccc(N4CCOCC4)cc3)c(Cl)cc2[nH]1)C(=O)O] | 1H-NMR (DMSO-d6) δ: 1.02 (t, J = 7.4 Hz, 3H), 1.99 (td, J = 14.2, 7.1 Hz, 2H), 3.20 (t, J = 4.8 Hz, 4H), 3.76 (t, J = 4.8 Hz, 4H), 4.57 (t, J = 6.8 Hz, 1H), 7.02 (d, J = 9.1 Hz, 2H), 7.57 (d, J = 8.6 Hz, 2H), 8.06 (s, 1H), 13.08 (s, 2H). | 1.79 | 433.2 | B |
| I-1-59 | 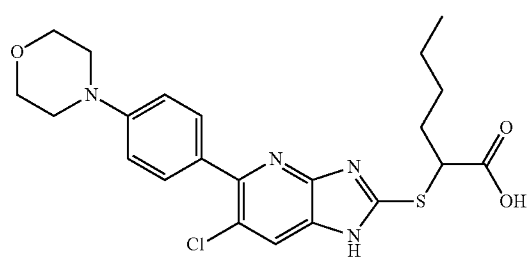 [SMILES: CCCCC(Sc1nc2nc(-c3ccc(N4CCOCC4)cc3)c(Cl)cc2[nH]1)C(=O)O] | 1H-NMR (DMSO-d6) δ: 0.87 (t, J = 7.4 Hz, 3H), 1.28-1.44 (m, 4H), 1.85-2.01 (m, 2H), 3.20 (t, J = 4.8 Hz, 4H), 3.76 (t, J = 4.8 Hz, 4H), 4.47 (t, J = 6.8 Hz, 1H), 7.02 (d, J = 9.1 Hz, 2H), 7.57 (d, J = 8.6 Hz, 2H), 8.03 (s, 1H). | 2.09 | 405.1 | B |
| I-1-60 | 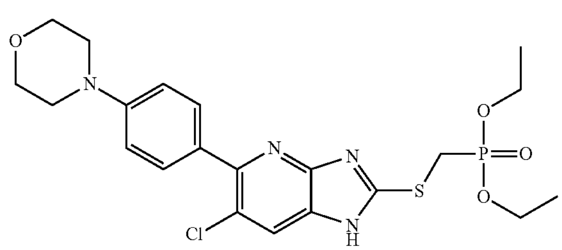 [SMILES: CCOP(=O)(CSc1nc2nc(-c3ccc(N4CCOCC4)cc3)c(Cl)cc2[nH]1)OCC] | 1H-NMR (DMSO-d6) δ: 1.19 (t, J = 6.8 Hz, 6H), 3.20 (t, J = 4.8 Hz, 4H), 3.76 (t, J = 4.8 Hz, 4H), 3.84 (d, J = 13.2 Hz, 2H), 4.06 (dt, J = 15.2, 7.1 Hz, 4H), 7.02 (d, J = 8.6 Hz, 2H), 7.58 (d, J = 8.6 Hz, 2H), 8.08 (s, 1H), 13.44 (s, 1H). | 1.82 | 497.1 | B |

TABLE 11-continued

| No. | Structure | NMR (δ) | retention time | Mass (M + H) | method |
|---|---|---|---|---|---|
| I-1-61 | 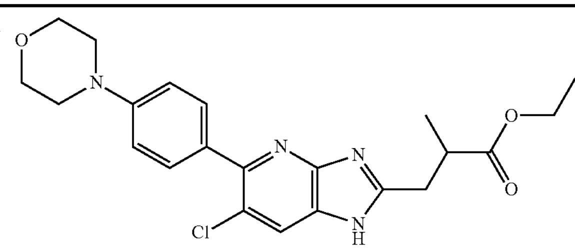 | 1H-NMR (DMSO-d6) δ: 1.12 (t, J = 7.10 Hz, 3H), 1.19 (d, J = 7.10 Hz, 3H), 2.94 (dd, J = 13.94, 5.83 Hz, 1H), 3.12-3.17 (m, 6H), 3.76 (t, J = 4.56 Hz, 4H), 4.05 (q, J = 7.10 Hz, 2H), 7.02 (d, J = 8.62 Hz, 2H), 7.57 (d, J = 8.62 Hz, 2H), 8.08 (s, 1H). | | | |

TABLE 12

| No. | Structure | NMR (δ) | retention time | Mass (M + H) | method |
|---|---|---|---|---|---|
| I-1-62 | 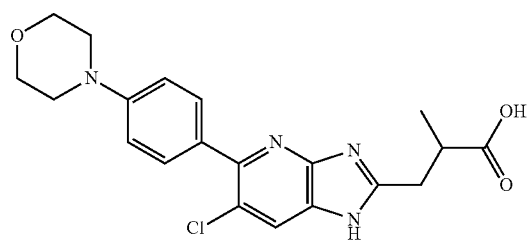 | 1H-NMR (DMSO-d6) δ: 1.18 (d, J = 6.59 Hz, 3H), 2.89 (dd, J = 14.70, 7.10 Hz, 1H), 3.00-3.23 (m, 6H), 3.76 (t, J = 4.82 Hz, 4H), 7.02 (d, J = 8.62 Hz, 2H), 7.57 (d, J = 8.62 Hz, 2H), 8.09 (s, 1H), 12.29 (s, 1H), 13.00 (s, 1H). | | | |
| I-1-63 | 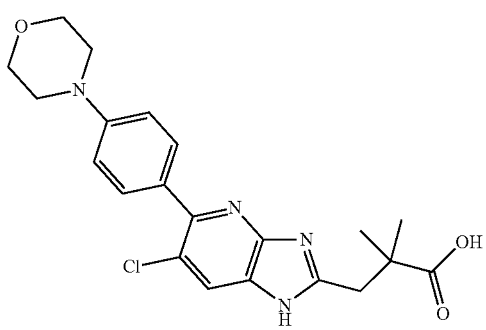 [SMILES: CC(C)(Cc1nc2nc(-c3ccc(N4CCOCC4)cc3)c(Cl)cc2[nH]1)C(=O)O] | 1H-NMR (DMSO-d6) δ: 1.24 (s, 6H), 3.05 (s, 2H), 3.20 (t, J = 4.82 Hz, 4H), 3.76 (t, J = 4.82 Hz, 4H), 7.02 (d, J = 8.62 Hz, 2H), 7.58 (d, J = 8.62 Hz, 2H), 8.11 (s, 1H), 12.31 (s, 1H), 12.97 (s, 1H). | | | |
| I-1-64 | 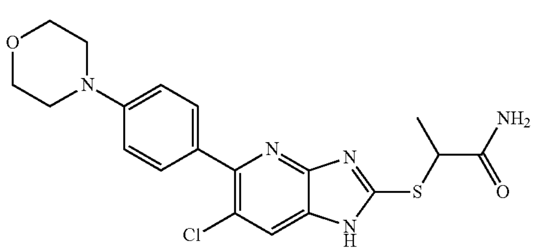 [SMILES: CC(Sc1nc2nc(-c3ccc(N4CCOCC4)cc3)c(Cl)cc2[nH]1)C(N)=O] | 1H-NMR (DMSO-d6) δ: 1.58 (d, J = 7.1 Hz, 3H), 3.20 (t, J = 3.8 Hz, 4H), 3.77 (t, J = 5.1 Hz, 4H), 4.64 (q, J = 6.9 Hz, 1H), 7.02 (d, J = 8.6 Hz, 2H), 7.25 (s, 1H), 7.57 (d, J = 8.6 Hz, 2H), 7.84 (s, 1H), 8.00 (s, 1H). | 1.54 | 418.3 | B |
| I-1-65 | 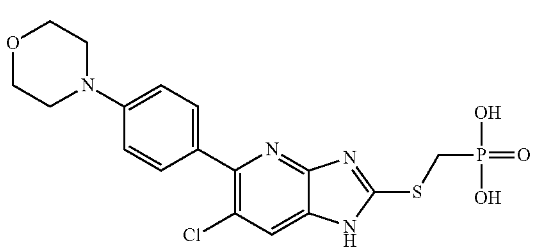 [SMILES: O=P(O)(O)CSc1nc2nc(-c3ccc(N4CCOCC4)cc3)c(Cl)cc2[nH]1] | 1H-NMR (DMSO-d6) δ: 3.20 (t, J = 4.6 Hz, 4H), 3.52 (d, J = 13.7 Hz, 2H), 3.76 (t, J = 4.6 Hz, 4H), 7.02 (d, J = 8.6 Hz, 2H), 7.57 (d, J = 8.6 Hz, 2H), 8.03 (s, 1H). | 1.29 | 444.2 | B |

TABLE 12-continued

| No. | Structure | NMR (δ) | retention time | Mass (M + H) | method |
|---|---|---|---|---|---|
| I-1-66 | 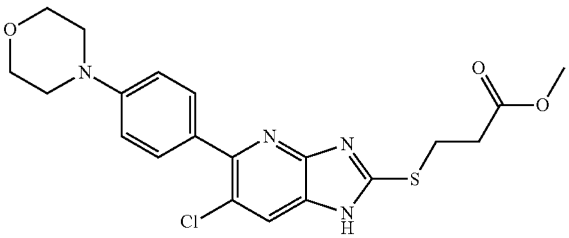 [SMILES: COC(=O)CCSc1nc2nc(-c3ccc(N4CCOCC4)cc3)c(Cl)cc2[nH]1] | 1H-NMR (DMSO-d6) δ: 2.88 (t, J = 6.8 Hz, 2H), 3.20 (t, J = 4.6 Hz, 4H), 3.60 (s, 3H), 3.76 (t, J = 4.8 Hz, 4H), 4.45 (t, J = 6.8 Hz, 2H), 7.02 (d, J = 8.6 Hz, 2H), 7.55 (d, J = 8.6 Hz, 2H), 8.09 (s, 1H), 13.49 (s, 1H). | 1.93 | 433.0 | B |

TABLE 13

| No. | Structure | NMR (δ) | retention time | Mass (M + H) | method |
|---|---|---|---|---|---|
| I-1-67 | 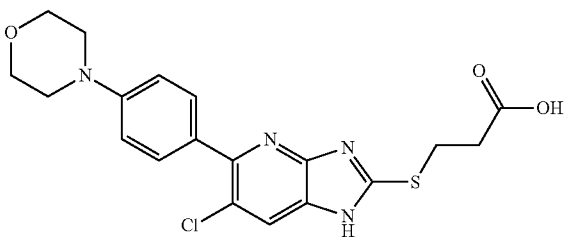 [SMILES: O=C(O)CCSc1nc2nc(-c3ccc(N4CCOCC4)cc3)c(Cl)cc2[nH]1] | 1H-NMR (DMSO-d6) δ: 2.79 (t, J = 7.1 Hz, 2H), 3.20 (t, J = 4.8 Hz, 4H), 3.76 (t, J = 4.8 Hz, 4H), 4.41 (t, J = 7.1 Hz, 2H), 7.02 (d, J = 9.1 Hz, 2H), 7.55 (d, J = 9.1 Hz, 2H), 8.08 (s, 1H), 12.43 (s, 1H), 13.48 (s, 1H). | 1.59 | 419.1 | B |
| I-1-68 | 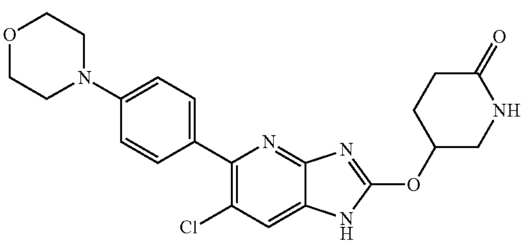 [SMILES: O=C1CCC(Oc2nc3nc(-c4ccc(N5CCOCC5)cc4)c(Cl)cc3[nH]2)CN1] | (DMSO-d6) δ: 2.14-2.32 (m, 4H), 3.19 (dd, J = 5.2, 4.4 Hz, 4H), 3.46-3.50 (m, 1H), 3.57-3.61 (m, 1H), 3.76 (dd, J = 5.2, 4.4 Hz, 4H), 5.41 (brs, 1H), 7.01 (d, J = 8.6 Hz, 2H), 7.51 (s, 1H), 7.55 (d, J = 8.6 Hz, 2H), 7.90 (brs, 1H). | | | |
| I-1-69 | 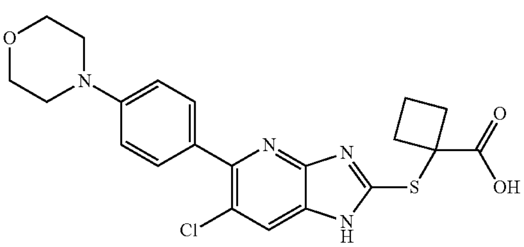 [SMILES: O=C(O)C1(Sc2nc3nc(-c4ccc(N5CCOCC5)cc4)c(Cl)cc3[nH]2)CCC1] | 1H-NMR (DMSO-d6) δ: 1.80-1.90 (m, 1H), 2.02-2.14 (m, 3H), 2.73 (t, J = 9.9 Hz, 2H), 3.19 (t, J = 4.6 Hz, 4H), 3.76 (t, J = 4.8 Hz, 4H), 7.01 (d, J = 8.6 Hz, 2H), 7.57 (d, J = 8.6 Hz, 2H), 7.96 (s, 1H). | 1.86 | 445.1 | B |
| I-1-70 | 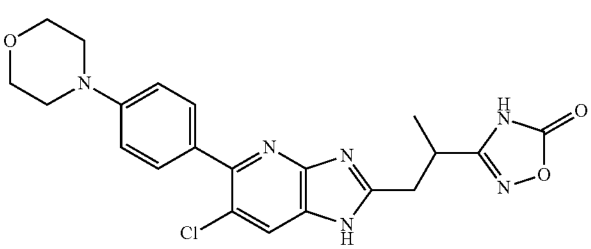 [SMILES: CC(Cc1nc2nc(-c3ccc(N4CCOCC4)cc3)c(Cl)cc2[nH]1)c1noc(=O)[nH]1] | 1H-NMR (CDCl3) δ: 1.19 (d, J = 7.10 Hz, 3H), 2.05-3.05 (m, 3H), 3.30 (t, J = 4.56 Hz, 4H), 3.91 (t, J = 4.56 Hz, 4H), 7.04 (d, J = 8.62 Hz, 2H), 7.72 (d, J = 8.62 Hz, 2H), 8.14 (s, 1H), 13.44 (s, 1H). | | | |

TABLE 13-continued

| No. | Structure | NMR (δ) | retention time | Mass (M + H) | method |
|---|---|---|---|---|---|
| I-1-71 | 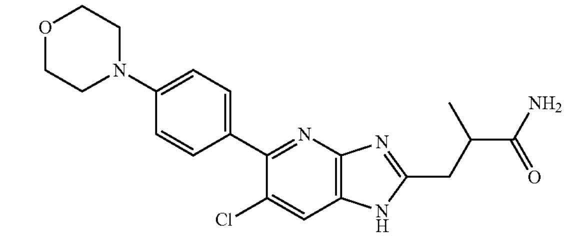 [SMILES: CC(Cc1nc2nc(-c3ccc(N4CCOCC4)cc3)c(Cl)cc2[nH]1)C(N)=O] | 1H-NMR (DMSO-d6) δ: 1.10 (d, J = 7.10 Hz, 3H), 2.73-3.14 (m, 3H), 3.20 (t, J = 4.82 Hz, 4H), 3.77 (t, J = 4.82 Hz, 4H), 6.78 (s, 1H), 7.02 (d, J = 8.62 Hz, 2H), 7.37 (s, 1H), 7.57 (d, J = 8.62 Hz, 2H), 8.08 (s, 1H), 12.94 (s, 1H). | | | |

TABLE 14

| No. | Structure | NMR (δ) | retention time | Mass (M + H) | method |
|---|---|---|---|---|---|
| I-1-72 | 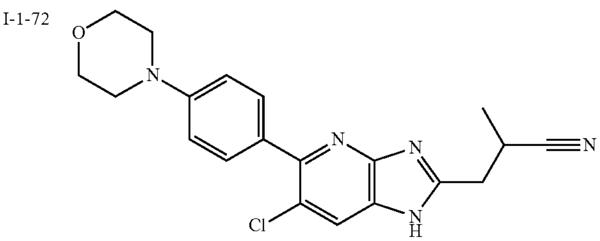 | 1H-NMR (DMSO-d6) δ: 1.38 (d, J = 7.10 Hz, 3H), 3.17-3.22 (m, 6H), 3.46 (m, 1H), 3.77 (t, J = 4.56 Hz, 4H), 7.03 (d, J = 8.62 Hz, 2H), 7.58 (d, J = 9.12 Hz, 2.0H), 8.16 (s, 1.0H). | | | |
| I-1-73 | 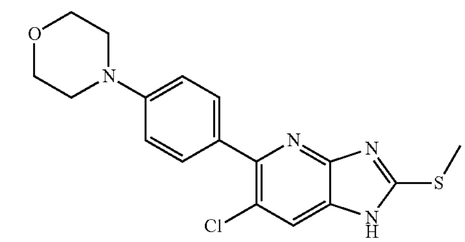 [SMILES: CSc1nc2nc(-c3ccc(N4CCOCC4)cc3)c(Cl)cc2[nH]1] | 1H-NMR (DMSO-d6) δ: 2.72 (s, 3H), 3.19 (t, J = 4.8 Hz, 4H), 3.76 (t, J = 4.8 Hz, 4H), 7.02 (d, J = 8.6 Hz, 2H), 7.57 (d, J = 8.6 Hz, 2H), 8.01 (s, 1H), 13.20 (s, 1H). | 1.71 | 361.0 | B |
| I-1-74 | 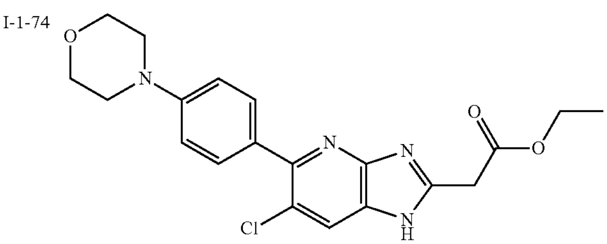 | 1H-NMR (DMSO-d6) δ: 1.21 (t, J = 7.86 Hz, 3H), 3.20 (t, J = 4.56 Hz, 4H), 3.77 (t, J = 4.56 Hz, 4H), 4.00 (s, 2H), 4.15 (q, J = 7.86 Hz, 2H), 7.03 (d, J = 8.62 Hz, 2H), 7.55-7.61 (m, 2H), 8.16 (s, 1H), 13.15 (s, 1H). | | | |
| I-1-75 | 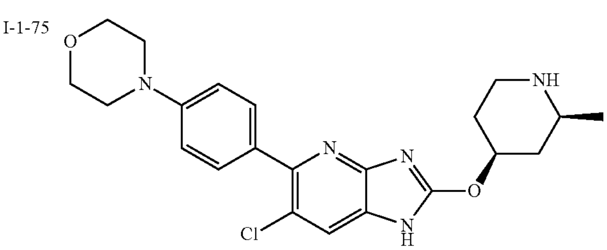 | (DMSO-d6) δ: 1.21 (d, J = 6.4 Hz, 3H), 1.47-1.58 (m, 2H), 1.61-1.737 (m, 1H), 2.33-2.41 (m, 2H), 2.98-3.03 (m, 1H), 3.18-3.36 (m, 5H), 3.52 (dd, J = 5.2, 4.4 Hz, 4H), 5.19-5.24 (m, 1H), 7.01 (d, J = 8.6 Hz, 2H), 7.55 (d, J = 8.6 Hz, 2H), 7.85 (s, 1H). | | | |

TABLE 14-continued

| No. | Structure | NMR (δ) | retention time | Mass (M + H) | method |
|---|---|---|---|---|---|
| I-1-76 | 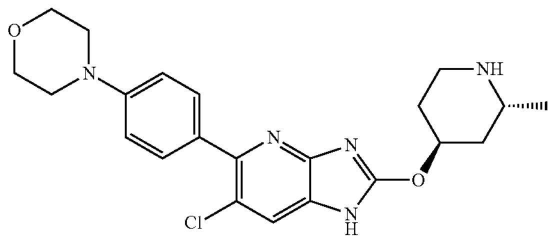 [SMILES: C[C@@H]1C[C@@H](Oc2nc3nc(-c4ccc(N5CCOCC5)cc4)c(Cl)cc3[nH]2)CCN1] | (DMSO-d6) δ: 1.00 (d, J = 6.6 Hz, 3H), 1.39-1.45 (m, 1H), 1.69-1.75 (m, 1H), 1.92-2.02 (m, 2H), 2.82-2.96 (m, 3H), 3.18 (dd, J = 5.2, 4.4 Hz, 4H), 3.76 (dd, J = 5.2, 4.4 Hz, 4H), 5.37 (brs, 1H), 7.00 (d, J = 8.6 Hz, 2H), 7.54 (d, J = 8.6 Hz, 2H), 7.78 (s, 1H). | | | |

TABLE 15

| No. | Structure | NMR (δ) | retention time | Mass (M + H) | method |
|---|---|---|---|---|---|
| I-1-77 | 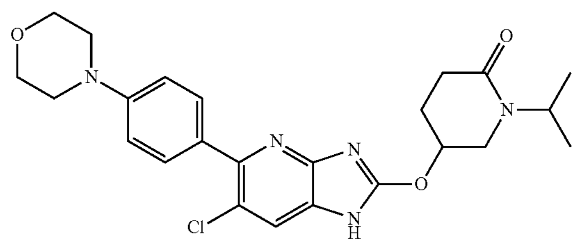 [SMILES: CC(C)N1CC(Oc2nc3nc(-c4ccc(N5CCOCC5)cc4)c(Cl)cc3[nH]2)CCC1=O] | (DMSO-d6) δ: 0.94 (d, J = 6.8 Hz, 3H), 1.05 (d, J = 6.8 Hz, 3H), 2.10-2.22 (m, 2H), 2.35-2.39 (m, 2H), 3.19 (dd, J = 5.2, 4.4 Hz, 4H), 3.56 (brs, 2H), 3.76 (dd, J = 5.2, 4.4 Hz, 4H), 4.68-4.75 (m, 1H), 5.49 (brs, 1H), 7.01 (d, J = 8.6 Hz, 2H), 7.55 (d, J = 8.6 Hz, 2H), 7.92 (brs, 1H). | | | |
| I-1-78 | 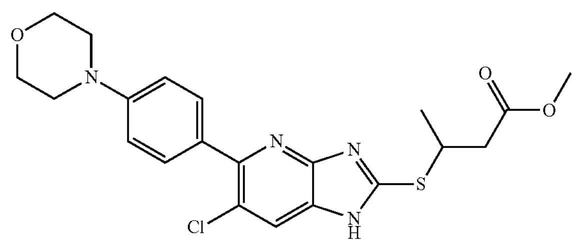 [SMILES: COC(=O)CC(C)Sc1nc2nc(-c3ccc(N4CCOCC4)cc3)c(Cl)cc2[nH]1] | 1H-NMR (DMSO-d6) δ: 1.53 (d, J = 6.6 Hz, 3H), 3.11 (dd, J = 15.7, 7.1 Hz, 1H), 3.20 (t, J = 4.6 Hz, 4H), 3.56 (s, 3H), 3.76 (t, J = 4.6 Hz, 4H), 5.57 (s, 1H), 7.02 (d, J = 8.6 Hz, 2H), 7.55 (d, J = 8.6 Hz, 2H), 8.25 (s, 1H), 13.46 (s, 1H). | 2.00 | 447.1 | B |
| I-1-79 | 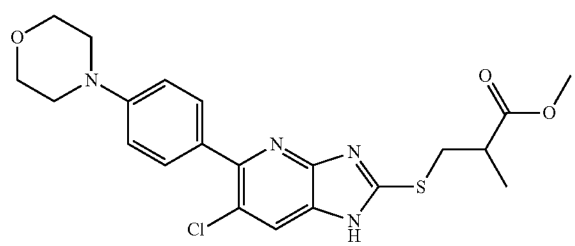 [SMILES: COC(=O)C(C)CSc1nc2nc(-c3ccc(N4CCOCC4)cc3)c(Cl)cc2[nH]1] | 1H-NMR (DMSO-d6) δ: 1.15 (d, J = 7.1 Hz, 3H), 3.20 (t, J = 4.6 Hz, 4H), 3.25 (dd, J = 14.7, 7.6 Hz, 2H), 3.54 (s, 3H), 3.76 (t, J = 4.8 Hz, 4H), 4.29 (dd, J = 13.9, 6.8 Hz, 1H), 4.47 (dd, J = 13.7, 8.1 Hz, 1H), 7.02 (d, J = 8.6 Hz, 2H), 7.56 (d, J = 8.6 Hz, 2H), 8.06 (s, 1H), 13.51 (s, 1H). | 2.07 | 447.1 | B |
| I-1-80 | 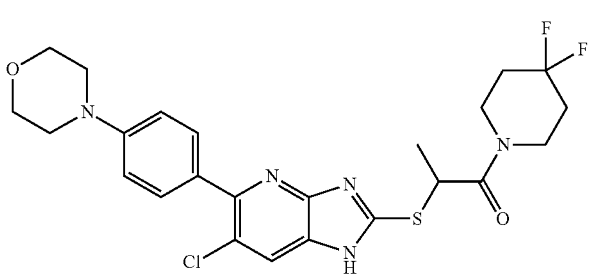 [SMILES: CC(Sc1nc2nc(-c3ccc(N4CCOCC4)cc3)c(Cl)cc2[nH]1)C(=O)N1CCC(F)(F)CC1] | 1H-NMR (DMSO-d6) δ: 0.85-1.30 (m, 1H), 1.58 (s, 3H), 1.99 (br s, 3H), 2.94-2.99 (m, 1H), 3.20 (s, 4H), 3.44 (br s, 2H), 3.63 (br s, 1H), 3.76 (s, 4H), 5.21 (br s, 1H), 7.02 (d, J = 8.6 Hz, 2H), 7.58 (d, J = 7.6 Hz, 2H), 8.00 (s, 1H), 13.24 (s, 1H). | 2.05 | 522.4 | B |

TABLE 15-continued

| No. | Structure | NMR (δ) | retention time | Mass (M + H) | method |
|---|---|---|---|---|---|
| I-1-81 | 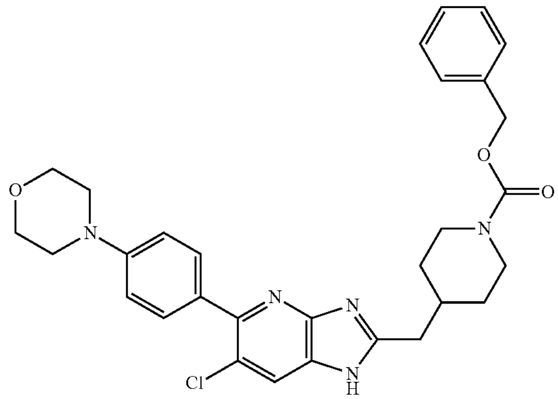 [SMILES: O=C(OCc1ccccc1)N1CCC(Cc2nc3nc(-c4ccc(N5CCOCC5)cc4)c(Cl)cc3[nH]2)CC1] | 1H-NMR (CDCl3) δ: 0.88-1.01 (m, 2H), 1.43-1.54 (m, 2H), 1.85-2.01 (m, 3H), 2.70 (br s, 2H), 3.24 (t, J = 4.56 Hz, 4H), 3.85 (t, J = 4.82 Hz, 4H), 4.10 (br s, 2H), 5.13 (s, 2H), 6.97 (d, J = 8.62 Hz, 2H), 7.31-7.36 (m, 5H), 7.67 (d, J = 8.62 Hz, 2H), 8.08 (s, 1H), 12.81 (s, 1H). | | | |

TABLE 16

| No. | Structure | NMR (δ) | retention time | Mass (M + H) | method |
|---|---|---|---|---|---|
| I-1-82 | 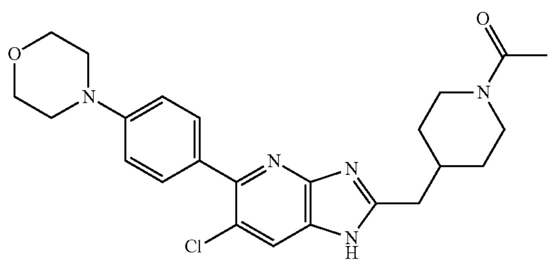 [SMILES: CC(=O)N1CCC(Cc2nc3nc(-c4ccc(N5CCOCC5)cc4)c(Cl)cc3[nH]2)CC1] | 1H-NMR (DMSO-d6) δ: 1.01-1.22 (m, 2H), 1.62-1.72 (m, 2H), 1.97 (s, 3H), 2.12 (m, 1H), 2.54 (m, 1H), 2.76-2.82 (m, 2H), 3.00 (t, J = 11.91 Hz, 1H), 3.20 (t, J = 4.82 Hz, 4H), 3.73-3.83 (m, 5H), 4.35 (d, J = 13.18 Hz, 1H), 7.02 (d, J = 9.12 Hz, 2H), 7.53-7.60 (m, 2H), 8.10 (s, 1H), 12.99 (s, 1H). | | | |
| I-1-83 | 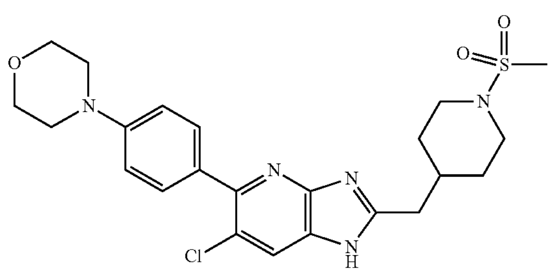 [SMILES: CS(=O)(=O)N1CCC(Cc2nc3nc(-c4ccc(N5CCOCC5)cc4)c(Cl)cc3[nH]2)CC1] | 1H-NMR (DMSO-d6) δ: 1.26-1.38 (m, 2H), 1.77 (d, J = 11.66 Hz, 2H), 2.00 (m, 1 H), 2.65-2.85 (m, 7H), 3.20 (t, J = 4.82 Hz, 4H), 3.55 (d, J = 11.66 Hz, 2H), 3.77 (t, J = 4.82 Hz, 4H), 7.02 (d, J = 8.62 Hz, 2H), 7.57 (d, J = 8.62 Hz, 2H), 8.08 (s, 1H), 12.99 (s, 1H). | | | |
| I-1-84 | 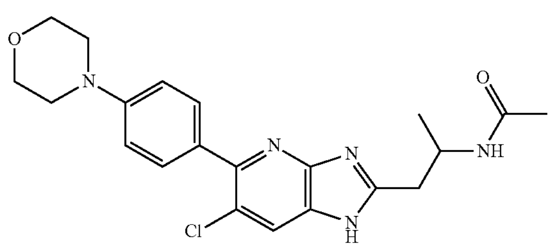 [SMILES: CC(=O)NC(C)Cc1nc2nc(-c3ccc(N4CCOCC4)cc3)c(Cl)cc2[nH]1] | 1H-NMR (DMSO-d6) δ: 1.09 (d, J = 6.08 Hz, 3H), 1.77 (s, 3H), 2.84-3.06 (m, 2H), 3.20 (t, J = 4.82 Hz, 4H), 3.77 (t, J = 4.82 Hz, 4H), 4.31 (m, 1H), 7.03 (d, J = 8.62 Hz, 2H), 7.58 (d, J = 8.62 Hz, 2H), 7.87 (d, J = 8.11 Hz, 1H), 8.11 (s, 1H), 12.98 (s, 1H). | | | |

TABLE 16-continued

| No. | Structure | NMR (δ) | retention time | Mass (M + H) | method |
|---|---|---|---|---|---|
| I-1-85 | 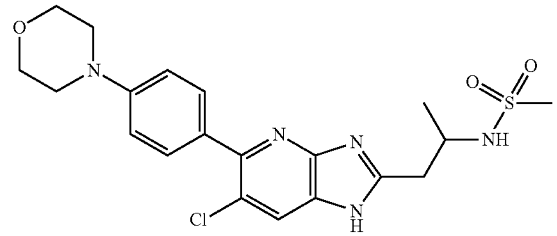 [SMILES: CC(Cc1nc2nc(-c3ccc(N4CCOCC4)cc3)c(Cl)cc2[nH]1)NS(C)(=O)=O] | 1H-NMR (DMSO-d6) δ: 1.19 (d, J = 6.59 Hz, 3H), 2.86 (s, 3H), 2.88-3.15 (m, 2H), 3.20 (t, J = 4.82 Hz, 4H), 3.77 (t, J = 4.82 Hz, 4H), 3.93 (m, 1H), 7.03 (d, J = 8.62 Hz, 2H), 7.24 (d, J = 8.11 Hz, 1H), 7.58 (d, J = 8.62 Hz, 2H), 8.12 (s, 1H), 13.04 (s, 1H). | | | |
| I-1-86 | 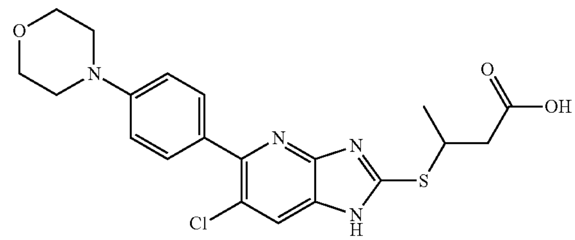 [SMILES: CC(CC(=O)O)Sc1nc2nc(-c3ccc(N4CCOCC4)cc3)c(Cl)cc2[nH]1] | 1H-NMR (DMSO-d6) δ: 1.51 (d, J = 7.1 Hz, 3H), 1.74-1.78 (m, 2H), 3.20 (t, J = 4.6 Hz, 4H), 3.60 (t, J = 6.3 Hz, 1H), 3.76 (t, J = 4.6 Hz, 4H), 5.54 (s, 1H), 7.02 (d, J = 8.6 Hz, 2H), 7.55 (d, J = 8.6 Hz, 2H), 8.22 (s, 1H), 12.35 (s, 1H), 13.45 (s, 1H). | 1.70 | 433.2 | B |

TABLE 17

| No. | Structure | NMR (δ) | retention time | Mass (M + H) | method |
|---|---|---|---|---|---|
| I-1-87 | 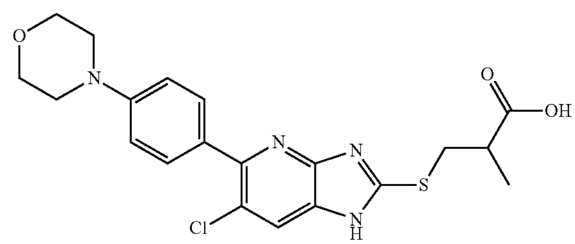 [SMILES: CC(CSc1nc2nc(-c3ccc(N4CCOCC4)cc3)c(Cl)cc2[nH]1)C(=O)O] | 1H-NMR (DMSO-d6) δ: 1.12 (d, J = 7.1 Hz, 3H), 3.16-3.22 (m, 5H), 3.76 (t, J = 4.8 Hz, 4H), 4.24-4.46 (m, 2H), 7.02 (d, J = 8.6 Hz, 2H), 7.55 (d, J = 8.6 Hz, 2H), 8.03 (s, 1H), 12.48 (s, 1H), 13.51 (s, 1H). | 1.72 | 433.1 | B |
| I-1-88 | 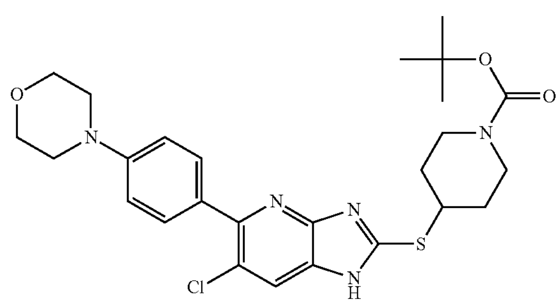 [SMILES: CC(C)(C)OC(=O)N1CCC(Sc2nc3nc(-c4ccc(N5CCOCC5)cc4)c(Cl)cc3[nH]2)CC1] | 1H-NMR (DMSO-d6) δ: 1.41 (s, 9H), 1.61 (q, J = 10.0 Hz, 2H), 2.11 (d, J = 10.1 Hz, 2H), 3.06 (s, 2H), 3.20 (t, J = 4.6 Hz, 4H), 3.76 (t, J = 4.6 Hz, 4H), 3.84 (d, J = 14.2 Hz, 2H), 4.07 (t, J = 10.4 Hz, 1H), 7.02 (d, J = 8.6 Hz, 2H), 7.57 (d, J = 8.6 Hz, 2H), 8.04 (s, 1H), 13.28 (s, 1H). | 2.35 | 530.3 | B |
| I-1-89 | 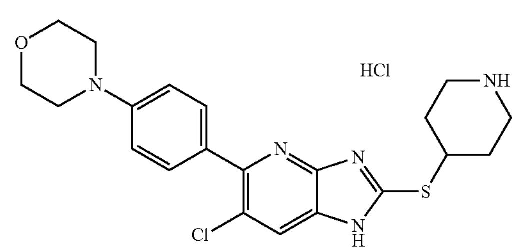 [SMILES: Clc1cc2[nH]c(SC3CCNCC3)nc2nc1-c1ccc(N2CCOCC2)cc1 ; Cl] | 1H-NMR (DMSO-d6) δ: 1.88-1.97 (m, 2H), 2.32 (d, J = 10.1 Hz, 2H), 3.11 (t, J = 9.6 Hz, 2H), 3.22 (t, J = 4.8 Hz, 4H), 3.31 (d, J = 13.2 Hz, 2H), 3.78 (t, J = 4.8 Hz, 4H), 4.14 (s, 1H), 7.07 (d, J = 9.1 Hz, 2H), 7.59 (d, J = 8.6 Hz, 2H), 8.05 (s, 1H), 8.94 (s, 2H). | 1.13 | 428.1 | B |

TABLE 17-continued

| No. | Structure | NMR (δ) | retention time | Mass (M + H) | method |
|---|---|---|---|---|---|
| I-1-90 | 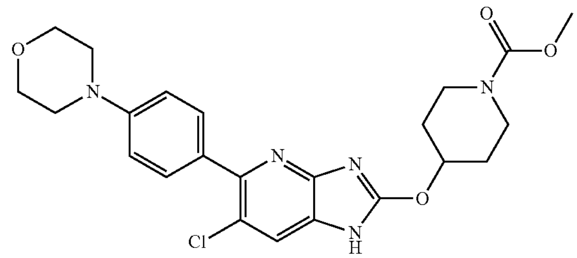 | (DMSO-d6) δ: 1.70-1.73 (m, 2H), 2.08-2.12 (m, 2H), 3.18 (dd, J = 5.2, 4.4 Hz, 4H), 3.26-3.28 (m, 2H), 3.61 (s, 3H), 3.73-3.77 (m, 6H), 5.21-5.25 (m, 1H), 7.01 (d, J = 8.6 Hz, 2H), 7.55 (d, J = 8.6 Hz, 2H), 7.84 (s, 1H). | | | |

TABLE 18

| No. | Structure | NMR (δ) | retention time | Mass (M + H) | method |
|---|---|---|---|---|---|
| I-2-5 | 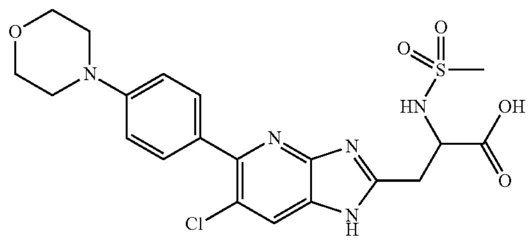 [SMILES: CS(=O)(=O)NC(Cc1nc2nc(-c3ccc(N4CCOCC4)cc3)c(Cl)cc2[nH]1)C(=O)O] | (DMSO-d6) δ: 2.87-3.15 (br m, 5H), 3.20 (t, J = 4.56 Hz, 4H), 3.77 (t, J = 4.56 Hz, 4H), 4.95-5.04 (m, 1H), 7.03 (d, J = 8.62 Hz, 2H), 7.58 (d, J = 8.62 Hz, 2H), 7.94 (br s, 1H), 8.15 (br s, 1H). | | | |
| I-2-6 | 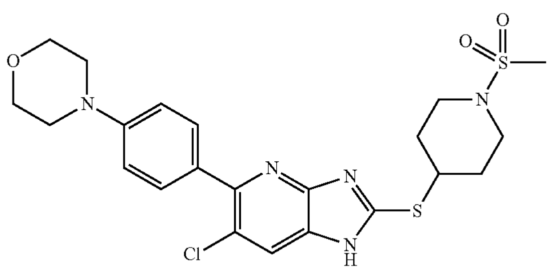 | 1H-NMR (DMSO-d6) δ: 1.80 (q, J = 9.8 Hz, 2H), 2.24 (d, J = 10.1 Hz, 2H), 2.91 (s, 3H), 3.02 (t, J = 10.1 Hz, 4H), 3.50-3.53 (m, 2H), 3.76 (t, J = 4.8 Hz, 4H), 4.02-4.05 (m, 1H), 7.02 (d, J = 8.6 Hz, 2H), 7.58 (d, J = 8.6 Hz, 2H), 8.05 (s, 1H), 13.32 (s, 1H). | 1.81 | 508.2 | B |
| I-2-7 | 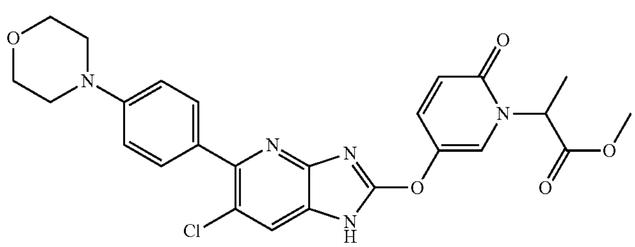 [SMILES: COC(=O)C(C)n1cc(Oc2nc3nc(-c4ccc(N5CCOCC5)cc4)c(Cl)cc3[nH]2)ccc1=O] | (CDCl3) δ: 1.69 (d, J = 7.10 Hz, 3H), 3.18 (t, J = 4.82 Hz, 4H), 3.78 (s, 3H), 3.83 (t, J = 4.82 Hz, 4H), 5.57 (q, J = 7.35 Hz, 1H), 6.64 (d, J = 10.14 Hz, 1H), 6.97 (d, J = 8.62 Hz, 2H), 7.30 (d, J = 10.00 Hz, 1H), 7.65-7.67 (m, 3H), 7.89 (s, 1H). | 1.65 | 510.15 | B |
| I-2-8 | 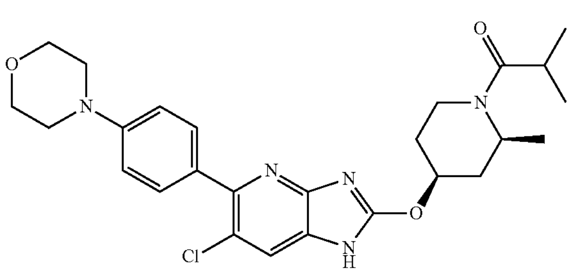 [SMILES: CC(C)C(=O)N1CC[C@H](Oc2nc3nc(-c4ccc(N5CCOCC5)cc4)c(Cl)cc3[nH]2)C[C@@H]1C] | 1H-NMR (DMSO-d6) δ: 1.00-1.04 (m, 8H), 1.18-1.32 (m, 3H), 1.77-2.09 (m, 5H), 2.84-2.90 (m, 1H), 3.19 (dd, J = 5.2, 4.4 Hz, 4H), 3.76 dd, J = 5.2, 4.4 Hz, 4H), 5.39 (brs, 1H), 7.01 (d, J = 8.6 Hz, 2H), 7.55 (d, J = 8.6 Hz, 2H), 7.85 (s, 1H). | | | |

TABLE 18-continued

| No. | Structure | NMR (δ) | retention time | Mass (M + H) | method |
|---|---|---|---|---|---|
| I-2-9 | 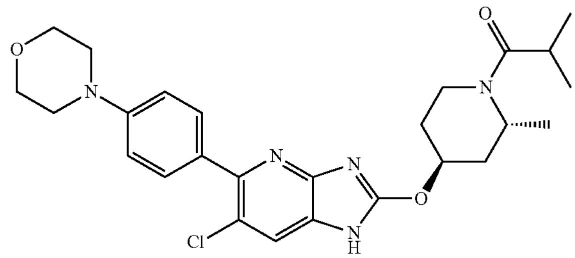 [SMILES: CC(C)C(=O)N1CC[C@H](Oc2nc3nc(-c4ccc(N5CCOCC5)cc4)c(Cl)cc3[nH]2)C[C@H]1C] | 1H-NMR (DMSO-d6) δ: 0.91-1.04 (m, 9H), 1.16-1.33 (m, 5H) 2.18-2.33 (m, 2H), 2.84-2.92 (m, 1H), 3.19 (brs, 4H), 3.76 dd, J = 5.2, 4.4 Hz, 4H), 5.37-5.45 (m, 1H), 7.01 (d, J = 8.6 Hz, 2H), 7.54 (d, J = 8.6 Hz, 2H), 7.91 (s, 1H). | | | |

TABLE 19

| No. | Structure | NMR (δ) | retention time | Mass (M + H) | method |
|---|---|---|---|---|---|
| I-2-10 | 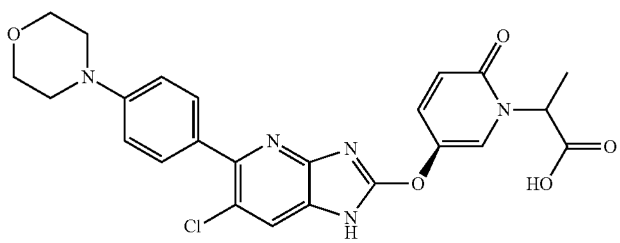 | (DMSO-d6) δ: 1.46 (d, J = 7.60 Hz, 3H), 3.19 (t, J = 4.82 Hz, 4H), 3.76 (t, J = 4.82 Hz, 4H), 5.17 (q, J = 7.10 Hz, 1H), 6.41 (d, J = 9.63 Hz, 1H), 7.01 (d, J = 9.12 Hz, 2H), 7.56-7.59 (m, 3H), 7.86 (s, 1H), 7.90 (d, J = 3.55 Hz, 1H). | 1.48 | 496.15 | B |
| I-2-11 | 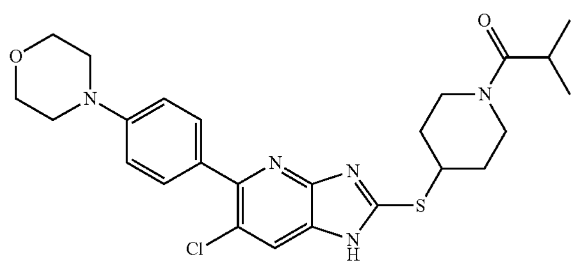 | 1H-NMR (DMSO-d6) δ: 1.00 (d, J = 6.1 Hz, 6H), 1.57-1.67 (br m, 2H), 2.15-2.17 (br m, 2H), 2.88-2.94 (m, 2H), 3.20 (t, J = 4.8 Hz, 4H), 3.76 (t, J = 4.6 Hz, 4H), 3.88-3.91 (br m, 1H), 4.15-4.17 (m, 2H), 7.02 (d, J = 9.1 Hz, 2H), 7.58 (d, J = 8.6 Hz, 2H), 8.09 (s, 1H), 13.36 (s, 1H). | 1.93 | 500.2 | B |
| I-2-12 | 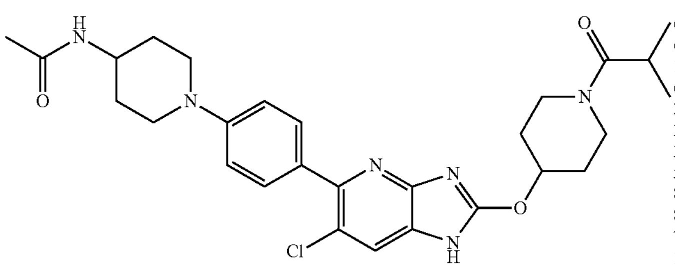 [SMILES: CC(=O)NC1CCN(c2ccc(-c3nc4nc(OC5CCN(C(=O)C(C)C)CC5)[nH]c4cc3Cl)cc2)CC1] | (DMSO-d6) δ: 1.01 (d, J = 6.59 Hz, 6H), 1.47 (q, J = 10.48 Hz, 2H), 1.60-1.84 (m, 4H), 1.80 (s, 3H), 2.04-2.20 (m, 2H), 2.83-2.95 (m, 3H), 3.20-3.48 (m, 2H), 3.70-3.99 (m, 5H), 5.23-5.31 (m, 1H), 7.00 (d, J = 8.62 Hz, 2H), 7.53 (d, J = 8.62 Hz, 2H), 7.83 (d, J = 7.60 Hz, 1H), 7.85 (br s, 1H), 12.69 (s, 1H). | | | |
| I-2-13 | 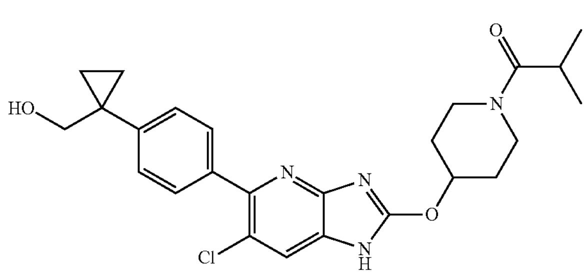 [SMILES: CC(C)C(=O)N1CCC(Oc2nc3nc(-c4ccc(C5(CO)CC5)cc4)c(Cl)cc3[nH]2)CC1] | (DMSO-d6) δ: 0.77-0.90 (m, 4H), 1.01 (d, J = 6.59 Hz, 6H), 1.60-1.80 (m, 2H), 2.02-2.20 (m, 2H), 2.93 (m, 1H), 3.24 (m, 1H), 3.42 (m, 1H), 3.59 (d, J = 5.58 Hz, 2H), 3.78-4.00 (m, 2H), 4.72 (t, J = 5.58 Hz, 1H), 5.28 (m, 1H), 7.37 (d, J = 8.11 Hz, 2H), 7.54 (d, J = 8.11 Hz, 2H), 7.91 (s, 1H), 12.79 (s, 1H). | | | |

TABLE 19-continued

| No. | Structure | NMR (δ) | retention time | Mass (M + H) | method |
|---|---|---|---|---|---|
| I-2-14 | 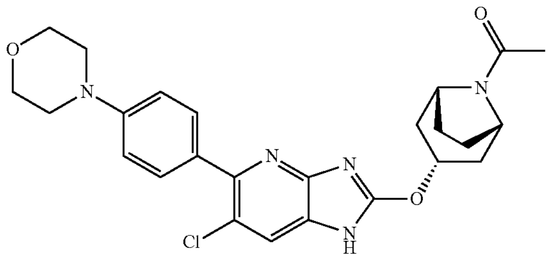 [SMILES: CC(=O)N1[C@@H]2CC[C@H]1C[C@H](Oc1nc3nc(-c4ccc(N5CCOCC5)cc4)c(Cl)cc3[nH]1)C2] | (DMSO-d6) δ: 1.59-1.91 (m, 5H), 1.98-2.10 (m, 1H), 2.02 (s, 3H), 2.24-2.42 (m, 2H), 3.19 (t, J = 4.82 Hz, 4H), 3.76 (t, J = 4.82 Hz, 4H), 4.34 (d, J = 6.59 Hz, 1H), 4.55 (d, J = 6.59 Hz, 1H), 5.46-5.55 (m, 1H), 7.01 (d, J = 8.62 Hz, 2H), 7.55 (d, J = 8.62 Hz, 2H), 7.90 (s, 1H), 12.70 (s, 1H). | | | |

TABLE 20

| No. | Structure | NMR (δ) | retention time | Mass (M + H) | method |
|---|---|---|---|---|---|
| I-2-15 | 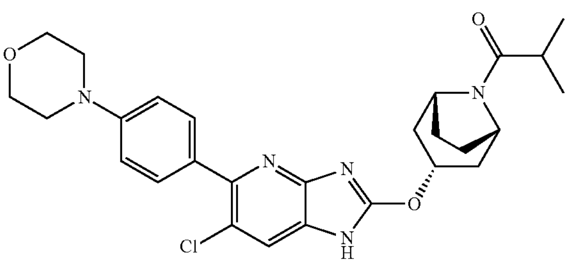 [SMILES: CC(C)C(=O)N1[C@@H]2CC[C@H]1C[C@H](Oc1nc3nc(-c4ccc(N5CCOCC5)cc4)c(Cl)cc3[nH]1)C2] | (DMSO-d6) δ: 1.03 (dd, J = 9.63, 7.10 Hz, 6H), 1.61 (t, J = 11.41 Hz, 2H), 1.71-2.10 (m, 4H), 2.26-2.47 (m, 2H), 2.76-2.82 (m, 1H), 3.18 (t, J = 4.82 Hz, 4H), 3.76 (t, J = 4.82 Hz, 4H), 4.45-4.62 (m, 2H), 5.47-5.56 (m, 1H), 7.01 (d, J = 8.62 Hz, 2H), 7.55 (d, J = 8.62 Hz, 2H), 7.88 (s, 1H), 12.67 (s, 1H). | | | |
| I-2-16 | 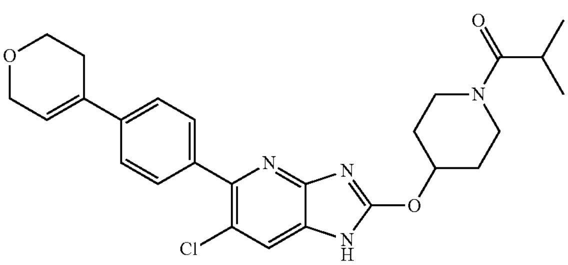 [SMILES: CC(C)C(=O)N1CCC(Oc2nc3nc(-c4ccc(C5=CCOCC5)cc4)c(Cl)cc3[nH]2)CC1] | (CDCl3) δ: 1.15 (d, J = 7.10 Hz, 6H), 1.79 (s, 2H). 2.11 (br s, 2H), 2.57 (br s, 2H), 2.79-2.86 (m, 1H), 3.36-3.47 (m, 2H), 3.69-4.03 (m, 4H), 4.33-4.39 (m, 2H), 5.33 (m, 1H), 6.23 (s, 1H), 7.49 (d, J = 8.11 Hz, 2H), 7.71 (d, J = 8.11 Hz, 2H), 7.85 (s, 1H), 9.79 (s, 1H). | | | |
| I-2-17 | 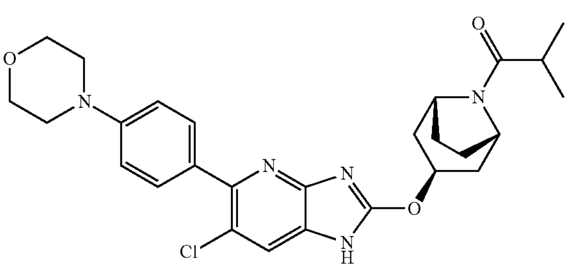 [SMILES: CC(C)C(=O)N1[C@@H]2CC[C@H]1C[C@@H](Oc1nc3nc(-c4ccc(N5CCOCC5)cc4)c(Cl)cc3[nH]1)C2] | (DMSO-d6) δ: 1.02 (dd, J = 12.67, 6.59 Hz, 6H), 1.83 (m, 1H), 1.98-2.16 (m, 7H), 2.72-2.79 (m, 1H), 3.19 (t, J = 4.56 Hz, 4H), 3.76 (t, J = 4.56 Hz, 4H), 4.36 (br s, 1H), 4.51 (br s, 1H), 5.35 (s, 1H), 7.01 (d, J = 8.62 Hz, 2H), 7.55 (d, J = 8.62 Hz, 2H), 7.87 (s, 1H), 12.72 (s, 1H). | | | |
| I-2-18 | 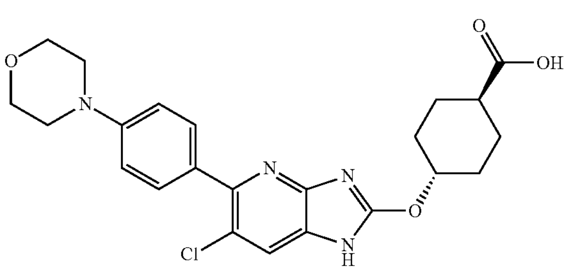 [SMILES: O=C(O)[C@H]1CC[C@H](Oc2nc3nc(-c4ccc(N5CCOCC5)cc4)c(Cl)cc3[nH]2)CC1] | (DMSO-d6) δ: 1.45-1.60 (m, 4H), 1.96-2.03 (m, 2H), 2.19-2.36 (m, 3H), 3.18 (t, J = 4.82 Hz, 4H), 3.76 (t, J = 4.82 Hz, 4H), 4.97 (m, 1H), 7.01 (d, J = 8.62 Hz, 2H). 7.55 (d, J = 8.62 Hz, 2H), 7.90 (s, 1H), 12.17 (s, 1H), 12.66 (s, 1H). | | | |

TABLE 20-continued

| No. | Structure | NMR (δ) | retention time | Mass (M + H) | method |
|---|---|---|---|---|---|
| I-2-19 | 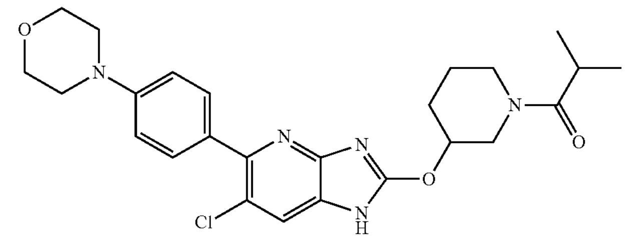 [SMILES: CC(C)C(=O)N1CCCC(Oc2nc3nc(-c4ccc(N5CCOCC5)cc4)c(Cl)cc3[nH]2)C1] | (DMSO-d6) δ: 0.89-1.02 (m, 6H), 1.45-2.14 (m, 4H), 2.67-2.94 (m, 1H), 3.19 (t, J = 4.56 Hz, 4H), 3.50-3.54 (m, 1H), 3.75-3.89 (m, 3H), 3.76 (t, J = 4.56 Hz, 4H), 5.10 (d, J = 26.87 Hz, 1H), 7.01 (d, J = 8.62 Hz, 2H), 7.55 (d, J = 8.62 Hz, 2H), 7.89 (s, 1H), 12.72 (br s, 1H). | | | |

TABLE 21

| No. | Structure | NMR (δ) | retention time | Mass (M + H) | method |
|---|---|---|---|---|---|
| I-2-20 | 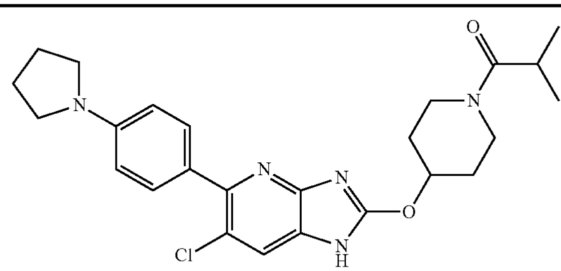 | (DMSO-d6) δ: 1.01 (d, J = 6.59 Hz, 6H), 1.65-1.75 (m, 2H), 1.97-1.98 (m, 4H), 2.13-2.15 (br m, 2H), 2.88-2.94 (m, 1H), 3.28 (t, J = 6.59 Hz, 6H), 3.79-3.81 (m, 1H), 3.94-4.00 (m, 1H), 5.26-5.27 (m, 1H), 6.59 (d, J = 9.12 Hz, 2H), 7.51 (d, J = 8.62 Hz, 2H), 7.82 (s, 1H). | 2.24 | 468.25 | B |
| I-2-21 | 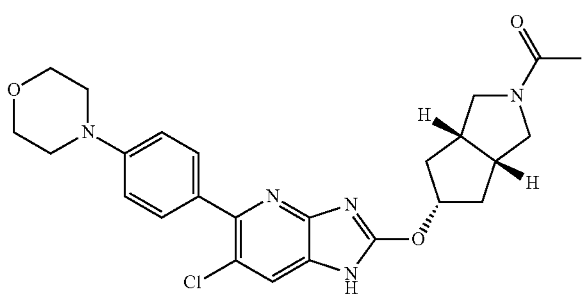 [SMILES: CC(=O)N1C[C@H]2C[C@@H](Oc3nc4nc(-c5ccc(N6CCOCC6)cc5)c(Cl)cc4[nH]3)C[C@H]2C1] | (DMSO-d6) δ: 1.71-1.84 (m, 2H), 1.95 (s, 3H), 2.37-2.47 (m, 2H), 2.65-2.83 (m, 2H), 3.18 (t, J = 4.56 Hz, 4H), 3.27-3.42 (m, 2H), 3.55 (dd, J = 11.91, 8.62 Hz, 1H), 3.68 (dd, J = 11.91, 8.62 Hz, 1H), 3.76 (t, J = 4.56 Hz, 4H), 5.45-5.46 (m, 1H), 7.01 (d, J = 8.62 Hz, 2H), 7.55 (d, J = 8.62 Hz, 2H), 7.84 (s, 1H), 12.61 (br s, 1H). | | | |
| I-2-22 | 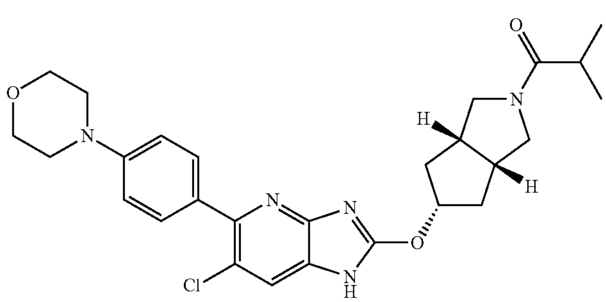 [SMILES: CC(C)C(=O)N1C[C@H]2C[C@@H](Oc3nc4nc(-c5ccc(N6CCOCC6)cc5)c(Cl)cc4[nH]3)C[C@H]2C1] | (DMSO-d6) δ: 0.97-1.03 (m, 6H), 1.74 (br s, 2H), 2.36-2.48 (m, 2H), 2.62-2.83 (m, 3H), 3.18 (t, J = 4.82 Hz, 4H), 3.45 (dd, J = 10.65, 4.56 Hz, 1H), 3.58 (dd, J = 12.17, 8.62 Hz, 1H), 3.70-3.79 (m, 1H), 3.76 (t, J = 4.82 Hz, 4H), 5.45 (m, 1H), 7.01 (d, J = 8.62 Hz, 2H), 7.54 (d, J = 8.62 Hz, 2H), 7.81 (d, J = 62.86 Hz, 1H), 12.67 (s, 1H). | | | |
| I-2-23 | 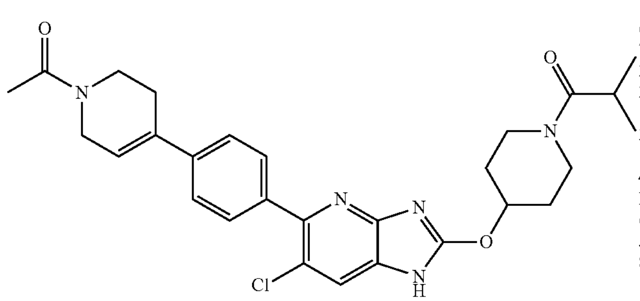 [SMILES: CC(=O)N1CC=C(c2ccc(-c3nc4nc(OC5CCN(C(=O)C(C)C)CC5)[nH]c4cc3Cl)cc2)CC1] | (DMSO-d6) δ: 1.02 (d, J = 7.86 Hz, 6H), 1.66-1.74 (m, 2H), 2.05-2.09 (m, 5H), 2.61 (s, 1H), 2.89-2.92 (m, 1H), 3.31-3.33 (br m, 3H), 3.64-3.70 (m, 2H), 3.80 (s, 1H), 3.95-4.00 (m, 1H), 4.15 (dd, J = 21.29, 10.65 Hz, 2H), 5.27-5.29 (m, 1H), 6.27-6.29 (m, 1H), 7.54 (t, J = 7.10 Hz, 2H), 7.64 (d, J = 8.62 Hz, 2H), 7.90 (s, 1H), 12.7 (br, 1H). | 1.79 | 522.25 | B |

TABLE 21-continued

| No. | Structure | NMR (δ) | retention time | Mass (M + H) | method |
|---|---|---|---|---|---|
| I-2-24 | 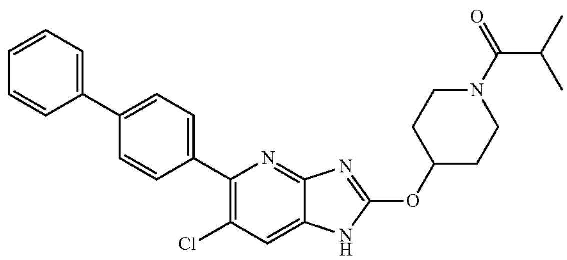 [SMILES: CC(C)C(=O)N1CCC(Oc2nc3nc(-c4ccc(-c5ccccc5)cc4)c(Cl)cc3[nH]2)CC1] | (DMSO-d6) δ: 1.02 (6H, d, J = 6.59 Hz), 1.66-1.77 (2H, m), 2.10-2.16 (m, 2H), 2.88-2.93 (1H, m), 3.20-3.35 (2H, m), 3.94-4.04 (2H, m), 5.27-5.34 (1H, m), 7.38-7.42 (m, 1H), 7.49-7.53 (m, 2H), 7.74-7.79 (m, 6H), 7.94 (s, 1H) | | | |

TABLE 22

| No. | Structure | NMR (δ) | retention time | Mass (M + H) | method |
|---|---|---|---|---|---|
| I-2-25 | 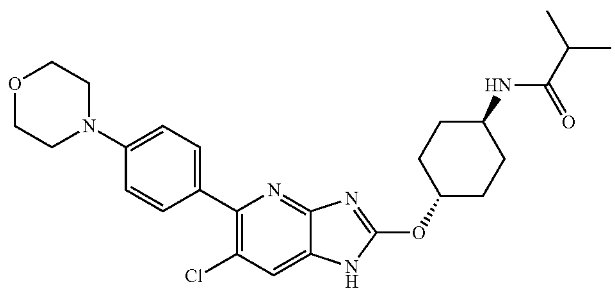 [SMILES: CC(C)C(=O)N[C@H]1CC[C@H](Oc2nc3nc(-c4ccc(N5CCOCC5)cc4)c(Cl)cc3[nH]2)CC1] | 1H-NMR (DMSO-d6) δ: 0.99 (d, J = 6.7 Hz, 6H), 1.30-1.41 (m, 2H), 1.52-1.65 (m, 2H), 1.84-1.88 (m, 2H), 2.20-2.23 (m, 2H), 2.29-2.38 (m, 1H), 3.19 (dd, J = 5.2, 4.4 Hz, 4H), 3.60-3.62 (m, 1H), 3.77 (dd, J = 5.2, 4.4 Hz, 4H), 4.93-5.00 (m, 1H), 7.01 (d, J = 8.7 Hz, 2H), 7.55 (d, J = 8.7 Hz, 2H), 7.64 (d, J = 7.4 Hz, 1H), 7.83 (s, 1H). | | | |
| I-2-26 | 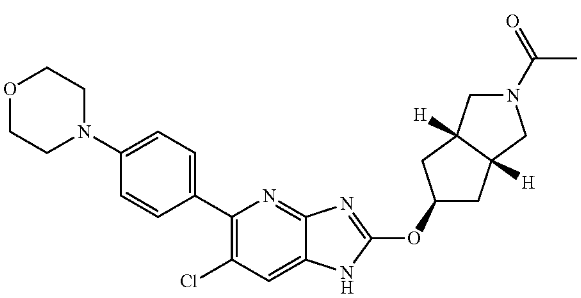 [SMILES: CC(=O)N1C[C@H]2C[C@H](Oc3nc4nc(-c5ccc(N6CCOCC6)cc5)c(Cl)cc4[nH]3)C[C@H]2C1] | (DMSO-d6) δ: 1.88-2.02 (m, 2H), 1.94 (s, 3H), 2.10-2.22 (m, 2H), 2.77-2.95 (m, 2H), 3.15-3.30 (m, 2H), 3.18 (t, J = 4.82 Hz, 4H), 3.47 (m, 1H), 3.64 (m, 1H), 3.76 (t, J = 4.82 Hz, 4H), 5.56 (br s, 1H), 7.01 (d, J = 8.11 Hz, 2H), 7.55 (d, J = 8.11 Hz, 2H), 7.87 (s, 1H), 12.65 (s, 1H). | | | |
| I-2-27 | 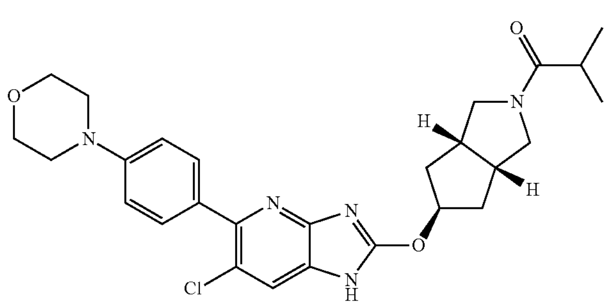 [SMILES: CC(C)C(=O)N1C[C@H]2C[C@H](Oc3nc4nc(-c5ccc(N6CCOCC6)cc5)c(Cl)cc4[nH]3)C[C@H]2C1] | (DMSO-d6) δ: 1.00 (dd, J = 10.14, 7.10 Hz, 6H), 1.87-2.00 (m, 2H), 2.11-2.22 (m, 2H), 2.62-2.71 (m, 1H), 2.75-2.95 (m, 2H), 3.18 (t, J = 4.82 Hz, 4H), 3.20-3.54 (m, 3H), 3.69 (dd, J = 10.39, 7.86 Hz, 1H), 3.76 (t, J = 4.82 Hz, 4H), 5.53-5.59 (m, 1H), 7.01 (d, J = 8.62 Hz, 2H), 7.55 (d, J = 8.62 Hz, 2H), 7.85 (s, 1H), 12.65 (s, 1H). | | | |

TABLE 22-continued

| No. | Structure | NMR (δ) | retention time | Mass (M + H) | method |
|---|---|---|---|---|---|
| I-2-28 | 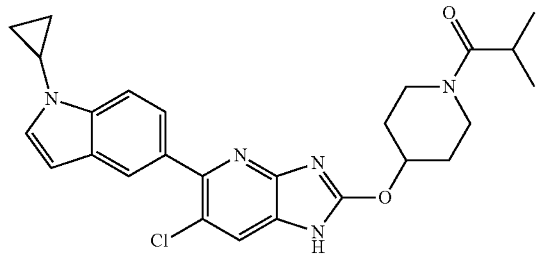 [SMILES: CC(C)C(=O)N1CCC(Oc2nc3nc(-c4ccc5c(ccn5C5CC5)c4)c(Cl)cc3[nH]2)CC1] | (DMSO-d6) δ: 0.98-1.11 (m, 10H), 1.66-1.76 (m, 2H), 2.09-2.15 (m, 2H), 2.88-2.95 (m, 1H), 3.31-3.33 (br m, 2H), 3.47-3.48 (m, 1H), 3.79-3.82 (m, 1H), 3.94-3.97 (m, 1H), 5.28-5.29 (m, 1H), 6.46 (d, J = 3.04 Hz, 1H), 7.37 (d, J = 3.04 Hz, 1H), 7.44 (dd, J = 8.62, 1.52 Hz, 1H), 7.61 (d, J = 8.62 Hz, 1H), 7.79 (s, 1H), 7.88 (s, 1H), 12.6 (brs, 1H). | 2.18 | 478.25 | B |

TABLE 23

| No. | Structure | NMR (δ) | retention time | Mass (M + H) | method |
|---|---|---|---|---|---|
| I-2-29 | 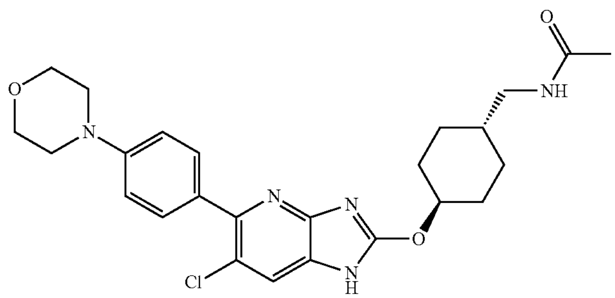 [SMILES: CC(=O)NC[C@H]1CC[C@H](Oc2nc3nc(-c4ccc(N5CCOCC5)cc4)c(Cl)cc3[nH]2)CC1] | (DMSO-d6) δ: 1.05-1.11 (m, 2H), 1.25-1.28 (m, 1H), 1.43-1.46 (m, 2H), 1.78-1.81 (m, 5H), 2.21-2.23 (m, 2H), 2.93 (t, J = 6.3 Hz, 2H), 3.18-3.19 (m, 4H), 3.75-3.77 (m, 4H), 4.92-4.96 (m, 1H), 7.01 (d, J = 9.1 Hz, 2H), 7.55 (d, J = 9.1 Hz, 2H), 7.84-7.86 (m, 2H), 12.58 (s, 1H). | 1.65 | 484.25 | B |
| I-2-30 | 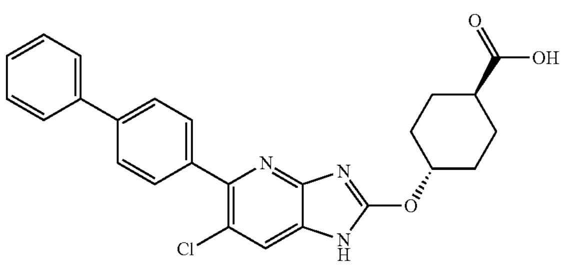 [SMILES: O=C(O)[C@H]1CC[C@H](Oc2nc3nc(-c4ccc(-c5ccccc5)cc4)c(Cl)cc3[nH]2)CC1] | (DMSO-d6) δ: 1.46-1.62 (m, 4H), 1.97-2.04 (m, 2H), 2.21-2.37 (m, 3H), 4.95-5.05 (m, 1H), 7.40 (t, J = 7.35 Hz, 1H), 7.50 (t, J = 7.60 Hz, 2H), 7.72-7.79 (m, 6H), 7.97 (s, 1H), 12.19 (s, 1H), 12.78 (s, 1H). | | | |
| I-2-31 | 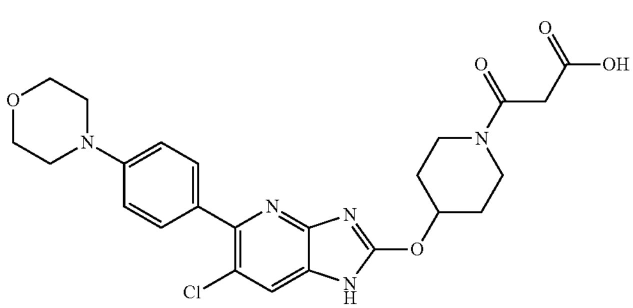 [SMILES: O=C(O)CC(=O)N1CCC(Oc2nc3nc(-c4ccc(N5CCOCC5)cc4)c(Cl)cc3[nH]2)CC1] | (DMSO-D6) δ: 1.63-1.73 (m, 1H), 1.75-1.87 (m, 1H), 2.06-2.17 (m, 2H), 3.17-3.20 (m, 4H), 3.19-3.30 (m, 2H), 3.66-3.73 (m, 2H), 3.75-3.77 (m, 4H), 3.88-3.97 (m, 2H), 5.24-5.33 (m, 1H), 7.01 (d, J = 8.62 Hz, 2H), 7.55 (d, J = 8.62 Hz, 2H), 7.86 (s, 1H) | | | |

TABLE 23-continued

| No. | Structure | NMR (δ) | retention time | Mass (M + H) | method |
|---|---|---|---|---|---|
| I-2-32 | 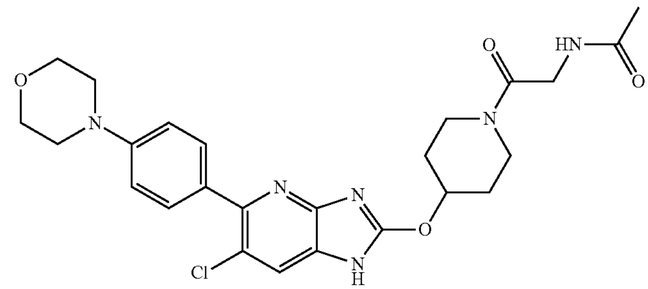 [SMILES: CC(=O)NCC(=O)N1CCC(Oc2nc3nc(-c4ccc(N5CCOCC5)cc4)c(Cl)cc3[nH]2)CC1] | (DMSO-D6) δ: 1.60-1.71 (m, 1H), 1.74-1.83 (m, 1H), 1.87 (s, 3H), 2.04-2.18 (m, 2H), 3.17-3.23 (m, 4H), 3.19-3.29 (m, 2H), 3.67-3.74 (m, 2H), 3.75-3.77 (m, 4H), 3.96-4.00 (m, 2H), 3.97 (t, J = 5.58 Hz, 2H), 5.23-5.32 (m, 1H), 7.01 (d, J = 8.62 Hz, 2H), 7.55 (d, J = 8.62 Hz, 2H), 7.85 (s, 1H), 7.97 (t, J = 5.58 Hz, 1H) | | | |
| I-2-33 | 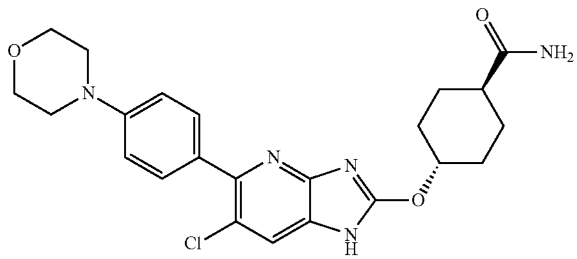 [SMILES: NC(=O)[C@H]1CC[C@H](Oc2nc3nc(-c4ccc(N5CCOCC5)cc4)c(Cl)cc3[nH]2)CC1] | (DMSO-D6) δ: 1.41-1.91 (m, 6H), 2.03-2.30 (m, 3H), 3.18 (t, J = 4.82 Hz, 4H), 3.76 (t, J = 4.82 Hz, 4H), 4.90-5.28 (br m, 1H), 6.74 (d, J = 17.74 Hz, 1H), 7.01 (d, J = 8.62 Hz, 2H), 7.25 (s, 1H), 7.55 (dd, J = 8.62, 3.04 Hz, 2H), 7.82 (d, J = 11.66 Hz, 1H), 12.56 (s, 1H). | | | |

TABLE 24

| No. | Structure | NMR (δ) | retention time | Mass (M + H) | method |
|---|---|---|---|---|---|
| I-2-34 | 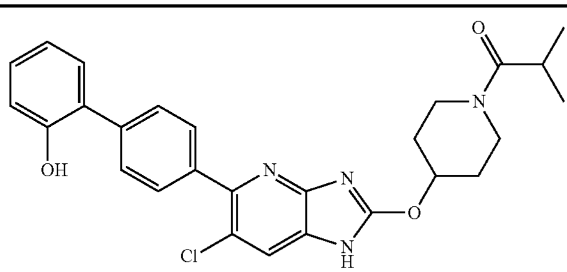 | (DMSO-d6) δ: 1.02 (d, J = 6.6 Hz, 6H), 1.66-1.76 (m, 2H), 2.07-2.09 (m, 2H), 2.91-2.93 (m, 1H), 3.29-3.38 (m, 2H), 3.88 (m, 2H), 5.29-5.31 (m, 1H), 6.89-6.98 (m, 2H), 7.18-7.20 (m, 1H), 7.32-7.34 (m, 1H), 7.60-7.68 (m, 5H), 9.60 (s, 1H), 12.84 (s, 1H). | 2.06 | 491.2 | B |
| I-2-35 | 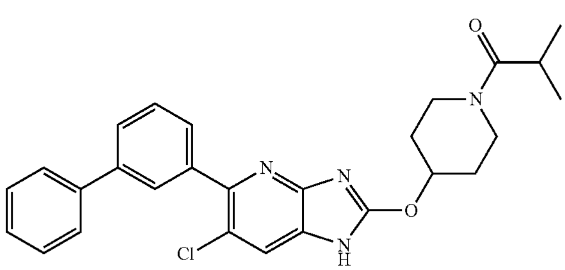 [SMILES: CC(C)C(=O)N1CCC(Oc2nc3nc(-c4cccc(-c5ccccc5)c4)c(Cl)cc3[nH]2)CC1] | (DMSO-d6) δ: 1.01 (d, J = 6.6 Hz, 6H), 1.66-1.76 (m, 2H), 2.07-2.09 (m, 2H), 2.91-2.92 (m, 1H), 3.25-3.27 (m, 2H), 3.81-3.96 (m, 2H), 5.29 (br s, 1H), 7.37-7.71 (m, 9H), 7.89 (s, 1H), 12.85 (s, 1H). | 2.35 | 475.25 | B |
| I-2-36 | 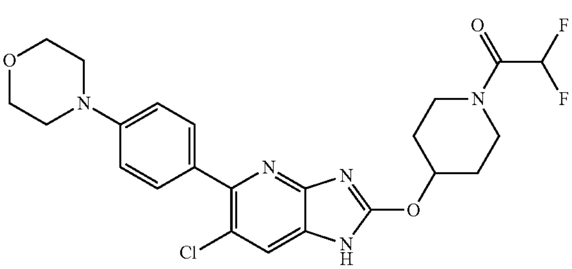 [SMILES: O=C(C(F)F)N1CCC(Oc2nc3nc(-c4ccc(N5CCOCC5)cc4)c(Cl)cc3[nH]2)CC1] | | 1.79 | 492.35 | B |

TABLE 24-continued

| No. | Structure | NMR (δ) | retention time | Mass (M + H) | method |
|---|---|---|---|---|---|
| I-2-37 | 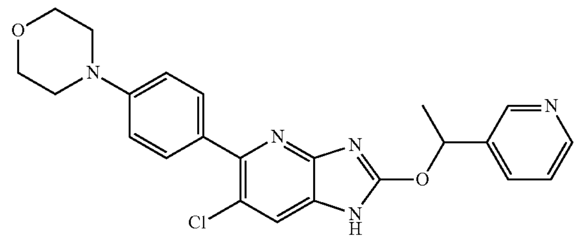 [SMILES: CC(Oc1nc2nc(-c3ccc(N4CCOCC4)cc3)c(Cl)cc2[nH]1)c1cccnc1] | (DMSO-D6) δ: 1.74 (d, J = 6.59 Hz, 3H), 3.18 (t, J = 4.82 Hz, 4H), 3.76 (t, J = 4.82 Hz, 4H), 6.26 (q, J = 6.59 Hz, 1H), 7.00 (d, J = 8.62 Hz, 2H), 7.44 (dd, J = 7.60, 5.07 Hz, 1H), 7.53 (d, J = 8.62 Hz, 2H), 7.85 (s, 1H), 7.92 (d, J = 7.60 Hz, 1H), 8.54 (dd, J = 5.07, 1.52 Hz, 1H), 8.74 (d, J = 1.52 Hz, 1H), 12.81 (s, 1H). | | | |
| I-2-38 | 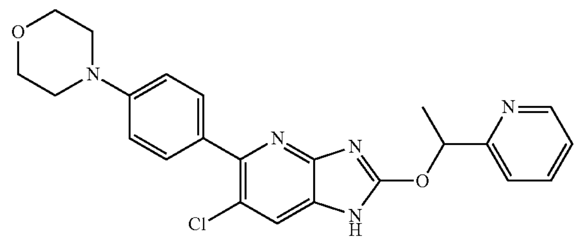 [SMILES: CC(Oc1nc2nc(-c3ccc(N4CCOCC4)cc3)c(Cl)cc2[nH]1)c1ccccn1] | (DMSO-D6) δ: 1.72 (d, J = 6.59 Hz, 3H), 3.18 (t, J = 4.82 Hz, 4H), 3.76 (t, J = 4.82 Hz, 4H), 6.20 (q, J = 6.59 Hz, 1H), 7.00 (d, J = 8.62 Hz, 2H), 7.35 (dd, J = 7.10, 5.07 Hz, 1H), 7.49-7.56 (m, 3H), 7.80-7.90 (m, 2H), 8.58 (d, J = 4.06 Hz, 1H), 12.86 (s, 1H). | | | |

TABLE 25

| No. | Structure | NMR (δ) | retention time | Mass (M + H) | method |
|---|---|---|---|---|---|
| I-2-39 | 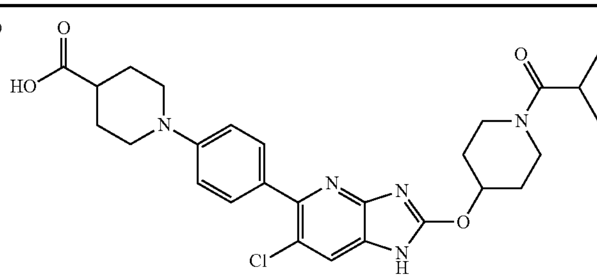 | (DMSO-D6) δ: 1.01 (d, J = 6.6 Hz, 6H), 1.60-1.79 (m, 4H), 1.89-1.94 (m, 2H), 2.05-2.17 (m, 2H), 2.40-2.51 (m, 1H), 2.54-2.61 (m, 1H), 2.80-2.95 (m, 3H), 3.71-3.85 (m, 3H), 3.94-4.00 (m, 1H), 5.24-5.28 (m, 1H), 7.00 (d, J = 8.6 Hz, 2H), 7.53 (d, J = 8.6 Hz, 2H), 7.83 (s, 1H). | | | |
| I-2-40 | 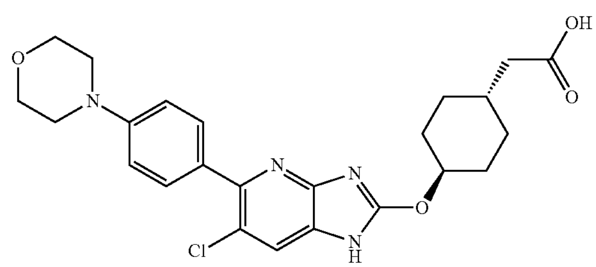 [SMILES: O=C(O)C[C@H]1CC[C@H](Oc2nc3nc(-c4ccc(N5CCOCC5)cc4)c(Cl)cc3[nH]2)CC1] | (DMSO-D6) δ: 1.10-1.23 (m, 2H), 1.43-1.55 (m, 2H), 1.68-1.86 (m, 3H), 2.13-2.25 (m, 4H), 3.18 (t, J = 4.82 Hz, 4H), 3.76 (t, J = 4.82 Hz, 4H), 4.91-4.99 (m, 1H), 7.01 (d, J = 9.12 Hz, 2H), 7.55 (d, J = 9.12 Hz, 2H), 7.83 (s, 1H), 11.80-12.75 (br m, 2H). | | | |
| I-2-41 | 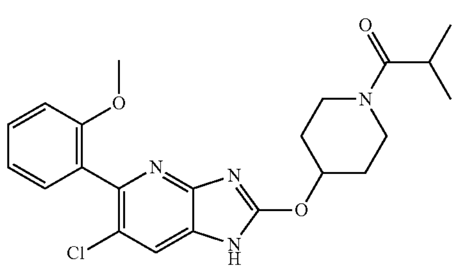 [SMILES: COc1ccccc1-c1nc2nc(OC3CCN(C(=O)C(C)C)CC3)[nH]c2cc1Cl] | (DMSO-d6) δ: 1.01 (d, J = 6.6 Hz, 6H), 1.66-1.76 (m, 2H), 2.09-2.13 (m, 2H), 2.88-2.95 (m, 1H), 3.24-3.27 (m, 1H), 3.42-3.44 (m, 1H), 3.71 (s, 3H), 3.78-3.80 (m, 1H), 3.92-3.94 (m, 1H), 5.27-5.29 (m, 1H), 7.01-7.03 (m, 1H), 7.09-7.11 (m, 1H), 7.18-7.23 (m, 1H), 7.39-7.43 (m, 1H), 7.84 (s, 1H), 12.64 (s, 1H). | 1.82 | 429.25 | B |

TABLE 25-continued

| No. | Structure | NMR (δ) | retention time | Mass (M + H) | method |
|---|---|---|---|---|---|
| I-2-42 | 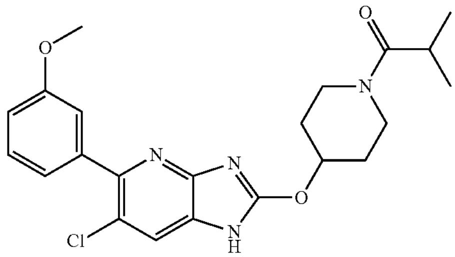 [SMILES: COc1cccc(-c2nc3nc(OC4CCN(C(=O)C(C)C)CC4)[nH]c3cc2Cl)c1] | (DMSO-d6) δ: 1.01 (d, J = 7.1 Hz, 6H), 1.66-1.76 (m, 2H), 2.10-2.15 (m, 2H), 2.90-2.92 (m, 1H), 3.23-3.26 (m, 1H), 3.41-3.44 (m, 1H), 3.83-3.95 (m, 5H), 5.28-5.29 (m, 1H), 6.98-7.00 (m, 1H), 7.15-7.20 (m, 2H), 7.37-7.39 (m, 1H), 7.91 (s, 1H), 12.80 (s, 1H), | 1.93 | 429.25 | B |
| I-2-43 | 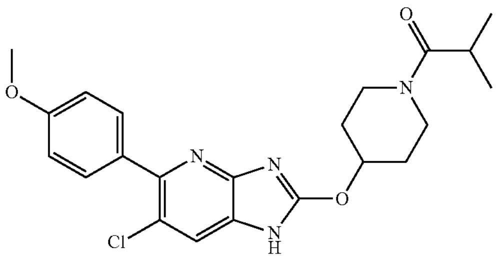 [SMILES: COc1ccc(-c2nc3nc(OC4CCN(C(=O)C(C)C)CC4)[nH]c3cc2Cl)cc1] | (DMSO-d6) δ: 1.01 (d, J = 6.6 Hz, 6H), 1.63-1.75 (m, 2H), 2.09-2.14 (m, 2H), 2.88-2.95 (m, 1H), 3.22-3.25 (m, 1H), 3.41-3.43 (m, 1H), 3.74-3.82 (m, 4H), 3.93-3.96 (m, 1H), 5.26-5.30 (m, 1H), 7.02 (d, J = 9.1 Hz, 2H), 7.59 (d, J = 9.1 Hz, 2H), 7.88 (s, 1H), 12.75 (s, 1H). | 1.91 | 429.25 | B |

TABLE 26

| No. | Structure | NMR (δ) | retention time | Mass (M + H) | method |
|---|---|---|---|---|---|
| I-2-44 | 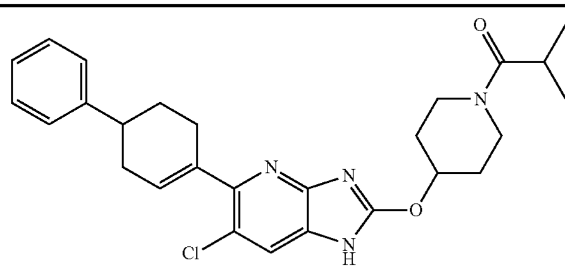 | (DMSO-d6) δ: 1.01 (d, J = 6.6 Hz, 6H), 1.64-1.72 (m, 2H), 1.85-1.90 (m, 1H), 2.06-2.13 (m, 4H), 2.29-2.32 (m, 1H), 2.44-2.47 (m, 2H), 2.88-2.94 (m, 2H), 3.24-3.26 (m, 1H), 3.38-3.41 (m, 1H), 3.78-3.80 (m, 1H), 3.92-3.95 (m, 1H), 5.23-5.28 (m, 1H), 6.01 (s, 1H), 7.19-7.23 (m, 1H), 7.31-7.33 (m, 4H), 7.79 (s, 1H), 12.56 (s, 1H). | 2.46 | 479.25 | B |
| I-2-45 | 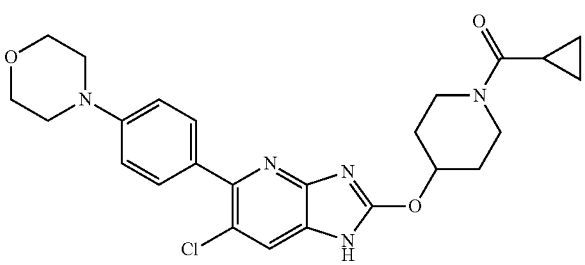 [SMILES: O=C(C1CC1)N1CCC(Oc2nc3nc(-c4ccc(N5CCOCC5)cc4)c(Cl)cc3[nH]2)CC1] | (DMSO-D6) δ: 0.71-0.74 (m, 4H), 1.60-1.83 (m, 2H), 1.99-2.23 (m, 2H), 3.17-3.20 (m, 4H), 3.20-3.33 (m, 1H), 3.48-3.64 (m, 2H), 3.75-3.77 (m, 4H), 3.96-4.09 (m, 2H), 5.27-5.31 (m, 1H), 7.01 (d, J = 8.62 Hz, 2H), 7.55 (d, J = 8.62 Hz, 2H), 7.86 (s, 1H) | | | |
| I-2-46 | 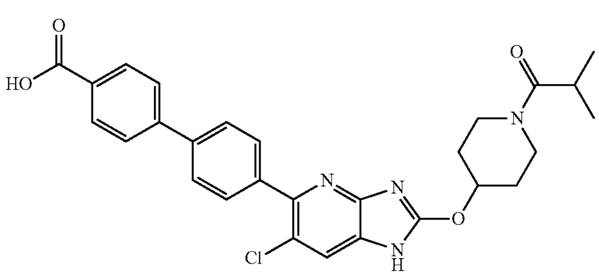 [SMILES: CC(C)C(=O)N1CCC(Oc2nc3nc(-c4ccc(-c5ccc(C(=O)O)cc5)cc4)c(Cl)cc3[nH]2)CC1] | (DMSO-d6) δ: 1.02 (d, J = 6.6 Hz, 6H), 1.67-1.77 (m, 2H). 2.09-2.15 (m, 2H), 2.88-2.95 (m, 1H), 3.30-3.39 (m, 2H), 3.80-3.82 (m, 1H), 3.94-3.97 (m, 1H), 5.29-5.31 (m, 1H), 7.76-7.78 (m, 2H), 7.83-7.85 (m, 4H), 7.94 (s, 1H), 8.05-8.07 (m, 2H), 12.83 (s, 1H). | 1.91 | 519.25 | B |

TABLE 26-continued

| No. | Structure | NMR (δ) | retention time | Mass (M + H) | method |
|---|---|---|---|---|---|
| I-2-47 | 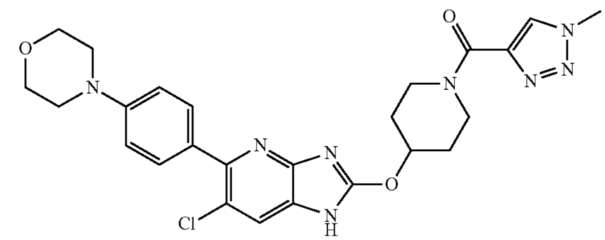 [SMILES: Cn1cc(C(=O)N2CCC(Oc3nc4nc(-c5ccc(N6CCOCC6)cc5)c(Cl)cc4[nH]3)CC2)nn1] | (DMSO-D6) δ: 1.73-1.91 (m, 2H), 2.11-2.24 (m, 2H), 3.17-3.20 (m, 4H), 3.33-3.40 (m, 2H), 3.75-3.91 (m, 5H), 4.09 (s, 3H), 4.38-4.49 (m, 1H), 5.31-5.39 (m, 1H), 7.01 (d, J = 8.62 Hz, 2H), 7.55 (d, J = 8.62 Hz, 2H), 7.85 (s, 1H), 8.49 (s, 1H) | | | |
| I-2-48 | 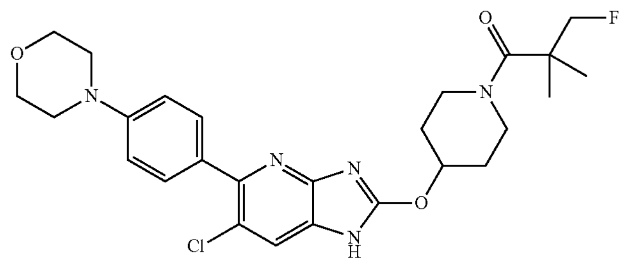 [SMILES: CC(C)(CF)C(=O)N1CCC(Oc2nc3nc(-c4ccc(N5CCOCC5)cc4)c(Cl)cc3[nH]2)CC1] | (DMSO-D6) δ: 1.27 (s, 6H), 1.64-1.75 (m, 2H), 2.09-2.17 (m, 2H), 3.19 (t, J = 4.56 Hz, 4H), 3.33-3.42 (m, 4H), 3.76 (t, J = 4.56 Hz, 4H), 4.34 (s, 1H), 4.46 (s, 1H), 5.25-5.32 (m, 1H), 7.01 (d, J = 8.62 Hz, 2H), 7.55 (d, J = 8.62 Hz, 2H), 7.85 (s, 1H), 12.68 (s, 1H). | | | |

TABLE 27

| No. | Structure | NMR (δ) | retention time | Mass (M + H) | method |
|---|---|---|---|---|---|
| I-2-49 | 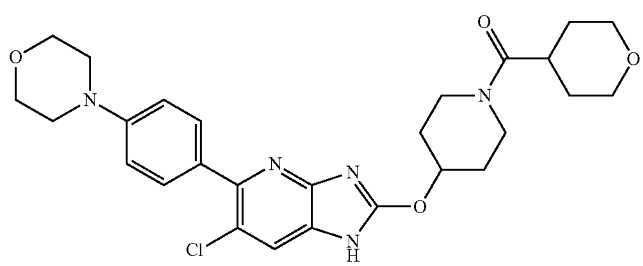 [SMILES: O=C(C1CCOCC1)N1CCC(Oc2nc3nc(-c4ccc(N5CCOCC5)cc4)c(Cl)cc3[nH]2)CC1] | | 1.65 | 526.25 | B |
| I-2-50 | 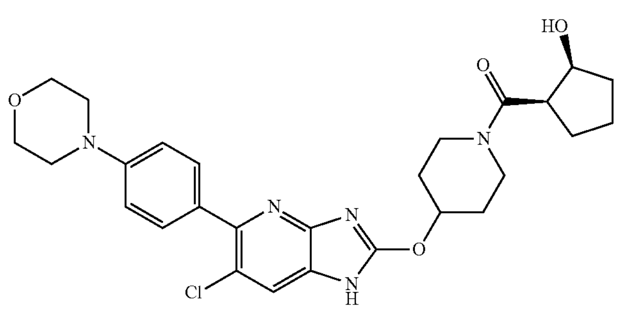 [SMILES: O=C([C@@H]1CCC[C@@H]1O)N1CCC(Oc2nc3nc(-c4ccc(N5CCOCC5)cc4)c(Cl)cc3[nH]2)CC1] | 1H-NMR (DMSO-d6) δ: 1.46-1.78 (m, 8H), 2.03-2.19 (m, 4H), 2.93-2.99 (m 1H), 3.19 (dd, J = 5.2, 4.4 Hz, 4H), 3.76 (dd, J = 5.2, 4.4 Hz, 4H), 3.82-3.87 (m, 1H). 3.97-4.00 (m, 1H), 4.29 (br s, 1H), 4.92 (d, J = 3.5 Hz, 1H), 5.25-5.29 (m, 1H), 7.01 (d, J = 8.6 Hz, 2H), 7.55 (d, J = 8.6 Hz, 2H), 7.85 (s, 1H). | | | |

TABLE 27-continued

| No. | Structure | NMR (δ) | retention time | Mass (M + H) | method |
|---|---|---|---|---|---|
| I-2-51 | 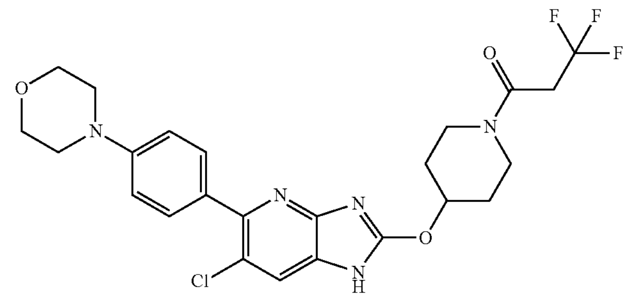 [SMILES: O=C(CC(F)(F)F)N1CCC(Oc2nc3nc(-c4ccc(N5CCOCC5)cc4)c(Cl)cc3[nH]2)CC1] | (DMSO-D6) δ: 1.75 (d, J = 45.12 Hz, 2H), 2.12 (br s, 2H), 3.19 (t, J = 4.56 Hz, 4H), 3.36-3.48 (m, 2H), 3.65-3.78 (m, 3H), 3.76 (t, J = 4.56 Hz, 4H), 3.88-3.97 (m, 1H), 5.28 (s, 1H), 7.01 (d, J = 8.62 Hz, 2H), 7.55 (d, J = 8.62 Hz, 2H), 7.87 (s, 1H), 12.73 (s, 1H). | | | |
| I-2-52 | 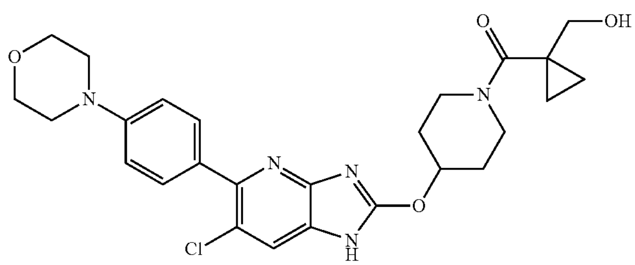 [SMILES: O=C(N1CCC(Oc2nc3nc(-c4ccc(N5CCOCC5)cc4)c(Cl)cc3[nH]2)CC1)C1(CO)CC1] | (DMSO-D6) δ: 0.72 (d, J = 16.28 Hz, 4H), 1.73 (br s, 2H), 2.10 (br s, 2H), 3.20 (d, J = 4.62 Hz, 4H), 3.47 (d, J = 5.88 Hz, 4H), 3.77 (t, J = 4.62 Hz, 4H), 3.97 (br s, 2H), 4.87 (t, J = 5.88 Hz, 1H), 5.28 (br s, 1H), 7.01 (d, J = 8.73 Hz, 2H), 7.56 (d, J = 8.73 Hz, 2H), 7.90 (s, 1H), 12.75 (s, 1H). | | | |
| I-2-53 | 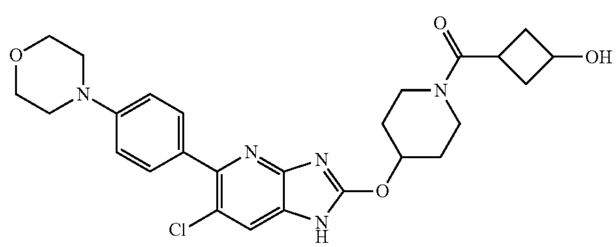 [SMILES: O=C(C1CC(O)C1)N1CCC(Oc2nc3nc(-c4ccc(N5CCOCC5)cc4)c(Cl)cc3[nH]2)CC1] | (DMSO-D6) δ: 1.65 (br s, 2H), 2.04 (d, J = 28.54 Hz, 4H), 2.30-2.41 (m, 2H), 2.77 (t, J = 8.98 Hz, 1H), 3.15-3.27 (m, 6H), 3.60-3.80 (m, 5H), 3.89-4.05 (m, 2H), 5.06 (d, J = 7.05 Hz, 1H), 5.26 (s, 1H), 7.01 (d, J = 8.56 Hz, 2H), 7.55 (d, J = 8.56 Hz, 2H), 7.90 (s, 1H), 12.74 (s, 1H). | | | |

TABLE 28

| No. | Structure | NMR (δ) | retention time | Mass (M + H) | method |
|---|---|---|---|---|---|
| I-2-54 | 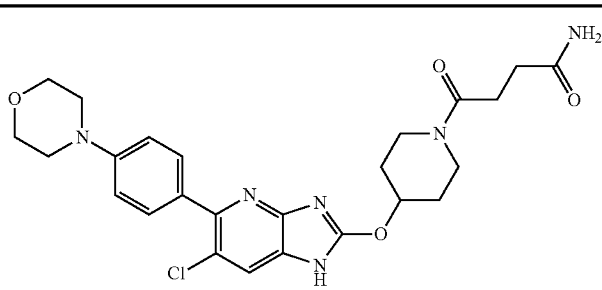 | | 1.43 | 513.25 | B |

TABLE 28-continued

| No. | Structure | NMR (δ) | retention time | Mass (M + H) | method |
|---|---|---|---|---|---|
| I-2-55 | 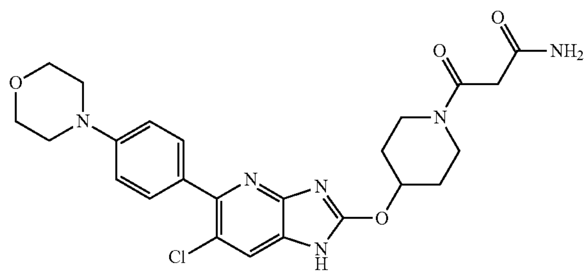 [SMILES: NC(=O)CC(=O)N1CCC(Oc2nc3nc(-c4ccc(N5CCOCC5)cc4)c(Cl)cc3[nH]2)CC1] | | 1.4 | 499.2 | B |
| I-2-56 | 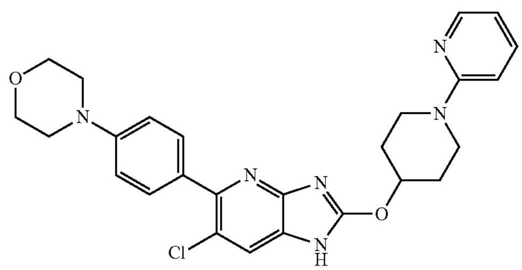 [SMILES: Clc1cc2[nH]c(OC3CCN(c4ccccn4)CC3)nc2nc1-c1ccc(N2CCOCC2)cc1] | 1H-NMR (DMSO-d6) δ: 1.71-1.80 (m, 2H), 2.16-2.20 (m, 2H), 3.19 (dd, J = 5.2, 4.4 Hz, 4H), 3.25-3.30 (m, 2H), 3.76 (dd, J = 5.2, 4.4 Hz, 4H), 4.00-4.06 (m, 2H), 5.27-5.31 (m, 1H), 6.62-6.66 (m, 1H), 6.90 (d, J = 8.7 Hz, 1H), 7.01 (d, J = 9.1 Hz, 2H), 7.52-7.57 (m, 3H), 7.86 (s, 1H), 8.11-8.14 (m, 1H). | | | |
| I-2-57 | 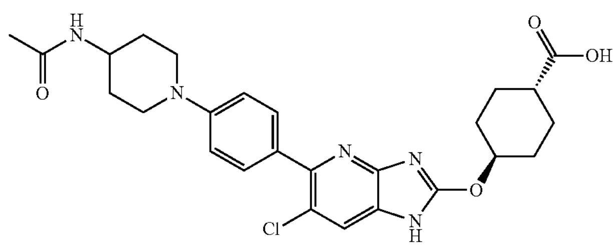 [SMILES: CC(=O)NC1CCN(c2ccc(-c3nc4nc(O[C@H]5CC[C@H](C(=O)O)CC5)[nH]c4cc3Cl)cc2)CC1] | (DMSO-d6) δ: 1.45-1.48 (m, 5H), 1.80-1.83 (m, 5H), 1.95-1.98 (m, 2H), 2.15-2.20 (m, 3H), 2.84-2.87 (m, 2H), 3.72-3.76 (m, 4H), 4.92 (s, 1H), 6.99 (d, J = 8.8 Hz, 2H), 7.52 (d, J = 8.8 Hz, 2H), 7.71 (s, 1H), 7.86 (d, J = 7.8 Hz, 1H). | | | |
| I-2-58 | 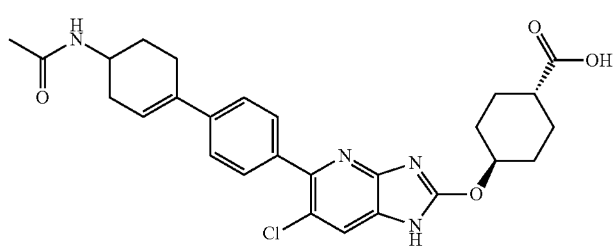 [SMILES: CC(=O)NC1CC=C(c2ccc(-c3nc4nc(O[C@H]5CC[C@H](C(=O)O)CC5)[nH]c4cc3Cl)cc2)CC1] | (DMSO-d6) δ: 1.53-1.61 (m, 5H), 1.83 (s, 3H), 1.92-1.99 (m, 3H), 2.06-2.10 (m, 1H), 2.24-2.29 (m, 3H), 2.46-2.51 (m, 3H), 3.85 (s, 1H), 4.98 (s, 1H), 6.19 (s, 1H), 7.51 (d, J = 8.3 Hz, 2H), 7.60 (d, J = 8.3 Hz, 2H), 7.88-7.90 (m, 2H). | | | |
| I-2-59 | 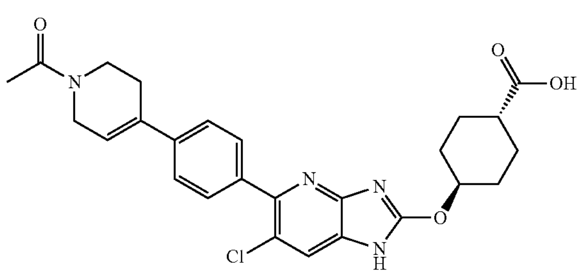 [SMILES: CC(=O)N1CC=C(c2ccc(-c3nc4nc(O[C@H]5CC[C@H](C(=O)O)CC5)[nH]c4cc3Cl)cc2)CC1] | (DMSO-d6) δ: 1.50-1.57 (m, 4H), 2.01-2.07 (m, 6H), 2.25-2.29 (m, 3H), 2.61 (s, 1H), 3.64-3.70 (m, 2H), 4.12-4.18 (m, 2H), 4.97-4.98 (m, 1H), 6.28 (s, 1H), 7.53-7.55 (m, 2H), 7.62-7.65 (m, 2H), 7.91 (s, 1H). | | | |

TABLE 29

| No. | Structure | NMR (δ) | retention time | Mass (M + H) | method |
|---|---|---|---|---|---|
| I-2-60 | 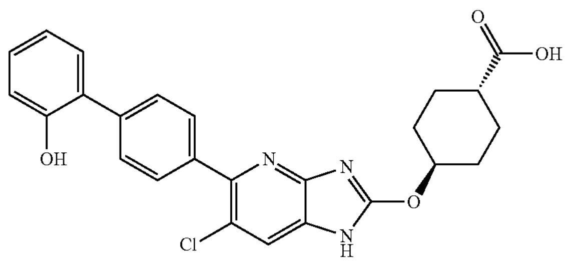 [SMILES: O=C(O)[C@H]1CC[C@H](Oc2nc3nc(-c4ccc(-c5ccccc5O)cc4)c(Cl)cc3[nH]2)CC1] | (DMSO-d6) δ: 1.52-1.56 (m, 4H), 1.99-2.01 (m, 2H), 2.25-2.29 (m, 3H), 4.98-4.99 (m, 1H), 6.90-6.91 (m, 1H), 6.96-6.98 (m, 1H), 7.17-7.20 (m, 1H), 7.32-7.34 (m, 1H), 7.62-7.69 (m, 4H), 7.92 (s, 1H), 9.65 (s, 1H). | | | |
| I-2-61 | 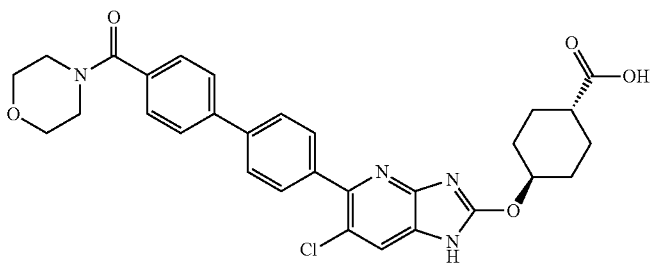 [SMILES: O=C(c1ccc(-c2ccc(-c3nc4nc(O[C@H]5CC[C@H](C(=O)O)CC5)[nH]c4cc3Cl)cc2)cc1)N1CCOCC1] | (DMSO-d6) δ: 1.52-1.56 (m, 4H), 1.99-2.02 (m, 2H), 2.24-2.32 (m, 3H), 3.59-3.61 (m, 9H), 5.00-5.01 (m, 1H), 7.54-7.56 (m, 2H), 7.76-7.87 (m, 6H), 7.94 (s, 1H). | 1.77 | 561.2 | B |
| I-2-62 | 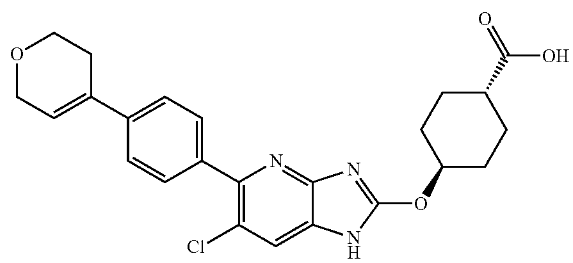 [SMILES: O=C(O)[C@H]1CC[C@H](Oc2nc3nc(-c4ccc(C5=CCOCC5)cc4)c(Cl)cc3[nH]2)CC1] | (DMSO-d6) δ: 1.50-1.53 (m, 4H), 1.98-2.00 (m, 2H), 2.22-2.33 (m, 5H), 3.84-3.86 (m, 2H), 4.25-4.26 (m, 2H), 4.96-4.99 (m, 1H), 6.35 (s, 1H), 7.54 (d, J = 8.5 Hz, 2H), 7.63 (d, J = 8.5 Hz, 2H), 7.87 (s, 1H). | 1.9 | 454.15 | B |
| I-2-63 | 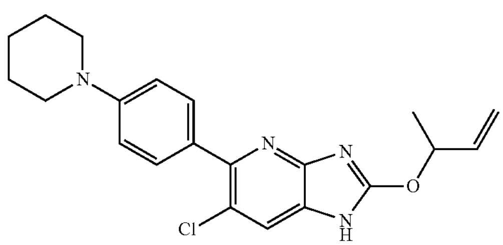 [SMILES: C=CC(C)Oc1nc2nc(-c3ccc(N4CCCCC4)cc3)c(Cl)cc2[nH]1] | (DMSO-d6) δ: 1.48 (d, J = 5.4 Hz, 3H), 1.56-1.63 (m, 6H), 3.18-3.24 (m, 4H), 5.21-5.24 (m, 1H), 5.36-5.40 (m, 1H), 5.64-5.69 (m, 1H), 6.06 (dq, J = 17.3, 5.4 Hz, 1H), 6.98 (d, J = 8.9 Hz, 2H), 7.52 (d, J = 8.9 Hz, 2H), 7.82 (s, 1H). | | | |
| I-2-64 | 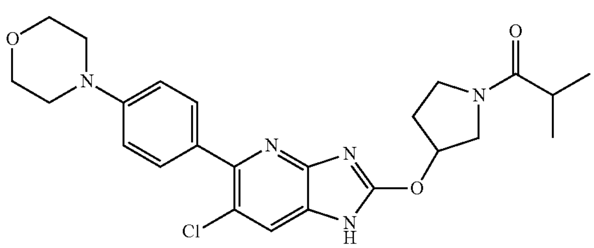 [SMILES: CC(C)C(=O)N1CCC(Oc2nc3nc(-c4ccc(N5CCOCC5)cc4)c(Cl)cc3[nH]2)C1] | (DMSO-d6) δ: 0.97-1.02 (m, 6H), 2.20-2.23 (m, 1H), 2.33-2.34 (m, 1H), 2.60-2.75 (m, 1H), 3.18-3.19 (m, 4H), 3.59-3.65 (m, 2H), 3.77-3.84 (m, 6H), 5.58-5.67 (m, 1H), 7.02 (d, J = 9.1 Hz, 2H), 7.55 (d, J = 8.8 Hz, 2H), 7.87 (s, 1H). | 1.76 | 470.05 | B |

TABLE 29-continued

| No. | Structure | NMR (δ) | retention time | Mass (M + H) | method |
|---|---|---|---|---|---|
| I-2-65 | 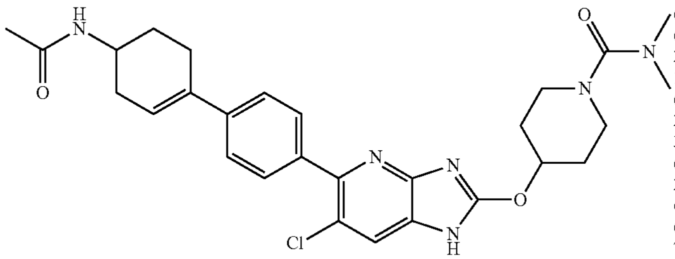 | (DMSO-d6) δ: 1.57-1.66 (m, 1H), 1.72-1.79 (m, 2H), 1.83 (s, 3H), 1.91-1.99 (m, 1H), 2.04-2.15 (m, 3H), 2.53-2.59 (m, 2H), 2.75 (s, 6H), 3.01-3.06 (m, 2H), 3.41-3.47 (m, 2H), 3.80-3.92 (m, 2H), 5.21-5.23 (m, 1H), 6.17-6.22 (m, 1H), 7.52 (d, J = 8.62 Hz, 2H), 7.60 (d, J = 8.62 Hz, 2H), 7.89 (d, 8.62 Hz, 1H), 8.01 (s, 1H) | | | |

TABLE 30

| No. | Structure | NMR (δ) | retention time | Mass (M + H) | method |
|---|---|---|---|---|---|
| I-2-66 | 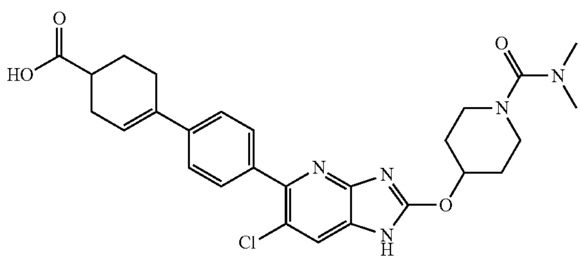 [SMILES: CN(C)C(=O)N1CCC(Oc2nc3nc(-c4ccc(C5=CCC(C(=O)O)CC5)cc4)c(Cl)cc3[nH]2)CC1] | (DMSO-d6) δ: 1.68-1.79 (m, 3H), 2.05-2.18 (m, 3H), 2.34-2.51 (m, 5H), 2.76 (s, 6H), 3.01-3.06 (m, 2H), 3.43-3.50 (m, 2H), 5.18-5.25 (m, 1H), 6.25-6.29 (m, 1H), 7.51 (d, J = 8.62 Hz, 2H), 7.60 (d, J = 8.62 Hz, 2H), 7.91 (s, 1H), 12.26 (bs, 1H), 12.83 (bs, 1H) | | | |
| I-2-67 | 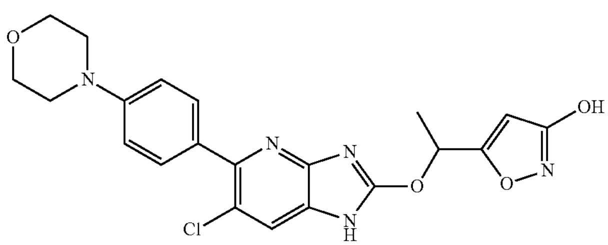 [SMILES: CC(Oc1nc2nc(-c3ccc(N4CCOCC4)cc3)c(Cl)cc2[nH]1)c1cc(O)no1] | (DMSO-d6) δ: 1.72 (d, J = 6.02 Hz, 3H), 3.19 (t, J = 4.82 Hz, 4H), 3.76 (t, J = 4.82 Hz, 4H), 6.18 (s, 1H), 6.25 (q, J = 6.02 Hz, 1H), 7.02 (d, J = 8.16 Hz, 2H), 7.55 (d, J = 8.16 Hz, 2H), 7 95 (s, 1H), 11.45 (s, 1H), 12.93 (s, 1H). | | | |
| I-2-68 | 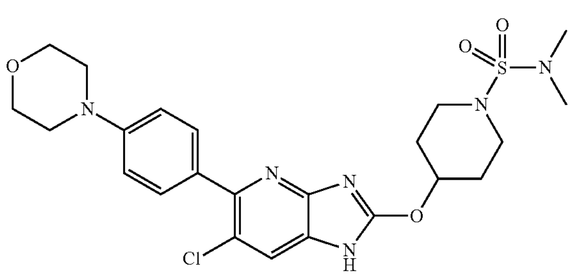 [SMILES: CN(C)S(=O)(=O)N1CCC(Oc2nc3nc(-c4ccc(N5CCOCC5)cc4)c(Cl)cc3[nH]2)CC1] | (DMSO-d6) δ: 1.74-1.91 (m, 2H), 2.13-2.17 (m, 2H), 2.77 (s, 6H), 3.17-3.24 (m, 6H), 3.43-3.46 (m, 2H), 3.76-3.77 (m, 4H), 5.19-5.23 (m, 1H), 7.01 (d, J = 8.9 Hz, 2H), 7.55 (d, J = 8.8 Hz, 2H), 7.85 (s, 1H). | | | |

TABLE 30-continued

| No. | Structure | NMR (δ) | retention time | Mass (M + H) | method |
|---|---|---|---|---|---|
| I-2-69 | 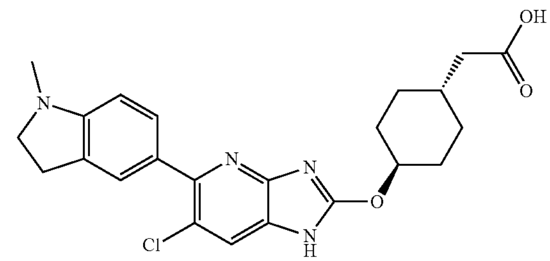 [SMILES: CN1CCc2cc(-c3nc4nc(O[C@H]5CC[C@H](CC(=O)O)CC5)[nH]c4cc3Cl)ccc21] | 1H-NMR (CDCl3) δ: 1.10-1.25 (m, 4H), 1.45-1.55 (m, 2H), 1.70-1.75 (m, 1H), 1.80-1.85 (m, 2H), 2.15-2.22 (m, 4H), 2.75 (s, 3H), 2.93 (t, J = 8.2 Hz, 2H), 4.93-4.96 (br m, 1H), 6.54 (d, J = 8.8 Hz, 1H), 7.30-7.35 (m, 2H), 7.85-7.86 (m, 1H). | 1.91 | 441.1 | B |
| I-2-70 | 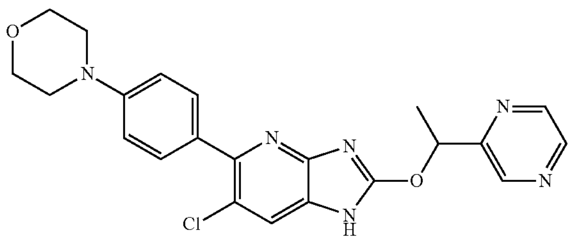 | (DMSO-d6) δ: 1.77 (d, J = 6.53 Hz, 3H), 3.18 (t, J = 4.64 Hz, 4H), 3.76 (t, J = 4.64 Hz, 4H), 6.28 (q, J = 6.53 Hz, 1H), 7.00 (d, J = 8.78 Hz, 2H), 7.54 (d, J = 8.53 Hz, 2H), 7.85 (s, 1H), 8.62-8.69 (m, 2H), 8.84 (s, 1H), 12.85 (s, 1H). | | | |

TABLE 31

| No. | Structure | NMR (δ) | retention time | Mass (M + H) | method |
|---|---|---|---|---|---|
| I-2-71 | 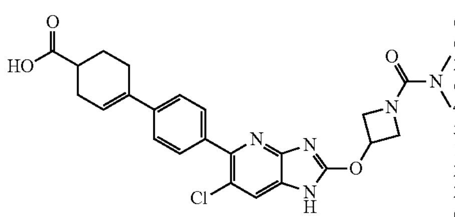 | (DMSO-d6) δ: 1.67-1.79 (m, 1H), 2.06-2.14 (m, 1H), 2.32-2.51 (m, 5H), 2.78 (s, 6H), 3.97-4.02 (m, 2H), 4.33-4.38 (m, 2H), 5.44-5.50 (m, 1H), 6.24-6.28 (m, 1H), 7.50 (d, J = 8.62 Hz, 2H), 7.61 (d, J = 8.62 Hz, 2H), 7.98 (s, 1H), 12.20 (s, 1H), 13.01 (s, 1H) | | | |
| I-2-72 | 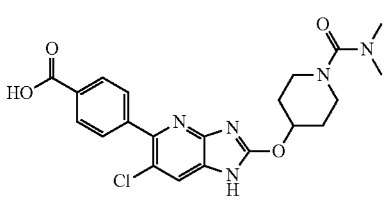 [SMILES: CN(C)C(=O)N1CCC(Oc2nc3nc(-c4ccc(C(=O)O)cc4)c(Cl)cc3[nH]2)CC1] | (DMSO-d6) δ: 1.68-1.80 (m, 2H), 2.05-2.16 (m, 2H), 2.76 (s, 6H), 3.02-3.07 (m, 2H), 3.42-3.46 (m, 2H), 5.19-5.28 (m, 1H), 7.76 (d, J = 8.62 Hz, 2H), 8.01 (s, 1H), 803 (d, J = 8.62 Hz, 2H), 12.92 (bs, 1H), 13.08 (bs, 1H) | | | |
| I-2-73 | 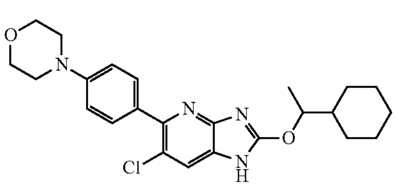 [SMILES: CC(Oc1nc2nc(-c3ccc(N4CCOCC4)cc3)c(Cl)cc2[nH]1)C1CCCCC1] | 1H-NMR (DMSO-d6) δ: 1.04-1.25 (m, 5H), 1.34 (d, J = 6.5 Hz, 3H), 1.63-1.84 (m, 6H), 3.18 (dd, J = 5.2, 4.4 Hz, 4H), 3.76 (dd, J = 5.2, 4.4 Hz, 4H), 5.02-5.05 (m, 1H), 7.01 (d, J = 9.0 Hz, 2H), 7.54 (d, J = 9.0 Hz, 2H), 7.81 (s, 1H). | | | |

TABLE 31-continued

| No. | Structure | NMR (δ) | retention time | Mass (M + H) | method |
|---|---|---|---|---|---|
| I-2-74 | 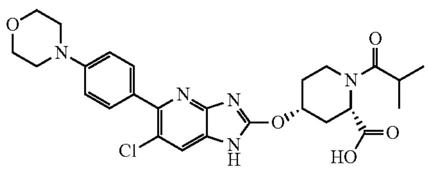 [SMILES: CC(C)C(=O)N1CC[C@@H](Oc2nc3nc(-c4ccc(N5CCOCC5)cc4)c(Cl)cc3[nH]2)C[C@H]1C(=O)O] | (DMSO-d6) δ: 1.02-1.04 (m, 6H), 1.91-2.01 (m, 2H), 2.93-3.00 (m, 3H), 3.18-3.20 (m, 4H), 3.56-3.60 (m, 1H), 3.75-3.78 (m, 4H), 3.89-3.92 (m, 1H), 5.06-5.08 (m, 1H), 5.32 (s, 1H), 7.02 (d, J = 8.3 Hz, 2H), 7.54 (d, J = 7.7 Hz, 2H), 7.90 (s, 1H). | 1.75 | 528.1 | B |
| I-2-75 | 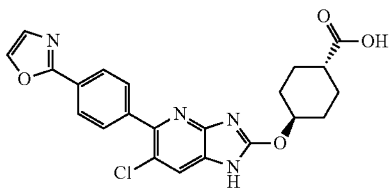 [SMILES: O=C(O)[C@H]1CC[C@H](Oc2nc3nc(-c4ccc(-c5ncco5)cc4)c(Cl)cc3[nH]2)CC1] | 1H-NMR (DMSO-d6) δ: 1.54 (br s, 4H), 1.99 (s, 2H), 2.22-2.31 (m, 3H), 4.98-5.00 (br m, 1H), 7.45 (d, J = 8.4 Hz, 1H), 7.82 (d, J = 8.0 Hz, 2H), 7.99 (d, J = 26.1 Hz, 1H), 8.08 (d, J = 7.9 Hz, 2H), 8.28 (s, 1H). | 1.83 | 428.9 | B |

TABLE 32

| No. | Structure | NMR (δ) | retention time | Mass (M + H) | method |
|---|---|---|---|---|---|
| I-2-76 | 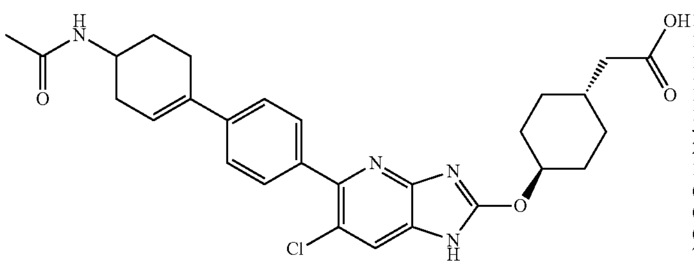 [SMILES: CC(=O)NC1CC=C(c2ccc(-c3nc4nc(O[C@H]5CC[C@H](CC(=O)O)CC5)[nH]c4cc3Cl)cc2)CC1] | 1H-NMR (DMSO-d6) δ: 1.15 (q, J = 11.8 Hz, 2H), 1.50 (q, J = 11.7 Hz, 2H), 1.62 (br s, 1H), 1.72 (br s, 1H), 1.83 (s, 5H), 1.93 (d, J = 12.0 Hz, 1H), 2.11-2.20 (m, 5H), 2.56 (s, 1H), 3.86 (s, 2H), 4.95 (s, 1H), 6.19 (s, 1H), 7.51 (d, J = 7.5 Hz, 2H), 7.60 (d, J = 7.7 Hz, 2H), 7.88-7.90 (m, 2H). | 1.82 | 523.3 | B |
| I-2-77 | 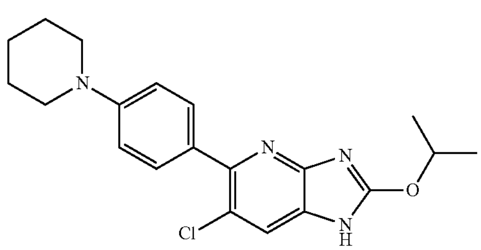 [SMILES: CC(C)Oc1nc2nc(-c3ccc(N4CCCCC4)cc3)c(Cl)cc2[nH]1] | (DMSO-d6) δ: 1.40 (d, J = 6.0 Hz, 6H), 1.55-1.66 (m, 6H), 3.19-3.26 (m, 4H), 5.24-5.30 (m, 1H), 6.97 (d, J = 8.8 Hz, 2H), 7.52 (d, J = 8.8 Hz, 2H), 7.79 (s, 1H). | | | |
| I-2-78 | 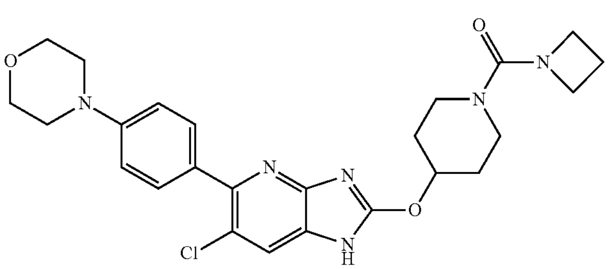 [SMILES: O=C(N1CCC1)N1CCC(Oc2nc3nc(-c4ccc(N5CCOCC5)cc4)c(Cl)cc3[nH]2)CC1] | (DMSO-d6) δ: 1.61-1.70 (m, 2H), 2.07-2.18 (m, 4H), 3.07-3.13 (m, 2H), 3.17-3.19 (m, 4H), 3.54-3.58 (m, 2H), 3.75-3.77 (m, 4H), 3.88-3.92 (m, 4H), 5.18-5.23 (m, 1H), 7.01 (d, J = 8.91 Hz, 2H), 7.55 (d, J = 8.91 Hz, 2H), 7.86 (s, 1H) | | | |

TABLE 32-continued

| No. | Structure | NMR (δ) | retention time | Mass (M + H) | method |
|---|---|---|---|---|---|
| I-2-79 | 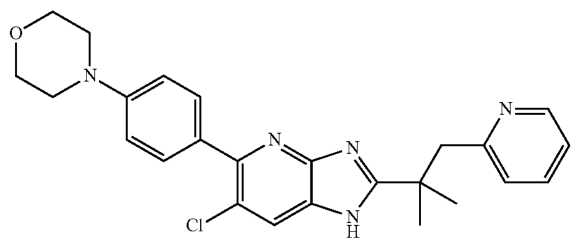 [SMILES: CC(C)(Cc1ccccn1)c1nc2nc(-c3ccc(N4CCOCC4)cc3)c(Cl)cc2[nH]1] | (DMSO-d6) δ: 1.41 (s, 6H), 3.20 (t, J = 4.77 Hz, 4H), 3.23 (s, 2H), 3.77 (t, J = 4.77 Hz, 4H), 6.94 (d, J = 7.65 Hz, 1H), 7.04 (d, J = 8.91 Hz, 2H), 7.16 (dd, J = 6.96, 5.21 Hz, 1H), 7.55-7.64 (m, 3H), 8.11 (s, 1H), 8.38 (d, J = 3.89 Hz, 1H), 13.11 (s, 1H). | | | |
| I-2-80 | 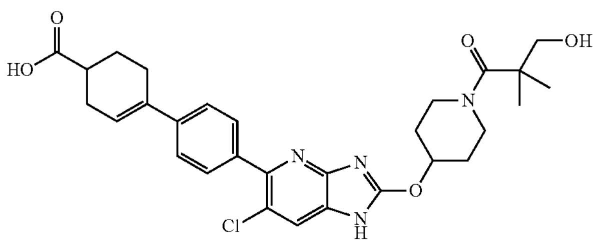 [SMILES: CC(C)(CO)C(=O)N1CCC(Oc2nc3nc(-c4ccc(C5=CCC(C(=O)O)CC5)cc4)c(Cl)cc3[nH]2)CC1] | (DMSO-d6) δ: 1.17 (s, 6H), 1.70-1.74 (m, 4H), 2.09-2.10 (m, 3H), 2.33-2.46 (m, 4H), 3.43-3.44 (m, 4H), 3.96-3.99 (m, 2H), 4.59 (t, J = 5.6 Hz, 1H), 5.27-5.29 (m, 1H), 6.26 (s, 1H), 7.50 (d, J = 8.4 Hz, 2H), 7.60 (d, J = 8.4 Hz, 2H), 7.89 (s, 1H). | 1.84 | 553.05 | B |
| I-2-81 | 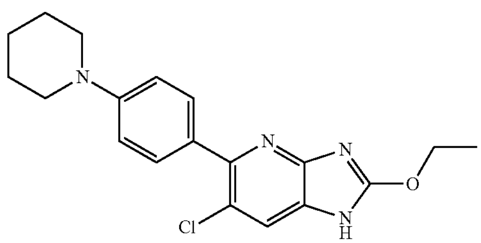 [SMILES: CCOc1nc2nc(-c3ccc(N4CCCCC4)cc3)c(Cl)cc2[nH]1] | (DMSO-d$_6$) δ: 1.40 (t, J = 7.1 Hz, 3H), 1.56-1.63 (m, 6H), 3.22-3.23 (m, 4H), 4.52 (q, J = 7.1 Hz, 2H), 6.98 (d, J = 8.8 Hz, 2H), 7.52 (d, J = 8.8 Hz, 2H), 7.83 (s, 1H). | | | |

TABLE 33

| No. | Structure | NMR (δ) | retention time | Mass (M + H) | method |
|---|---|---|---|---|---|
| I-2-82 | 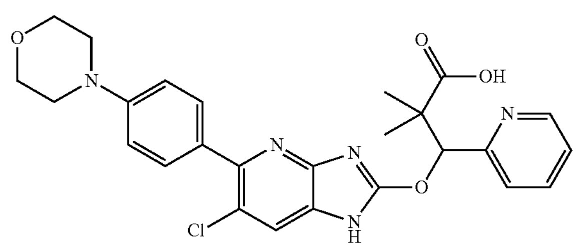 [SMILES: CC(C)(C(=O)O)C(Oc1nc2nc(-c3ccc(N4CCOCC4)cc3)c(Cl)cc2[nH]1)c1ccccn1] | 1H-NMR (DMSO-d6) δ: 1.13 (s, 3H), 1.19 (s, 3H), 3.17 (t, J = 4.77 Hz, 4H), 3.76 (t, J = 4.77 Hz, 4H), 6.37 (s, 1H), 7.00 (d, J = 8.66 Hz, 2H), 7.34 (ddd, J = 7.91, 4.86, 0.91 Hz, 1H), 7.42 (d. J = 7.91 Hz, 1H), 7.50 (d, J = 8.66 Hz, 2H), 7.75-7.85 (m, 2H), 8.57 (dd, J = 4.86, 0.91 Hz, 1H), 12.68 (s, 1H), 12.95 (s, 1H). | | | |
| I-2-83 | 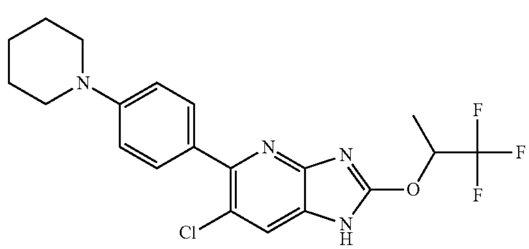 [SMILES: CC(Oc1nc2nc(-c3ccc(N4CCCCC4)cc3)c(Cl)cc2[nH]1)C(F)(F)F] | (DMSO-d$_6$) δ: 1.58-1.62 (m, 9H), 3.23-3.26 (m, 4H), 5.84-5.91 (m, 1H), 6.98 (d, J = 8.9 Hz, 2H), 7.53 (d, J = 8.9 Hz, 2H), 7.92 (s, 1H). | | | |

TABLE 33-continued

| No. | Structure | NMR (δ) | retention time | Mass (M + H) | method |
|---|---|---|---|---|---|
| I-2-84 | 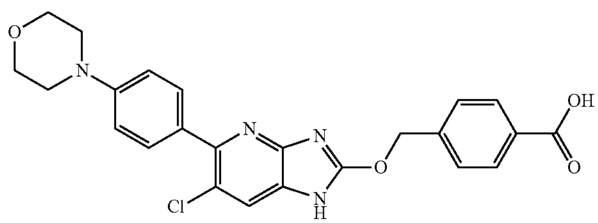 [SMILES: O=C(O)c1ccc(COc2nc3nc(-c4ccc(N5CCOCC5)cc4)c(Cl)cc3[nH]2)cc1] | 1H-NMR (DMSO-d6) δ: 3.19 (dd, J = 5.2, 4.4 Hz, 4H), 3.76 (dd, J = 5.2, 4.4 Hz, 4H), 5.65 (s, 2H), 7.02 (d, J = 8.9 Hz, 2H), 7.56 (d, J = 8.9 Hz, 2H), 7.63 (d, J = 8.3 Hz, 2H), 7.91 (s, 1H), 7.99 (d, J = 8.3 Hz, 2H). | | | |
| I-2-85 | 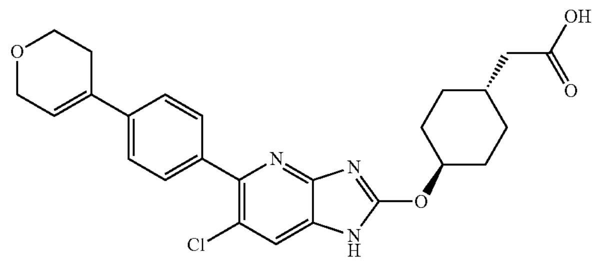 [SMILES: O=C(O)C[C@H]1CC[C@H](Oc2nc3nc(-c4ccc(C5=CCOCC5)cc4)c(Cl)cc3[nH]2)CC1] | 1H-NMR (DMSO-d6) δ: 1.15-1.25 (m, 4H), 1.51 (dd, J = 24.1, 9.3 Hz, 2H), 1.73-1.74 (br m, 3H), 1.83 (d, J = 12.0 Hz, 2H), 2.16 (d, J = 7.0 Hz, 2H), 2.22 (d, J = 9.3 Hz, 2H), 3.85 (t, J = 5.4 Hz, 2H), 4.26 (d, J = 2.8 Hz, 2H), 4.96 (s, 1H), 6.36 (s, 1H), 7.54 (d, J = 8.5 Hz, 2H), 7.63 (d, J = 8.3 Hz, 2H), 12.08 (s, 1H), 12.74 (s, 1H). | 2.03 | 468.4 | B |
| I-2-86 | 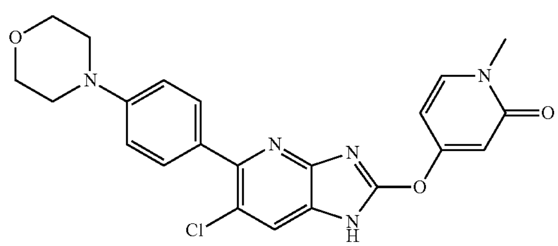 [SMILES: Cn1ccc(Oc2nc3nc(-c4ccc(N5CCOCC5)cc4)c(Cl)cc3[nH]2)cc1=O] | (DMSO-d6) δ: 3.20 (t, J = 4.77 Hz, 4H), 3.44 (s, 3H), 3.76 (t, J = 4.64 Hz, 4H), 6.40 (dd, J = 7.53, 3.76 Hz, 1H), 6.50 (d, J = 10.00 Hz, 1H), 7.03 (d, J = 8.78 Hz, 2H), 7.57 (d, J = 8.78 Hz, 2H), 7.83 (d, J = 7.53 Hz, 1H), 8.02 (s, 1H), 13.3 (brs, 1H). | 1.53 | 439.15 | B |

TABLE 34

| No. | Structure | NMR (δ) | retention time | Mass (M + H) | method |
|---|---|---|---|---|---|
| I-2-87 | 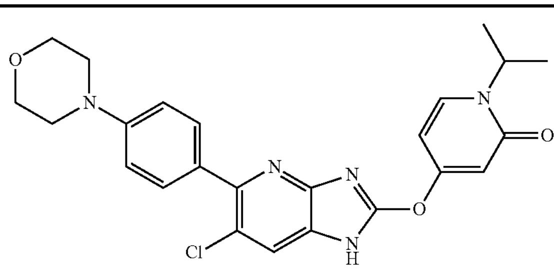 | (DMSO-d6) δ: 1.31 (d, J = 6.78 Hz, 6H), 3.20 (t, J = 4.77 Hz, 4H), 3.76 (t, J = 4.77 Hz, 4H), 5.03-5.05 (m, 1H), 6.43-6.47 (m, 2H), 7.03 (d, J = 9.03 Hz, 2H), 7.57 (d, J = 8.78 Hz, 2H), 7.87 (d, J = 7.53 Hz, 1H), 8.02 (s, 1H), 13.4 (brs, 1H). | 1.77 | 467.25 | B |
| I-2-88 | 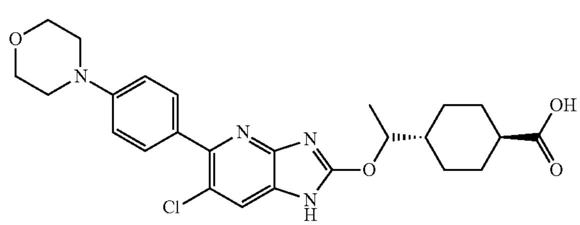 [SMILES: CC(Oc1nc2nc(-c3ccc(N4CCOCC4)cc3)c(Cl)cc2[nH]1)[C@H]1CC[C@H](C(=O)O)CC1] | 1H-NMR (DMSO-d6) δ: 1.12-1.16 (m, 1H), 1.24-1.35 (m, 6H), 1.56-1.65 (m, 2H), 1.77-1.80 (m, 1H), 1.88-1.97 (m, 2H), 2.12-2.18 (m, 1H), 3.18 (t, J = 5.2, 4.4 Hz, 4H), 3.76 (t, J = 5.2, 4.4 Hz, 4H), 5.02-5.05 (m, 1H), 7.01 (d, J = 9.0 Hz, 2H), 7.54 (d, J = 9.0 Hz, 2H), 7.87 (s, 1H). | | | |

TABLE 34-continued

| No. | Structure | NMR (δ) | retention time | Mass (M + H) | method |
|---|---|---|---|---|---|
| I-2-89 | 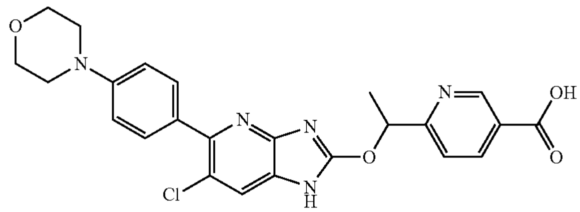 [SMILES: CC(Oc1nc2nc(-c3ccc(N4CCOCC4)cc3)c(Cl)cc2[nH]1)c1ccc(C(=O)O)cn1] | (DMSO-d6) δ: 1.73 (d, J = 6.65 Hz, 3H), 3.18 (t, J = 4.64 Hz, 4H), 3.76 (t, J = 4.64 Hz, 4H), 6.24 (q, J = 6.53 Hz, 1H), 7.01 (d, J = 8.41 Hz, 2H), 7.54 (d, J = 8.41 Hz, 2H), 7.63 (d, J = 7.91 Hz, 1H), 7.87 (s, 1H), 8.31 (dd, J = 7.91, 1.51 Hz, 1H), 9.06 (d, J = 1.51 Hz, 1H), 12.96 (s, 1H), 13.46 (s, 1H). | | | |
| I-2-90 | 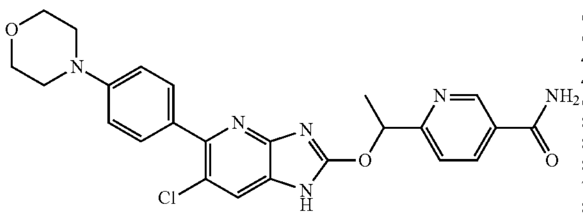 [SMILES: CC(Oc1nc2nc(-c3ccc(N4CCOCC4)cc3)c(Cl)cc2[nH]1)c1ccc(C(N)=O)cn1] | (DMSO-d6) δ: 1.72 (d, J = 6.65 Hz, 3H), 3.18 (t, J = 4.58 Hz, 4H), 3.76 (t, J = 4.58 Hz, 4H), 6.22 (q, J = 6.65 Hz, 1H), 7.00 (d, J = 8.78 Hz, 2H), 7.53 (d, J = 8.78 Hz, 2H), 7.59 (d, J = 8.09 Hz, 1H), 7.62 (s, 1H), 7.84 (s, 1H), 8.16 (s, 1H), 8.23 (dd, J = 8.09, 1.94 Hz, 1H), 9.00 (d, J = 1.94 Hz, 1H), 12.86 (s, 1H). | | | |
| I-2-91 | 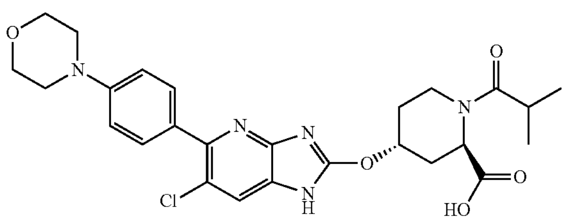 [SMILES: CC(C)C(=O)N1CC[C@@H](Oc2nc3nc(-c4ccc(N5CCOCC5)cc4)c(Cl)cc3[nH]2)C[C@@H]1C(=O)O] | (DMS0-d6) δ: 0.98-1.02 (m, 6H), 1.73-1.75 (m, 2H), 259-2.33 (m, 1H), 2.87-2.95 (m, 2H), 3.18-3.19 (m, 4H), 3.76-3.77 (m, 4H), 3.99-4.02 (m, 1H), 5.10-5.22 (m, 2H), 7.01 (d, J = 8.8 Hz, 2H), 7 55 (d, J = 8.7 Hz, 2H), 7.86 (s, 1H). | 1.67 | 528.1 | B |

TABLE 35

| No. | Structure | NMR (δ) | retention time | Mass (M + H) | method |
|---|---|---|---|---|---|
| I-2-92 | 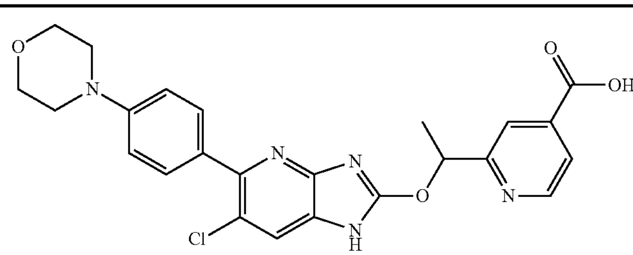 | (DMSO-d6) δ: 1.74 (d, J = 6.53 Hz, 3H), 3.18 (t, J = 4.64 Hz, 4H), 3.76 (t, J = 4.64 Hz, 4H), 6.28 (q, J = 6.53 Hz, 1H), 7.01 (d, J = 8.78 Hz, 2H), 7.54 (d, J = 8.78 Hz, 2H), 7.78 (dd, J = 4.89, 1.38 Hz, 1H), 7.89 (s, 1H), 7.92 (s, 1H), 8.78 (d, J = 4.89 Hz, 1H), 12.95 (s, 1H), 13.81 (s, 1H). | | | |
| I-2-93 | 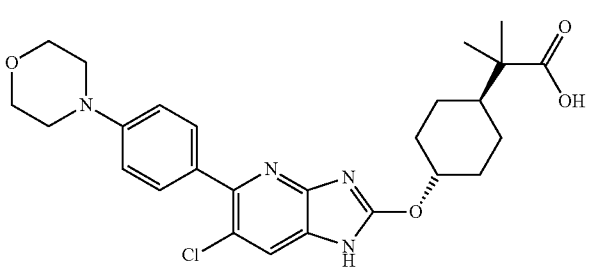 | 1H-NMR (DMSO-d6) δ: 1.05 (s, 6H), 1.24 (t, J = 11.8 Hz, 2H), 1.47 (dd, J = 22.8,11.0 Hz, 2H), 1.61 (t, J= 11.9 Hz, 1H), 1.69 (d, J = 12.5 Hz, 2H), 2.27 (d, J = 8.5 Hz, 2H), 3.18 (t, J = 4.8 Hz, 4H), 3.76 (t, J = 4.8 Hz, 4H), 4.91-4.94 (m, 1H), 7.01 (d, J = 8.9 Hz, 2H), 7.55 (d, J = 8.8 Hz, 2H), 7.85 (s, 1H), 12.17 (s, 1H), 12.68 (s, 1H). | 2.05 | 499.3 | B |

TABLE 35-continued

| No. | Structure | NMR (δ) | retention time | Mass (M + H) | method |
|---|---|---|---|---|---|
| I-2-94 | 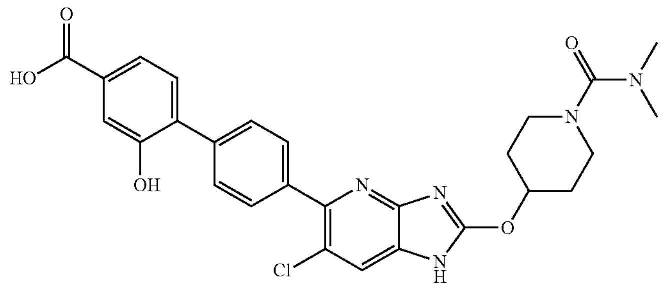 [SMILES: CN(C)C(=O)N1CCC(Oc2nc3nc(-c4ccc(-c5ccc(C(=O)O)cc5O)cc4)c(Cl)cc3[nH]2)CC1] | (DMSO-d6) δ: 1.71-1.78 (m, 2H), 2.11-2.13 (m, 2H), 2.76 (s, 6H), 3.02-3.07 (m, 2H), 3.43-4.46 (m, 2H), 5.21-5.26 (m, 1H), 7.44-7.50 (m, 2H), 7.58 (s, 1H), 7.70 (bs, 4H), 7.96 (bs, 1H), 10.06 (s, 1H), 12.86 (bs, 1H) | | | |
| I-2-95 | 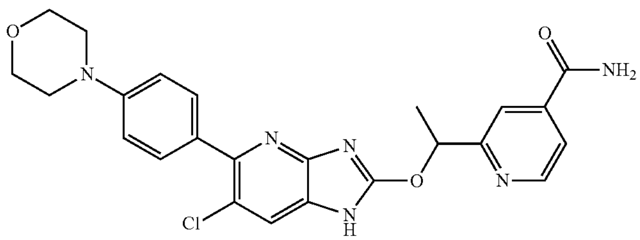 [SMILES: CC(Oc1nc2nc(-c3ccc(N4CCOCC4)cc3)c(Cl)cc2[nH]1)c1cc(C(N)=O)ccn1] | (DMSO-d6) δ: 1.73 (d, J = 6.48 Hz, 3H), 3.18 (t, J = 4.71 Hz, 4H), 3.76 (t, J = 4.71 Hz, 4H), 6.24 (q, J = 6.48 Hz, 1H), 7.00 (d, J = 8.78 Hz, 2H), 7.54 (d, J = 8.78 Hz, 2H), 7.73 (dd, J = 5.02, 1.38 Hz, 1H), 7.75-7.94 (m, 3H), 8.30 (s, 1H), 8.71 (d, J = 5.02 Hz, 1H), 12.91 (s, 1H). | | | |
| I-2-96 | 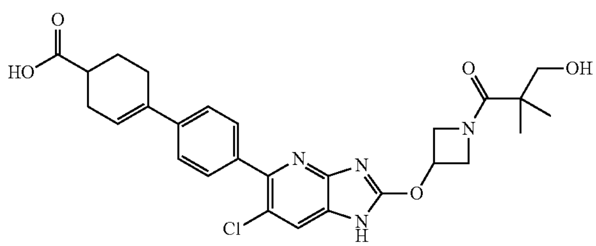 [SMILES: CC(C)(CO)C(=O)N1CC(Oc2nc3nc(-c4ccc(C5=CCC(C(=O)O)CC5)cc4)c(Cl)cc3[nH]2)C1] | (DMSO-d6) δ: 1.06 (s, 6H), 1.68-1.78 (m, 1H), 2.09-2.11 (m, 1H), 2.33-2.43 (m, 5H), 3.46-3.49 (m, 2H), 4.05-4.45 (m, 4H), 4.83 (t, J = 5.3 Hz, 1H), 5.46-547 (m, 1H), 6.26 (s, 1H), 7.50 (d, J = 8.5 Hz, 2H), 7.60 (d, J = 8.3 Hz, 2H), 7.90 (s, 1H). | 1.69 | 525.1 | B |

TABLE 36

| No. | Structure | NMR (δ) | retention time | Mass (M + H) | method |
|---|---|---|---|---|---|
| I-2-97 | 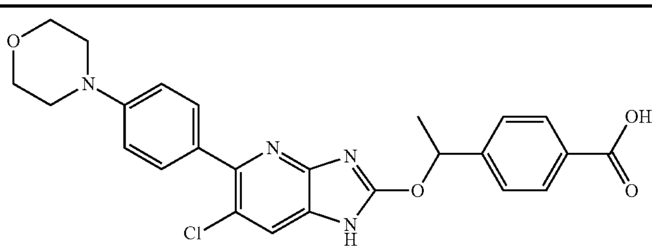 | 1H-NMR (DMSO-d6) δ: 1.70 (d, J = 6.5 Hz, 3H), 3.18 (dd, J = 5.2, 4.4 Hz, 4H), 3.76 (dd, J = 5.2, 4.4 Hz, 4H), 6.26-6.27 (m, 1H), 7.00 (d, J = 8.8 Hz, 2H), 7.53 (d, J = 8.8 Hz, 2H), 7.60 (d, J = 8.2 Hz, 2H), 7.88 (s, 1H), 7.96 (d, J = 8.2 Hz, 2H). | | | |
| I-2-98 | 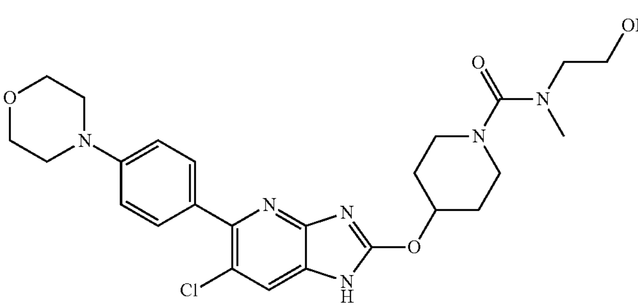 | (DMSO-d6) δ: 1.69-1.76 (m, 2H), 2.06-2.14 (m, 2H), 2.82 (s, 3H), 2.99-3.04 (m, 2H), 3.15-3.22 (m, 4H), 3.75-3.77 (m, 4H), 3.41-3.49 (m, 4H), 3.49-3.54 (m, 2H), 4.71 (bs, 1H), 5.18-5.22 (m, 1H), 7.01 (d, J = 8.66 Hz, 2H), 7.55 (d, J = 8.66 Hz, 2H), 7.83 (s, 1H) | | | |

TABLE 36-continued

| No. | Structure | NMR (δ) | retention time | Mass (M + H) | method |
|---|---|---|---|---|---|
| I-2-99 | 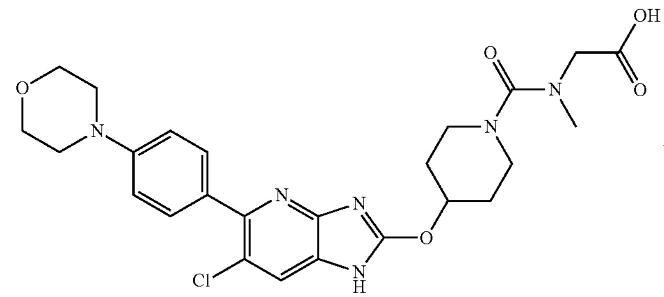 [SMILES: CN(CC(=O)O)C(=O)N1CCC(Oc2nc3nc(-c4ccc(N5CCOCC5)cc4)c(Cl)cc3[nH]2)CC1] | (DMSO-d6) δ: 1.67-1.78 (m, 2H), 2.04-2.13 (m, 2H), 2.80 (s, 3H), 2.97-3.04 (m, 2H), 3.17-3.20 (m, 4H), 3.34-3.51 (m, 2H), 3.57-3.68 (m, 2H), 3.75-3.77 (m, 4H), 5.15-5.26 (m, 1H), 7.01 (d, J = 8.78 Hz, 2H), 7.55 (d, J = 8.78 Hz, 2H), 7.85 (bs, 1H) | | | |
| I-2-100 | 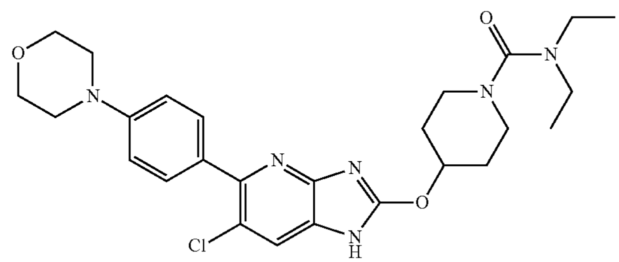 [SMILES: CCN(CC)C(=O)N1CCC(Oc2nc3nc(-c4ccc(N5CCOCC5)cc4)c(Cl)cc3[nH]2)CC1] | (DMSO-d6) δ: 1.05 (t, J = 6.90 Hz, 6H), 1.66-1.78 (m, 2H), 2.05-2.16 (m, 2H), 2.99-3.04 (m, 2H), 3.13 (q, J = 6.90 Hz, 4H), 3.17-3.20 (m, 4H), 3.35-3.45 (m, 2H), 3.75-3.78 (m, 4H), 5.16-5.24 (m, 1H), 7.01 (d, J = 8.53 Hz, 2H), 7.55 (d, J = 8.53 Hz, 2H), 7.89 (bs, 1H), 12.75 (bs, 1H) | | | |
| I-2-101 | 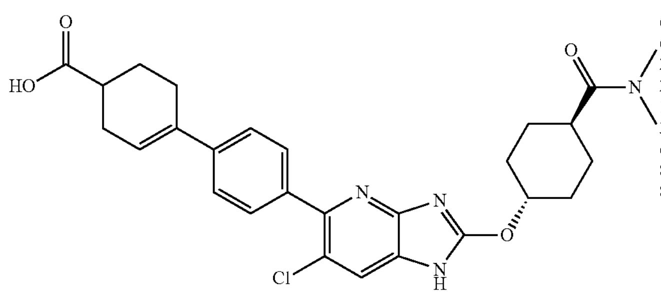 [SMILES: CN(C)C(=O)[C@H]1CC[C@H](Oc2nc3nc(-c4ccc(C5=CCC(C(=O)O)CC5)cc4)c(Cl)cc3[nH]2)CC1] | (DMSO-d6) δ: 1.49-1.60 (m, 4H), 1.77-1.80 (m, 3H), 2.08-2.10 (m, 1H), 2.29-2.40 (m, 7H), 2.68-2.69 (m, 1H), 2.81 (s, 3H), 3 04 (s, 3H), 4.96-4.99 (m, 1H), 6 26 (s, 1H), 7.50 (d, J = 8.3 Hz, 2H), 7.60 (d, J = 8.5 Hz, 2H), 7.96 (s, 1H). | 1.85 | 523.05 | B |

TABLE 37

| No. | Structure | NMR (δ) | retention time | Mass (M + H) | method |
|---|---|---|---|---|---|
| I-2-102 | 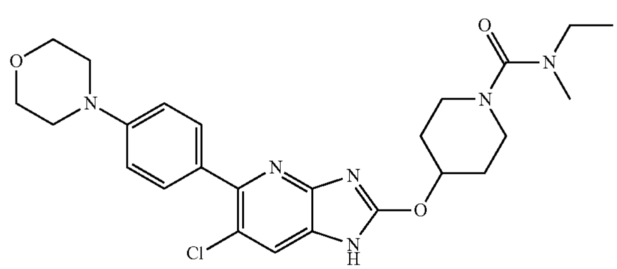 [SMILES: CCN(C)C(=O)N1CCC(Oc2nc3nc(-c4ccc(N5CCOCC5)cc4)c(Cl)cc3[nH]2)CC1] | (DMSO-d6) δ: 1.06 (t, J = 7.19, 3H), 1.65-1.76 (m, 2H), 2.05-2.14 (m, 2H), 2.75 (s, 3H), 2.97-3.03 (m, 2H), 3.13 (q, T = 7.19 Hz, 2H), 3.17-3.19 (m, 4H), 3.40-3.55 (m, 2H), 3.75-3.78 (m, 4H), 5.13-5.20 (m, 1H), 7.00 (d, J = 8.78 Hz, 2H), 7.54 (d, J = 8.78 Hz, 2H), 7.75 (bs, 1H) | | | |

TABLE 37-continued

| No. | Structure | NMR (δ) | retention time | Mass (M + H) | method |
|---|---|---|---|---|---|
| I-2-103 | 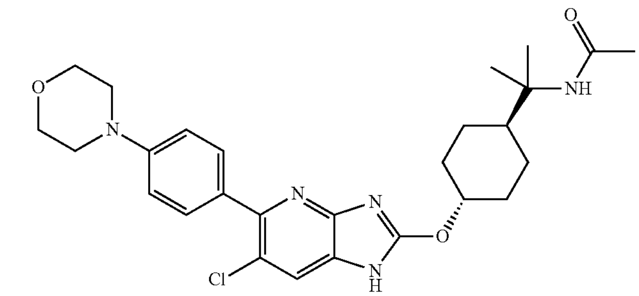 [SMILES: CC(=O)NC(C)(C)[C@H]1CC[C@H](Oc2nc3nc(-c4ccc(N5CCOCC5)cc4)c(Cl)cc3[nH]2)CC1] | (DMSO-d6) δ: 1.16-1.25 (m, 8H), 1.38-1.43 (m, 2H), 1.76 (t, J = 6.4 Hz, 5H), 2.02-2.05 (m, 1H), 2.25-2.28 (m, 2H), 3.18-3.19 (m, 4H), 3.76-3.77 (m, 4H), 4.92-4.95 (m, 1H), 7.01 (d, J = 9.0 Hz, 2H), 7.31 (s, 1H), 7.55 (d, J = 8.8 Hz, 2H), 7.84 (s, 1H), | | | |
| I-2-104 | 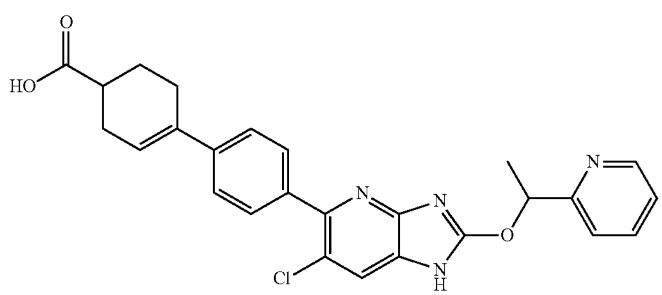 [SMILES: CC(Oc1nc2nc(-c3ccc(C4=CCC(C(=O)O)CC4)cc3)c(Cl)cc2[nH]1)c1ccccn1] | 1H-NMR (DMSO-d6) δ: 1.66-1.78 (m, 4H), 2.10 (d, J = 12.05 Hz, 1H), 2.28-2.61 (m, 5H), 6.20 (q, J = 6.44 Hz, 1H), 6.26 (s, 1H), 7.35 (dd, J = 6.27, 5.27 Hz, 1H), 7.47-7.54 (m, 3H), 7.59 (d, J = 8.03 Hz, 2H), 7.84 (dd, J = 8.03, 6.27 Hz, 1H), 7.88 (s, 1H), 8.58 (d, J = 5.27 Hz, 1H), 12.27 (s, 1H), 12.87 (s, 1H), | | | |
| I-2-105 | 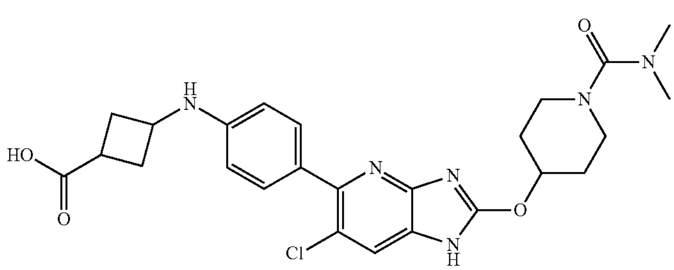 [SMILES: CN(C)C(=O)N1CCC(Oc2nc3nc(-c4ccc(NC5CC(C(=O)O)C5)cc4)c(Cl)cc3[nH]2)CC1] | | 1.53 | 513.25 | B |
| I-2-106 | 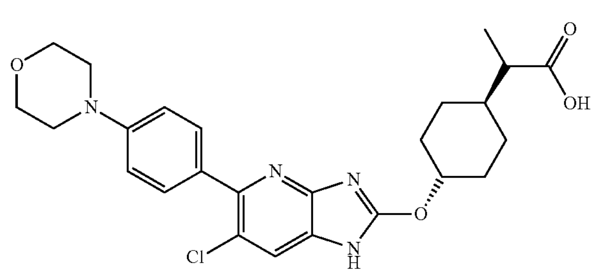 | 1H-NMR (DMSO-d6) δ: 1.05 (d, J = 7.0 Hz, 3H), 1.25 (t, J = 11.7 Hz, 2H), 1.43-1.56 (m, 3H), 1.73 (d, J = 12.3 Hz, 1H), 1.80 (d, J = 12.8 Hz, 1H), 2.20 (dd, J = 17.4, 10.4 Hz, 3H), 3.18 (t, J = 4.4 Hz, 4H), 3.76 (t, J = 4.6 Hz, 4H), 4.91-4.97 (m, 1H), 7.01 (d, J = 8.5 Hz, 2H), 7.55 (d, J = 8.5 Hz, 2H), 7.72-7.89 (m, 1H), 12.13 (s, 1H), 12.26-12.66 (m, 1H). | 1.94 | 485 | A |

TABLE 38

| No. | Structure | NMR (δ) | retention time | Mass (M + H) | method |
|---|---|---|---|---|---|
| I-2-107 | 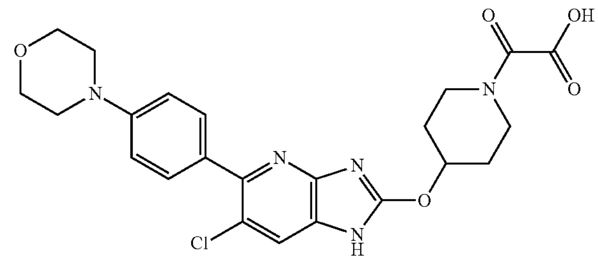 [SMILES: O=C(O)C(=O)N1CCC(Oc2nc3nc(-c4ccc(N5CCOCC5)cc4)c(Cl)cc3[nH]2)CC1] | (DMSO-d6) δ: 1.67-1 85 (m, 2H), 2.15-2.23 (m, 2H), 3.15-3.23 (m, 4H), 3.52-3.56 (m, 2H), 3.73-3.81 (m, 4H), 3.81-3.94) m, 2H), 5.27-5.37 (m, 1H), 7.02 (d, J = 8.62 Hz, 2H), 7.54 (d, J = 8.62 Hz, 2H), 7.91 (s, 1H), 12.79 (s, 1H) | | | |
| I-2-108 | 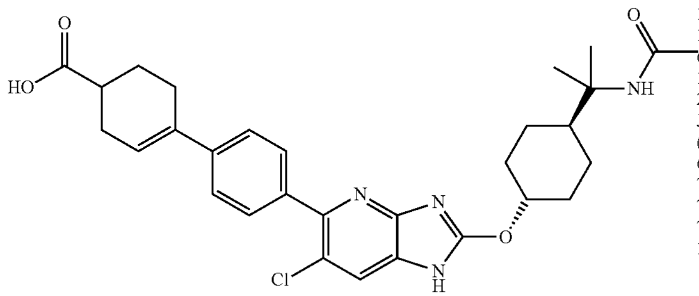 | 1H-NMR (DMSO-d6) δ: 1.17-1.25 (m, 3H), 1.19 (s, 6H), 1.37-1.46 (m, 2H), 1.76 (m, 3H), 1.78 (s, 3H), 2.01-2.12 (m, 3H), 2.27 (d, J = 9.0 Hz, 2H), 2.33-2.45 (m, 2H), 4.92-4.97 (m, 1H), 6.26 (s, 1H), 7.31 (s, 1H), 7.50 (d, J = 8.3 Hz, 2H), 7.60 (d, J = 8.3 Hz, 2H), 7.90 (s, 1H), 12.24 (s, 1H), 12.73 (s, 1H). | 2.05 | 551.3 | B |
| I-2-109 | 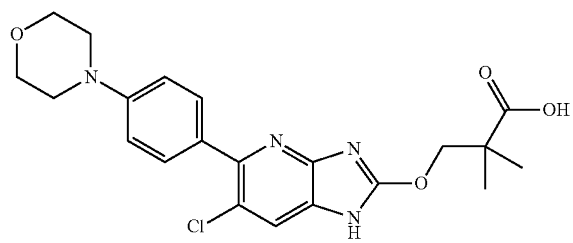 [SMILES: CC(C)(COc1nc2nc(-c3ccc(N4CCOCC4)cc3)c(Cl)cc2[nH]1)C(=O)O] | 1H-NMR (DMSO-d6) δ: 1.24 (s, 6H), 3.18 (dd, J = 5.2, 4.4 Hz, 4H), 3.76 (dd, J = 5.2, 4.4 Hz, 4H), 4.51 (s, 2H), 7.01 (d, J = 8.8 Hz, 2H), 7.54 (d, J = 8.8 Hz, 2H), 7.85 (s, 1H). | | | |
| I-2-110 | 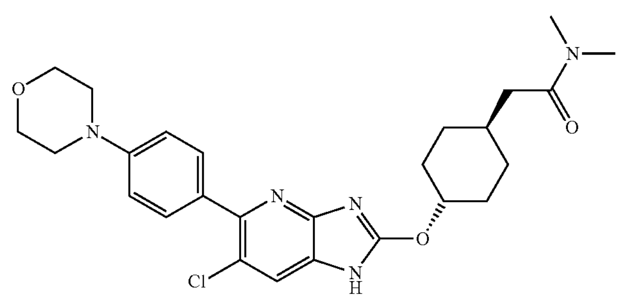 | 1H-NMR (DMSO-d6) δ: 1.14 (dd, J = 23.8, 10.5 Hz, 2H), 1.49 (dd, J = 22.5, 10.7 Hz, 2H), 1.73-1.79 (m, 1H), 1.83 (d, J = 13.8 Hz, 2H), 2.22 (d, J = 6.5 Hz, 4H), 2.81 (s, 3H), 2.97 (s, 3H), 3.18 (t, J = 4.8 Hz, 4H), 3.76 (t, J = 4.8 Hz, 4H), 4.90-4.98 (m, 1H), 7.01 (d, J = 8.8 Hz, 2H), 7.55 (d, J = 8.8 Hz, 2H), 7.84 (s, 1H), 12.54 (s, 1H). | 1.8 | 500.2 | A |
| I-2-111 | 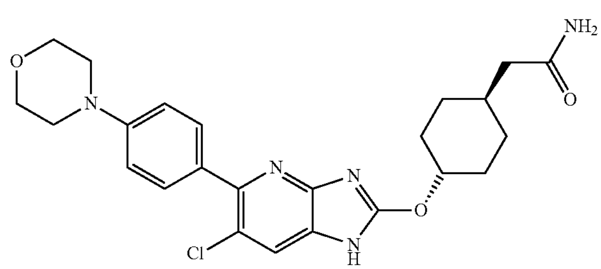 | 1H-NMR (DMSO-d6) δ: 1.11 (dd, J = 24.0, 11.2 Hz, 2H), 1.48 (dd, J = 22.2, 10.9 Hz, 2H), 1.70-1.75 (m, 1H), 1.80 (d, J = 13.3 Hz, 2H), 1.98 (d, J = 7.3 Hz, 2H), 2.21 (d, J = 9.5 Hz, 2H), 3.18 (t, J = 4.8 Hz, 4H), 3.76 (t, J = 4.8 Hz, 4H), 4.92-4.97 (m, 1H), 6.76 (s, 1H), 7.01 (d, J = 8.8 Hz, 2H), 7.28 (s, 1H), 7.55 (d, J = 8.8 Hz, 2H), 7.88 (s, 1H), 12.65 (s, 1H). | 1.59 | 470.2 | A |

TABLE 39

| No. | Structure | NMR (δ) | retention time | Mass (M + H) | method |
|---|---|---|---|---|---|
| I-2-112 | 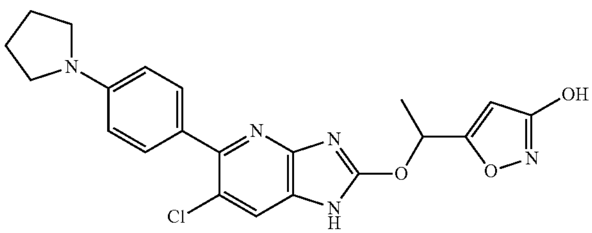 [SMILES: CC(Oc1nc2nc(-c3ccc(N4CCCC4)cc3)c(Cl)cc2[nH]1)c1cc(O)no1] | 1.72 (d, J = 6.78 Hz, 3H), 1.98 (t, J = 6.40 Hz, 4H), 3.28 (t, J = 6.40 Hz, 4H), 6.17 (s, 1H), 6.24 (q, J = 6.78 Hz, 1H), 6.59 (d, J = 8.78 Hz, 2H), 7.52 (d, J = 8.78 Hz, 2H), 7.89 (s, 1H), 11.45 (s, 1H), 12.86 (s, 1H). | | | |
| I-2-113 | 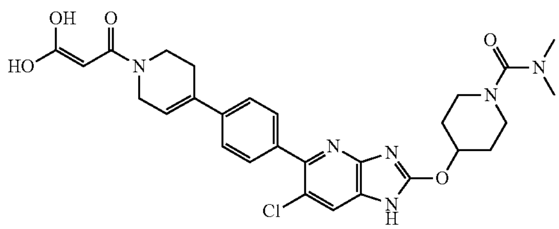 [SMILES: CN(C)C(=O)N1CCC(Oc2nc3nc(-c4ccc(C5=CCN(C(=O)C=C(O)O)CC5)cc4)c(Cl)cc3[nH]2)CC1] | | 1.6 | 567 | A |
| I-2-114 | 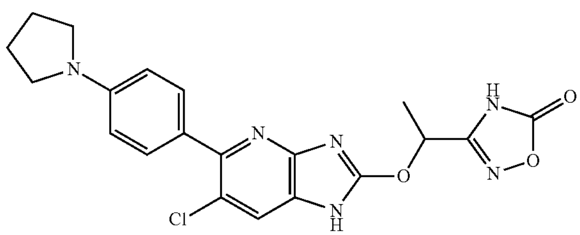 [SMILES: CC(Oc1nc2nc(-c3ccc(N4CCCC4)cc3)c(Cl)cc2[nH]1)c1noc(=O)[nH]1] | 1H-NMR (DMSO-d6) δ: 1.72 (d, J = 6.78 Hz, 3H), 1.98 (t, J = 6.40 Hz, 4H), 3.28 (t, J = 6.40 Hz, 4H), 6.11 (q, J = 6.69 Hz, 1H), 6.60 (d, J = 8.53 Hz, 2H), 7.52 (d, J = 8.53 Hz, 2H), 7.92 (s, 1H), 12.50-13.10 (m, 2H). | | | |
| I-2-115 | 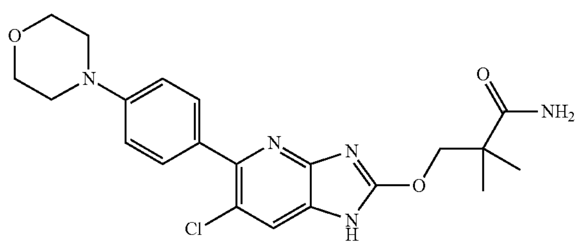 [SMILES: CC(C)(COc1nc2nc(-c3ccc(N4CCOCC4)cc3)c(Cl)cc2[nH]1)C(N)=O] | 1H-NMR (DMSO-d6) δ: 1.20 (s, 6H), 3.18 (dd, J = 5.2, 4.4 Hz, 4H), 3.76 (dd, J = 5.2, 4.4 Hz, 4H), 4.49 (s, 2H), 7.00-7.02 (m, 3H), 7.29 (s, 1H), 7.54 (d, J = 8.5 Hz, 2H), 7.83 (s, 1H). | | | |
| I-2-116 | 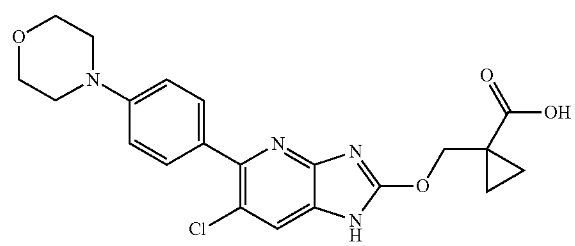 [SMILES: O=C(O)C1(COc2nc3nc(-c4ccc(N5CCOCC5)cc4)c(Cl)cc3[nH]2)CC1] | 1H-NMR (DMSO-d6) δ: 1.14 (s, 2H), 1.24 (s, 2H), 3.18 (dd, J = 5.2, 4.4 Hz, 4H), 3.75 (dd, J = 5.2, 4.4 Hz, 4H), 4.60 (s, 2H), 7.01 (d, J = 8.4 Hz, 2H), 7.55 (d, J = 8.4 Hz, 2H), 7.85 (s, 1H). | | | |
| I-2-117 | 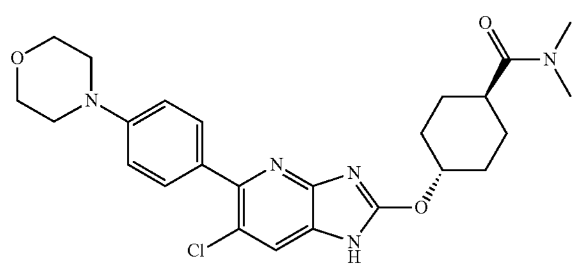 [SMILES: CN(C)C(=O)[C@H]1CC[C@H](Oc2nc3nc(-c4ccc(N5CCOCC5)cc4)c(Cl)cc3[nH]2)CC1] | (DMSO-d6) δ: 1.50-1.57 (m, 5H), 1.78-1.81 (m, 2H), 2.24-2.26 (m, 2H), 2.81 (s, 3H), 3.04 (s, 3H), 3.17-3.20 (m, 4H), 3.75-3.77 (m, 4H), 4.94-4.96 (m, 1H), 7.01 (d, J = 8.2 Hz, 2H), 7.55 (d, J = 8.4 Hz, 2H), 7.90 (s, 1H). | 1.75 | 484.1 | B |

TABLE 40

| No. | Structure | NMR (δ) | retention time | Mass (M + H) | method |
|---|---|---|---|---|---|
| I-2-118 | 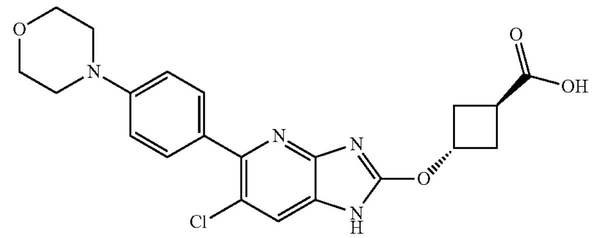 [SMILES: O=C(O)[C@H]1C[C@H](Oc2nc3nc(-c4ccc(N5CCOCC5)cc4)c(Cl)cc3[nH]2)C1] | (DMSO-d6) δ: 2.26-2.33 (m, 2H), 2.72-2.77 (m, 3H), 3.18-3.19 (m, 4H), 3.75-3.77 (m, 4H), 5.21-5.23 (m, 1H), 7.01 (d, J = 8.8 Hz, 2H), 7.55 (d, J = 8.8 Hz, 2H), 7.85 (s, 1H). | 1.61 | 429.85 | B |
| I-2-119 | 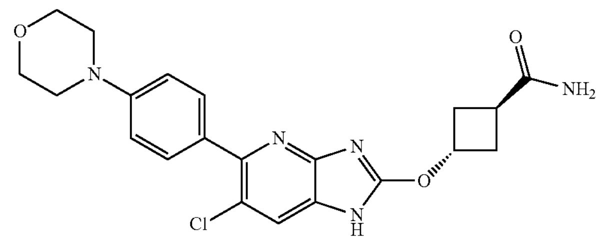 [SMILES: NC(=O)[C@H]1C[C@H](Oc2nc3nc(-c4ccc(N5CCOCC5)cc4)c(Cl)cc3[nH]2)C1] | (DMSO-d6) δ: 2.24-2.26 (m, 2H), 2.62-2.68 (m, 3H), 3.19-3.20 (m, 4H), 3.76-3.77 (m, 4H), 5.19-5.23 (m, 1H), 6.90 (s, 1H), 7.01 (d, J = 8.5 Hz, 2H), 7.38 (s, 1H), 7.55 (d, J = 8.5 Hz, 2H), 7.85 (s, 1H). | 1.46 | 428.25 | B |
| I-2-120 | 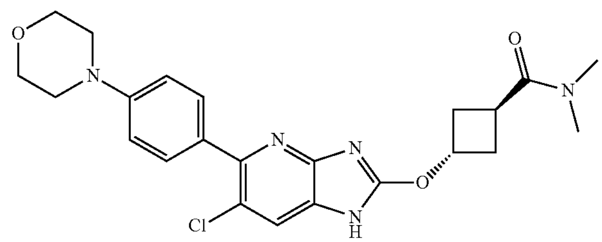 [SMILES: CN(C)C(=O)[C@H]1C[C@H](Oc2nc3nc(-c4ccc(N5CCOCC5)cc4)c(Cl)cc3[nH]2)C1] | (DMSO-d6) δ: 2.26-2.31 (m, 2H), 2.68-2.71 (m, 2H), 2.83 (s, 3H), 2.93 (s, 3H), 3.04-3.12 (m, 1H), 3.18-3.19 (m, 4H), 3.76-3.77 (m, 4H), 5.23-5.25 (m, 1H), 7.01 (d, J = 8.5 Hz, 2H), 7.55 (d, J = 8.4 Hz, 2H), 7.84 (s, 1H). | 1.67 | 456.3 | B |
| I-2-121 | 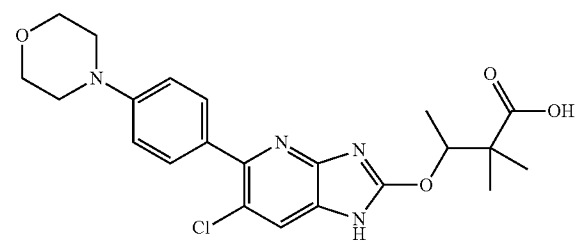 [SMILES: CC(Oc1nc2nc(-c3ccc(N4CCOCC4)cc3)c(Cl)cc2[nH]1)C(C)(C)C(=O)O] | 1H-NMR (DMSO-d6) δ: 1.17 (s, 3H), 1.22 (s, 3H), 1.35 (d, J = 6.1 Hz, 3H), 3.18 (brs, 4H), 3.76 (brs, 4H), 5.46-5.47 (m, 1H), 7.01 (d, J = 8.2 Hz, 2H), 7.54 (d, J = 8.2 Hz, 2H), 7.85 (brs, 1H). | | | |
| I-2-122 | 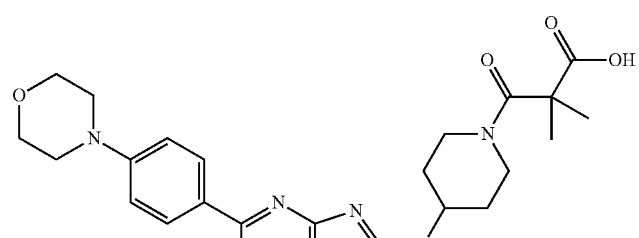 | | 1.68 | 528.4 | B |
| I-2-123 | 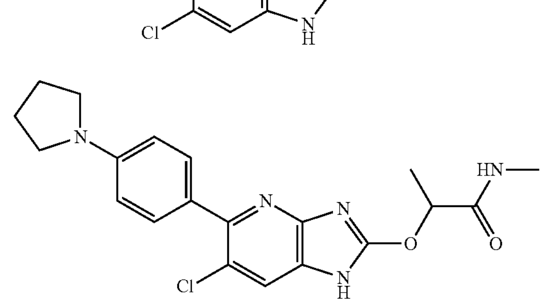 | 1H-NMR (DMSO-d6) δ: 1.51 (d, J = 6.78 Hz, 3H), 1.98 (t, J = 6.40 Hz, 4H), 2.61 (d, J = 4.52 Hz, 3H), 3.28 (t, J = 6.40 Hz, 4H), 5.34 (q, J = 6.78 Hz, 1H), 6.59 (d, J = 8.78 Hz, 2H), 7.51 (d, J = 8.78 Hz, 2H), 7.86 (s, 1H), 8.14 (q, J = 4.27 Hz, 1H), 12.76 (s, 1H). | | | |

TABLE 41

| No. | Structure | NMR (δ) | retention time | Mass (M + H) | method |
|---|---|---|---|---|---|
| I-2-124 | 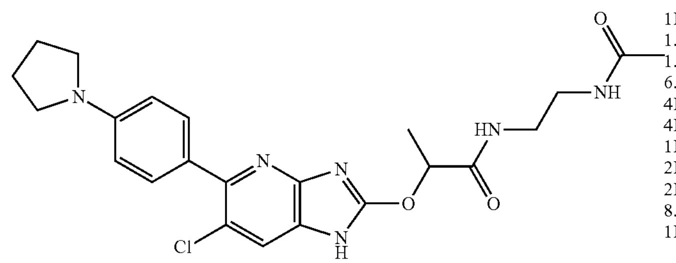 | 1H-NMR (DMSO-d6) δ: 1.52 (d, J = 6.53 Hz, 3H), 1.75 (s, 3H), 1.98 (t, J = 6.27 Hz, 4H), 3.05-3.20 (m, 4H), 3.28 (t, J = 6.27 Hz, 4H), 5.33 (q, J = 6.53 Hz, 1H), 6.59 (d, J = 8.78 Hz, 2H), 7.51 (d, J = 8.78 Hz, 2H), 7.73-7.90 (m, 2H), 8.20-8.30 (m, 1H), 12.77 (s, 1H). | | | |
| I-2-125 | 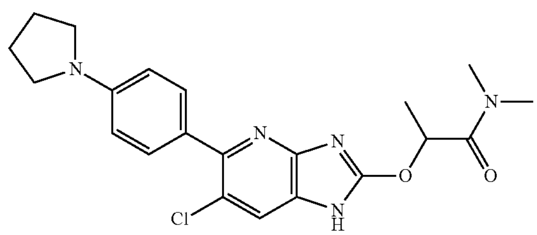 [SMILES: CC(Oc1nc2nc(-c3ccc(N4CCCC4)cc3)c(Cl)cc2[nH]1)C(=O)N(C)C] | 1H-NMR (DMSO-d6) δ: 1.50 (d, J = 6.61 Hz, 3H), 1.98 (t, J = 6.40 Hz, 4H), 2.85 (s, 3H), 3.11 (s, 3H), 3.28 (t, J = 6.40 Hz, 4H), 5.83 (q, J = 6.61 Hz, 1H), 6.59 (d, J = 8.78 Hz, 2H), 7.50 (d, J = 8.78 Hz, 2H), 7.84 (s, 1H), 12.79 (s, 1H), | | | |
| I-2-126 | 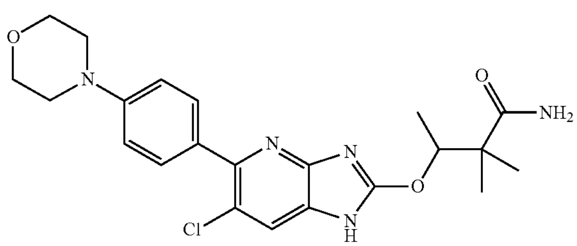 [SMILES: CC(Oc1nc2nc(-c3ccc(N4CCOCC4)cc3)c(Cl)cc2[nH]1)C(C)(C)C(N)=O] | 1H-NMR (DMSO-d6) δ: 1.15 (s, 3H), 1.18 (s, 3H), 1.31 (d, J = 6.3 Hz, 3H), 3.19 (dd, J = 5.2, 4.4 Hz, 4H), 3.76 (dd, J = 5.2, 4.4 Hz, 4H), 5.44-5.49 (m, 1H), 6.98-7.02 (m, 3H), 7.24 (s, 1H), 7.54 (d, J = 8.5 Hz, 2H), 7.82 (brs, 1H). | | | |
| I-2-127 | 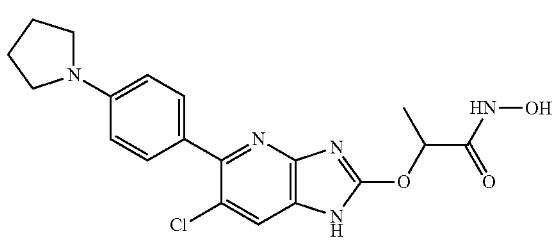 [SMILES: CC(Oc1nc2nc(-c3ccc(N4CCCC4)cc3)c(Cl)cc2[nH]1)C(=O)NO] | 1H-NMR(DMSO-d6) δ: 1.52 (d, J = 6.78 Hz, 3H), 1.98 (t, J = 6.40 Hz, 4H), 3.28 (t, J = 6.40 Hz, 4H), 5.30 (q, J = 6.78 Hz, 1H), 6.59 (d, J = 8.78 Hz, 2H), 7.51 (d, J = 8.78 Hz, 2H), 7.82 (s, 1H), 9.03 (s, 1H), 10.95 (s, 1H), 12.78 (s, 1H). | | | |
| I-2-128 | 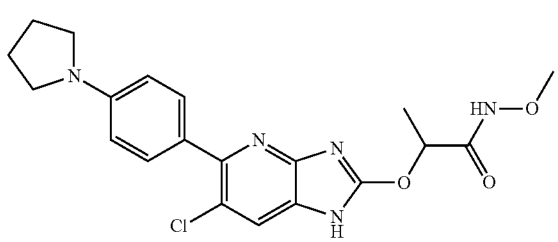 [SMILES: CONC(=O)C(C)Oc1nc2nc(-c3ccc(N4CCCC4)cc3)c(Cl)cc2[nH]1] | 1H-NMR(DMSO-d6) δ: 1.53 (d, J = 6.53 Hz, 3H), 1.98 (t, J = 6.40 Hz, 4H), 3.28 (t, J = 6.40 Hz, 4H), 3.60 (s, 3H), 5.25 (q, J = 6.53 Hz, 1H), 6.59 (d, J = 8.53 Hz, 2H), 7.51 (d, J = 8.53 Hz, 2H), 7.87 (s, 1H), 11.58 (s, 1H), 12.82 (s, 1H). | | | |

TABLE 42

| No. | Structure | NMR (δ) | retention time | Mass (M + H) | method |
|---|---|---|---|---|---|
| I-2-129 | 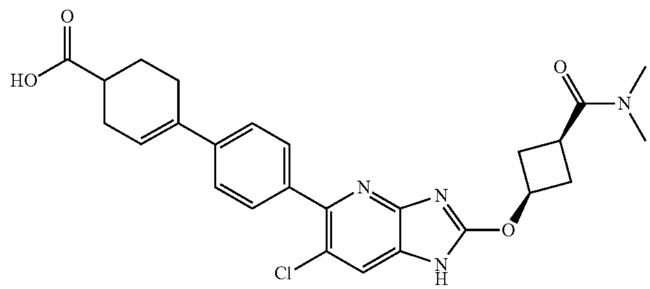 [SMILES: CN(C)C(=O)[C@H]1C[C@@H](Oc2nc3nc(-c4ccc(C5=CCC(C(=O)O)CC5)cc4)c(Cl)cc3[nH]2)C1] | (DMSO-d6) δ: 1.75-1.77 (m, 2H), 2.09-2.12 (m, 1H), 2.28-2.43 (m, 5H), 2.70-2.72 (m, 3H), 2.84 (s, 3H), 2.92 (s, 3H), 3.06-3.10 (m, 1H), 5.21-5.28 (m, 1H), 6.27 (s, 1H), 7.50 (d, J = 7.9 Hz, 2H), 7.60 (d, J = 7.9 Hz, 2H), 7.90 (s, 1H). | 1.79 | 495.35 | B |
| I-2-130 | 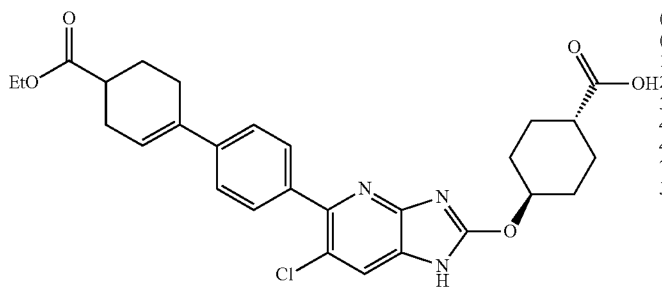 | (DMSO-d6) δ: 1.21-1.22 (m, 3H), 1.41-1.46 (m, 4H), 1.75-1.78 (m, 1H), 1.95-2.13 (m, 7H), 2.35-2.38 (m, 3H), 2.62-2.67 (m, 1H), 4.10-4.12 (m, 2H), 4.81-4.84 (m, 1H), 6.23 (s, 1H), 7.44-7.46 (m, 3H), 7.59 (d, J = 8.0 Hz, 2H). | 2.37 | 524.1 | B |
| I-2-131 | 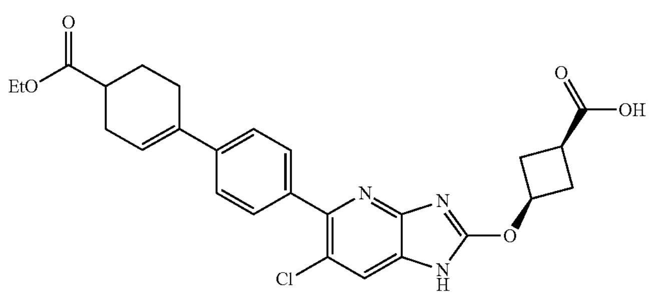 [SMILES: CCOC(=O)C1CC=C(c2ccc(-c3nc4nc(O[C@H]5C[C@@H](C(=O)O)C5)[nH]c4cc3Cl)cc2)CC1] | (DMSO-d6) δ: 1.21 (t, J = 7.0 Hz, 3H), 1.73-1.75 (m, 1H), 2.08-2.10 (m, 1H), 2.36-2.41 (m, 6H), 2.61-2.63 (m, 4H), 4.11 (q, J = 7.0 Hz, 2H), 5.13-5.16 (m, 1H), 6.24 (s, 1H), 7.46 (d, J = 8.2 Hz, 2H), 7.58-7.60 (m, 3H). | 2.27 | 496.35 | B |
| I-2-132 | 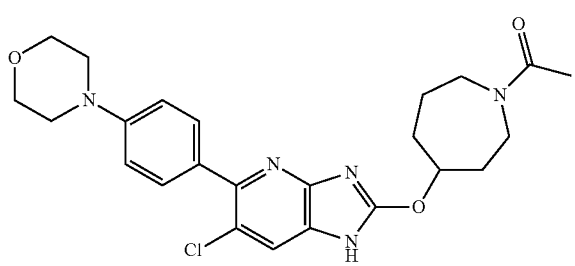 [SMILES: CC(=O)N1CCCC(Oc2nc3nc(-c4ccc(N5CCOCC5)cc4)c(Cl)cc3[nH]2)CC1] | | 1.67 | 470.95 | B |
| I-2-133 | 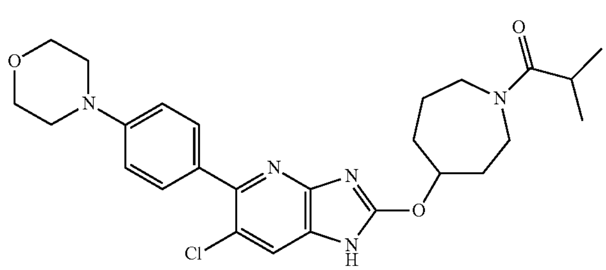 [SMILES: CC(C)C(=O)N1CCCC(Oc2nc3nc(-c4ccc(N5CCOCC5)cc4)c(Cl)cc3[nH]2)CC1] | | 1.91 | 499.00 | B |

TABLE 42-continued
| No. | Structure | NMR (δ) | retention time | Mass (M + H) | method |
|---|---|---|---|---|---|
| I-2-134 | 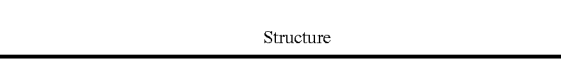 | | 1.82 | 500.00 | B |
TABLE 43
| No. | Structure | NMR (δ) | retention time | Mass (M + H) | method |
|---|---|---|---|---|---|
| I-2-135 | 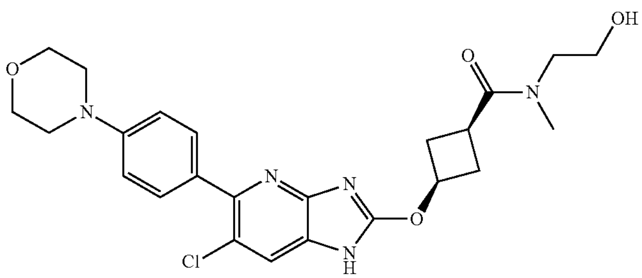 [SMILES: CN(CCO)C(=O)[C@H]1C[C@@H](Oc2nc3nc(-c4ccc(N5CCOCC5)cc4)c(Cl)cc3[nH]2)C1] | (DMSO-d6) δ: 2.24-2.37 (m, 3H), 2.59-2.78 (m, 3H), 2.79-3.12 (m, 5H), 3.12-3.25 (m, 4H), 3.43-3.58 (m, 2H), 3.70-3.86 (m, 4H), 4.58-4.87 (m, 1H), 5.20-5.25 (m, 1H), 7.01 (d, J = 8.4 Hz, 2H), 7.55 (d, J = 8.3 Hz, 2H), 7.89 (s, 1H). | 1.51 | 486.05 | B |
| I-2-136 | 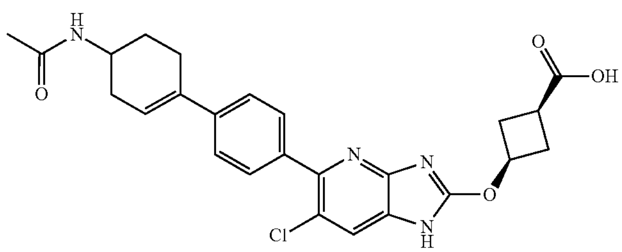 [SMILES: CC(=O)NC1CC=C(c2ccc(-c3nc4nc(O[C@H]5C[C@@H](C(=O)O)C5)[nH]c4cc3Cl)cc2)CC1] | (DMSO-d6) δ: 1.60-1.63 (m, 1H), 1.82 (s, 3H), 1.90-1.92 (m, 1H), 2.10-2.13 (m, 1H), 2.28-2.31 (m, 2H), 2.42-2.44 (m, 2H), 2.67-2.83 (m, 4H), 3.84-3.87 (m, 1H), 5.23-5.25 (m, 1H), 6.20 (s, 1H), 7.51 (d, J = 7.8 Hz, 2H), 7.60 (d, J = 7.9 Hz, 2H), 7.87-7.89 (m, 2H). | 1.59 | 481.2 | B |
| I-2-137 | 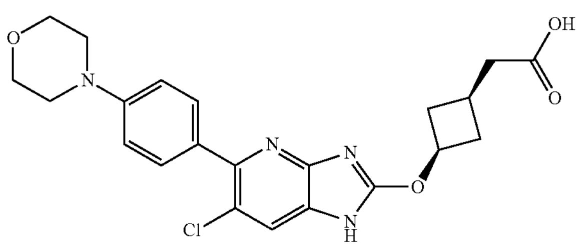 [SMILES: O=C(O)C[C@H]1C[C@@H](Oc2nc3nc(-c4ccc(N5CCOCC5)cc4)c(Cl)cc3[nH]2)C1] | (DMSO-d6) δ: 1.84-1.92 (m, 2H), 2.20-2.28 (m, 1H), 2.44 (d, J = 7.3 Hz, 2H), 2.63-2.69 (m, 2H), 3.18-3.19 (m, 4H), 3.75-3.77 (m, 4H), 5.12-5.19 (m, 1H), 7.01 (d, J = 8.8 Hz, 2H), 7.55 (d, J = 8.8 Hz, 2H), 7.85 (s, 1H). | 1.66 | 443.2 | B |
| I-2-138 | 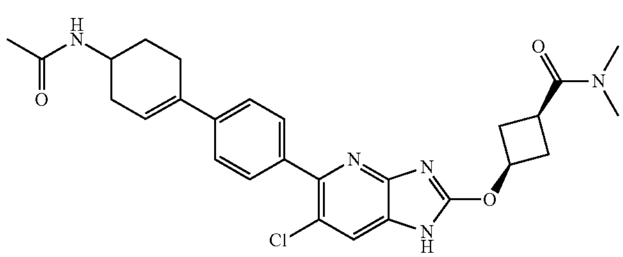 [SMILES: CC(=O)NC1CC=C(c2ccc(-c3nc4nc(O[C@H]5C[C@@H](C(=O)N(C)C)C5)[nH]c4cc3Cl)cc2)CC1] | (DMSO-d6) δ: 1.58-1.64 (m, 1H), 1.82 (s, 3H), 1.91-1.95 (m, 1H), 2.06-2.10 (m, 1H), 2.27-2.32 (m, 2H), 2.42-2.45 (m, 3H), 2.69-2.71 (m, 2H), 2.84 (s, 3H), 2.92 (s, 3H), 3.04-3.13 (m, 1H), 3.86 (s, 1H), 5.20-5.28 (m, 1H), 6.19 (s, 1H), 7.51 (d, J = 8.0 Hz, 2H), 7.60 (d, J = 7.9 Hz, 2H), 7.87-7.89 (m, 2H). | 1.67 | 508.2 | B |

TABLE 43-continued

| No. | Structure | NMR (δ) | retention time | Mass (M + H) | method |
|---|---|---|---|---|---|
| I-2-139 | 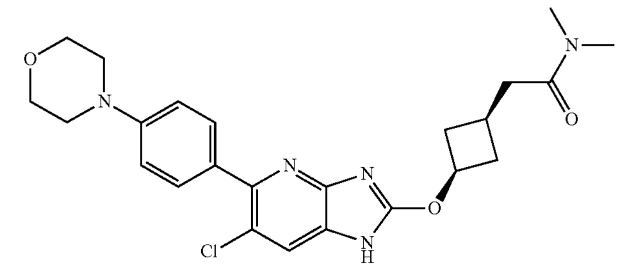 [SMILES: CN(C)C(=O)C[C@H]1C[C@@H](Oc2nc3nc(-c4ccc(N5CCOCC5)cc4)c(Cl)cc3[nH]2)C1] | (DMSO-d6) δ: 1.82-1.85 (m, 2H), 2.21-2.29 (m, 1H), 2.53-2.55 (m, 2H), 2.61-2.64 (m, 2H), 2.80 (s, 3H), 2.94 (s, 3H), 3.18-3.19 (m, 4H), 3.75-3.77 (m, 4H), 5.10-5.18 (m, 1H), 7.01 (d, J = 8.4 Hz, 2H), 7.54 (d, J = 8.4 Hz, 2H), 7.81 (s, 1H), | 1.69 | 470.25 | B |

TABLE 44

| No. | Structure | NMR (δ) | retention time | Mass (M + H) | method |
|---|---|---|---|---|---|
| I-2-140 | 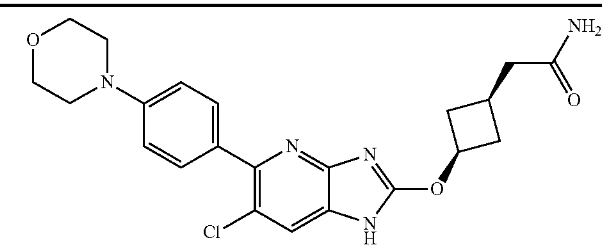 | (DMSO-d6) δ: 1.86-1.88 (m, 2H), 2.24-2.29 (m, 3H), 2.61-2.64 (m, 2H), 3.18-3.19 (m, 4H), 3.76-3.77 (m, 4H), 5.13-5.15 (m, 1H), 6.77 (s, 1H), 7.01 (d, J = 8.5 Hz, 2H), 7.27 (s, 1H), 7.55 (d, J = 8.3 Hz, 2H), 7.83 (s, 1H). | 1.49 | 442.25 | B |

TABLE 45

| No. | Structure | NMR (δ) | retention time | Mass (M + H) | method |
|---|---|---|---|---|---|
| I-3-2 | 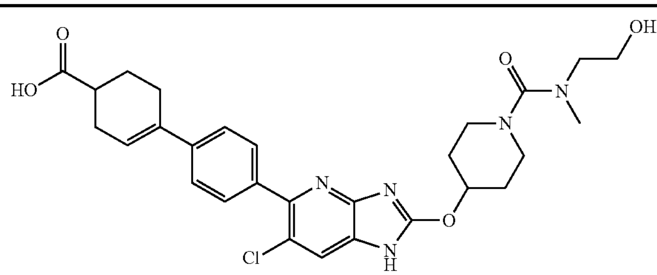 | (DMSO-d6) δ: 1.66-1.80 (m, 3H), 1.99-2.17 (m, 3H), 2.33-2.60 (m, 5H), 2.82 (s, 3H), 3.00-3.05 (m, 2H), 3.17-3.20 (m, 2H), 3.41-3.48 (m, 2H), 3.51-3.58 (m, 2H), 4.71 (t, J = 4.9 Hz, 1H), 5.22 (s, 1H), 6.27 (s, 1H), 7.51 (d, J = 8.0 Hz, 2H), 7.60 (d, J = 8.0 Hz, 2H), 7.95 (s, 1H), 12.25 (s, 1H), 12.82 (s, 1H) | | | |
| I-3-3 | 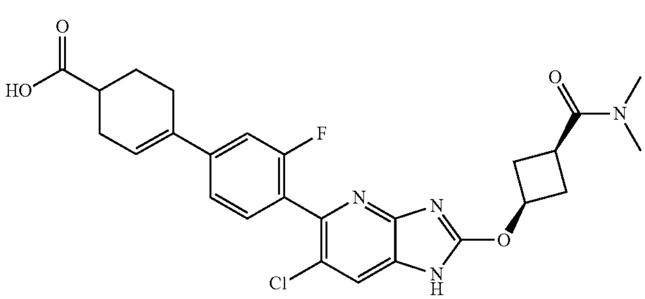 [SMILES: CN(C)C(=O)[C@H]1C[C@@H](Oc2nc3nc(-c4ccc(C5=CCC(C(=O)O)CC5)cc4F)c(Cl)cc3[nH]2)C1] | (DMSO-D6) δ: 1.69-1.75 (1H, m), 2.07-2.12 (1H, m), 2.26-2.43 (4H, m), 2.67-2.75 (2H, m), 2.83 (3H, s), 2.93 (3H, s), 3.04-3.20 (4H, m), 5.24 (1H, m), 6.36 (1H, brs), 7.31-7.40 (3H, m), 7.90 (1H, s). | | | |

TABLE 45-continued

| No. | Structure | NMR (δ) | retention time | Mass (M + H) | method |
|---|---|---|---|---|---|
| I-3-4 | 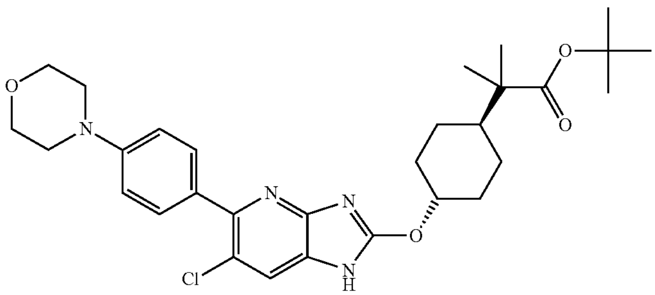 | 1H-NMR (DMSO-D6) δ: 1.03 (s, 6H), 1.18-1.26 (m, 2H), 1.38-1.52 (m, 11H), 1.58 (t, J = 11.9 Hz, 1H), 1.68 (d, J = 11.9 Hz, 2H), 2.27 (d, J = 7.8 Hz, 2H), 3.18 (t, J = 4.6 Hz, 4H), 3.76 (t, J = 4.6 Hz, 4H), 4.86-4.96 (m, 1H), 7.01 (d, J = 8.9 Hz, 2H), 7.55 (d, J = 8.8 Hz, 2H), 7.80 (br s, 1H), 12.44 (br s, 1H). | 2.87 | 557.3 | A |
| I-3-5 | 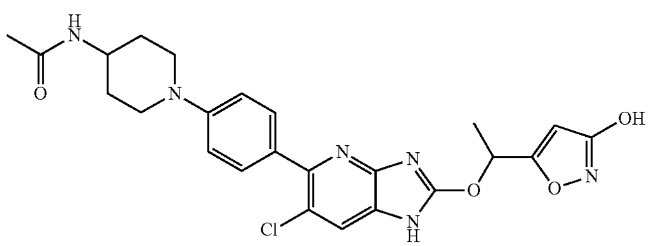 [SMILES: CC(=O)NC1CCN(c2ccc(-c3nc4nc(OC(C)c5cc(O)no5)[nH]c4cc3Cl)cc2)CC1] | (DMSO-D6) δ: 1.40-1.54 (m, 2H), 1.72 (d, J = 6.53 Hz, 3H), 1.78-1.85 (m, 2H), 1.80 (s, 3H), 2.87 (t, J = 11.17 Hz, 2H), 3.71- 3.80 (m, 3H), 6.18 (s, 1H), 6.24 (q, J = 6.53 Hz, 1H), 7.00 (d, J = 8.78 Hz, 2H), 7.53 (d, J = 8.78 Hz, 2H), 7.84 (d, J = 7.53 Hz, 1H), 7.91 (br s, 1H), 11.45 (br s, 1H), 12.89 (br s, 1H). | | | |
| I-3-6 | 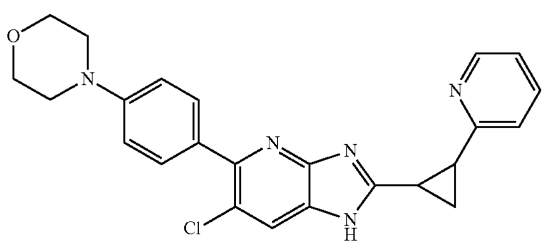 [SMILES: Clc1cc2[nH]c(C3CC3c3ccccn3)nc2nc1-c1ccc(N2CCOCC2)cc1] | (DMSO-D6) δ: 1.76-1.85 (m, 2H), 2.67 (m, 1H), 2.80 (m, 1H), 3.20 (t, J = 4.64 Hz, 4H), 3.76 (t J = 4.64 Hz, 4H), 7.03 (d, J = 9.03 Hz, 2H), 7.22 (dd, J = 6.90, 5.14 Hz, 1H), 7.48 (d, J = 7.65 Hz, 1H), 7.57 (d, J = 9.03 Hz, 2H), 7.71 (dd, J = 7.65, 6.90 Hz, 1H), 8.05 (s, 1H), 8.50 (d, J = 5.14 Hz, 1H), 13.12 (br s, 1H). | | | |
| I-3-7 | 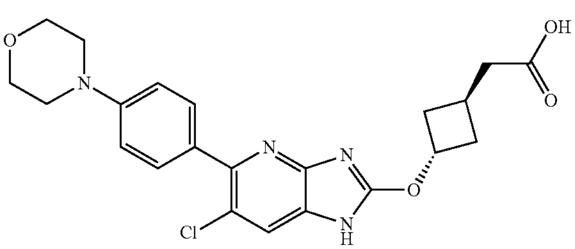 [SMILES: O=C(O)C[C@H]1C[C@H](Oc2nc3nc(-c4ccc(N5CCOCC5)cc4)c(Cl)cc3[nH]2)C1] | 1H-NMR (DMSO-D6) δ: 2.29-2.36 (m, 3H), 2.46-2.48 (m, 2H), 2.62-2.66 (m, 2H), 3.17-3.19 (m, 4H), 3.75-3.77 (m, 4H), 5.34-5.41 (m, 1H), 7.00 (d, J = 8.9 Hz, 2H), 7.54 (d, J = 8.8 Hz, 2H), 7.79 (s, 1H). | 1.59 | 443.0 | A |

TABLE 46

| No. | Structure | NMR (δ) | retention time | Mass (M + H) | method |
|---|---|---|---|---|---|
| I-3-8 | 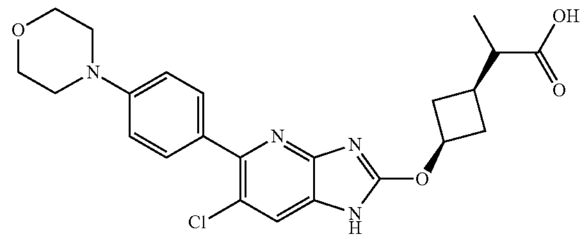 [SMILES: CC(C(=O)O)[C@H]1C[C@@H](Oc2nc3nc(-c4ccc(N5CCOCC5)cc4)c(Cl)cc3[nH]2)C1] | 1H-NMR (DMSO-D6) δ: 1.01 (d, J = 7.0 Hz, 3H), 1.81-2.09 (m, 3H), 2.30-2.39 (m, 1H), 2.55-2.62 (m, 2H), 3.17-3.19 (m, 4H), 3.75-3.77 (m, 4H), 5.09-5.16 (m, 1H), 7.00 (d, J = 9.0 Hz, 2H), 7.54 (d, J = 8.8 Hz, 2H), 7.79 (s, 1H). | 1.71 | 457.0 | A |
| I-3-9 | 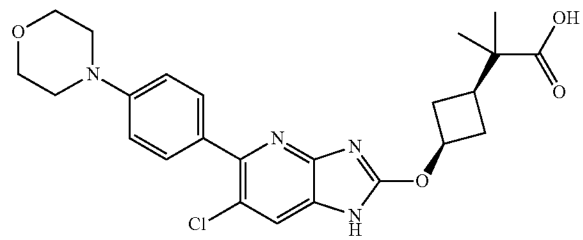 [SMILES: CC(C)(C(=O)O)[C@H]1C[C@@H](Oc2nc3nc(-c4ccc(N5CCOCC5)cc4)c(Cl)cc3[nH]2)C1] | 1H-NMR (DMSO-D6) δ: 1.06 (s, 6H), 1.93-1.99 (m, 2H), 2.13-2.22 (m, 1H), 2.45-2.47 (m, 2H), 3.18 (t, J = 4.9 Hz, 4H), 3.76 (t, J = 4.6 Hz, 4H), 5.08-5.15 (m, 1H), 7.01 (d, J = 9.0 Hz, 2H), 7.55 (d, J = 8.8 Hz, 2H), 7.88 (s, 1H). | 1.91 | 472.0 | B |
| I-3-10 | 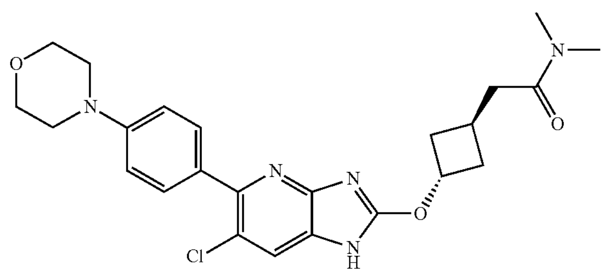 [SMILES: CN(C)C(=O)C[C@H]1C[C@H](Oc2nc3nc(-c4ccc(N5CCOCC5)cc4)c(Cl)cc3[nH]2)C1] | 1H-NMR (DMSO-D6) δ: 2.22-2.25 (m, 2H), 2.30-2.37 (m, 2H), 2.57-2.59 (m, 2H), 2.62-2.67 (m, 1H), 2.81 (s, 3H), 2.98 (s, 3H), 3.19 (dd, J = 10.4, 5.6 Hz, 4H), 3.76 (t, J = 4.8 Hz, 4H), 5.37-5.43 (m, 1H), 7.00 (d, J = 8.8 Hz, 2H), 7.54 (d, J = 8.8 Hz, 2H), 7.79 (s, 1H). | 1.70 | 470.0 | B |
| I-3-11 | 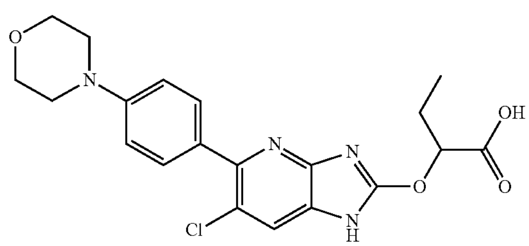 [SMILES: CCC(Oc1nc2nc(-c3ccc(N4CCOCC4)cc3)c(Cl)cc2[nH]1)C(=O)O] | (DMSO-D6) δ: 1.04 (t, J = 7.4 Hz, 3H), 1.90-2.05 (m, 2H), 3.19 (dd, J = 4.8, 4.4 Hz, 4H), 3.76 (dd, J = 4.8, 4.4 Hz, 4H), 5.23-5.26 (m, 1H), 7.01 (d, J = 9.0 Hz, 2H), 7.55 (d, J = 9.0 Hz, 2H), 7.88 (s, 1H). | | | |
| I-3-12 | 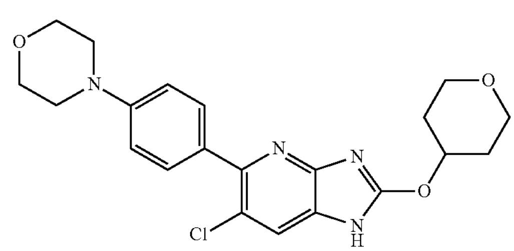 [SMILES: Clc1cc2[nH]c(OC3CCOCC3)nc2nc1-c1ccc(N2CCOCC2)cc1] | (DMSO-d6) δ: 1.16-1.78 (m, 2H), 2.08-2.17 (m, 2H), 3.17-3.20 (m, 4H), 3.48-3.55 (m, 2H), 3.86-3.91 (m, 4H), 4.00-4.06 (m, 2H), 5.20-5.27 (m, 1H), 7.01 (d, J = 9.0 Hz, 2H), 7.55 (d, J = 9.0 Hz, 2H), 7.86 (s, 1H) | | | |
| I-3-13 | 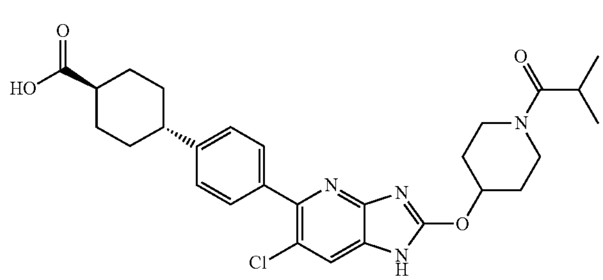 [SMILES: CC(C)C(=O)N1CCC(Oc2nc3nc(-c4ccc([C@H]5CC[C@H](C(=O)O)CC5)cc4)c(Cl)cc3[nH]2)CC1] | (DMSO-D6) δ: 1.01 (6H, J = 6.5 Hz, d), 1.48-1.53 (3H, m), 1.54-1.75 (2H, m), 1.87-1.91 (2H, m), 1.98-2.16 (4H, m), 2.26-2.32 (1H, m), 2.50-2.60 (2H, m), 2.88-2.95 (1H, m), 3.20-3.30 (2H, m), 3.78-3.83 (1H, m), 3.93-3.99 (1H, m), 5.21-5.29 (1H, m), 7.31 (2H, J = 8.3 Hz, d), 7.55 (2H, J = 8.3 Hz, d), 7.83 (1H, s). | | | |

TABLE 47

| No. | Structure | NMR (δ) | retention time | Mass (M + H) | method |
|---|---|---|---|---|---|
| I-3-14 | 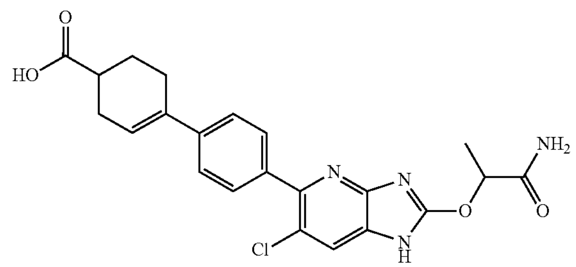 [SMILES: CC(Oc1nc2nc(-c3ccc(C4=CCC(C(=O)O)CC4)cc3)c(Cl)cc2[nH]1)C(N)=O] | (DMSO-D6) δ: 1.53 (d, J = 6.78 Hz, 3H), 1.73 (m, 1H), 2.11 (m, 1H), 2.33-2.56 (m, 4H), 5.32 (q, J = 6.78 Hz, 1H), 6.26 (br s, 1H), 7.26 (s, 1H), 7.50 (d, J = 8.53 Hz, 2H), 7.60 (d, J = 8.53 Hz, 2H), 7.64 (s, 1H), 7.90 (s, 1H), 12.27 (s, 1H), 12.84 (s, 1H). | | | |
| I-3-15 | 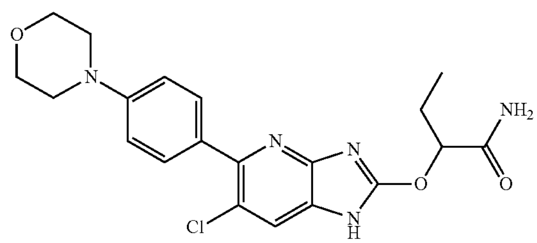 [SMILES: CCC(Oc1nc2nc(-c3ccc(N4CCOCC4)cc3)c(Cl)cc2[nH]1)C(N)=O] | (DMSO-D6) δ: 1.00 (t, J = 7.4 Hz, 3H), 1.86-1.96 (m, 2H), 3.19 (dd, J = 4.8, 4.4 Hz, 4H), 3.76 (dd, J = 4.8, 4.4 Hz, 4H), 5.17-5.20 (m, 1H), 7.01 (d, J = 9.0 Hz, 2H), 7.28 (s, 1H), 7.55 (d, J = 9.0 Hz, 2H), 7.63 (s, 1H), 7.84 (s, 1H). | | | |
| I-3-16 | 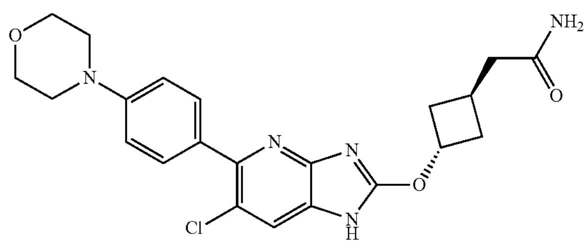 [SMILES: NC(=O)C[C@H]1C[C@H](Oc2nc3nc(-c4ccc(N5CCOCC5)cc4)c(Cl)cc3[nH]2)C1] | 1H-NMR (DMSO-D6) δ: 2.27-2.34 (m, 5H), 2.63-2.66 (m, 2H), 3.18-3.19 (m, 4H), 3.75-3.77 (m, 4H), 5.38 (t, J = 6.7 Hz, 1H), 6.80 (s, 1H), 7.01 (d, J = 8.9 Hz, 2H), 7.34 (s, 1H), 7.55 (d, J = 8.8 Hz, 2H), 7.85 (s, 1H). | 1.42 | 442.0 | A |
| I-3-17 | 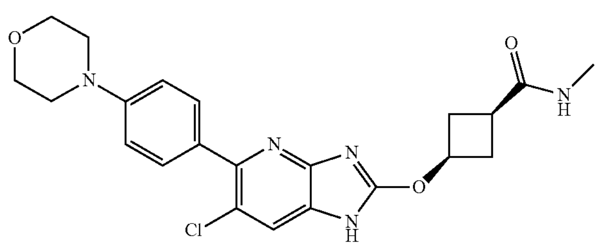 [SMILES: CNC(=O)[C@H]1C[C@@H](Oc2nc3nc(-c4ccc(N5CCOCC5)cc4)c(Cl)cc3[nH]2)C1] | 1H-NMR (DMSO-D6) δ: 2.24-2.33 (m, 2H), 2.60-2.66 (m, 6H), 3.18-3.19 (m, 4H), 3.76-3.77 (m, 4H), 5.20-5.22 (m, 1H), 7.01 (d, J = 8.9 Hz, 2H), 7.55 (d, J = 8.8 Hz, 2H), 7.86-7.87 (m, 2H). | 1.42 | 442.0 | A |
| I-3-18 | 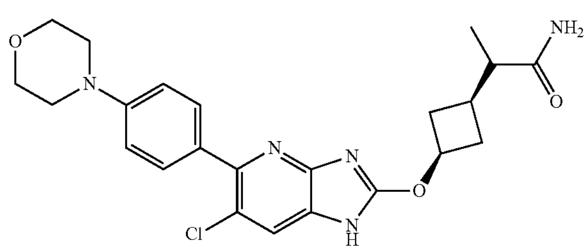 [SMILES: CC(C(N)=O)[C@H]1C[C@@H](Oc2nc3nc(-c4ccc(N5CCOCC5)cc4)c(Cl)cc3[nH]2)C1] | 1H-NMR (DMSO-D6) δ: 0.94 (d, J = 6.8 Hz, 3H), 1.77-1.82 (m, 1H), 1.96-2.00 (m, 2H), 2.23-2.26 (m, 1H), 2.47-2.49 (m, 1H), 2.61-2.64 (m, 1H), 3.18-3.19 (m, 4H), 3.75-3.77 (m, 4H), 5.11-5.13 (m, 1H), 6.77 (s, 1H), 7.01 (d, J = 8.9 Hz, 2H), 7.28 (s, 1H), 7.55 (d, J = 8.8 Hz, 2H), 7.85 (s, 1H), | 1.49 | 456.0 | A |
| I-3-19 | 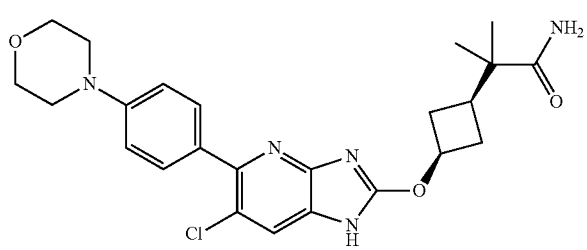 [SMILES: CC(C)(C(N)=O)[C@H]1C[C@@H](Oc2nc3nc(-c4ccc(N5CCOCC5)cc4)c(Cl)cc3[nH]2)C1] | 1H-NMR (DMSO-D6) δ: 1.03 (s, 6H), 1.92-1.98 (m, 2H), 2.10-2.18 (m, 1H), 2.40-2.43 (m, 2H), 3.18-3.19 (m, 4H), 3.76-3.78 (m, 4H), 5.05-5.12 (m, 1H), 6.83 (s, 1H), 6.97-7.01 (m, 3H), 7.55 (d, J = 8.8 Hz, 2H), 7.83-7.84 (m, 1H). | 1.59 | 470.0 | A |

TABLE 48

| No. | Structure | NMR (δ) | retention time | Mass (M + H) | method |
|---|---|---|---|---|---|
| I-3-20 | 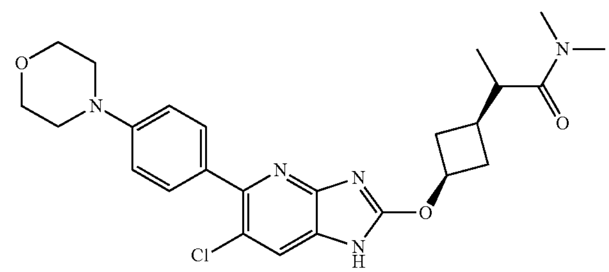 [SMILES: CC(C(=O)N(C)C)[C@H]1C[C@@H](Oc2nc3nc(-c4ccc(N5CCOCC5)cc4)c(Cl)cc3[nH]2)C1] | 1H-NMR (DMSO-D6) δ: 0.94 (d, J = 6.8 Hz, 3H), 1.78-1.87 (m, 2H), 2.09-2.13 (m, 1H), 2.43-2.46 (m, 1H), 2.58-2.62 (m, 1H), 2.82 (s, 3H), 2.85-2.91 (m, 1H), 3.03 (s, 3H), 3.18-3.19 (m, 4H), 3.75-3.77 (m, 4H), 5.06-5.14 (m, 1H), 7.01 (d, J = 8.9 Hz, 2H), 7.54 (d, J = 8.8 Hz, 2H), 7.81 (s, 1H). | 1.78 | 485.0 | A |
| I-3-21 | 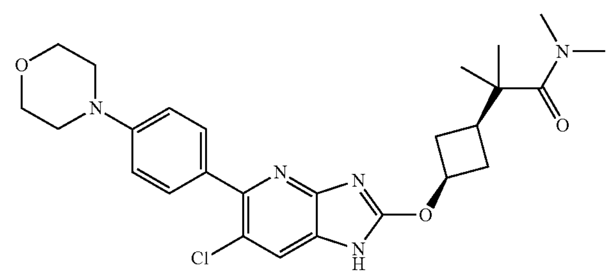 [SMILES: CN(C)C(=O)C(C)(C)[C@H]1C[C@@H](Oc2nc3nc(-c4ccc(N5CCOCC5)cc4)c(Cl)cc3[nH]2)C1] | 1H-NMR (DMSO-D6) δ: 1.17 (s, 6H), 1.89-1.93 (m, 2H), 2.42-2.44 (m, 3H), 2.95 (s, 6H), 3.18-3.19 (m, 4H), 3.75-3.77 (m, 4H), 5.07-5.14 (m, 1H), 7.01 (d, J = 8.9 Hz, 2H), 7.55 (d, J = 8.8 Hz, 2H), 7.84 (s, 1H). | 1.92 | 499.0 | B |
| I-3-22 | 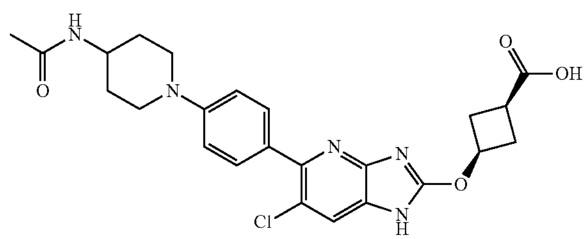 [SMILES: CC(=O)NC1CCN(c2ccc(-c3nc4nc(O[C@H]5C[C@@H](C(=O)O)C5)[nH]c4cc3Cl)cc2)CC1] | 1H-NMR (DMSO-D6) δ: 1.44-1.49 (m, 2H), 1.78-1.80 (m, 5H), 2.30-2.32 (m, 2H), 2.62-2.64 (m, 2H), 2.84-2.87 (m, 2H), 3.72-3.75 (m, 4H), 5.16 (s, 1H), 6.98 (d, J = 8.9 Hz, 2H), 7.52 (d, J = 8.7 Hz, 2H), 7.73 (s, 1H), 7.85 (d, J = 7.7 Hz, 1H). | 1.20 | 484.0 | B |
| I-3-23 | 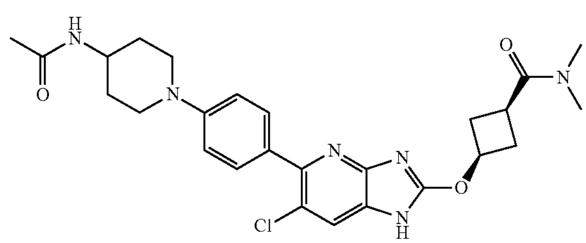 [SMILES: CC(=O)NC1CCN(c2ccc(-c3nc4nc(O[C@H]5C[C@@H](C(=O)N(C)C)C5)[nH]c4cc3Cl)cc2)CC1] | 1H-NMR (DMSO-D6) δ: 1.45-1.48 (m, 2H), 1.80-1.82 (m, 5H), 2.28-2.30 (m, 2H), 2.67-2.71 (m, 2H), 2.84-2.88 (m, 5H), 2.93 (s, 3H), 3.03-3.12 (m, 1H), 3.74-3.76 (m, 3H), 5.21-5.23 (m, 1H), 7.00 (d, J = 8.8 Hz, 2H), 7.52 (d, J = 8.8 Hz, 2H), 7.82-7.84 (m, 2H). | 1.12 | 511.0 | A |
| I-3-24 | 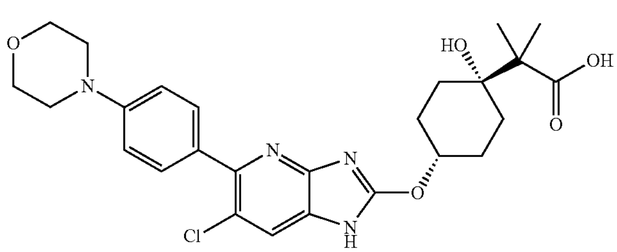 [SMILES: CC(C)(C(=O)O)[C@]1(O)CC[C@@H](Oc2nc3nc(-c4ccc(N5CCOCC5)cc4)c(Cl)cc3[nH]2)CC1] | (DMSO-D6) δ: 1.53 (d, J = 6.78 Hz, 3H), 1.73 (m, 1H), 2.11 (m, 1H), 2.33-2.56 (m, 4H), 5.32 (q, J = 6.78 Hz, 1H), 6.26 (br s, 1H), 7.26 (s, 1H), 7.50 (d, J = 8.53 Hz, 2H), 7.60 (d, J = 8.53 Hz, 2H), 7.64 (s, 1H), 7.90 (s, 1H), 12.27 (s, 1H), 12.84 (s, 1H). | | | |

TABLE 48-continued

| No. | Structure | NMR (δ) | retention time | Mass (M + H) | method |
|---|---|---|---|---|---|
| I-3-25 | 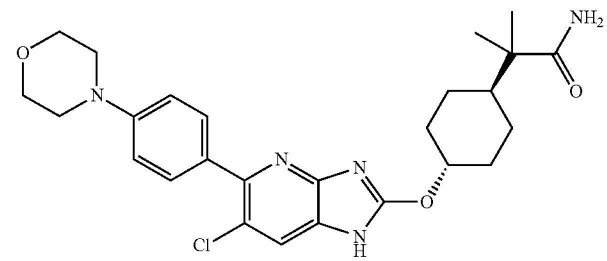 [SMILES: CC(C)(C(N)=O)[C@H]1CC[C@H](Oc2nc3nc(-c4ccc(N5CCOCC5)cc4)c(Cl)cc3[nH]2)CC1] | 1H-NMR (CDCl3) δ: 1.01 (s, 6H), 1.20 (t, J = 13.7 Hz, 2H), 1.36-1.47 (m, 2H), 1.63 (t, J = 15.6 Hz, 1H), 1.68 (d, J = 12.8 Hz, 2H), 2.27 (d, J = 9.3 Hz, 2H), 3.18 (t, J = 4.8 Hz, 4H), 3.76 (t, J = 4.6 Hz, 4H), 4.87-4.95 (m, 1H), 6.66 (s, 1H), 6.80 (s, 1H), 7.00-7.02 (m, 3H), 7.55 (d, J = 8.8 Hz, 2H), 7.84 (br s, 1H). | 1.73 | 500.2 | A |

TABLE 49

| No. | Structure | NMR (δ) | retention time | Mass (M + H) | method |
|---|---|---|---|---|---|
| I-3-26 | 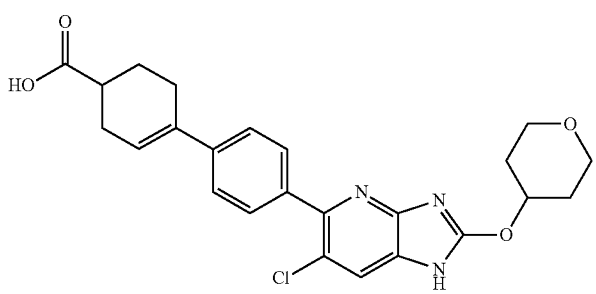 [SMILES: O=C(O)C1CC=C(c2ccc(-c3nc4nc(OC5CCOCC5)[nH]c4cc3Cl)cc2)CC1] | (DMSO-d6) δ: 1.68-1.78 (m, 3H), 2.09-2.15 (m, 3H), 2.33-2.51 (m, 5H), 3.50-3.55 (m, 2H), 3.86-3.91 (m, 2H), 5.22-5.26 (m, 1H), 6.26 (s, 1H), 7.50 (d, J = 8.4 Hz, 2H), 7.60 (d, J = 8.4 Hz, 2H), 7.89 (s, 1H) | | | |
| I-3-27 | 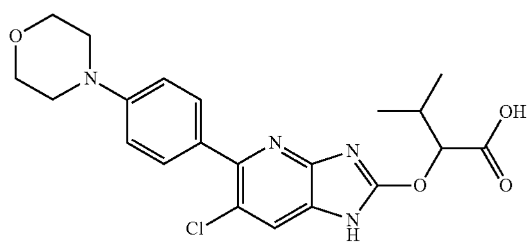 [SMILES: CC(C)C(Oc1nc2nc(-c3ccc(N4CCOCC4)cc3)c(Cl)cc2[nH]1)C(=O)O] | (DMSO-D6) δ: 1.03-1.08 (m, 6H), 2.30-2.34 (m, 1H), 3.19 (dd, J = 4.8, 4.4 Hz, 4H), 3.76 (dd, J = 4.8, 4.4 Hz, 4H), 5.15 (d, J = 4.0 Hz, 1H), 7.01 (d, J = 9.0 Hz, 2H), 7.55 (d, J = 9.0 Hz, 2H), 7.86 (s, 1H). | | | |
| I-3-28 | 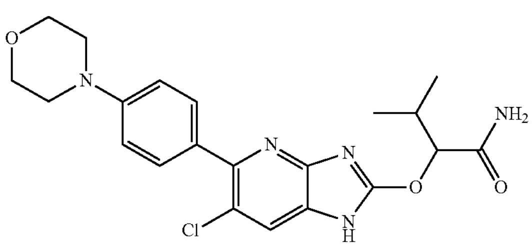 [SMILES: CC(C)C(Oc1nc2nc(-c3ccc(N4CCOCC4)cc3)c(Cl)cc2[nH]1)C(N)=O] | (DMSO-D6) δ: 0.99-1.04 (m, 6H), 2.24-2.27 (m, 1H), 3.18 (dd, J = 4.8, 4.4 Hz, 4H), 3.76 (dd, J = 4.8, 4.4 Hz, 4H), 5.10 (d, J = 4.0 Hz, 1H), 7.02 (d, J = 9.0 Hz, 2H), 7.31 (s, 1H), 7.55 (d, J = 9.0 Hz, 2H), 7.63 (s, 1H), 7.84 (s, 1H). | | | |
| I-3-29 | 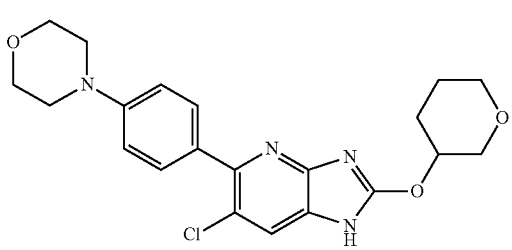 [SMILES: Clc1cc2[nH]c(OC3CCCOC3)nc2nc1-c1ccc(N2CCOCC2)cc1] | | 1.78 | 415.0 | B |

TABLE 49-continued

| No. | Structure | NMR (δ) | retention time | Mass (M + H) | method |
|---|---|---|---|---|---|
| I-3-30 | 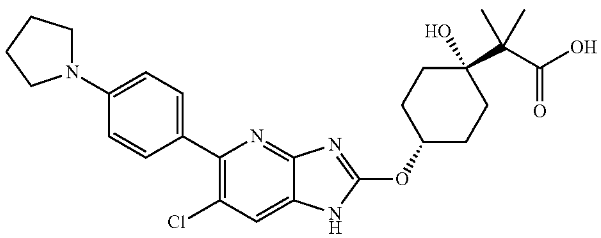 [SMILES: CC(C)(C(=O)O)[C@]1(O)CC[C@@H](Oc2nc3nc(-c4ccc(N5CCCC5)cc4)c(Cl)cc3[nH]2)CC1] | (DMSO-D6) δ: 1.13 (s, 6H), 1.62 (t, J = 11.80 Hz, 2H), 1.74-1.88 (m, 4H), 1.96-2.05 (m, 2H), 3.18 (t, J = 4.64 Hz, 4H), 3.76 (t, J = 4.64 Hz, 4H), 4.47 (s, 1H), 4.91 (m, 1H), 7.01 (d, J = 8.78 Hz, 2H), 7.55 (d, J = 8.78 Hz, 2H), 7.87 (s, 1H), 12.24 (s, 1H), 12.65 (s, 1H). | | | |
| I-3-31 | 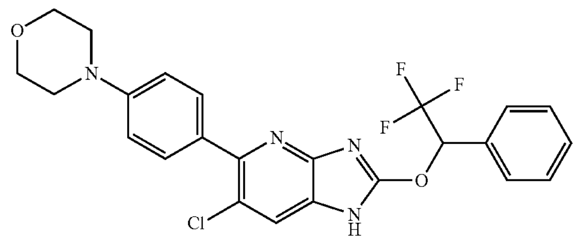 [SMILES: FC(F)(F)C(Oc1nc2nc(-c3ccc(N4CCOCC4)cc3)c(Cl)cc2[nH]1)c1ccccc1] | (DMSO-D6) δ: 3.18 (t, J = 4.6 Hz, 4H), 3.76 (t, J = 4.8 Hz, 4H), 6.87 (t, J = 6.8 Hz, 1H), 7.00 (d, J = 9.0 Hz, 2H), 7.49-7.54 (m, 5H), 7.65 (d, J = 4.3 Hz, 2H), 7.92 (s, 1H), 13.3 (brs, 1H). | | | |

TABLE 50

| No. | Structure | NMR (δ) | retention time | Mass (M + H) | method |
|---|---|---|---|---|---|
| I-3-32 | 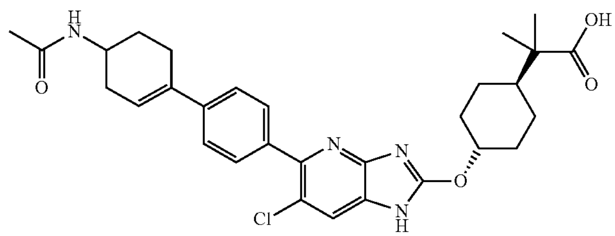 | 1H-NMR (DMSO-D6) δ: 1.06 (s, 6H), 1.23 (dd, J = 22.5, 9.9 Hz, 2H), 1.48 (q, J = 11.7 Hz, 2H), 1.61 (t, J = 11.3 Hz, 2H), 1.70 (d, J = 12.0 Hz, 2H), 1.83 (s, 3H), 1.88-1.96 (m, 1H), 2.03-2.15 (m, 1H), 2.28 (d, J = 9.0 Hz, 2H), 2.46 (d, J = 18.6 Hz, 1H), 2.52 (d, J = 13.8 Hz, 2H), 3.81-3.90 (m, 1H), 4.93 (br s, 1H), 6.19 (s, 1H), 7.51 (d, J = 8.3 Hz, 2H), 7.60 (d, J = 8.3 Hz, 2H), 7.84 (br s, 1H), 7.85 (d, J = 7.5 Hz, 1H), 12.14 (s, 1H), 12.52 (br s, 1H). | 2.01 | 551.3 | A |
| I-3-33 | 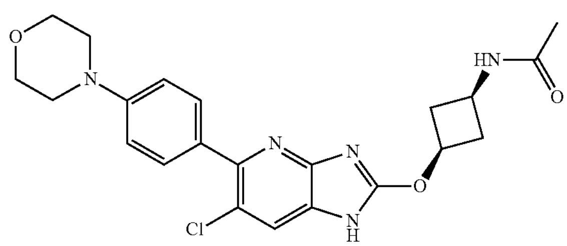 [SMILES: CC(=O)N[C@H]1C[C@@H](Oc2nc3nc(-c4ccc(N5CCOCC5)cc4)c(Cl)cc3[nH]2)C1] | 1H-NMR (DMSO-D6) δ: 1.79 (s, 3H), 2.11-2.13 (m, 2H), 2.81-2.83 (m, 2H), 3.18-3.19 (m, 4H), 3.75-3.77 (m, 4H), 5.00-5.01 (m, 1H), 7.01 (d, J = 8.9 Hz, 3H), 7.55 (d, J = 8.9 Hz, 2H), 7.84 (s, 1H), 8.22 (d, J = 7.7 Hz, 1H). | 1.45 | 442.0 | A |
| I-3-34 | 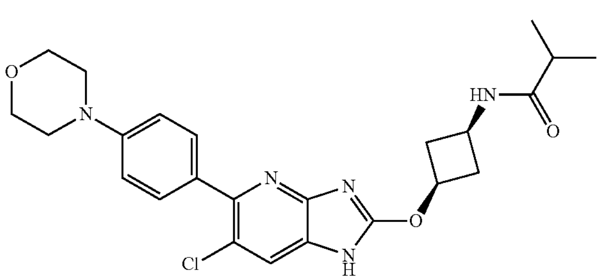 [SMILES: CC(C)C(=O)N[C@H]1C[C@@H](Oc2nc3nc(-c4ccc(N5CCOCC5)cc4)c(Cl)cc3[nH]2)C1] | 1H-NMR (DMSO-D6) δ: 0.99 (d, J = 6.8 Hz, 6H), 2.10-2.12 (m, 2H), 2.28-2.32 (m, 1H), 2.82-284 (m, 2H), 3.18-3.19 (m, 4H), 3.76-3.77 (m, 4H), 3.97 (dd, J = 15.9, 8.3 Hz, 1H), 5.02-5.03 (m, 1H), 7.01 (d, J = 8.9 Hz, 2H), 7.55 (d, J = 8.9 Hz, 2H), 7.86 (s, 1H), 8.08 (d, J = 7.9 Hz, 1H). | 1.72 | 470.0 | B |

TABLE 50-continued

| No. | Structure | NMR (δ) | retention time | Mass (M + H) | method |
|---|---|---|---|---|---|
| I-3-35 | 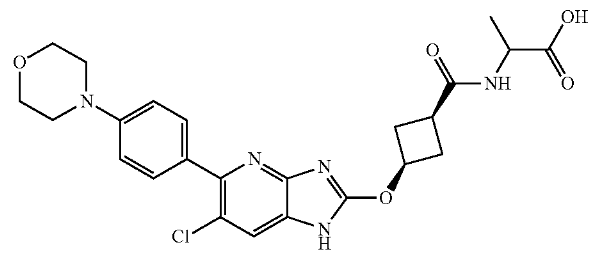 [SMILES: CC(NC(=O)[C@H]1C[C@@H](Oc2nc3nc(-c4ccc(N5CCOCC5)cc4)c(Cl)cc3[nH]2)C1)C(=O)O] | 1H-NMR (DMSO-D6) δ: 1.26 (d, J = 7.3 Hz, 3H), 2.26-2.31 (m, 2H), 2.62-2.66 (m, 2H), 2.73-2.82 (m, 1H), 3.18-3.19 (m, 4H), 3.76-3.77 (m, 4H), 4.16-4.23 (m, 1H), 5.19-5.27 (m, 1H), 7.01 (d, J = 8.9 Hz, 2H), 7.55 (d, J = 8.8 Hz, 2H), 7.86 (s, 1H), 8.26 (d, J = 7.3 Hz, 1H). | 1.54 | 500.0 | B |
| I-3-36 | 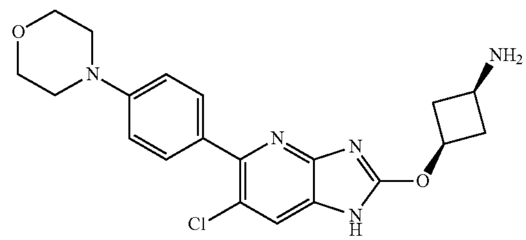 [SMILES: N[C@H]1C[C@@H](Oc2nc3nc(-c4ccc(N5CCOCC5)cc4)c(Cl)cc3[nH]2)C1] | 1H-NMR(DMSO-D6) δ: 2.18-2.20 (m, 2H), 2.83-2.86 (m, 2H), 3.17-3.20 (m, 4H), 3.75-3.76 (m, 5H), 5.02-5.04 (m, 1H), 7.01 (d, J = 9.0 Hz, 2H), 7.55 (d, J = 8.5 Hz, 2H), 7.86 (s, 1H). | 1.19 | 400.0 | B |

TABLE 51

| No. | Structure | NMR (δ) | retention time | Mass (M + H) | method |
|---|---|---|---|---|---|
| I-3-37 | 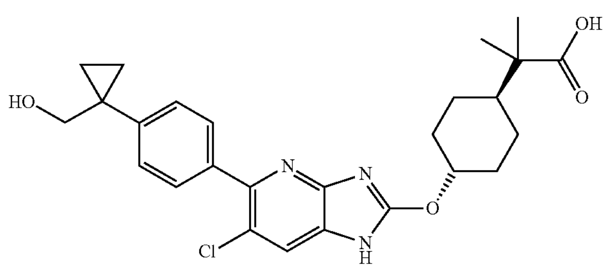 | 1H-NMR (DMSO-D6) δ: 0.79 (t, J = 4.9 Hz, 2H), 0.88 (t, J = 4.9 Hz, 2H), 1.05 (s, 6H), 1.24 (t, J = 12.5 Hz, 2H), 1.47 (q, J = 11.1 Hz, 2H), 1.61 (t, J = 12.0 Hz, 1H), 1.70 (d, J = 12.3 Hz, 2H), 2.27 (d, J = 9.3 Hz, 2H), 3.58 (s, 2H), 4.73 (br s, 1H), 4.88-4.98 (m, 1H), 7.37 (d, J = 8.0 Hz, 2H), 7.54 (d, J = 8.3 Hz, 2H), 7.84 (br s, 1H), 12.16 (s, 1H), 12.52 (br s, 1H), | 2.00 | 486.2 | A |
| I-3-38 | 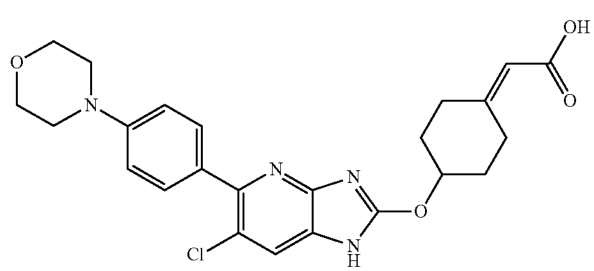 [SMILES: O=C(O)C=C1CCC(Oc2nc3nc(-c4ccc(N5CCOCC5)cc4)c(Cl)cc3[nH]2)CC1] | 1H-NMR (DMSO-D6) δ: 1.73-1.89 (m, 2H), 2.09-2.22 (m, 2H), 2.28-2.37 (m, 1H), 2.39-2.46 (m, 1H), 2.66 (t, J = 13.1 Hz, 1H), 3.19 (t, J = 4.8 Hz, 4H), 3.25 (br s, 1H), 3.76 (t, J = 4.6 Hz, 4H), 5.26-5.31 (m, 1H), 5.68 (s, 1H), 7.01 (d, J = 8.8 Hz, 2H), 7.55 (d, J = 8.8 Hz, 2H), 7.88 (s, 1H), 12.07 (s, 1H), 12.72 (s, 1H), | 1.81 | 471.2 | A |

TABLE 51-continued

| No. | Structure | NMR (δ) | retention time | Mass (M + H) | method |
|---|---|---|---|---|---|
| I-3-39 | 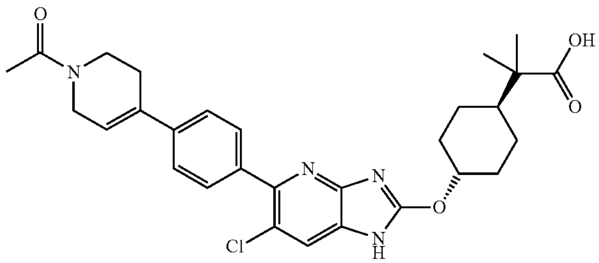 | 1H-NMR (DMSO-D6) δ: 1.05 (s, 6H), 1.23 (dd, J = 24.0, 11.2 Hz, 2H), 1.47 (dd, J = 22.7, 10.9 Hz, 2H), 1.61 (t, J = 11.9 Hz, 1H), 1.70 (d, J = 12.4 Hz, 2H), 2.07 (d, J = 15.2 Hz, 3H), 2.27 (d, J = 9.0 Hz, 2H), 2.61 (s, 1H), 3.17 (s, 1H), 3.64-3.70 (m, 2H), 4.15 (dd, J = 21.8. 2.4 Hz, 2H), 4.88-4.98 (m, 1H), 6.28 (d, J = 3.1 Hz, 1H), 7.54 (dd, J = 8.2, 6.3 Hz, 2H), 7.63 (d, J = 8.4 Hz, 2H), 7.88 (s, 1H), 12.43 (s, 2H), | 1.99 | 537.3 | A |
| I-3-40 | 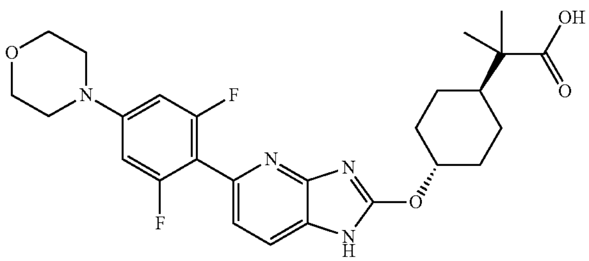 [SMILES: CC(C)(C(=O)O)[C@H]1CC[C@H](Oc2nc3nc(-c4c(F)cc(N5CCOCC5)cc4F)ccc3[nH]2)CC1] | (DMSO-D6) δ: 1.06 (6H, s), 1.22-1.25 (2H, m), 1.44-1.50 (2H, m), 1.58-1.71 (3H, m), 2.27-2.31 (2H, m), 3.22 (4H, J = 4.5 Hz, t), 3.73 (4H, J = 4.3 Hz, t), 4.91-4.95 (1H, m), 6.74 (2H, J = 11.5 Hz, d), 7.10-7.16 (1H, m), 7.62 (0.4H, J = 8.0 Hz, d), 7.75 (0.6H, J = 8.0 Hz, d). | | | |
| I-3-41 | 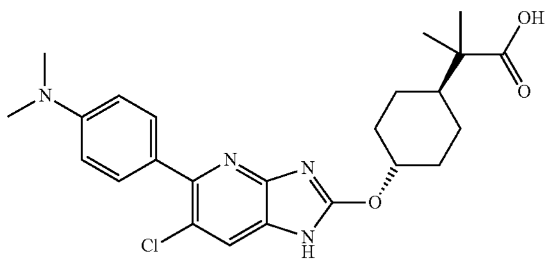 | 1H-NMR (CDCl3) δ: 1.05 (s, 6H), 1.22 (dd, J = 25.5, 12.7 Hz, 1H), 1.32 (dd, J = 14.9, 7.4 Hz, 1H), 1.47 (dd, J = 23.7, 12.2 Hz, 2H), 1.59 (d, J = 11.8 Hz, 1H), 1.69 (d, J = 12.3 Hz, 2H), 2.26 (d, J = 8.0 Hz, 2H), 2.96 (s, 6H), 4.89-4.95 (m, 1H), 6.77 (d, J = 8.8 Hz, 2H), 7.52 (d, J = 8.8 Hz, 2H), 7.78 (br s, 1H). | 1.93 | 458.2 | A |

TABLE 52

| No. | Structure | NMR (δ) | retention time | Mass (M + H) | method |
|---|---|---|---|---|---|
| I-3-42 | 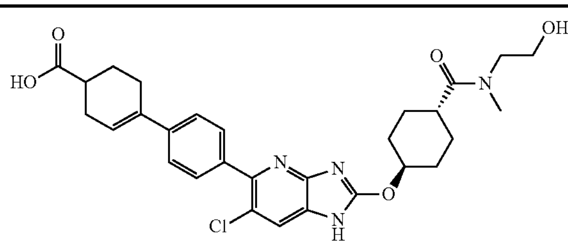 | 1H-NMR (DMSO-D6) δ: 7.90 (1H, s), 7.60 (2H, d, J = 8.4 Hz), 7.50 (2H, d, J = 8.4 Hz), 6.27 (1H, s), 4.97 (1H, s), 4.89-4.61 (1H, m), 3.61-3.23 (4H, m), 3.14-2.77 (3H, m), 2.71-2.66 (1H, m), 2.59-2.20 (7H, m), 2.10 (1H, d, J = 11.8 Hz), 1.79-1.67 (3H, m), 1.65-1.44 (4H, m). | | | |
| I-3-43 | 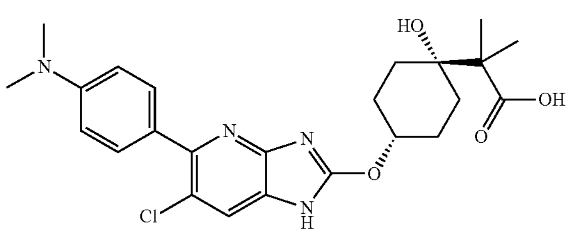 [SMILES: CN(C)c1ccc(-c2nc3nc(O[C@H]4CC[C@](O)(C(C)(C)C(=O)O)CC4)[nH]c3cc2Cl)cc1] | 1H-NMR (DMSO-D6) δ: 1.11 (s, 6H), 1.60 (dd, J = 9.0, 9.0 Hz, 2H), 1.73 (d, J = 9.0, 2H), 1.83 (m, 2H), 1.99 (m, 2H), 2.96 (s, 3H), 4.90 (m, 2H), 6.78 (d, J = 9.0 Hz, 2H), 7.52 (d, J = 9.0 Hz, 2H), 7.85 (br s, 1H), 12.62 (1H, br.s). | | | |

TABLE 52-continued

| No. | Structure | NMR (δ) | retention time | Mass (M + H) | method |
|---|---|---|---|---|---|
| I-3-44 | 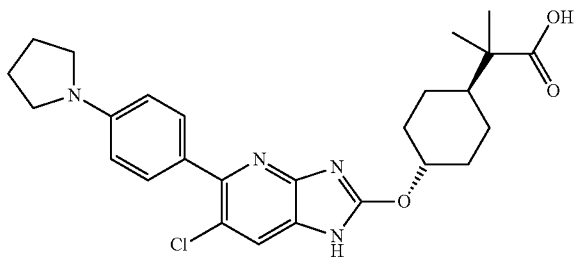 | 1H-NMR (DMSO-D6) δ: 1.05 (s, 6H), 1.24 (t, J = 11.8 Hz, 2H), 1.46 (q, J = 13.0 Hz, 2H), 1.61 (t, J = 11.9 Hz, 1H), 1.69 (d, J = 12.0 Hz, 2H), 1.98 (s, 4H), 2.27 (d, J = 9.3 Hz, 2H), 3.28 (s, 4H), 4.86-4.97 (m, 1H), 6.59 (d, J = 8.8 Hz, 2H), 7.51 (d, J = 8.5 Hz, 2H), 7.77 (br s, 1H), 12.15 (s, 1H), 12.60 (s, 1H). | 4.88 | 483.1 | B |
| I-3-45 | 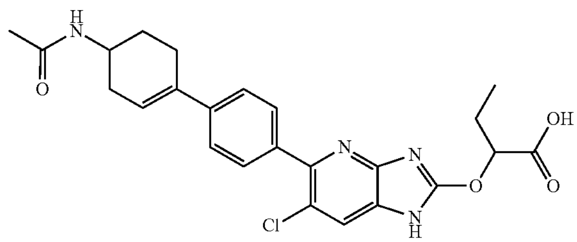 [SMILES: CCC(Oc1nc2nc(-c3ccc(C4=CCC(NC(C)=O)CC4)cc3)c(Cl)cc2[nH]1)C(=O)O] | (DMSO-d6) δ: 1.04 (t, J = 7.3 Hz, 3H), 1.57-1.66 (m, 1H), 1.83 (s, 3H), 1.91-2.11 (m, 6H), 4.00-4.05 (m, 2H), 5.24-5.27 (m, 1H), 6.19 (s, 1H), 7.52 (d, J = 8.3 Hz, 2H), 7.60 (d, J = 8.3 Hz, 2H), 7.88 (d, J = 7.7 Hz, 1H), 7.93 (s, 1H) | | | |
| I-3-46 | 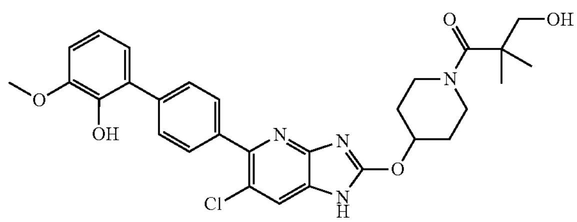 [SMILES: COc1cccc(-c2ccc(-c3nc4nc(OC5CCN(C(=O)C(C)(C)CO)CC5)[nH]c4cc3Cl)cc2)c1O] | (DMSO-d6) δ: 1.17 (s, 6H), 1.67-1.74 (m, 2H), 2.12-2.14 (m, 2H), 3.11-3.39 (m, 2H), 3.44 (d, J = 5.6 Hz, 2H), 3.93-4.02 (m, 2H), 4.59 (t, J = 5.8 Hz, 1H), 5.28-5.32 (m, 1H), 6.88 (t, J = 7.8 Hz, 1H), 6.94-7.00 (m, 2H), 7.63 (d, J = 8.5 Hz, 2H), 7.67 (d, J = 8.5 Hz, 2H), 7.93 (s, 1H), 8.74 (s, 1H) | | | |
| I-3-47 | 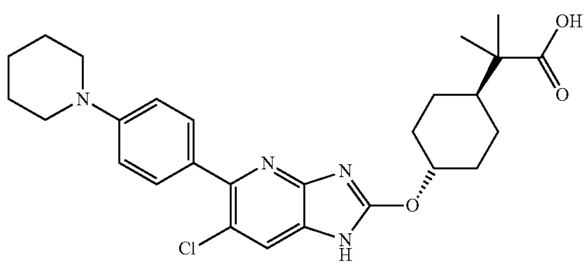 | 1H-NMR (DMSO-D6) δ: 1.05 (s, 6H), 1.24 (t, J = 11.8 Hz, 2H), 1.47 (dd, J = 23.0, 11.2 Hz, 2H), 1.53-1.73 (m, 9H), 2.27 (d, J = 9.3 Hz, 2H), 3.22 (t, J = 5.1 Hz, 4H), 4.87-4.96 (m, 1H), 6.97 (d, J = 8.8 Hz, 2H), 7.52 (d, J = 8.8 Hz, 2H), 7.87 (br s, 1H), 12.14-12.16 (br m, 1H), 12.64 (br s, 1H). | 1.84 | 497.2 | A |

TABLE 53

| No. | Structure | NMR (δ) | retention time | Mass (M + H) | method |
|---|---|---|---|---|---|
| I-3-48 | 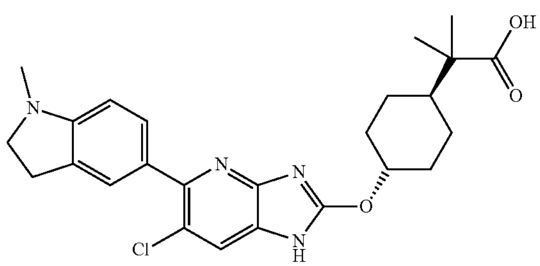 | 1H-NMR (DMSO-D6) δ: 1.05 (s, 6H), 1.24 (t, J = 11.9 Hz, 2H), 1.46 (dd, J = 23.1, 11.0 Hz, 2H), 1.61 (t, J = 11.8 Hz, 1H), 1.69 (d, J = 12.4 Hz, 2H), 2.27 (d, J = 9.0 Hz, 2H), 2.75 (s, 3H), 2.93 (t, J = 8.1 Hz, 2H), 3.32 (t, J = 7.3 Hz, 2H), 4.88-4.94 (m, 1H), 6.55 (d, J = 8.7 Hz, 1H), 7.34 (d, J = 5.5 Hz, 2H), 7.81 (s, 1H), 12.36 (br s, 2H). | 2.16 | 469.4 | B |

TABLE 53-continued

| No. | Structure | NMR (δ) | retention time | Mass (M + H) | method |
|---|---|---|---|---|---|
| I-3-49 | 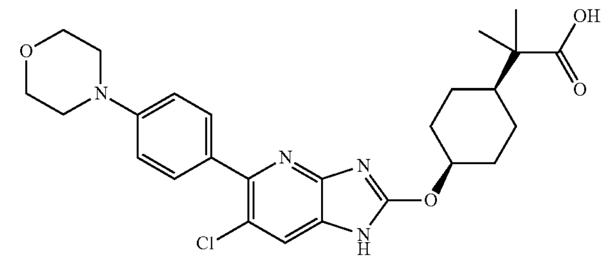 [SMILES: CC(C)(C(=O)O)[C@H]1CC[C@@H](Oc2nc3nc(-c4ccc(N5CCOCC5)cc4)c(Cl)cc3[nH]2)CC1] | 1H-NMR (CDCl3) δ: 1.05 (s, 6H), 1.30-1.50 (m, 4H), 1.58-1.72 (m, 3H), 2.17 (d, J = 13.6 Hz, 2H), 3.18 (t, J = 4.8 Hz, 4H), 3.76 (t, J = 4.6 Hz, 4H), 5.28 (s, 1H), 7.01 (d, J = 8.8 Hz, 2H), 7.54 (d, J = 8.8 Hz, 2H), 7.80 (s, 1H). | 2.04 | 501.3 | A |
| I-3-50 | 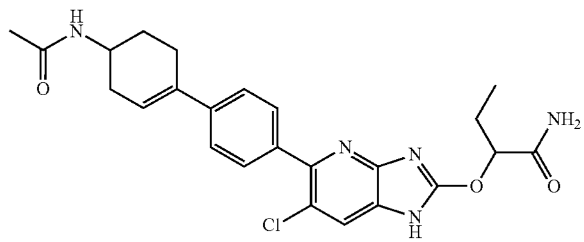 [SMILES: CCC(Oc1nc2nc(-c3ccc(C4=CCC(NC(C)=O)CC4)cc3)c(Cl)cc2[nH]1)C(N)=O] | (DMSO-d6) δ: 1.00 (t, J = 7.3 Hz, 3H), 1.57-1.66 (m, 1H), 1.83 (s, 3H), 1.91-1.99 (m, 4H), 2.05-2.11 (m, 2H), 3.80-3.90 (m, 2H), 5.19 (t, J = 6.0 Hz, 1H), 6.19 (s, 1H), 7.29 (s, 1H), 7.52 (d, J = 8.3 Hz, 2H), 7.59 (d, J = 8.3 Hz, 2H), 7.65 (s, 1H), 7.88 (d, J = 7.7 Hz, 1H), 7.94 (s, 1H), 12.9 (s, 1H) | | | |
| I-3-51 | 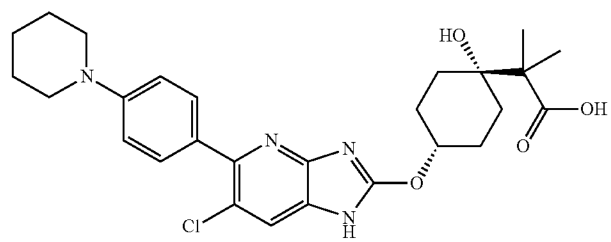 [SMILES: CC(C)(C(=O)O)[C@]1(O)CC[C@@H](Oc2nc3nc(-c4ccc(N5CCCCC5)cc4)c(Cl)cc3[nH]2)CC1] | 1H-NMR (DMSO-D6) δ: 1.09 (s, 6H), 1.56-1.69 (m, 10H), 1.85-1.97 (m, 4H), 3.22 (m, 4H), 4.92 (m, 1H), 6.97 (d, J = 8.8 Hz, 1H), 7.51 (d, J = 8.8 Hz, 1H), 7.81 (br s, 1H). | | | |
| I-3-52 | 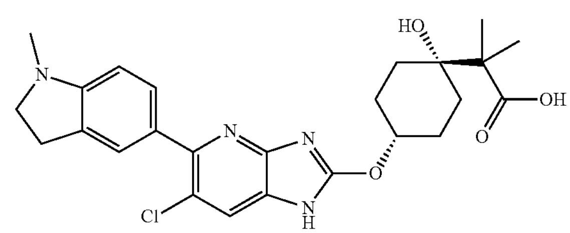 [SMILES: CN1CCc2cc(-c3nc4nc(O[C@H]5CC[C@](O)(C(C)(C)C(=O)O)CC5)[nH]c4cc3Cl)ccc21] | 1H-NMR (DMSO-D6) δ: 1.13 (s, 6H), 1.62 (dd, J = 10.8, 10.8 Hz, 2H), 1.74-1.78 (m, 4H), 1.99 (m, 2H), 2.75 (s, 3H), 2.93 (t, J = 8.0 Hz, 2H), 3.32 (t, J = 8.0 Hz, 2H), 4.90 (m, 1H), 6.54 (d, J = 8.8 Hz, 1H), 7.33 (s, 1H), 7.34 (d, J = 8.8 Hz, 1H), 7.85 (br s, 1H), 12.60 (1H, br.s). | | | |
| I-3-53 | 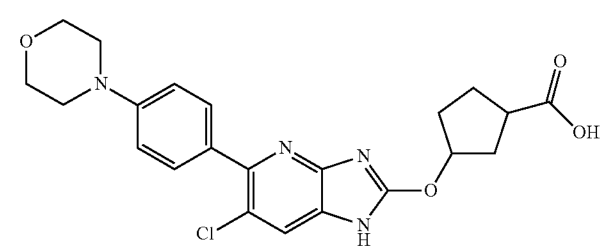 [SMILES: O=C(O)C1CCC(Oc2nc3nc(-c4ccc(N5CCOCC5)cc4)c(Cl)cc3[nH]2)C1] | (DMSO-D6) δ: 1.79-1.93 (m, 2H), 1.99-2.23 (m, 4H), 2.96 (m, 1H), 3.18 (t, J = 4.52 Hz, 4H), 3.76 (t, J = 4.52 Hz, 4H), 5.51 (m, 1H), 7.01 (d, J = 8.66 Hz, 2H), 7.55 (d, J = 8.66 Hz, 2H), 7.91 (s, 1H), 12.27 (s, 1H), 12.69 (s, 1H). | | | |

TABLE 54

| No. | Structure | NMR (δ) | retention time | Mass (M + H) | method |
|---|---|---|---|---|---|
| I-3-54 | 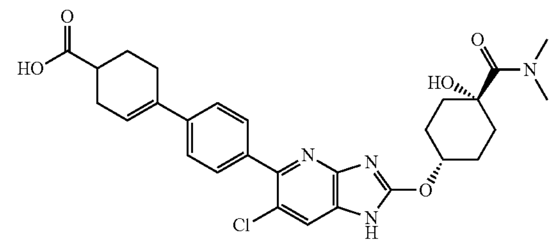 [SMILES: CN(C)C(=O)[C@]1(O)CC[C@@H](Oc2nc3nc(-c4ccc(C5=CCC(C(=O)O)CC5)cc4)c(Cl)cc3[nH]2)CC1] | (DMSO-D6) δ: 1.66-1.79 (1H, m), 1.86 (6H, s), 1.95-2.15 (3H, m), 2.29-2.60 (4H, m), 2.83 (2H, s), 3.18-3.42 (5H, m), 5.01 (1H, s), 5.47 (1H, s), 6.27 (1H, s), 7.50 (2H, d, J = 8.0 Hz), 7.60 (2H, d, J = 7.9 Hz), 7.78 (1H, s), 12.3-12.7 (2H, m). | 1.79 | 539.2 | B |
| I-3-55 | 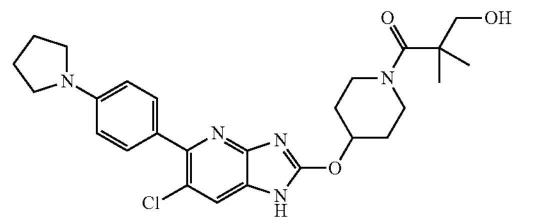 [SMILES: CC(C)(CO)C(=O)N1CCC(Oc2nc3nc(-c4ccc(N5CCCC5)cc4)c(Cl)cc3[nH]2)CC1] | 1H-NMR (CDCl3) δ: 1.17 (s, 6H), 1.17 (s, 6H), 1.63-1.74 (m, 2H), 1.96-1.99 (m, 1H), 1.98 (d, J = 3.8 Hz, 4H), 2.11 (d, J = 8.3 Hz, 2H), 3.28 (s, 2H), 3.36-3.38 (m, 2H), 3.44 (d, J = 5.8 Hz, 2H), 3.92-4.01 (m, 2H), 4.56 (t, J = 5.9 Hz, 1H), 5.22-5.31 (m, 1H), 6.59 (d, J = 8.8 Hz, 2H), 7.51 (d, J = 8.3 Hz, 2H), 7.79 (br s, 1H). | 2.15 | 498.3 | A |
| I-3-56 | 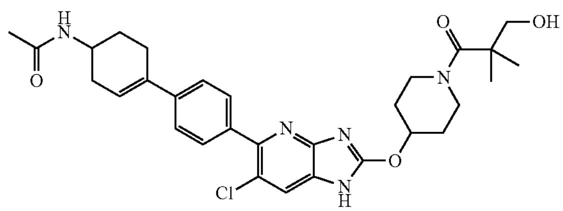 [SMILES: CC(=O)NC1CC=C(c2ccc(-c3nc4nc(OC5CCN(C(=O)C(C)(C)CO)CC5)[nH]c4cc3Cl)cc2)CC1] | 1H-NMR (DMSO-D6) δ: 1.18 (s, 6H), 1.57-1.75 (m, 3H), 1.83 (s, 3H), 1.93 (d, J = 12.3 Hz, 1H), 2.04-2.16 (m, 3H), 2.46 (d, J = 17.8 Hz, 1H), 2.54 (s, 2H), 3.44 (d, J = 6.0 Hz, 2H), 3.86 (br s, 1H), 3.96 (br s, 2H), 4.56 (t, J = 5.8 Hz, 1H), 5.29 (s, 1H), 6.19 (s, 1H), 7.51 (d, J = 8.5 Hz, 2H), 7.60 (d, J = 8.5 Hz, 2H), 7.85 (d, J = 7.5 Hz, 2H), 7.87 (br s, 2H), 12.61 (br s, 1H). | 1.74 | 566.1 | B |
| I-3-57 | 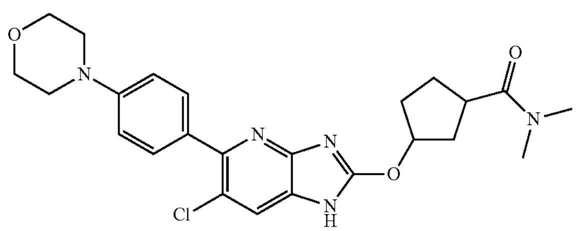 [SMILES: CN(C)C(=O)C1CCC(Oc2nc3nc(-c4ccc(N5CCOCC5)cc4)c(Cl)cc3[nH]2)C1] | (DMSO-D6) δ: 1.75 (m, 1H), 1.91 (m, 1H), 1.97-2.28 (m, 4H), 2.84 (s, 3H), 3.02 (s, 3H), 3.18 (t J = 4.77 Hz, 4H), 3.29 (m, 1H), 3.76 (t, J = 4.77 Hz, 4H), 5.53 (m, 1H), 7.01 (d, J = 8.78 Hz, 2H), 7.55 (d, J = 8.78 Hz, 2H), 7.87 (s, 1H), 12.63 (s, 1H). | | | |
| I-3-58 | 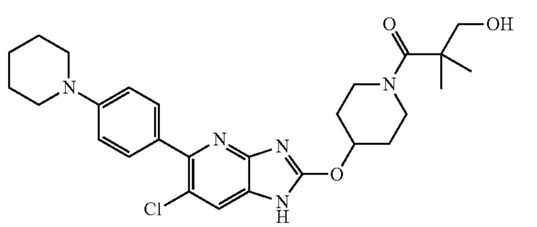 [SMILES: CC(C)(CO)C(=O)N1CCC(Oc2nc3nc(-c4ccc(N5CCCCC5)cc4)c(Cl)cc3[nH]2)CC1] | 1H-NMR (DMSO-D6) δ: 1.04 (d, J = 6.1 Hz, 1H), 1.17 (s, 6H), 1.56-1.70 (m, 8H), 2.11 (br s, 2H), 3.22 (d, J = 5.1 Hz, 4H), 3.31 (s, 1H), 3.44 (d, J = 5.6 Hz, 2H), 3.98 (d, J = 12.9 Hz, 2H), 4.60 (t, J = 5.6 Hz, 1H), 5.28 (s, 1H), 6.98 (d, J = 8.4 Hz, 2H), 7.52 (d, J = 8.3 Hz, 2H), 7.83 (br s, 1H), 12.55 (br s, 1H). | 1.38 | 514.3 | A |
| I-3-59 | 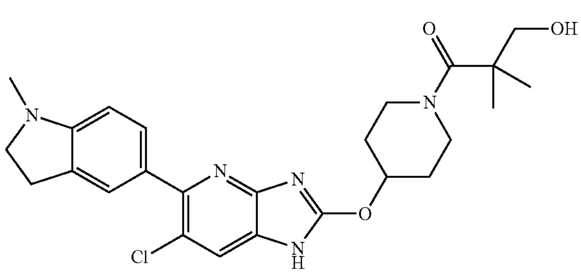 [SMILES: CN1CCc2cc(-c3nc4nc(OC5CCN(C(=O)C(C)(C)CO)CC5)[nH]c4cc3Cl)ccc21] | 1H-NMR (DMSO-D6) δ: 1.17 (s, 6H), 1.68 (br s, 2H), 2.12 (br s, 2H), 2.75 (s, 3H), 2.93 (t, J = 8.1 Hz, 2H), 3.30-3.38 (m, 4H), 3.44 (d, J = 5.6 Hz, 2H), 3.98 (d, J = 11.2 Hz, 2H), 4.59 (t, J = 5.5 Hz, 1H), 5.27 (s, 1H), 6.55 (d, J = 8.4 Hz, 1H), 7.34 (d, J = 5.5 Hz, 2H), 7.80 (br s, 1H), 12.51 (br s, 1H). | 1.75 | 486.3 | A |

TABLE 55

| No. | Structure | NMR (δ) | retention time | Mass (M + H) | method |
|---|---|---|---|---|---|
| I-3-60 | 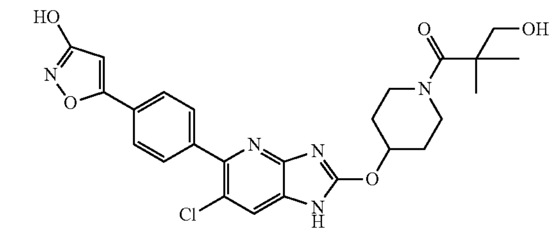 [SMILES: CC(C)(CO)C(=O)N1CCC(Oc2nc3nc(-c4ccc(-c5cc(O)no5)cc4)c(Cl)cc3[nH]2)CC1] | (DMSO-D6) δ: 1.18 (s, 6H), 1.65-1.77 (m, 2H), 2.08-2.17 (m, 2H), 3.32-3.46 (m, 4H), 3.92-4.02 (m, 2H), 4.56 (t, J = 5.77 Hz, 1H), 5.31 (m, 1H), 6.62 (s, 1H), 7.78 (d, J = 8.28 Hz, 2H), 7.90 (d, J = 8.28 Hz, 2H), 7.99 (s, 1H), 11.40 (s, 1H), 12.89 (s, 1H). | | | |
| I-3-61 | 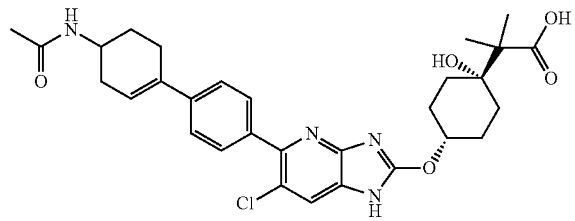 [SMILES: CC(=O)NC1CC=C(c2ccc(-c3nc4nc(O[C@H]5CC[C@](O)(C(C)(C)C(=O)O)CC5)[nH]c4cc3Cl)cc2)CC1] | 1H-NMR (DMSO-D6) δ: 1.13 (s, 6H), 1.62 (dd, J = 13.2, 13.2 Hz, 2H), 1.74-2.11 (m, 7H), 1.83 (s, 3H), 2.43-2.54 (m, 4H), 3.86 (m, 1H), 4.93 (m, 1H), 6.19 (m, 1H), 7.51 (d, J = 8.0 Hz, 2H), 7.61 (d, J = 8.0 Hz, 2H). | | | |
| I-3-62 | 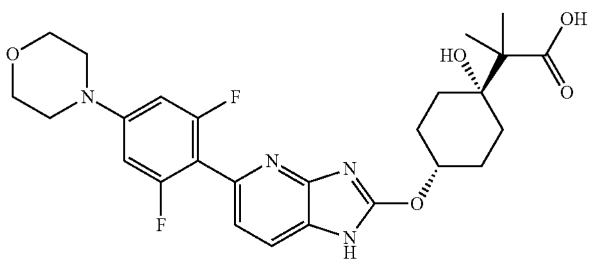 [SMILES: CC(C)(C(=O)O)[C@]1(O)CC[C@@H](Oc2nc3nc(-c4c(F)cc(N5CCOCC5)cc4F)ccc3[nH]2)CC1] | (DMSO-D6) δ: 1.23 (6H, s), 1.71-1.74 (2H, m), 1.86-1.95 (4H, m), 2.09-2.11 (2H, m), 3.33 (4H, J = 4.6 Hz, t), 3.83 (4H, J = 4.8 Hz, t), 4.22 (1H, br s), 4.97-5.06 (1H, m), 6.84 (2H, J = 11.3 Hz, d), 7.21 (0.4H, J = 7.8 Hz, d), 7.26 (0.6H, J = 8.0 Hz, d), 7.73 (0.4H, J = 7.8 Hz, d), 7.85 (0.6H, J = 8.0 Hz, d). | | | |
| I-3-63 | 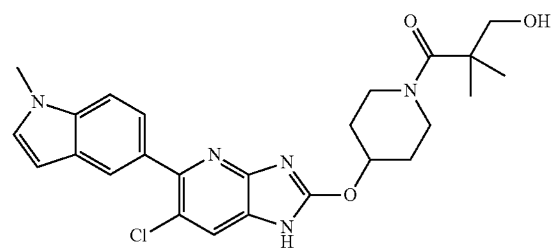 [SMILES: Cn1ccc2cc(-c3nc4nc(OC5CCN(C(=O)C(C)(C)CO)CC5)[nH]c4cc3Cl)ccc21] | 1H-NMR (DMSO-D6) δ: 1.18 (s, 6H), 1.72 (t, J = 10.3 Hz, 2H), 2.13 (d, J = 14.8 Hz, 2H), 3.36 (t, J = 11.8 Hz, 2H), 3.44 (d, J = 5.8 Hz, 2H), 3.83 (s, 3H), 3.98 (d, J = 14.1 Hz, 2H), 4.56 (t, J = 5.8 Hz, 1H), 5.27-5.31 (m, 1H), 6.49 (d, J = 3.0 Hz, 1H), 7.38 (d, J = 3.0 Hz, 1H), 7.42 (dd, J = 8.5, 1.0 Hz, 1H), 7.49 (d, J = 8.5 Hz, 1H), 7.80 (s, 1H), 7.92 (br s, 1H), 12.54 (br s, 1H). | 1.86 | 484.3 | A |
| I-3-64 | 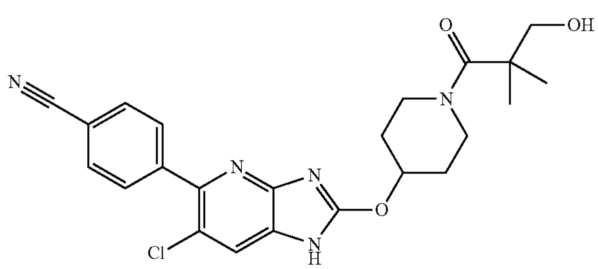 [SMILES: CC(C)(CO)C(=O)N1CCC(Oc2nc3nc(-c4ccc(C#N)cc4)c(Cl)cc3[nH]2)CC1] | (DMSO-D6) δ: 1.18 (s, 6H), 1.65-1.76 (m, 2H), 2.08-2.16 (m, 2H), 3.32-3.40 (m, 2H), 3.44 (d, J = 5.77 Hz, 2H), 3.92-4.01 (m, 2H), 4.56 (t, J = 5.77 Hz, 1H), 5.31 (m, 1H), 7.84 (d, J = 8.28 Hz, 2H), 7.93-8.02 (m, 3H), 12.93 (s, 1H). | | | |
| I-3-65 | 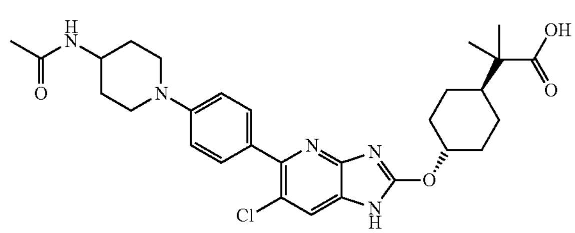 | 1H-NMR (CDCl3) δ: 1.05 (s, 6H), 1.18-1.27 (m, 2H), 1.40-1.52 (m, 4H), 1.61 (t, J = 11.9 Hz, 1H), 1.70 (d, J = 12.5 Hz, 2H), 1.80 (s, 3H), 1.81 (d, J = 10.0 Hz, 2H), 2.27 (d, J = 8.8 Hz, 2H), 2.87 (t, J = 11.3 Hz, 2H), 3.75 (d, J = 13.3 Hz, 3H), 4.92 (dd, J = 13.3, 9.3 Hz, 1H), 6.99 (d, J = 8.8 Hz, 2H), 7.53 (d, J = 8.5 Hz, 2H), 7.84 (d, J = 7.5 Hz, 2H). | 1.60 | 555.4 | A |

TABLE 56

| No. | Structure | NMR (δ) | retention time | Mass (M + H) | method |
|---|---|---|---|---|---|
| I-3-66 | 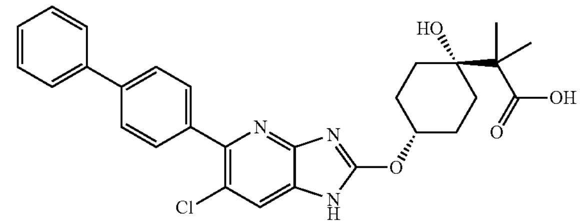 [SMILES: CC(C)(C(=O)O)[C@]1(O)CC[C@@H](Oc2nc3nc(-c4ccc(-c5ccccc5)cc4)c(Cl)cc3[nH]2)CC1] | 1H-NMR (DMSO-D6) δ: 1.13 (s, 6H), 1.63 (dd, J = 13.2, 13.2 Hz, 2H), 1.75-1.90 (m, 4H), 2.00 (m, 2H), 4.48 (s, 1H), 4.94 (m, 1H), 7.40 (t, J = 7.2 Hz, 1H), 7.50 (t, J = 7.2 Hz, 2H), 7.73-7.78 (d, J = 8.0 Hz, 6H), 12.27 (brs, 1H). | | | |
| I-3-67 | 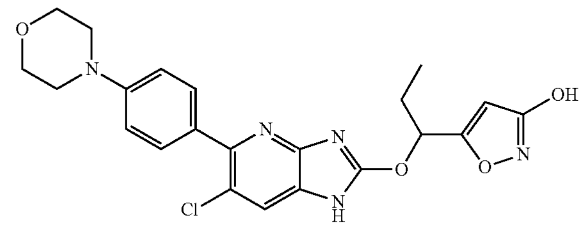 [SMILES: CCC(Oc1nc2nc(-c3ccc(N4CCOCC4)cc3)c(Cl)cc2[nH]1)c1cc(O)no1] | (DMSO-D6) δ: 0.97 (t, J = 7.03 Hz, 3H), 2.09 (dq, J = 7.03, 6.27 Hz, 2H), 3.19 (t, J = 4.77 Hz, 4H), 3.76 (t, J = 4.77 Hz, 4H), 6.08 (t, J = 6.27 Hz, 1H), 6.15 (s, 1H), 7.01 (d, J = 8.28 Hz, 2H), 7.55 (d, J = 8.28 Hz, 2H), 7.92 (s, 1H), 11.39 (s, 1H), 12.92 (s, 1H). | | | |
| I-3-68 | 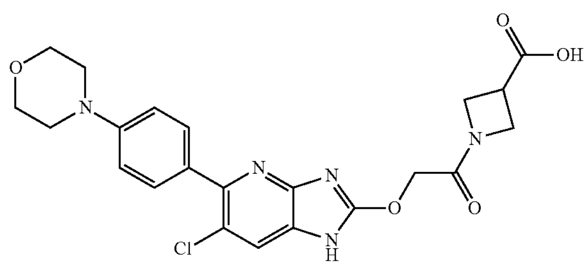 [SMILES: O=C(O)C1CN(C(=O)COc2nc3nc(-c4ccc(N5CCOCC5)cc4)c(Cl)cc3[nH]2)C1] | (DMSO-D6) δ: 3.19 (t, J = 4.77 Hz, 4H), 3.52 (m, 1H), 3.76 (t, J = 4.77 Hz, 4H), 3.92-4.15 (m, 2H), 4.30-4.46 (m, 2H), 5.02 (s, 2H), 7.01 (d, J = 8.78 Hz, 2H), 7.56 (d, J = 8.78 Hz, 2H), 7.91 (s, 1H), 12.78 (s, 1H), 12.93 (s, 1H). | | | |
| I-3-69 | 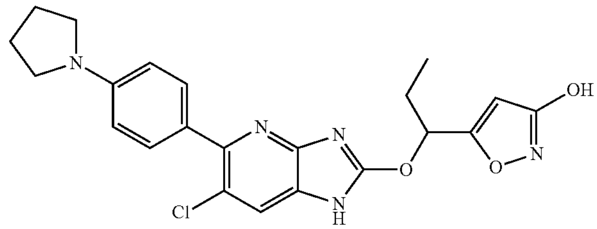 [SMILES: CCC(Oc1nc2nc(-c3ccc(N4CCCC4)cc3)c(Cl)cc2[nH]1)c1cc(O)no1] | (DMSO-D6) δ: 0.97 (t, J = 7.40 Hz, 3H), 1.98 (t, J = 6.40 Hz, 4H), 2.09 (dq, J = 7.40, 6.78 Hz, 2H), 3.28 (t, J = 6.40 Hz, 4H), 6.07 (t, J = 6.78 Hz, 1H), 6.14 (s, 1H), 6.59 (d, J = 8.53 Hz, 2H), 7.51 (d, J = 8.53 Hz, 2H), 7.89 (s, 1H), 11.39 (s, 1H), 12.87 (s, 1H). | | | |
| I-3-70 | 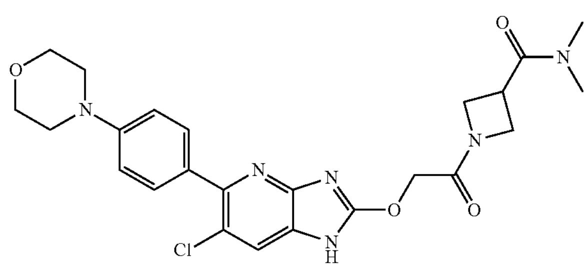 [SMILES: CN(C)C(=O)C1CN(C(=O)COc2nc3nc(-c4ccc(N5CCOCC5)cc4)c(Cl)cc3[nH]2)C1] | (DMSO-D6) δ: 2.86 (s, 6H), 3.19 (t, J = 4.77 Hz, 4H), 3.73-3.83 (m, 5H), 3.98 (m, 1H), 4.09 (m, 1H), 4.32-4.43 (m, 2H), 5.02 (s, 2H), 7.01 (d, J = 8.53 Hz, 2H), 7.56 (d, J = 8.53 Hz, 2H), 7.89 (s, 1H), 12.91 (s, 1H). | | | |
| I-3-71 | 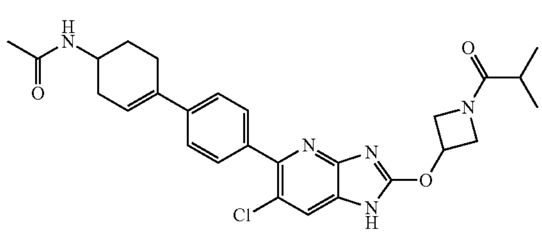 [SMILES: CC(=O)NC1CC=C(c2ccc(-c3nc4nc(OC5CN(C(=O)C(C)C)C5)[nH]c4cc3Cl)cc2)CC1] | 1H-NMR (DMSO-D6) δ: 0.99 (dd, J = 6.6, 2.8 Hz, 6H), 1.17 (t, J = 7.2 Hz, 1H), 1.55-1.67 (m, 1H), 1.82 (s, 3H), 1.93 (d, J = 12.5 Hz, 1H), 2.04-2.14 (m, 1H), 2.53-2.56 (m, 2H), 3.38-3.42 (m, 1H), 3.85 (br s, 1H), 3.94 (d, J = 10.2 Hz, 1H), 4.26-4.34 (m, 2H), 4.65 (t J = 8.4 Hz, 1H), 5.52 (s, 1H), 6.20 (s, 1H), 7.52 (d, J = 8.3 Hz, 2H), 7.61 (d, J = 8.2 Hz, 2H), 7.88 (d, J = 7.5 Hz, 1H), 8.00 (s, 1H), 12.87 (br s, 1H). | 1.74 | 508.2 | B |

TABLE 57

| No. | Structure | NMR (δ) | retention time | Mass (M + H) | method |
|---|---|---|---|---|---|
| I-3-72 | 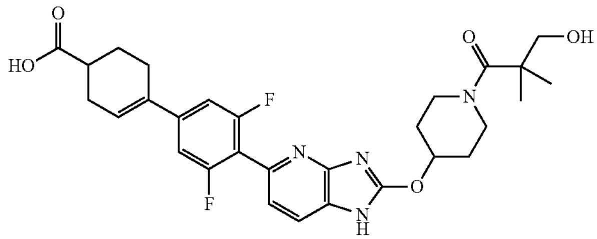 [SMILES: CC(C)(CO)C(=O)N1CCC(Oc2nc3nc(-c4c(F)cc(C5=CCC(C(=O)O)CC5)cc4F)ccc3[nH]2)CC1] | 1H-NMR (DMSO-D6) δ: 7.79 (1H, brs), 7.31-7.19 (3H, m), 6.42 (1H, s), 5.29 (1H, s), 4.60 (1H, t, J = 5.3 Hz), 4.05-3.90 (2H, m), 3.59-3.17 (4H, m), 2.71-2.28 (5H, m), 2.20-2.03 (3H, m), 1.78-1.62 (3H, m), 1.18 (6H, s). | | | |
| I-3-73 | 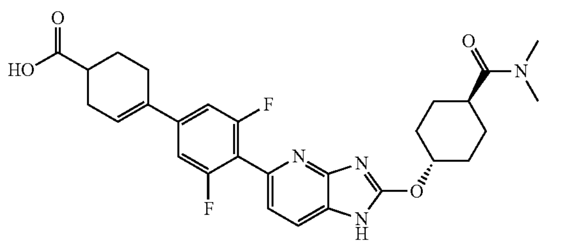 [SMILES: CN(C)C(=O)[C@H]1CC[C@H](Oc2nc3nc(-c4c(F)cc(C5=CCC(C(=O)O)CC5)cc4F)ccc3[nH]2)CC1] | $^1$H-NMR (DMSO-D$_6$) δ: 7.89-7.61 (1H, m), 7.33-7.13 (3H, m), 6.42 (1H, s), 5.04-4.91 (1H, m), 3.04 (3H, s), 2.82 (3H, s), 2.74-2.62 (1H, m), 2.61-2.21 (7H, m), 2.16-2.03 (1H, m), 1.91-1.42 (7H, m). | | | |
| I-3-74 | 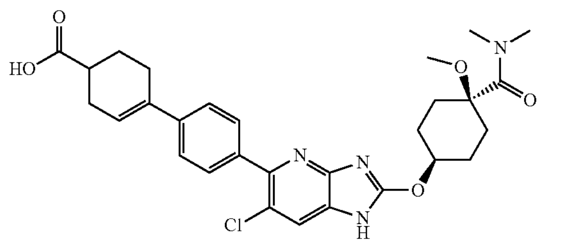 [SMILES: CO[C@]1(C(=O)N(C)C)CC[C@H](Oc2nc3nc(-c4ccc(C5=CCC(C(=O)O)CC5)cc4)c(Cl)cc3[nH]2)CC1] | (DMSO-D6) δ: 1.65-1.86 (5H, m), 2.00-2.15 (5H, m), 2.29-2.60 (4H, m), 2.86 (3H, s), 3.13 (3H, s), 3.21-3.47 (4H, m), 6.26 (1H, s), 7.48 (2H, d, J = 8.3 Hz), 7.60 (2H, d, J = 8.3 Hz), 7.89 (1H, s), 12.49 (2H, brs). | 1.99 | 553.1 | B |
| I-3-75 | 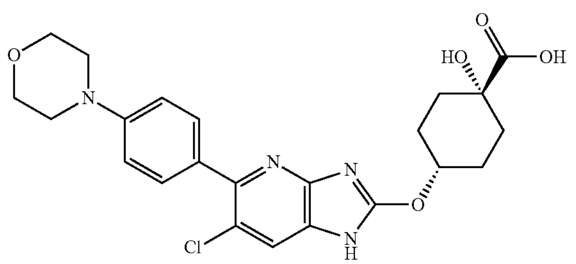 [SMILES: O=C(O)[C@]1(O)CC[C@@H](Oc2nc3nc(-c4ccc(N5CCOCC5)cc4)c(Cl)cc3[nH]2)CC1] | (DMSO-D6) δ: 1.71-1.90 (6H, m), 1.97-2.10 (2H, m), 3.18 (4H, t, J = 4.2 Hz), 3.76 (4H, t, J = 4.2 Hz), 5.03 (1H, s), 5.20 (1H, brs), 7.01 (2H, d, J = 8.5 Hz), 7.55 (2.0H, d, J = 8.5 Hz), 7.82 (1H, s), 12.20-12.80 (2H, m). | 1.58 | 473.1 | B |
| I-3-76 | 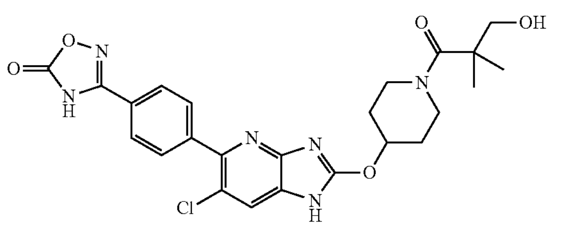 [SMILES: CC(C)(CO)C(=O)N1CCC(Oc2nc3nc(-c4ccc(-c5noc(=O)[nH]5)cc4)c(Cl)cc3[nH]2)CC1] | (DMSO-D6) δ: 1.18 (s, 6H), 1.65-1.77 (m, 2H), 2.08-2.17 (m, 2H), 3.30-3.40 (m, 2H), 3.44 (d, J = 4.27 Hz, 2H), 3.92-4.02 (m, 2H), 4.56 (t, J = 4.27 Hz, 1H), 5.31 (m, 1H), 7.84 (d, J = 8.28 Hz, 2H), 7.91 (d, J = 8.28 Hz, 2H), 8.01 (s, 1H), 12.91 (s, 1H), 13.04 (s, 1H). | | | |
| I-3-77 | 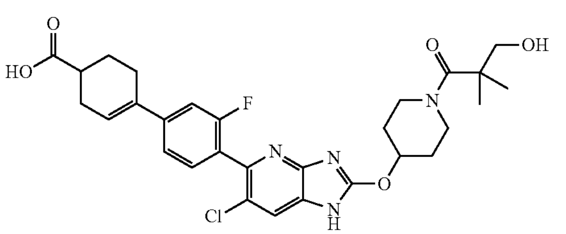 [SMILES: CC(C)(CO)C(=O)N1CCC(Oc2nc3nc(-c4ccc(C5=CCC(C(=O)O)CC5)cc4F)c(Cl)cc3[nH]2)CC1] | (DMSO-D6) δ: 1.17 (6H, s), 1.68-1.71 (3H, m), 2.10-2.12 (3H, m), 2.38-2.42 (5H, m), 3.34-3.44 (4H, m), 3.96-3.99 (2H, m), 4.59 (1H, J = 5.7 Hz, t), 5.27-5.30 (1H, m), 6.35-6.38 (1H, m), 7.35-7.39 (2H, m), 7.51 (1H, J = 7.9 Hz, t), 7.76-7.78 (1H, m). | | | |

TABLE 58

| No. | Structure | NMR (δ) | retention time | Mass (M + H) | method |
|---|---|---|---|---|---|
| I-3-78 | 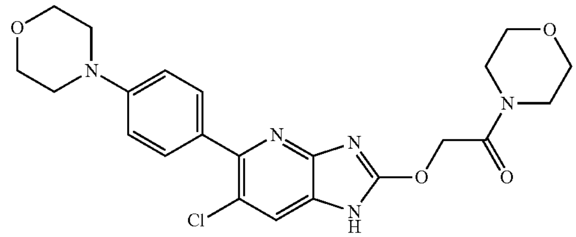 [SMILES: O=C(COc1nc2nc(-c3ccc(N4CCOCC4)cc3)c(Cl)cc2[nH]1)N1CCOCC1] | (DMSO-D6) δ: 3.19 (t, J = 4.77 Hz, 4H), 3.41-3.49 (brs, 4H), 3.55-3.67 (m, 4H), 3.76 (t J = 4.77 Hz, 4H), 5.30 (s, 2H), 7.01 (d, J = 8.78 Hz, 2H), 7.55 (d, J = 8.78 Hz, 2H), 7.87 (s, 1H), 12.90 (s, 1H). | | | |
| I-3-79 | 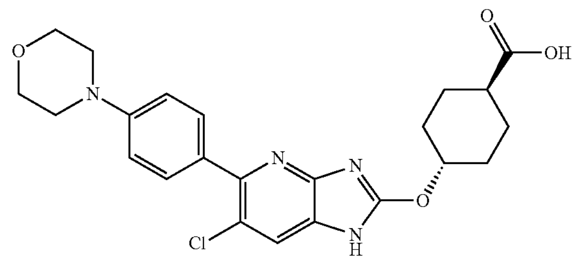 [SMILES: O=C(O)[C@H]1CC[C@H](Oc2nc3nc(-c4ccc(N5CCOCC5)cc4)c(Cl)cc3[nH]2)CC1] | 1H-NMR (DMSO-D6) δ: 2.42-2.45 (m, 2H), 2.63-2.65 (m, 2H), 3.01-3.04 (m, 1H), 3.18 (s, 4H), 3.76 (s, 4H), 5.38-5.40 (m, 1H), 7.01 (d, J = 8.4 Hz, 2H), 7.54 (d, J = 8.7 Hz, 2H), 7.79 (s, 1H). | 1.61 | 429.0 | B |
| I-3-80 | 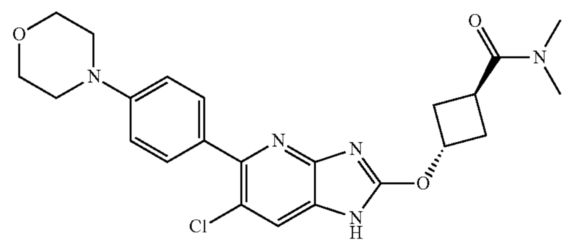 [SMILES: CN(C)C(=O)[C@H]1C[C@H](Oc2nc3nc(-c4ccc(N5CCOCC5)cc4)c(Cl)cc3[nH]2)C1] | 1H-NMR (DMSO-D6) δ: 2.41-2.48 (m, 2H), 2.67-2.68 (m, 2H), 2.86 (s, 3H), 2.90 (s, 3H), 3.18-3.19 (m, 4H), 3.41-3.50 (m, 1H), 3.76-3.77 (m, 4H), 5.24-5.30 (m, 1H), 7.01 (d, J = 8.5 Hz, 2H), 7.55 (d, J = 8.4 Hz, 2H), 7.86 (s, 1H). | 1.58 | 456.0 | B |
| I-3-81 | 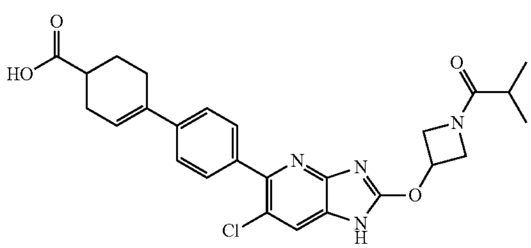 [SMILES: CC(C)C(=O)N1CC(Oc2nc3nc(-c4ccc(C5=CCC(C(=O)O)CC5)cc4)c(Cl)cc3[nH]2)C1] | 1H-NMR (DMSO-D6) δ: 0.99 (dd, J = 6.8, 2.8 Hz, 6H), 1.67-1.78 (m, 1H), 2.08-2.12 (m, 1H), 2.31-2.49 (m, 6H), 3.93 (dd, J = 11.0, 3.3 Hz, 1H), 4.26-4.33 (m, 2H), 4.65 (dd, J = 9.8, 6.5 Hz, 1H), 5.50-5.55 (m, 1H), 6.27 (s, 1H), 7.51 (d, J = 8.3 Hz, 2H), 7.61 (d, J = 8.3 Hz, 2H), 7.94 (s, 1H), 12.27 (s, 1H), 12.89 (s, 1H). | 1.81 | 497.2 | A |
| I-3-82 | 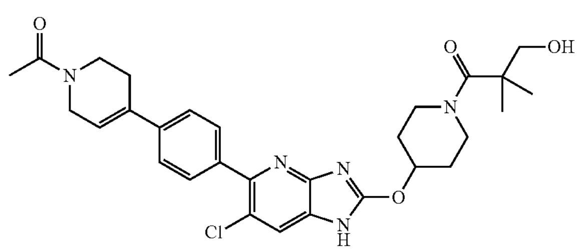 [SMILES: CC(=O)N1CC=C(c2ccc(-c3nc4nc(OC5CCN(C(=O)C(C)(C)CO)CC5)[nH]c4cc3Cl)cc2)CC1] | 1H-NMR (DMSO-D6) δ: 1.17 (s, 6H), 1.65-1.74 (m, 2H), 2.07 (d, J =15.2 Hz, 3H), 2.11 (d, J = 16.6 Hz, 2H), 2.61 (s, 1H), 3.35 (t, J = 10.3 Hz, 3H), 3.44 (s, 3H), 3.64-3.70 (m, 2H), 3.97 (d, J = 13.8 Hz, 2H), 4.15 (d, J = 22.1 Hz, 2H), 5.29 (t, J = 3.8 Hz, 1H), 6.28 (s, 1H), 7.54 (t, J = 7.0 Hz, 2H), 7.64 (d, J = 8.0 Hz, 2H), 7.90 (s, 1H), 12.79 (br s, 1H). | 1.64 | 552.3 | A |
| I-3-83 | 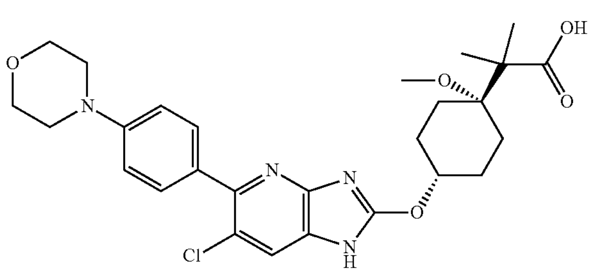 [SMILES: CO[C@]1(C(C)(C)C(=O)O)CC[C@H](Oc2nc3nc(-c4ccc(N5CCOCC5)cc4)c(Cl)cc3[nH]2)CC1] | 1H-NMR (DMSO-D6) δ: 1.16 (s, 6H), 1.61-1.64 (m, 4H), 2.00-2.13 (m, 4H), 3.18 (br t, 4H), 3.29 (s, 1H), 3.76 (br t, 4H), 4.95 (m, 1H), 7.00 (d, J = 8.8 Hz, 2H), 7.55 (d, J = 8.8 Hz, 2H), 7.73-7.78 (d, J = 8.0 Hz, 6H), 7.76 (brs, 1H), 12.25 (brs, 1H). | | | |

TABLE 59

| No. | Structure | NMR (δ) | retention time | Mass (M + H) | method |
|---|---|---|---|---|---|
| I-3-84 | 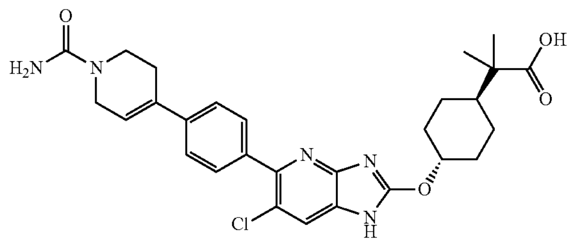 [SMILES: CC(C)(C(=O)O)[C@H]1CC[C@H](Oc2nc3nc(-c4ccc(C5=CCN(C(N)=O)CC5)cc4)c(Cl)cc3[nH]2)CC1] | 1H-NMR (DMSO-D6) δ: 1.05 (s, 6H), 1.23-1.26 (m, 2H), 1.45-1.48 (m, 2H), 1.59-1.71 (m, 3H), 2.25-2.28 (m, 2H), 3.53-3.54 (m, 2H), 4.00 (s, 2H), 4.94 (s, 1H), 6.05 (s, 2H), 6.27 (s, 1H), 7.54 (d, J = 7.9 Hz, 2H), 7.63 (d, J = 8.3 Hz, 2H), 7.94 (s, 1H). | 1.85 | 538.0 | B |
| I-3-85 | 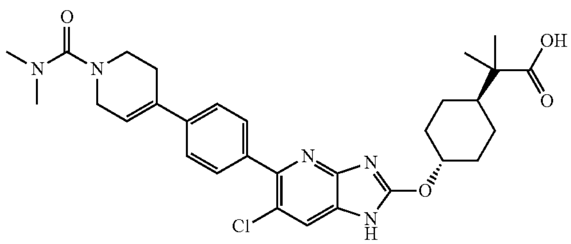 [SMILES: CN(C)C(=O)N1CC=C(c2ccc(-c3nc4nc(O[C@H]5CC[C@H](C(C)(C)C(=O)O)CC5)[nH]c4cc3Cl)cc2)CC1] | 1H-NMR (DMSO-D6) δ: 1.05 (s, 6H), 1.19-1.26 (m, 2H), 1.45-1.51 (m, 2H), 1.58-1.71 (m, 3H), 2.27-2.29 (m, 2H), 2.55-2.58 (m, 2H), 2.78 (s, 6H), 3.86-3.89 (m, 2H), 4.93 (s, 1H), 6.28 (s, 1H), 7.54 (d, J = 8.0 Hz, 2H), 7.63 (d, J = 8.2 Hz, 2H), 7.92 (s, 1H), 12.20 (s, 1H), 12.75 (s, 1H). | 2.09 | 566.0 | B |
| I-3-86 | 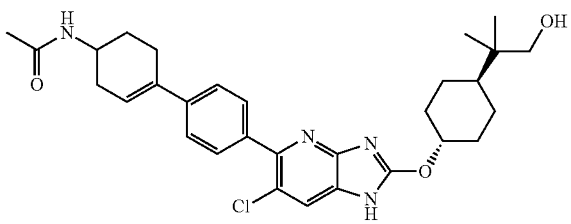 [SMILES: CC(=O)NC1CC=C(c2ccc(-c3nc4nc(O[C@H]5CC[C@H](C(C)(C)CO)CC5)[nH]c4cc3Cl)cc2)CC1] | 1H-NMR (DMSO-D6) δ: 0.78 (s, 6H), 1.14-1.23 (m, 3H), 1.32 (t, J = 11.9 Hz, 1H), 1.43 (dd, J = 22.5, 10.9 Hz, 2H), 1.57-1.68 (m, 1H), 1.81 (d, J= 15.8 Hz, 2H), 1.83 (s, 3H), 1.90-1.95 (m, 1H), 2.04-2.13 (m, 1H), 2.26 (d, J = 9.5 Hz, 2H), 2.46 (d, J = 18.6 Hz, 1H), 2.54 (s, 1H), 3.17 (d, J = 5.0 Hz, 2H), 3.86 (br s, 1H), 4.44 (t, J = 5.0 Hz, 1H), 4.88-4.96 (m, 1H), 6.18 (s, 1H), 7.51 (d, J = 8.3 Hz, 2H), 7.60 (d, J = 8.5 Hz, 2H), 7.85 (d, J = 7.5 Hz, 2H), 12.67 (br s, 1H). | 2.11 | 537.2 | B |
| I-3-87 | 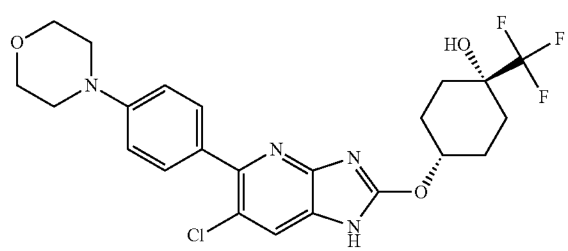 [SMILES: O[C@]1(C(F)(F)F)CC[C@H](Oc2nc3nc(-c4ccc(N5CCOCC5)cc4)c(Cl)cc3[nH]2)CC1] | (DMSO-D6) δ: 1.65-1.89 (m, 6H), 2.10-2.18 (m, 2H), 3.19 (t, J = 4.64 Hz, 4H), 3.76 (t, J = 4.64 Hz, 4H), 5.04 (m, 1H), 5.93 (s, 1H), 7.01 (d, J = 8.78 Hz, 2H), 7.55 (d, J = 8.78 Hz, 2H), 7.87 (s, 1H), 12.68 (s, 1H). | | | |
| I-3-88 | 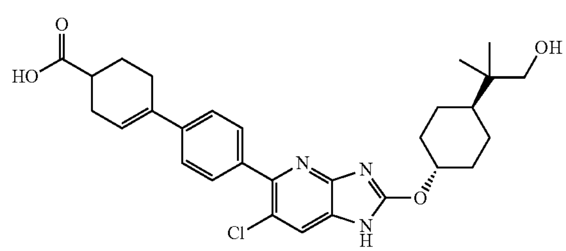 [SMILES: CC(C)(CO)[C@H]1CC[C@H](Oc2nc3nc(-c4ccc(C5=CCC(C(=O)O)CC5)cc4)c(Cl)cc3[nH]2)CC1] | 1H-NMR (DMSO-D6) δ: 0.78 (s, 6H), 1.20 (t, J = 10.0 Hz, 2H), 1.32 (t, J = 12.2 Hz, 1H), 1.43 (dd, J = 23.6, 9.7 Hz, 2H), 1.73 (dd, J= 10.0, 6.5 Hz, 1H), 1.80 (d, J =12.5 Hz, 2H), 2.10 (d, J = 14.6 Hz, 1H), 2.26 (d, J = 8.8 Hz, 1H), 2.30-2.46 (m, 2H), 2.55-2.58 (m, 2H), 3.17 (d, J = 4.5 Hz, 2H), 3.39-3.45 (m, 2H), 4.47 (t, J = 4.8 Hz, 1H), 4.88-4.97 (m, 1H), 6.27 (s, 1H), 7.50 (d, J = 8.2 Hz, 2H), 7.60 (d, J = 8.3 Hz, 2H), 7.89 (s,1H), 12.26 (s, 1H), 12.70 (s, 1H). | 2.23 | 526.3 | A |

TABLE 60

| No. | Structure | NMR (δ) | retention time | Mass (M + H) | method |
|---|---|---|---|---|---|
| I-3-89 | 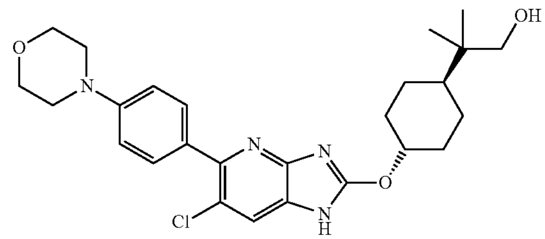 | 1H-NMR (DMSO-D6) δ: 0.78 (s, 6H), 1.20 (t, J = 9.3 Hz, 2H), 1.32 (t, J= 12.1 Hz, 1H), 1.42 (dd, J = 23.1, 11.3 Hz, 2H), 1.80 (d, J = 12.3 Hz, 2H), 2.26 (d, J = 9.8 Hz, 2H), 3.18 (t, J = 5.8 Hz, 6H), 3.76 (t, J = 4.3 Hz, 4H), 4.47 (t, J = 5.1 Hz, 1H), 4.91 (dd, J = 13.4, 9.1 Hz, 1H), 7.01 (d, J = 8.4 Hz, 2H), 7.55 (d, J = 8.3 Hz, 2H), 7.88 (s, 1H), 12.44 (br s, 1H). | 2.11 | 486.3 | A |
| I-3-90 | 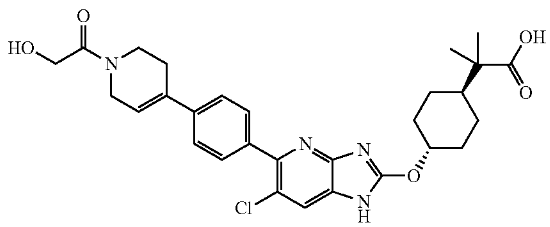 [SMILES: CC(C)(C(=O)O)[C@H]1CC[C@H](Oc2nc3nc(-c4ccc(C5=CCN(C(=O)CO)CC5)cc4)c(Cl)cc3[nH]2)CC1] | 1H-NMR (DMSO-D6) δ: 1.00-1.06 (m, 6H), 1.18-1.25 (m, 2H), 1.46-1.49 (m, 2H), 1.58-1.72 (m, 3H). 2.27-2.29 (m, 2H), 2.53-2.60 (m, 2H), 3.68 (s, 1H), 3.73 (s, 2H), 4.12-4.17 (m, 4H), 4.57-4.62 (m, 1H), 4.92-4.95 (m, 1H), 6.25-6.30 (m, 1H), 7.53 (d, J = 7.0 Hz, 2H), 7.63 (d, J = 7.8 Hz, 2H), 7.88 (s, 1H), 12.16 (s, 1H), 12.64 (s, 1H). | 1.91 | 553.0 | B |
| I-3-91 | 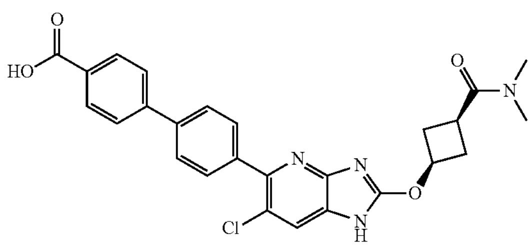 [SMILES: CN(C)C(=O)[C@H]1C[C@@H](Oc2nc3nc(-c4ccc(-c5ccc(C(=O)O)cc5)cc4)c(Cl)cc3[nH]2)C1] | (DMSO-D6) δ: 8.09 (2H, d, J = 8.0 Hz), 7.97 (1H, s), 7.94-7.85 (4H, m), 7.81 (2H, d, J = 8.0 Hz), 5.35-5.23 (1H, m), 3.20-3.06 (1H, m), 2.97 (3H, s), 2.86 (3H, s), 2.83-2.68 (2H, m), 2.41-2.27 (2H, m). | | | |
| I-3-92 | 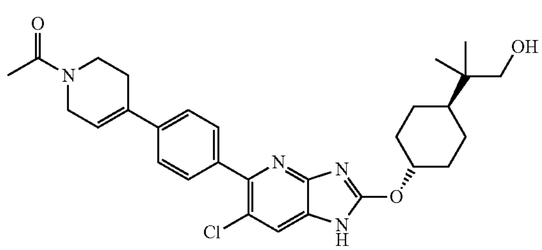 | 1H-NMR (DMSO-D6) δ: 0.78 (s, 6H), 1.21 (t, J = 8.3 Hz, 1H), 1.30 (d, J = 10.5 Hz, 1H), 1.43 (dd, J = 22.3, 10.3 Hz, 2H), 1.80 (d, J = 11.5 Hz, 2H), 2.07 (d, J = 15.1 Hz, 3H), 2.27 (d, J = 10.8 Hz, 2H), 3.17 (d, J = 5.3 Hz, 2H), 3.35-3.38 (m, 1H), 3.40-3.47 (m, 2H), 3.64-3.70 (m, 2H), 4.15 (d, J = 21.6 Hz, 2H), 4.44 (t, J = 5.0 Hz, 1H), 4.93 (br s, 1H), 6.28 (s, 1H), 7.54 (t, J = 6.9 Hz, 2H), 7.63 (d, J = 7.8 Hz, 2H), 7.86 (br s, 1H), 12.50 (br s, 1H). | 2.04 | 523.3 | A |
| I-3-93 | 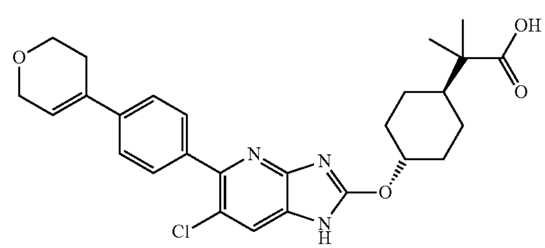 | 1H-NMR (DMSO-D6) δ: 1.06 (s, 6H), 1.19-1.30 (m, 3H), 1.48 (q, J = 11.9 Hz, 2H), 1.61 (t, J = 12.3 Hz, 1H), 1.70 (d, J = 12.0 Hz, 2H), 2.28 (d, J = 9.3 Hz, 2H), 3.37-3.39 (m, 1H), 3.85 (t, J = 5.3 Hz, 2H), 4.26 (s, 2H), 4.93 (br s, 1H), 6.36 (s, 1H), 7.54 (d, J = 8.0 Hz, 2H), 7.63 (d, J = 8.0 Hz, 2H), 7.92 (br s, 1H), 12.15 (br s, 1H), 12.72 (br s, 1H). | 2.27 | 498.2 | A |

TABLE 61

| No. | Structure | NMR (δ) | retention time | Mass (M + H) | method |
|---|---|---|---|---|---|
| I-3-94 | 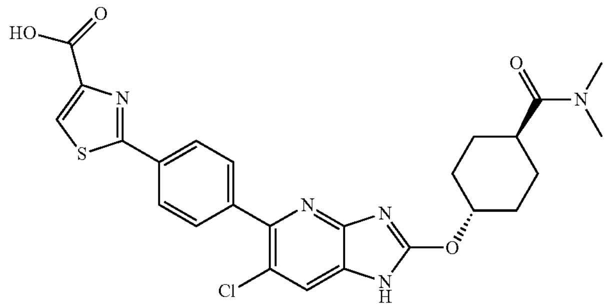 [SMILES: CN(C)C(=O)[C@H]1CC[C@H](Oc2nc3nc(-c4ccc(-c5nc(C(=O)O)cs5)cc4)c(Cl)cc3[nH]2)CC1] | (DMSO-D6) δ: 1.46-1.66 (m, 4H), 1.76-1.84 (m, 2H), 2.24-2.33 (m, 2H), 2.69 (m, 1H), 2.82 (s, 3H), 3.04 (s, 3H), 4.99 (s, 1H), 7.83 (d, J = 7.78 Hz, 2H), 8.01 (s, 1H), 8.08 (d, J = 8.03 Hz, 2H), 8.54 (s, 1H), 12.82 (s, 1H), 13.15 (s, 1H). | | | |
| I-3-95 | 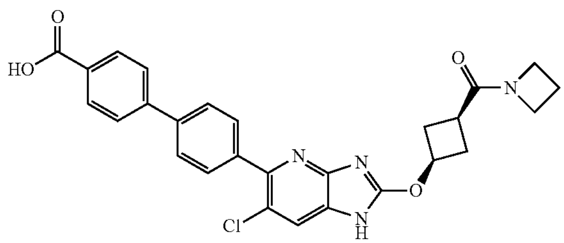 [SMILES: O=C(O)c1ccc(-c2ccc(-c3nc4nc(O[C@H]5C[C@@H](C(=O)N6CCC6)C5)[nH]c4cc3Cl)cc2)cc1] | (DMSO-D6) δ: 8.05 (2H, d, J = 8.0 Hz), 7.98 (1H, s), 7.92-7.82 (4H, m), 7.78 (2H, d, J = 7.9 Hz), 5.31-5.18 (1H, m), 4.10 (2H, t, J = 7.6 Hz), 3.85 (2H, t, J = 7.7 Hz), 2.84-2.71 (1H, m), 2.70-2.59 (2H, m), 2.37-2.11 (4H, m). | | | |
| I-3-96 | 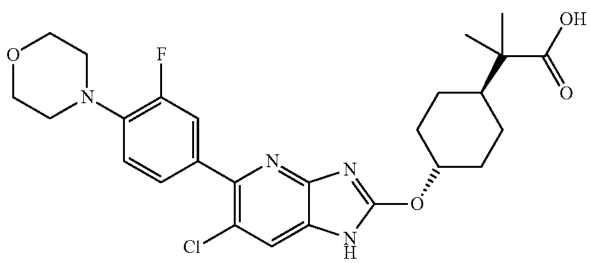 | 1H-NMR (DMSO-D6) δ: 1.05 (s, 6H), 1.24 (t, J = 12.5 Hz, 2H), 1.42 (d, J = 8.0 Hz, 1H), 1.49 (t, J = 11.9 Hz, 1H), 1.61 (t, J = 12.1 Hz, 1H), 1.69 (d, J = 13.2 Hz, 2H), 2.27 (d, J = 9.8 Hz, 2H), 3.08 (s, 4H), 3.77 (s, 4H), 4.90-4.96 (m, 1H), 7.11 (t, J = 8.8 Hz, 1H), 7.43 (t, J = 11.3 Hz, 2H), 7.91 (s, 1H), 12.18 (s, 1H), 12.55 (br s, 1H). | 2.20 | 517.2 | B |
| I-3-97 | 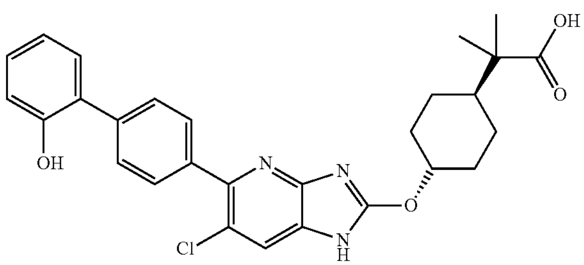 | 1H-NMR (DMSO-D6) δ: 1.06 (s, 6H), 1.14-1.30 (m, 2H), 1.48 (dd, J = 23.1, 11.3 Hz, 2H), 1.62 (t, J= 10.7 Hz, 1H), 1.70 (d, J = 11.3 Hz, 2H), 2.29 (d, J =10.4 Hz, 2H), 4.94 (s, 1H), 6.89-6.98 (m, 2H), 7.17-7.34 (m, 2H), 7.65-7.67 (m, 4H), 7.91 (s, 1H), 9.64 (s, 1H), 12.20 (br s, 1H), 12.74 (br s, 1H). | 2.25 | 506.1 | B |
| I-3-98 | 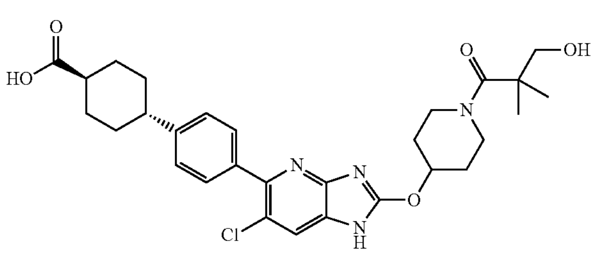 [SMILES: CC(C)(CO)C(=O)N1CCC(Oc2nc3nc(-c4ccc([C@H]5CC[C@H](C(=O)O)CC5)cc4)c(Cl)cc3[nH]2)CC1] | (DMSO-D6) δ: 1.17 (6H, s), 1.42-1.58 (4H, m), 1.65-1.74 (2H, m), 1.86-1.92 (2H, m), 1.98-2.05 (2H, m), 2.08-2.16 (2H, m), 2.25-2.35 (1H, m), 2.54-2.57 (1H, m), 3.40-3.46 (4H, m), 3.92-4.02 (2H, m), 4.59 (1H, J = 5.7 Hz, t), 5.25-5.31 (1H, m), 7.32 (2H, J = 8.0 Hz, d), 7.56 (2H, J = 8.0 Hz, d), 7.90 (1H, s). | | | |

TABLE 61-continued

| No. | Structure | NMR (δ) | retention time | Mass (M + H) | method |
|---|---|---|---|---|---|
| I-3-99 | 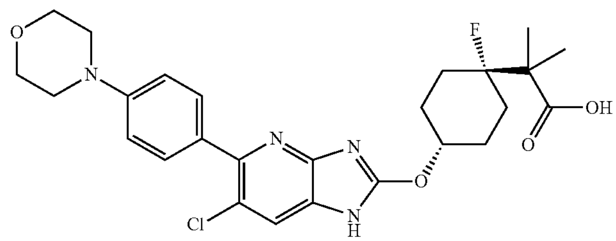 [SMILES: CC(C)(C(=O)O)[C@]1(F)CC[C@@H](Oc2nc3nc(-c4ccc(N5CCOCC5)cc4)c(Cl)cc3[nH]2)CC1] | 1H-NMR (DMSO-D6) δ: 1.16 (s, 6H), 1.61-1.64 (m, 4H), 2.00-2.13 (m, 4H), 3.18 (br t, 4H), 3.29 (s, 1H), 3.76 (br t, 4H), 5.00 (m, 1H), 7.00 (d, J = 8.4 Hz, 2H), 7.54 (d, J = 8.4 Hz, 2H), 7.80 (brs, 1H). | | | |

TABLE 62

| No. | Structure | NMR (δ) | retention time | Mass (M + H) | method |
|---|---|---|---|---|---|
| I-3-100 | 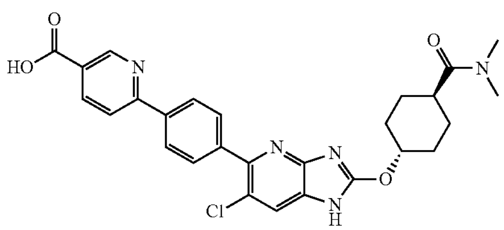 [SMILES: CN(C)C(=O)[C@H]1CC[C@H](Oc2nc3nc(-c4ccc(-c5ccc(C(=O)O)cn5)cc4)c(Cl)cc3[nH]2)CC1] | (DMSO-D6) δ: 1.45-1.66 (m, 4H), 1.76-1.85 (m, 2H), 2.25-2.33 (m, 2H), 2.69 (t, J = 9.41 Hz, 1H), 2.82 (s, 3H), 3.04 (s, 3H), 4.99 (m, 1H), 7.82 (d, J = 7.78 Hz, 2H), 8.00 (s, 1H), 8.18 (d, J = 8.28 Hz, 1H), 8.27 (d, J = 7.78 Hz, 2H), 8.36 (d, J = 8.28 Hz, 1H), 9.17 (s, 1H), 12.81 (s, 1H), 13.48 (s, 1H). | | | |
| I-3-101 | 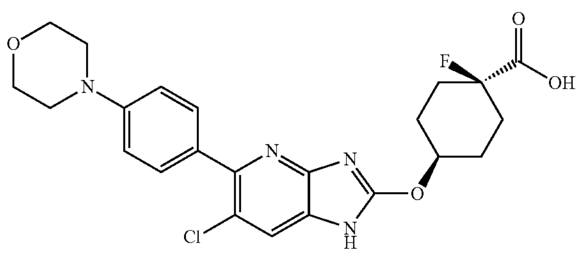 [SMILES: O=C(O)[C@]1(F)CC[C@@H](Oc2nc3nc(-c4ccc(N5CCOCC5)cc4)c(Cl)cc3[nH]2)CC1] | (DMSO-D6) δ: 1.71-1.90 (6H, m), 1.97-2.10 (2H, m), 3.18 (4H, t, J = 4.2 Hz), 3.76 (4H, t, J = 4.2 Hz), 5.03 (1H, s), 5.20 (1H, brs), 7.01 (2H, d, J = 8.5 Hz), 7.55 (2.0H, d, J = 8.5 Hz), 7.82 (1H, s), 12.20-12.80 (2H, m). | 1.58 | 473.1 | B |
| I-3-102 | 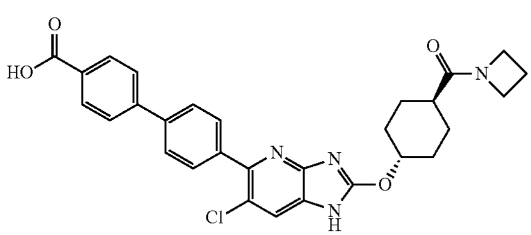 [SMILES: O=C(O)c1ccc(-c2ccc(-c3nc4nc(O[C@H]5CC[C@H](C(=O)N6CCC6)CC5)[nH]c4cc3Cl)cc2)cc1] | (DMSO-D6) δ: 8.05 (2H, d, J = 8.2 Hz), 7.97 (1H, s), 7.92-7.82 (4H, m), 7.78 (2H, d, J = 8.2 Hz), 5.02-4.90 (1H, m), 4.17 (2H, t, J = 7.5 Hz), 3.83 (2H, t, J = 7.6 Hz), 2.34-2.12 (5H, m), 1.83-1.73 (2H, m), 1.61-1.42 (4H, m). | | | |
| I-3-103 | 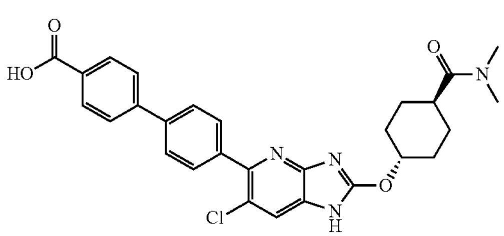 [SMILES: CN(C)C(=O)[C@H]1CC[C@H](Oc2nc3nc(-c4ccc(-c5ccc(C(=O)O)cc5)cc4)c(Cl)cc3[nH]2)CC1] | 1H-NMR (DMSO-D6) δ: 8.05 (2H, d, J = 8.2 Hz), 7.98 (1H, s), 7.93-7.81 (4H, m), 7.78 (2H, d, J = 8.2 Hz), 4.98 (1H, s), 3.04 (3H, s), 2.82 (3H, s), 2.75-2.63 (1H, m), 2.35-2.21 (2H, m), 1.86-1.73 (2H, m), 1.67-1.44 (4H, m). | | | |

TABLE 62-continued

| No. | Structure | NMR (δ) | retention time | Mass (M + H) | method |
|---|---|---|---|---|---|
| I-3-104 | 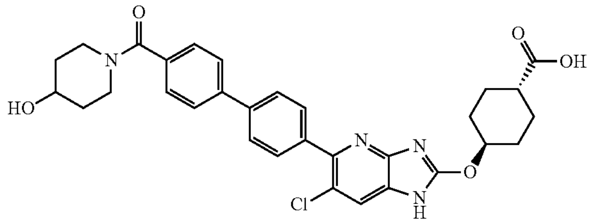 [SMILES: O=C(c1ccc(-c2ccc(-c3nc4nc(O[C@H]5CC[C@H](C(=O)O)CC5)[nH]c4cc3Cl)cc2)cc1)N1CCC(O)CC1] | 1H-NMR (DMSO-D6) δ: 1.38-1.61 (m, 6H), 1.76-1.79 (m, 2H), 1.99-2.01 (m, 2H), 2.25-2.29 (m, 3H), 3.21-3.23 (m, 2H), 3.53-3.56 (m, 1H), 3.76 (s, 1H), 4.01-4.03 (m, 1H), 4.83 (s, 1H), 4.99-5.00 (m, 1H), 7.50 (d, J = 7.9 Hz, 2H), 7.76-7.81 (m, 6H), 7.92 (s, 1H), 12.52 (s, 2H). | 1.58 | 575.0 | B |
| I-3-105 | 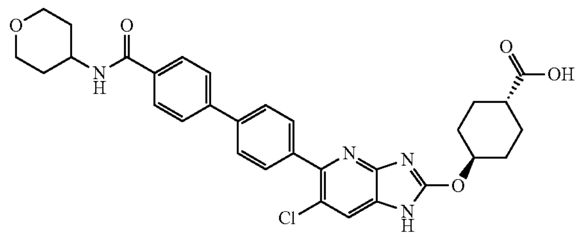 [SMILES: O=C(NC1CCOCC1)c1ccc(-c2ccc(-c3nc4nc(O[C@H]5CC[C@H](C(=O)O)CC5)[nH]c4cc3Cl)cc2)cc1] | 1H-NMR (DMSO-D6) δ: 1.53-1.62 (m, 6H), 1.76-1.79 (m, 2H), 2.00-2.02 (m, 2H), 2.23-2.32 (m, 3H), 3.39-3.43 (m, 1H), 3.88-3.91 (m, 2H), 4.04 (m, 1H), 4.99 (s, 1H), 7.77 (d, J = 7.8 Hz, 2H), 7.84-7.86 (m, 4H), 7.97-7.99 (m, 3H), 8.40 (d, J = 7.9 Hz, 1H), 12.23-12.75 (m, 2H). | 1.83 | 575.0 | B |

TABLE 63

| No. | Structure | NMR (δ) | retention time | Mass (M + H) | method |
|---|---|---|---|---|---|
| I-3-106 | 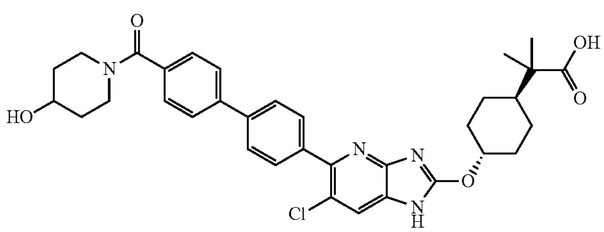 [SMILES: CC(C)(C(=O)O)[C@H]1CC[C@H](Oc2nc3nc(-c4ccc(-c5ccc(C(=O)N6CCC(O)CC6)cc5)cc4)c(Cl)cc3[nH]2)CC1] | 1H-NMR (DMSO-D6) δ: 1.06 (s, 6H), 1.16-1.52 (m, 6H), 1.59-1.72 (m, 5H), 2.27-2.30 (m, 2H), 3.20-3.22 (m, 2H), 3.47-3.58 (m, 1H), 3.76 (s, 1H), 4.02-4.04 (m, 1H), 4.80 (d, J = 3.3 Hz, 1H), 4.95 (s, 1H), 7.49 (d, J = 8.3 Hz, 2H), 7.76-7.81 (m, 6H), 7.90 (s, 1H), 12.44 (d, J = 208.8 Hz, 2H). | 1.87 | 617.0 | B |
| I-3-107 | 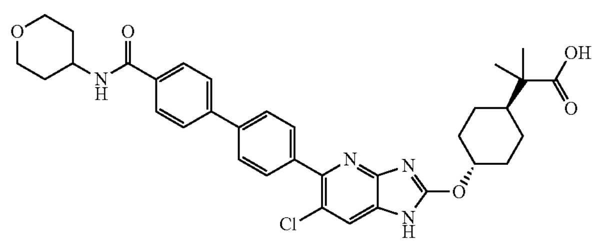 [SMILES: CC(C)(C(=O)O)[C@H]1CC[C@H](Oc2nc3nc(-c4ccc(-c5ccc(C(=O)NC6CCOCC6)cc5)cc4)c(Cl)cc3[nH]2)CC1] | 1H-NMR (DMSO-D6) δ: 1.06 (s, 6H), 1.18-1.26 (m, 2H), 1.45-1.51 (m, 2H), 1.61-1.75 (m, 7H), 2.27-2.30 (m, 2H), 3.40-3.43 (m, 2H), 3.89-3.91 (m, 2H), 4.01-4.04 (m, 1H), 4.94 (s, 1H), 7.77 (d, J = 8.2 Hz, 2H), 7.84-7.86 (m, 4H), 7.92 (s, 1H), 7.98 (d, J = 8.2 Hz, 2H), 8.40 (d, J = 7.5 Hz, 1H), 12.20-12.75 (m, 2H). | 2.12 | 617.0 | B |
| I-3-108 | 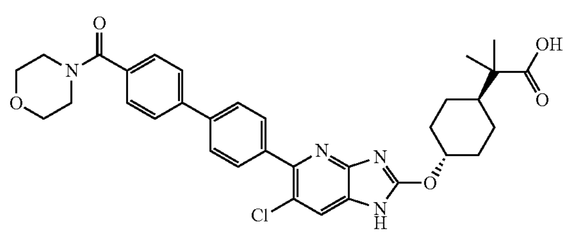 [SMILES: CC(C)(C(=O)O)[C@H]1CC[C@H](Oc2nc3nc(-c4ccc(-c5ccc(C(=O)N6CCOCC6)cc5)cc4)c(Cl)cc3[nH]2)CC1] | 1H-NMR (DMSO-D6) δ:1.06 (s, 6H), 1.22-1.25 (m, 2H), 1.41-1.53 (m, 2H), 1.59-1.72 (m, 3H), 2.27-2.30 (m, 2H), 3.49-3.58 (m, 8H), 4.93-4.96 (m, 1H), 7.54 (d, J = 8.0 Hz, 2H), 7.75-7.83 (m, 6H), 7.91 (s, 1H), 12.16-12.70 (m, 2H). | 2.12 | 603.0 | B |

TABLE 63-continued

| No. | Structure | NMR (δ) | retention time | Mass (M + H) | method |
|---|---|---|---|---|---|
| I-3-109 | 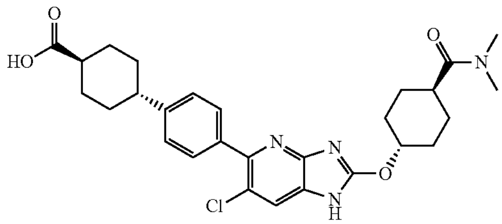 [SMILES: CN(C)C(=O)[C@H]1CC[C@H](Oc2nc3nc(-c4ccc([C@H]5CC[C@H](C(=O)O)CC5)cc4)c(Cl)cc3[nH]2)CC1] | (DMSO-D6) δ: 1.48-1.58 (9H, m), 1.76-1.82 (2H, m), 1.86-1.92 (2H, m), 1.98-2.04 (2H, m), 2.23-2.30 (3H, m), 2.53-2.60 (1H, m), 2.62-2.72 (1H, m), 2.81 (3H, s), 3.04 (3H, s), 4.92-5.02 (1H, m), 7.32 (2H, J = 8.0 Hz, d), 7.56 (2H, J = 8.0 Hz, d), 7.89 (1H, s). | | | |
| I-3-110 | 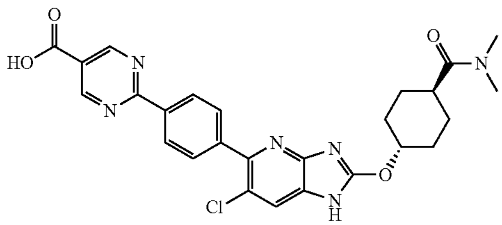 [SMILES: CN(C)C(=O)[C@H]1CC[C@H](Oc2nc3nc(-c4ccc(-c5ncc(C(=O)O)cn5)cc4)c(Cl)cc3[nH]2)CC1] | (DMSO-D6) δ: 1.45-1.65 (m, 4H), 1.76-1.84 (m, 2H), 2.25-2.33 (m, 2H), 2.70 (m, 1H), 2.82 (s, 3H), 3.04 (s, 3H), 4.99 (m, 1H), 7.83 (d, J = 8.28 Hz, 2H), 7.99 (s, 1H), 8.52 (d, J = 8.28 Hz, 2H), 9.22 (s, 2H), 12.84 (s, 1H). | | | |
| I-3-111 | 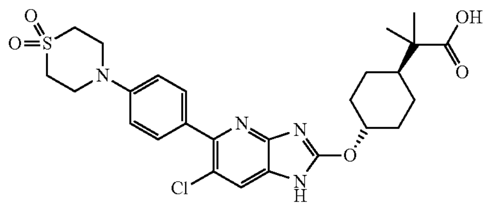 | 1H-NMR (DMSO-D6) δ:1.05 (s, 6H), 1.15-1.29 (m, 2H), 1.47 (d, J = 11.5 Hz, 2H), 1.61 (t J = 10.5 Hz, 1H), 1.70 (d, J = 11.8 Hz, 2H), 2.27 (d, J = 11.5 Hz, 2H), 3.15 (s, 4H), 3.86 (s, 4H), 4.88-4.97 (m, 1H), 5.76 (s, 1H), 7.10 (d, J = 7.8 Hz, 2H), 7.58 (d, J = 7.5 Hz, 2H), 7.84 (s, 1H), 12.11 (br s, 1H). | 1.89 | 547.1 | B |

TABLE 64

| No. | Structure | NMR (δ) | retention time | Mass (M + H) | method |
|---|---|---|---|---|---|
| I-3-112 | 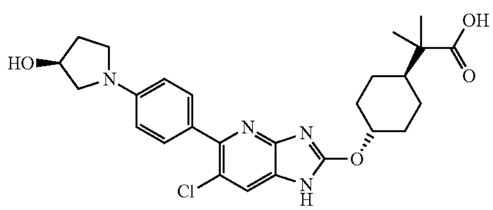 | 1H-NMR (DMSO-D6) δ: 1.06 (s, 6H), 1.16-1.29 (m, 3H), 1.41-1.51 (m, 2H), 1.61 (t, J = 12.4 Hz, 1H), 1.70 (d, J = 12.3 Hz, 2H), 1.88-1.95 (m, 1H), 2.02-2.09 (m, 1H), 2.27 (br s, 2H), 3.13 (d, J = 10.3 Hz, 1H), 3.36 (t, J = 8.8 Hz, 1H), 3.46 (dd, J = 10.2, 4.1 Hz, 1H), 4.42 (d, J = 1.5 Hz, 1H), 4.87-4.95 (m, 1H), 4.97 (d, J = 3.3 Hz, 1H), 6.57 (d, J = 8.0 Hz, 2H), 7.51 (d, J = 8.0 Hz, 2H), 7.76 (br s, 1H), 12.09 (s, 1H), 12.38 (br s, 1H). | 1.92 | 499.1 | B |
| I-3-113 | 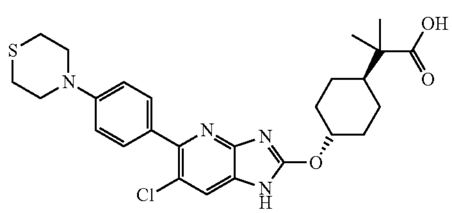 | 1H-NMR (DMSO-D6) δ: 1.05 (s, 6H), 1.24 (t, J = 11.9 Hz, 2H), 1.47 (dd, J = 24.0, 12.3 Hz, 2H), 1.61 (t, J = 11.9 Hz, 1H), 1.69 (d, J = 12.2 Hz, 2H), 2.27 (d, J = 9.3 Hz, 2H), 2.68 (t, J = 4.5 Hz, 4H), 3.63 (t, J = 4.4 Hz, 4H), 4.92 (br s, 1H), 6.98 (d, J = 8.5 Hz, 2H), 7.54 (d, J = 8.4 Hz, 2H), 7.87 (s, 1H), 12.17 (s, 1H), 12.87 (s, 1H). | 2.33 | 515.1 | B |

TABLE 64-continued

| No. | Structure | NMR (δ) | retention time | Mass (M + H) | method |
|---|---|---|---|---|---|
| I-3-114 | 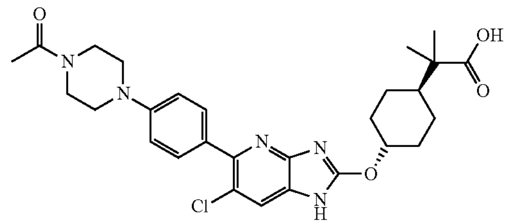 | 1H-NMR (DMSO-D6) δ: 0.94 (t, J = 6.1 Hz, 2H), 1.05 (s, 5H), 1.14-1.35 (m, 2H), 1.47 (d, J = 11.3 Hz, 2H), 1.55-1.61 (m, 1H), 1.70 (d, J = 11.8 Hz, 2H), 2.06 (s, 3H), 2.27 (s, 2H), 3.22 (d, J = 29.1 Hz, 3H), 3.60 (s, 4H), 4.92 (br s, 1H), 7.02 (d, J = 8.0 Hz, 2H), 7.55 (d, J = 7.8 Hz, 2H), 7.87 (br s, 1H), 11.88 (br s, 1H), 12.65 (s, 1H). | 1.87 | 540.2 | B |
| I-3-115 | 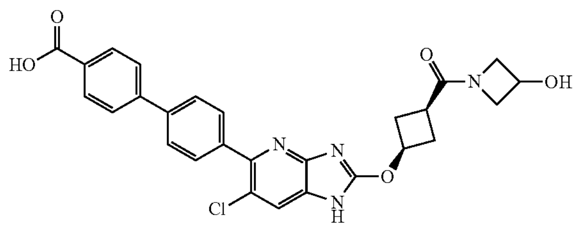 [SMILES: O=C(O)c1ccc(-c2ccc(-c3nc4nc(O[C@H]5C[C@@H](C(=O)N6CC(O)C6)C5)[nH]c4cc3Cl)cc2)cc1] | (DMSO-D6) δ: 8.05 (2H, d, J = 8.2 Hz), 7.94 (1H, br s), 7.91-7.82 (4H, m), 7.78 (2H, d, J = 8.2 Hz), 5.74 (1H, br s), 5.30-5.18 (1H, m), 4.45 (1H, br s), 4.33-4.23 (1H, m), 4.09-3.98 (1H, m), 3.83 (1H, dd, J = 8.8, 4.1 Hz), 3.58 (1H, dd, J = 10.2, 4.6 Hz), 2.85-2.60 (3H, m), 2.26 (2H. s). | | | |
| I-3-116 | 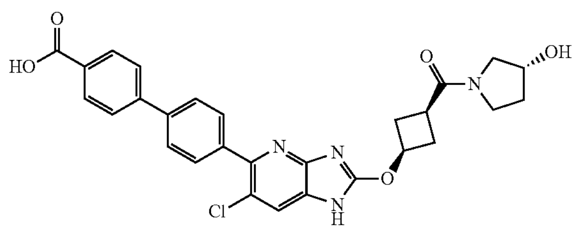 [SMILES: O=C(O)c1ccc(-c2ccc(-c3nc4nc(O[C@H]5C[C@@H](C(=O)N6CC[C@@H](O)C6)C5)[nH]c4cc3Cl)cc2)cc1] | (DMSO-D6) δ: 8.05 (2H, d, J = 8.3 Hz), 7.95 (1H, br s), 7.91-7.82 (4H, m), 7.78 (2H, d, J = 8.2 Hz), 5.33-5.20 (1H, m), 5.12-4.84 (1H, m), 4.27 (1H, d, J = 27.2 Hz), 3.56-3.17 (4H, m), 3.08-2.87 (1H, m), 2.80-2.63 (2H, m), 2.39-2.22 (2H, m), 1.97-1.67 (2H, m). | | | |

TABLE 65

| No. | Structure | NMR (δ) | retention time | Mass (M + H) | method |
|---|---|---|---|---|---|
| I-3-117 | 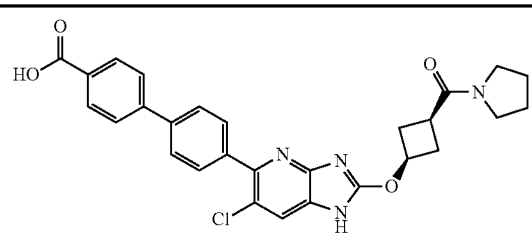 | (DMSO-D6) δ: 8.05 (2H, d, J = 8.2 Hz), 7.94 (1H, br s), 7.92-7.82 (4H, m), 7.78 (2H, d, J = 8.3 Hz), 5.30-5.22 (1H, m), 3.48-3.21 (4H, m), 3.02-2.94 (1H, m), 2.78-2.65 (2H, m), 2.39-2.25 (2H, m), 1.90-1.73 (4H, m). | | | |
| I-3-118 | 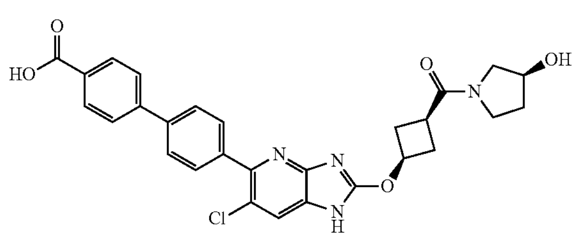 [SMILES: O=C(O)c1ccc(-c2ccc(-c3nc4nc(O[C@H]5C[C@@H](C(=O)N6CC[C@H](O)C6)C5)[nH]c4cc3Cl)cc2)cc1] | (DMSO-D6) δ: 8.05 (2H, d, J = 8.0 Hz), 7.94 (1H, s), 7.92-7.82 (4H, m), 7.78 (2H, d, J = 8.2 Hz), 5.33-5.19 (1H, m), 5.11-4.83 (1H, m), 4.27 (1H, d, J = 26.7 Hz), 3.54-3.19 (4H, m), 3.03-2.90 (1H, m), 2.79-2.64 (2H, m), 2.39-2.24 (2H, m), 1.97-1.68 (2H, m). | | | |
| I-3-119 | 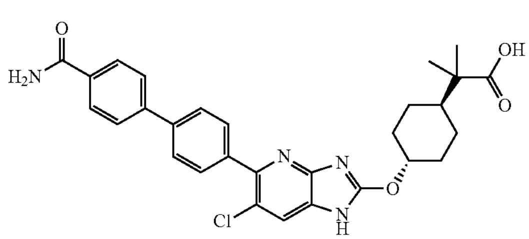 [SMILES: CC(C)(C(=O)O)[C@H]1CC[C@H](Oc2nc3nc(-c4ccc(-c5ccc(C(N)=O)cc5)cc4)c(Cl)cc3[nH]2)CC1] | 1H-NMR (DMSO-D6) δ: 1.06 (s, 6H), 1.20-1.26 (m, 2H), 1.47-1.49 (m, 2H), 1.59-1.72 (m, 3H), 2.28-2.31 (m, 2H), 4.94 (s, 1H), 7.43 (s, 1H), 7.76 (d, J = 8.0 Hz, 2H), 7.83-7.85 (m, 5H), 8.00 (d, J = 8.0 Hz, 2H), 8.06 (s, 1H), 12.18-12.71 (m, 2H). | 1.94 | 533.0 | B |

TABLE 65-continued

| No. | Structure | NMR (δ) | retention time | Mass (M + H) | method |
|---|---|---|---|---|---|
| I-3-120 | 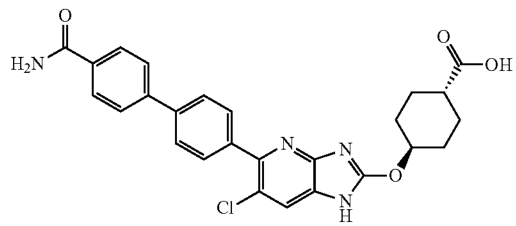 [SMILES: NC(=O)c1ccc(-c2ccc(-c3nc4nc(O[C@H]5CC[C@H](C(=O)O)CC5)[nH]c4cc3Cl)cc2)cc1] | 1H-NMR (DMSO-D6) δ: 1.50-1.58 (m, 4H), 1.99-2.01 (m, 2H), 2.23-2.33 (m, 3H), 4.98-5.01 (m, 1H), 7.43 (s, 1H), 7.77 (d, J = 7.9 Hz, 2H), 7.83-7.85 (m, 4H), 7.99-8.01 (m, 3H), 8.07 (s, 1H), 12.24-12.77 (m, 2H). | 1.65 | 491.0 | B |
| I-3-121 | 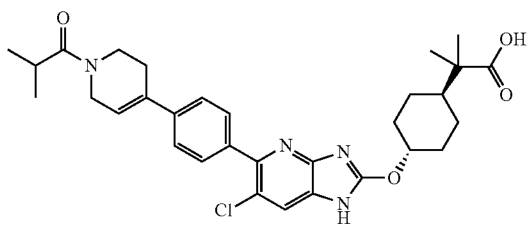 [SMILES: CC(C)C(=O)N1CC=C(c2ccc(-c3nc4nc(O[C@H]5CC[C@H](C(C)(C)C(=O)O)CC5)[nH]c4cc3Cl)cc2)CC1] | 1H-NMR (DMSO-D6) δ: 1.02-1.04 (m, 12H), 1.16-1.27 (m, 2H), 1.41-1.52 (m, 2H), 1.58-1.71 (m, 3H), 2.26-2.29 (m, 2H), 2.61 (s, 1H), 2.91-2.98 (m, 1H), 3.71-3.72 (m, 2H), 4.13 (s, 1H), 4.25 (s, 1H), 4.92-4.95 (m, 1H), 6.30 (s, 1H), 7.54 (d, J = 7.9 Hz, 2H), 7.63 (d, J = 8.0 Hz, 2H), 7.90 (s, 1H), 12.18 (s, 1H), 12.75 (s, 1H). | 2.28 | 565.0 | B |
| I-3-122 | 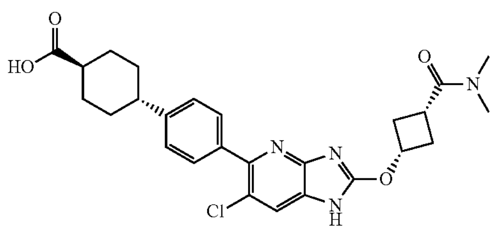 [SMILES: CN(C)C(=O)[C@H]1C[C@@H](Oc2nc3nc(-c4ccc([C@H]5CC[C@H](C(=O)O)CC5)cc4)c(Cl)cc3[nH]2)C1] | (DMSO-d6) δ: 1.47-1.58 (4H, m), 1.86-1.93 (2H, m), 1.98-2.04 (2H, m), 2.24-2.35 (4H, m), 2.65-2.75 (2H, m), 2.83 (3H, s), 2.93 (3H, s), 3.03-3.12 (1H, m), 5.19-5.27 (1H, m), 7.31 (2H, J = 7.8 Hz, d), 7.55 (2H, J = 7.8 Hz, d), 7.86 (1H, s). | | | |

TABLE 66

| No. | Structure | NMR (δ) | retention time | Mass (M + H) | method |
|---|---|---|---|---|---|
| I-3-123 | 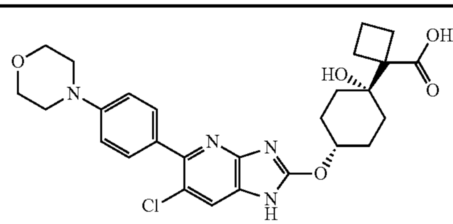 | 1H-NMR (DMSO-D6) δ: 1.16 (s, 6H), 1.51 (t, J =13.2 Hz, 2H), 1.60-1.71 (m, 4H), 1.83-1.86 (m, 2H), 1.99 (m, 2H), 2.16 (m, 2H), 2.36 (m, 2H), 3.18 (br t, 4H), 3.76 (br t, 4H), 4.89 (m, 1H), 7.01 (d, J = 8.4 Hz, 2H), 7.54 (d, J = 8.4 Hz, 2H), 7.88 (brs, 1 H), 12.67 (brs, 1H) | | | |
| I-3-124 | 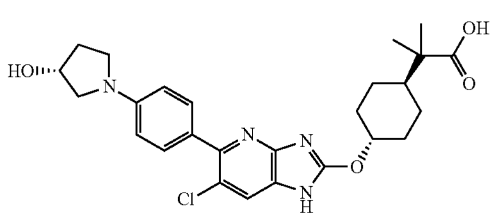 [SMILES: CC(C)(C(=O)O)[C@H]1CC[C@H](Oc2nc3nc(-c4ccc(N5CC[C@@H](O)C5)cc4)c(Cl)cc3[nH]2)CC1] | 1H-NMR (DMSO-D6) δ: 1.05 (s, 6H), 1.24 (t, J = 12.2 Hz, 3H), 1.46 (dd, J = 25.6, 13.3 Hz, 2H), 1.61 (t, J = 11.5 Hz, 1H), 1.70 (d, J = 11.8 Hz, 2H), 1.92 (s, 1H), 2.06 (dd, J = 12.8, 4.8 Hz, 1H), 2.27 (d, J = 9.8 Hz, 2H), 3.13 (d, J = 10.0 Hz, 1H), 3.37 (t, J = 8.2 Hz, 1H), 3.46 (dd, J=10.2, 4.9 Hz, 1H), 4.42 (s, 1H), 4.91 (t, J = 11. 3 Hz, 1H), 4.97 (d, J = 3.0 Hz, 1H), 6.57 (d, J = 8.0 Hz, 2H), 7.51 (d, J = 7.8 Hz, 2H), 7.77 (br s, 1H), 12.13 (s, 1H), 12.59 (s, 1H), | 1.91 | 499.5 | B |

TABLE 66-continued

| No. | Structure | NMR (δ) | retention time | Mass (M + H) | method |
|---|---|---|---|---|---|
| I-3-125 | 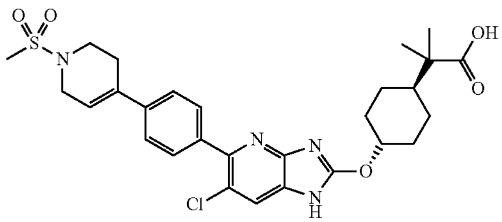 | 1H-NMR (DMSO-D6) δ: 1.06 (s, 6H), 1.24 (t, J = 12.8 Hz, 2H), 1.48 (dd, J = 23.3, 12.0 Hz, 2H), 1.61 (t, J = 12.7 Hz, 1H), 1.70 (d, J = 12.8 Hz, 2H), 2.28 (d, J = 11.0 Hz, 2H), 2.66 (d, J = 0.5 Hz, 2H), 3.41 (t, J = 5.4 Hz, 4H), 3.90 (s, 4H), 4.90-4.97 (m, 1H), 6.31 (s, 1H), 7.55 (d, J = 7.8 Hz, 2H), 7.64 (d, J = 7.8 Hz, 2H), 7.89 (s, 1H), 12.16 (s, 1H). | 2.12 | 573.1 | B |
| I-3-126 | 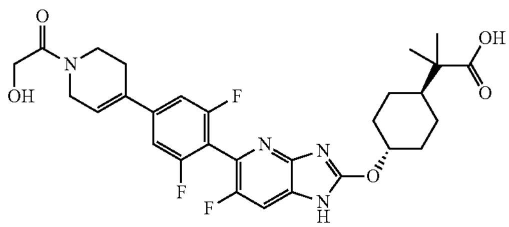 [SMILES: CC(C)(C(=O)O)[C@H]1CC[C@H](Oc2nc3nc(-c4c(F)cc(C5=CCN(C(=O)CO)CC5)cc4F)c(F)cc3[nH]2)CC1] | (DMSO-D6) δ: 1.05 (6H, s), 1.16-1.30 (2H, m), 1.42-1.52 (2H, m), 1.58-1.72 (3H, m), 2.26-2.33 (2H, m), 2.56-2.63 (2H, m), 3.57-3.64 (1H, m), 3.68-3.72 (1H, m), 4.09-4.21 (4H, m), 4.58-4.67 (1H, m), 4.88-4.93 (1H, m), 6.44-6.48 (1H, m), 7.34-7.39 (2H, m), 7.83 (1H, brs). | | | |
| I-3-127 | 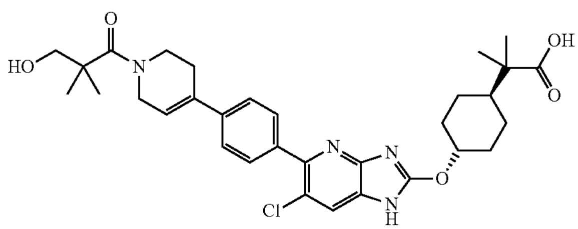 | 1H-NMR (DMSO-D6) δ: 1.05 (s, 6H), 1.20 (s, 6H), 1.24 (t, J = 11.7 Hz, 2H), 1.48 (dd, J = 25.2, 13.1 Hz, 2H), 1.62 (t, J = 13.1 Hz, 1H), 1.70 (d, J = 11.3 Hz, 2H), 2.27 (d, J = 8.0 Hz, 2H), 2.56 (s, 1H), 3.36-3.41 (m, 1H), 3.47 (d, J = 5.8 Hz, 2H), 3.79 (br s, 2H), 4.21 (s, 2H), 4.61 (t, J = 5.9 Hz, 1H), 4.94 (br s, 1H), 6.30 (s, 1H), 7.54 (d, J = 8.0 Hz, 2H), 7.63 (d, J = 8.2 Hz, 2H), 7.86 (br s, 1H), 12.17 (br s, 1H), 12.56 (d, J = 159.1 Hz, 1H). | 2.12 | 595.2 | B |

TABLE 67

| No. | Structure | NMR (δ) | retention time | Mass (M + H) | method |
|---|---|---|---|---|---|
| I-3-128 | 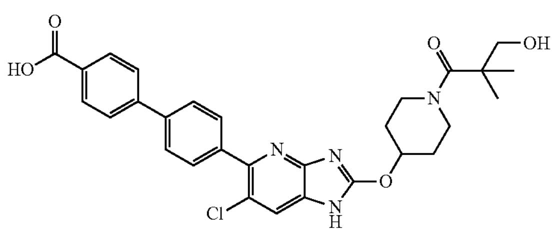 [SMILES: CC(C)(CO)C(=O)N1CCC(Oc2nc3nc(-c4ccc(-c5ccc(C(=O)O)cc5)cc4)c(Cl)cc3[nH]2)CC1] | (DMSO-D6) δ: 8.06 (2H, d, J = 8.2 Hz), 7.98 (1H, br s), 7.94-7.82 (4H, m), 7.78 (2H, d, J = 8.2 Hz), 5.38-5.22 (1H, m), 4.67-4.52 (1H, m), 4.10-3.86 (2H, m), 3.52-3.21 (4H, m), 2.24-2.03 (2H, m), 1.84-1.57 (2H, m), 1.18 (6H, s). | | | |
| I-3-129 | 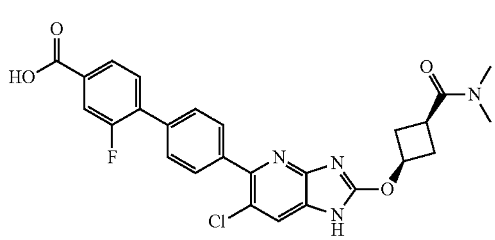 [SMILES: CN(C)C(=O)[C@H]1C[C@@H](Oc2nc3nc(-c4ccc(-c5ccc(C(=O)O)cc5F)cc4)c(Cl)cc3[nH]2)C1] | (DMSO-D6) δ: 7.99 (1H, br s), 7.89 (1H, d, J = 8.0 Hz), 7.82-7.71 (6H, m), 5.30-5.22 (1H, m), 3.17-3.02 (1H, m), 2.99-2.80 (6H, m), 2.79-2.66 (2H, m), 2.39-2.24 (2H, m). | | | |

TABLE 67-continued

| No. | Structure | NMR (δ) | retention time | Mass (M + H) | method |
|---|---|---|---|---|---|
| I-3-130 | 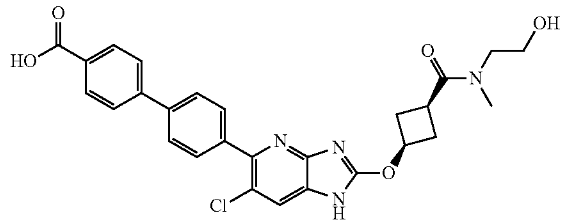 [SMILES: CN(CCO)C(=O)[C@H]1C[C@@H](Oc2nc3nc(-c4ccc(-c5ccc(C(=O)O)cc5)cc4)c(Cl)cc3[nH]2)C1] | (DMSO-D6) δ: 8.06 (2H, d, J = 8.2 Hz), 7.95 (1H, br s), 7.92-7.81 (4H, m), 7.78 (2H, d, J = 8.2 Hz), 5.32-5.17 (1H, m), 4.92-4.58 (1H, m), 3.58-3.26 (4H, m), 3.23-3.03 (1H, m), 3.00-2.80 (3H, m), 2.80-2.62 (2H, m), 2.40-2.24 (2H, m). | | | |
| I-3-131 | 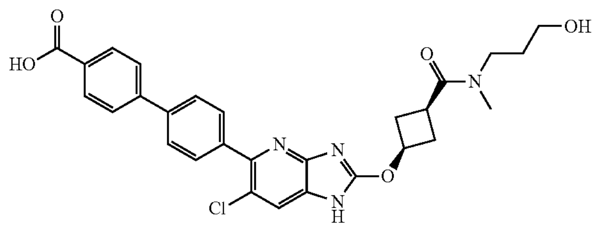 [SMILES: CN(CCCO)C(=O)[C@H]1C[C@@H](Oc2nc3nc(-c4ccc(-c5ccc(C(=O)O)cc5)cc4)c(Cl)cc3[nH]2)C1] | (DMSO-D6) δ: 8.05 (2H, d, J = 8.3 Hz), 7.96 (1H, br s), 7.93-7.82 (4H, m), 7.78 (2H, d, J = 8.2 Hz), 5.33-5.19 (1H, m), 4.72-4.36 (1H, m), 3.51-3.25 (4H, m), 3.17-3.07 (1H, m), 2.98-2.79 (3H, m), 2.79-2.63 (2H, m), 2.41-2.21 (2H, m), 1.74-1.50 (2H, m). | | | |
| I-3-132 | 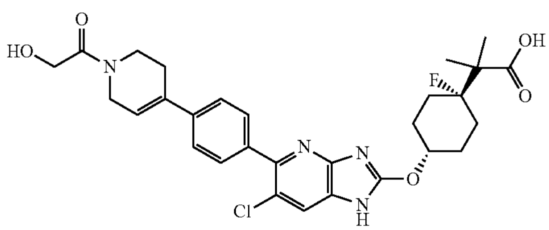 [SMILES: CC(C)(C(=O)O)[C@]1(F)CC[C@@H](Oc2nc3nc(-c4ccc(C5=CCN(C(=O)CO)CC5)cc4)c(Cl)cc3[nH]2)CC1] | 1H-NMR (DMSO-D6) δ: 1.18 (s, 6H), 1.68-1.85 (m, 4H), 2.00-2.18 (m, 4H), 2.60 (m, 2H), 4.08-4.20 (m, 4H), 4.60-4.66 (m, 1H), 5.04 (m, 1H), 6.26-6.30 (m, 1H), 7.53 (br t, J = 8.0 Hz, 2H), 7.63 (d, J = 8.0 Hz, 2H), 7.93 (brs, 1H), 12.52 (brs, 1H). | | | |
| I-3-133 | 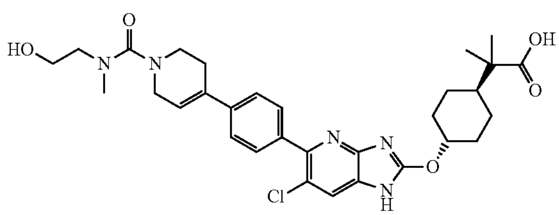 | 1H-NMR (DMSO-D6) δ: 1.16 (s, 6H), 1.34 (q, J = 11.0 Hz, 1H), 1.52-1.62 (m, 2H), 1.72(t, J = 12.0 Hz, 1H), 1.81 (d, J = 12.0 Hz, 2H), 2.39 (d, J = 9.3 Hz, 2H), 2.67 (s, 2H), 2.95 (s, 3H), 3.32 (t, J = 5.8 Hz, 2H), 3.46-3.50 (m, 3H), 3.66 (q, J = 5.4 Hz, 2H), 3.98 (s, 2H), 4.82 (t, J = 5.1 Hz, 1H), 5.04 (s, 1H), 6.39 (s, 1H), 7.65 (d, J = 7.8 Hz, 2H), 7.74 (d, J = 8.0 Hz, 2H), 8.03 (br s, 1H), 12.26 (br s, 1H), 12.84 (br s, 1H). | 1.96 | 596.2 | B |

TABLE 68

| No. | Structure | NMR (δ) | retention time | Mass (M + H) | method |
|---|---|---|---|---|---|
| I-3-134 | 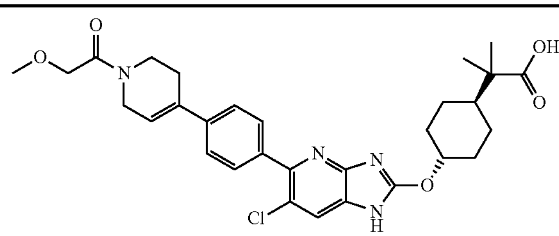 | 1H-NMR (DMSO-D6) δ: 1.06 (s, 6H), 1.25 (t, J = 12.5 Hz, 2H), 1.48 (dd, J = 25.8, 11.4 Hz, 2H), 1.62 (t, J = 9.5 Hz, 1H), 1.70 (d, J = 12.3 Hz, 2H), 2.28 (d, J = 9.7 Hz, 2H), 2.60 (s, 1H), 3.32 (s, 3H), 3.38-3.41 (m, 2H), 3.62 (t, J = 6.1 Hz, 1H), 3.70 (t, J = 5.6 Hz, 1H), 4.12-4.20 (m, 4H), 4.86-4.99 (m, 1H), 6.28 (d, J = 14.4 Hz, 1H), 7.54 (d, J = 7.4 Hz, 2H), 7.64 (d, J = 8.2 Hz, 2H), 7.90 (s, 1H), 12.19 (br s, 1H). | 2.01 | 567.1 | B |

TABLE 68-continued

| No. | Structure | NMR (δ) | retention time | Mass (M + H) | method |
|---|---|---|---|---|---|
| I-3-135 | 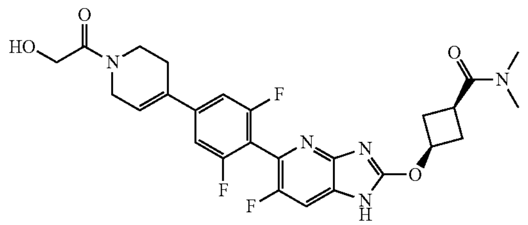 [SMILES: CN(C)C(=O)[C@H]1C[C@@H](Oc2nc3nc(-c4c(F)cc(C5=CCN(C(=O)CO)CC5)cc4F)c(F)cc3[nH]2)C1] | (DMSO-D6) δ: 2.22-2.35 (2H, m), 2.50-2.62 (2H, m), 2.65-2.75 (2H, m), 2.83 (3H, s), 2.93 (3H, s), 3.03-3.15 (1H, m), 3.54-3.59 (1H, m), 3.68-3.74 (1H, m), 4.08-4.20 (4H, m), 4.57-4.69 (1H, m), 5.19-5.27 (1H, m), 6.42-6.50 (1H, m), 7.30-7.38 (2H, m), 7.60-7.85 (1H, m). | | | |
| I-3-136 | 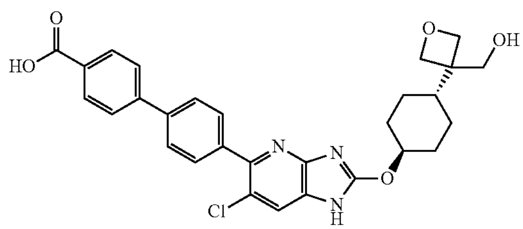 [SMILES: O=C(O)c1ccc(-c2ccc(-c3nc4nc(O[C@H]5CC[C@H](C6(CO)COC6)CC5)[nH]c4cc3Cl)cc2)cc1] | (DMSO-D6) δ: 1.20-1.55 (4H, m), 1.76 (3H, d, J = 8.7 Hz), 2.25-2.35 (2H, m), 3.44 (2H, s), 4.33 (4H, s), 4.98 (1H, s), 7.70-7.85 (7H, m), 8.01 (2H, s), 8.47 (1H, s). | | | |
| I-3-137 | 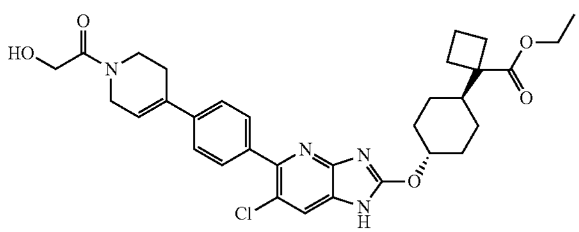 [SMILES: CCOC(=O)C1([C@H]2CC[C@H](Oc3nc4nc(-c5ccc(C6=CCN(C(=O)CO)CC6)cc5)c(Cl)cc4[nH]3)CC2)CCC1] | 1H-NMR (DMSO-D6) δ: 1.09-1.23 (m, 5H), 1.48 (dd, J = 23.34, 11.29 Hz, 2H), 1.69-1.82 (m, 5H), 1.99-2.08 (m, 2H), 2.28 (d, J = 9.79 Hz, 4H), 2.45-2.63 (m, 2H), 3.56-3.76 (m, 2H), 4.07-4.21 (m, 6H), 4.59 (br s, 1H), 4.92-4.95 (m, 1H), 6.27 (d, J = 15.56 Hz, 1H), 7.51-7.57 (m, 2H), 7.63 (d, J = 8.03 Hz, 2H), 7.93 (s, 1H), 12.73 (s, 1H). | | | |
| I-3-138 | 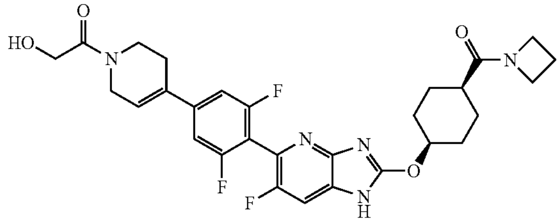 [SMILES: O=C(CO)N1CC=C(c2cc(F)c(-c3nc4nc(O[C@H]5CC[C@@H](C(=O)N6CCC6)CC5)[nH]c4cc3F)c(F)c2)CC1] | (DMSO-D6) δ: 2.14-2.33 (4H, m), 2.50-2.70 (4H, m), 2.71-2.81 (1H, m), 3.53-3.62 (1H, m), 3.69-3.75 (1H, m), 3.85 (2H, J = 7.6 Hz, t), 4.02-4.17 (6H, m), 4.53-4.67 (1H, m), 5.21-5.26 (1H, m), 6.41-6.50 (1H, m), 7.30-7.39 (2H, m), 7.78-7.85 (1H, s). | | | |

Evaluation Method of an Activator for AMP-Activated Protein Kinase (AMPK)

TEST EXAMPLE 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)—N,N,N',N'-tetraacetic acid (EGTA), 5 mM disodium β-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium β-glycerophosphate, 2 mM dithiothreitol, 0.4 mM ATP and 3 FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 1 are shown below.
Compound (I-1-1); EC150=1600 nM, Emax=218%
Compound (I-1-4): EC150=160 nM, Emax=283%
Compound (I-1-10); EC150=390 nM, Emax=270%
Compound (I-1-11); EC150=2100 nM, Emax=238%
Compound (I-1-12); EC150=320 nM, Emax=263%
Compound (I-1-21); EC150=730 nM, Emax=284%
Compound (I-1-25); EC150=3100 nM, Emax=226%
Compound (I-1-27); EC150=310 nM, Emax=226%
Compound (I-1-28); EC150=210 nM, Emax=231%
Compound (I-1-32): EC150=200 nM, Emax=280%
Compound (I-1-37); EC150=910 nM, Emax=228%
Compound (I-1-39); EC150=160 nM, Emax=258%
Compound (I-1-57); EC150=140 nM, Emax=277%
Compound (I-1-62): EC 150=540 nM, Emax=228%
Compound (I-1-65); EC150=550 nM, Emax=269%
Compound (I-1-68); EC150=4900 nM, Emax=174%
Compound (I-2-30); EC150=650 nM, Emax=178%
Compound (I-2-33); EC150=70 nM, Emax=236%
Compound (I-2-40); EC150=51 nM, Emax=293%
Compound (I-2-58); EC150=650 nM, Emax=169%
Compound (I-2-59); EC150=2300 nM, Emax=181%
Compound (I-2-60); EC150=49 nM, Emax=205%
Compound (I-2-61); EC150=72 nM, Emax=189%
Compound (I-2-71); EC150=2400 nM, Emax=193%
Compound (I-2-76); EC150=14 nM, Emax=232%
Compound (I-2-85); EC150=18 nM, Emax=255%
Compound (I-2-88); EC150=65 nM, Emax=288%
Compound (I-2-104): EC150=6400 nM, Emax=161%
Compound (I-2-109); EC150=250 nM, Emax=212%
Compound (I-2-112); EC150=25 nM, Emax=246%
Compound (I-2-114); EC150=49 nM, Emax=215%
Compound (I-2-116); EC150=130 nM, Emax=229%
Compound (I-2-118); EC150=230 nM, Emax=194%
Compound (I-2-121); EC150=160 nM, Emax=258%
Compound (I-2-129); EC150=15 nM, Emax=276%
Compound (I-3-2): EC150=1.4 nM, Emax=182%
Compound (I-3-3): EC150=19 nM, Emax=271%
Compound (I-3-11): EC150=61 nM, Emax=240%
Compound (I-3-12): EC150=21 nM, Emax=211%
Compound (I-3-14): EC150=130 nM, Emax=232%
Compound (I-3-24): EC150=0.79 nM, Emax=318%
Compound (I-3-25): EC150=230 nM, Emax=210%
Compound (I-3-26): EC150=68 nM, Emax=221%
Compound (I-3-27): EC150=280 nM, Emax=228%
Compound (I-3-30): EC150=0.49 nM, Emax=345%
Compound (I-3-37): EC150=5.6 nM, Emax=257%
Compound (I-3-39): EC150=5.1 nM, Emax=286%
Compound (I-3-40): EC150=23 nM, Emax=244%
Compound (I-3-44): EC150=7.6 nM, Emax=275%
Compound (I-3-50): EC150=160 nM, Emax=228%
Compound (I-3-51): EC150=4.5 nM, Emax=338%
Compound (I-3-52): EC150=2.3 nM, Emax=400%
Compound (I-3-53): EC150=51 nM, Emax=261%
Compound (I-3-54): EC150=270 nM, Emax=201%
Compound (I-3-62): EC150=22 nM, Emax=333%
Compound (I-3-65): EC150=24 nM, Emax=233%
Compound (I-3-66): EC150=3.4 nM, Emax=389%
Compound (I-3-69): EC150=60 nM, Emax=259%
Compound (I-3-75): EC150=47 nM, Emax=236%
Compound (I-3-83): EC150=24 nM, Emax=278%
Compound (I-3-85): EC150=4.9 nM, Emax=276%
Compound (I-3-86): EC150=23 nM, Emax=277%
Compound (I-3-89): EC150=65 nM, Emax=236%
Compound (I-3-90): EC150=17 nM, Emax=320%
Compound (I-3-91): EC150=21 nM, Emax=287%
Compound (I-3-92): EC150=23 nM, Emax=303%
Compound (I-3-93): EC150=9.6 nM, Emax=301%
Compound (I-3-97): EC150=0.68 nM, Emax=343%
Compound (I-3-99): EC150=3.7 nM, Emax=310%
Compound (I-3-104): EC150=21 nM, Emax=203%
Compound (I-3-106): EC150=9.1 nM, Emax=311%
Compound (I-3-108): EC150=8.2 nM, Emax=291%
Compound (I-3-115): EC150=23 nM, Emax=260%
Compound (I-3-119): EC150=1.6 nM, Emax=300%
Compound (I-3-120): EC150=28 nM, Emax=216%
Compound (I-3-123): EC150=18 nM, Emax=243%

Preparation Method of Human AMPK α2β2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6× His tag at the 5' terminus) expressing plasmid. The plasmid was contransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK β from 720 ml of broth.

Evaluation Method of an Activator for AMP-Activated Protein Kinase (AMPK)

TEST EXAMPLE 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)—N,N,N',N'-tetraacetic acid (EGTA), 5 mM disodium β-glycerophosphate, 1 mM dithiothreitol and 0.2 mM ATP, and the obtained liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophaphate, 2 mM dithiothreitol, 0.4 mM ATP and 3 µM FL-Peptide 7 (manufactured by Caliper Life Sciences, Inc.) was added in equal amount (10 µl in total). The obtained liquid was allowed to react at 25° C. for 2 hours, and 10 µl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound (I-2-76): EC150=85 nM, Emax=175%
Compound (I-2-112): EC150=74 nM, Emax=269%
Compound (I-2-129): EC150=9.2 nM, Emax=339%
Compound (I-3-24): EC150=11 nM, Emax=271%
Compound (I-3-30): EC150=12 nM, Emax=271%
Compound (I-3-37): EC150=5 nM, Emax=237%
Compound (I-3-40): EC150=69 nM, Emax=228%
Compound (I-3-54): EC150=2.2 nM, Emax=373%
Compound (I-3-86): EC150=11 nM, Emax=259%
Compound (I-3-90): EC150=21 nM, Emax=274%
Compound (I-3-99): EC150=15 nM, Emax=261%
Compound (I-3-120): EC150=7 nM, Emax=262%

As can be seen from the above Test Examples, the compounds of the present invention have an excellent activating effect on both of an AMPK al trimer and an AMPK α2 trimer.

Usefulness as a medicament can be examined by the following tests etc.

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a co-factor was added to initiate a reaction as an *index* (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each *index* reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and IC50 was calculated by reverse presumption by a logistic model using a concentration and an inhibition rate.

FAT Test

Each 20 µL of freeze-stored *Salmonella typhimurium* (TA98 and TA100 strain) was inoculated in 10 mL of liquid nutrient medium (2.5% Oxoid nutrient broth No. 2), and the cultures were incubated at 37° C. under shaking for 10 hours. 9 mL of TA98 culture was centrifuged (2000×g, 10 minutes) to remove medium, and the bacteria was suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of Exposure medium (Micro F buffer containing Biotin: 8 μg/mL, histidine 0.2 μg/mL, glucose: 8 mg/mL). 3.16 mL of TA100 culture was added to 120 mL of Exposure medium to prepare the test bacterial solution. 588 μL of the test bacterial solution (or mixed solution of 498 μl of the test bacterial solution and 90 μL of the S9 mix in the case with metabolic activation system) was mixed with each 12 μL of the following solution: DMSO solution of the test substance (eight dose levels from maximum dose 50 mg/mL at 2-fold ratio); DMSO as negative control; 50 μg/mL of 4-nitroquinoline-1-oxide DMSO solution as positive control for TA98 without metabolic activation system; 0.25 μg/mL of 2-(2-furyl)-3-(5-nitro-2-furyl)acrylamide DMSO solution as positive control for TA100 without metabolic activation system; 40 μ/g/mL of 2-aminoanthracene DMSO solution as positive control for TA98 with metabolic activation system; or 20 μg/mL of 2-aminoanthracene DMSO solution as positive control for TA100 with metabolic activation system. 12 μL of the solution and 588 μL of the test bacterial solution (a mixed solution of 498 μl of the test bacterial solution and 90 μL of S9 mix with metabolic activation condition) were mixed and incubated at 37° C. under shaking for 90 minutes. 460 μL of the bacterial solution exposed to the test substance was mixed with 2300 μL of Indicator medium (Micro F buffer containing biotin: 8 pg/mL, histidine 0.2 μg/mL, glucose: 8 mg/mL, Bromo Cresol Purple: 37.5 μg/mL), each 50 μL was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose was counted, and evaluated the mutagenicity by comparing with the negative control group.

Solubility Test

The solubility of a compound was determined under a condition in which 1% DMSO was added. 10 mM compound solution was prepared using DMSO, and then 6 μL of the compound solution was added to 594 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on Ix, Powder Solubility Test Appropriate amounts of the test substances were put into appropriate containers. To the respective containers were added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures were filtered, and 100 μL of methanol was added to each of the filtrate (100 μL) so that the filtrates were two-fold diluted. The dilution ratio was changed if necessary. After confirmation of no bubbles and precipitates, the containers were sealed and shaken. Quantification was performed by HPLC with an absolute calibration method.

BA Test

Materials and Methods for Studies on Oral Absorption
(1) Animals: mice or rats
(2) Animal husbandry:
Mice and rats had free access to solid food and sterilized bottled tap water.
(3) Setting of Dose and group compositions:
orally or intravenously administered at a predetermined dose; Group compositions were as shown below (Dose depends on the compound)
Oral: 1 to 30 mg/kg (n=2 to 3)
Intravenous: 0.5 to 10 mg/kg (n=2 to 3)
(4) Preparation for dosing formulation:
for oral administration, in a solution or a suspension state; for intravenous administration, in a solubilized state (5) Dosing procedure:

In oral administration study, the test suspension was dosed to the stomach of rats by using a gavage tube In intravenous administration study, the test solution was dosed to rats via tail vein using a syringe with a needle.

(6) Evaluation items:

Blood was collected at each time point, and plasma concentration of the test substance was determined by a LC/MS/MS system.

(7) Data analysis:

Regarding the transition of the plasma concentration, area under the plasma concentration-time curve (AUC) was calculated by means of WinNonlin® program, respectively. Bioavailability (BA) was calculated by using AUC values in oral administration study and in intravenous administration study.

Fluctuation Ames Test

In 10 ml of nutrient liquid medium (2.5% Oxoid nutrient broth No. 2), 20 µL of freeze-stored *Salmonella typhimurium* (TA 98 strain, TA 100 strain) is seeded, and the medium is pre-cultured with shaking at 37° C. for 10 hours. For the TA 98 strain, 9 mL of bacterial liquid is centrifuged (2000×g, 10 min) to remove broth. The bacteria are suspended in 9 mL of Micro F buffer solution ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension is added to 110 mL of Exposure medium (Micro F buffer solution containing biotin: 8 µg/mL, histidine: 0.2 µg/mL and glucose: 8 mg/mL). For the TA 100 strain, 3.16 mL of bacterial liquid is added to 120 mL of Exposure medium to prepare a test bacterial liquid. Each 12 µL of a solution of a compound of the present invention in DMSO (a few-stage dilution from a maximum dose of 50 mg/mL at a common ratio of 2 or 3), DMSO as a negative control, a 50 µg/mL solution of 4-nitroquinoline-1-oxide in DMSO for the TA 98 strain and a 0.25 µg/mL solution of 2-(2-furyl-3-(5-nitro-2-furyl)acrylamide in DMSO for the TA 100 strain under non-metabolic activation conditions, a 40 µg/mL solution of 2-aminoanthracene in DMSO for the TA 98 strain and a 20 µg/mL solution of 2-aminoanthracene in DMSO for the TA 100 strain under metabolic activation conditions as positive controls is mixed with 588 µL of a test bacterial liquid (a mixed liquid of 498 µL of test bacterial liquid and 90 µL of S9 mix under metabolic activation conditions), and the obtained liquid is cultured with shaking at 37° C. for 90 minutes. A bacterial liquid exposed to a compound of the present invention, 460 µL, is mixed with 2300 µL of Indicator medium (Micro F buffer solution containing biotin: 8 µg/mL, histidine: 0.2 µg/mL, glucose: 8 mg/mL and bromocresol purple: 37.5 µg/mL), and 50 µL each of the obtained liquid is dispensed into a microplate 48 wells/dose. The plate is static-cultured at 37° C. for 3 days. A well which contains bacteria acquiring the ability to proliferate by mutation of an amino acid (histidine)-synthesizing enzyme gene is changed from purple to yellow by pH changes. Therefore, the number of bacteria-proliferation wells, whose color has been changed to yellow, of 48 wells per dose is counted, and compared with that of the negative control group for evaluation. Negative mutagenicity is shown as (−), and positive is shown as (+).

FORMULATION EXAMPLE 1

A hard gelatin capsule is prepared using the following ingredients.

|  | Dose (mg/capsule) |
| --- | --- |
| Active ingredient | 250 |
| Starch (dry) | 200 |
| Magnesium stearate | 10 |
| Total | 460 mg |

FORMULATION EXAMPLE 2

A tablet is prepared using the following ingredients.

|  | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed and compressed to form tablets, each of which has a weight of 665 mg.

FORMULATION EXAMPLE 3

An aerosol solution containing the following ingredients is prepared.

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to a part of propellant 22. The obtained mixture is cooled to −30° C., and transferred to a packing machine. Thereafter, the amount to be required is supplied to a stainless steel container, and diluted with remaining propellant. A bubbling unit is attached to the container.

FORMULATION EXAMPLE 4

A tablet containing 60 ma of active ingredient is prepared as follows.

| Active ingredient | 60 mg |
| --- | --- |
| Starch | 45 mg |
| Microcrystalline cellulose | 35 mg |
| Polyvinylpyrrolidone (a 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and then adequately mixed. An aqueous solution containing polyvinylpyrrolidone is mixed with the obtained powder, and the mixture is then passed through a No. 14 mesh U.S. sieve. Granules obtained in this manner are dried at 50° C. and passed through a No. 18 mesh U.S. sieve. The sodium carboxymethyl starch, magnesium stearate and talc that are passed through a No. 60 mesh U.S. sieve in advance, are added to the granules, and the obtained mixture is mixed and then compressed by a tablet machine to obtain tablets, each of which has a weight of 150 mg.

FORMULATION EXAMPLE 5

A capsule containing 80 mg of active ingredient is prepared as follows.

| Active ingredient | 80 mg |
|---|---|
| Starch | 59 mg |
| Microcrystalline cellulose | 59 mg |
| Magnesium stearate | 2 mg |
| Total | 200 mg |

The active ingredient, starch, cellulose and magnesium stearate are mixed and passed through a No. 45 mesh U.S. sieve, and each 200 mg of the mixture is filled into a hard gelatin capsule.

FORMULATION EXAMPLE 6

A suppository containing 225 mg of active ingredient is prepared as follows.

| Active ingredient | 225 mg |
|---|---|
| Saturated fatty acid glyceride | 2000 mg |
| Total | 2225 mg |

The active ingredient is passed through a No. 60 mesh U.S. sieve and suspended in a saturated fatty acid glyceride, which has been melted by minimum heating in advance. Thereafter, the resultant mixture is put into a mold with an apparent weight of 2 g and cooled.

FORMULATION EXAMPLE 7

A suspension containing 50 mg of active ingredient is prepared as follows.

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Pigment | q.v. |
| Total after adding purified water | 5 ml |

The active ingredient is passed through a No. 45 mesh U.S. sieve and mixed with sodium carboxymethyl cellulose and syrup to form a smooth paste. The benzoic acid solution and the flavor diluted with part of water are added, and stirred. A sufficient amount of water is then added thereto to obtain a required volume.

FORMULATION EXAMPLE 8

An intravenous formulation is prepared as follows.

| Active ingredient | 100 mg |
|---|---|
| Saturated fatty acid glyceride | 1000 ml |

A solution of the above-described ingredients is usually intravenously administered to a patient at a rate of 1 ml per 1 min.

INDUSTRIAL APPLICABILITY

As is apparent from the above test examples, the compounds of the present invention show an AMPK activating effect. Therefore, the compounds of the present invention are very useful as a therapeutic agent for type II diabetes, hyperglycemia, metabolic syndrome, obesity, hypercholesterolemia and hypertension.

The invention claimed is:
1. A compound of formula (I):

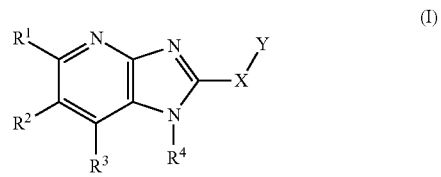

or a pharmaceutically acceptable salt thereof,
wherein $R^4$ is hydrogen,
$R^1$, $R^2$ and $R^3$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino, with the proviso that $R^1$, $R^2$ and $R^3$ are not simultaneously hydrogen, X is —O—, Y is substituted or unsubstituted heterocyclyl, with the proviso that c) when R¹ is substituted aryl having at least one substituent, the at least one substituent of substituted aryl is each independently selected from the group consisting of ca) hydroxy, carboxy, nitro, cyano;

cb) substituted or unsubstituted alkyl, wherein a substituent of substituted alkyl is halogen, carboxy, nitro, cyano, alkyl, aryl, cycloalkyl, cycloalkenyl, heteroaryl, heterocyclyl, alkyloxycarbonyl, acylamino, or substituted or unsubstituted carbamoyl (wherein a substituent of substituted carbamoyl is alkyl);

cc) substituted or unsubstituted alkenyl, wherein a substituent of substituted alkenyl is halogen, hydroxy, carboxy, nitro, cyano, alkyl, aryl, cycloalkyl, cycloalkenyl, heteroaryl or heterocyclyl;

cd) substituted or unsubstituted alkynyl, wherein a substituent of substituted alkynyl is halogen, hydroxy, carboxy, nitro, cyano, aryl, cycloalkenyl, or heteroaryl;

cg) substituted or unsubstituted cycloalkenyl, wherein a substituent of substituted cycloalkenyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, alkyloxycarbonyl, substituted or unsubstituted carbamoyl (wherein a substituent of substituted carbamoyl is substituted or unsubstituted alkyl (wherein a substituent of substituted alkyl is hydroxy)) or alkylsulfonyl;

ch) substituted or unsubstituted heteroaryl, wherein a substituent of substituted heteroaryl is selected from halogen, hydroxy, carboxy, nitro, cyano, alkyl, aryl, cycloalkyl, cycloalkenyl, or heterocyclyl;

ci) substituted heterocyclyl, wherein a substituent of substituted heterocyclyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, oxo, substituted or unsubstituted carbamoyl (wherein a substituent of substituted carbamoyl is substituted or unsubstituted alkyl (wherein a substituent of substituted alkyl is hydroxy)) or alkylsulfonyl;

ck) substituted or unsubstituted alkenyloxy, wherein a substituent of substituted alkenyloxy is halogen, hydroxy, carboxy, nitro, cyano, alkyl, aryl, cycloalkyl, cycloalkenyl, heteroaryl or heterocyclyl;

cl) substituted or unsubstituted aryloxy, wherein a substituent of substituted aryloxy is halogen, hydroxy, carboxy, nitro, cyano, alkyl, aryl, cycloalkyl, cycloalkenyl, heteroaryl or heterocyclyl;

cm) substituted or unsubstituted cycloalkyloxy, wherein a substituent of substituted cycloalkyloxy is halogen, hydroxy, carboxy, nitro, cyano, alkyl, aryl, cycloalkyl, cycloalkenyl, heteroaryl or heterocyclyl;

cn) substituted or unsubstituted cycloalkenyloxy, wherein a substituent of substituted cycloalkenyloxy is halogen, hydroxy, carboxy, nitro, cyano, alkyl, aryl, cycloalkyl, cycloalkenyl, heteroaryl or heterocyclyl;

co) substituted or unsubstituted heteroaryloxy, wherein a substituent of substituted heteroaryloxy is halogen, hydroxy, carboxy, nitro, cyano, alkyl, aryl, cycloalkyl, cycloalkenyl, heteroaryl or heterocyclyl;

cp) substituted or unsubstituted heterocyclyloxy, wherein a substituent of substituted heterocyclyloxy is halogen, hydroxy, carboxy, nitro, cyano, alkyl, aryl, cycloalkyl, cycloalkenyl, heteroaryl or heterocyclyl;

cq) substituted or unsubstituted arylalkyl, wherein a substituent of substituted arylalkyl is halogen, hydroxy, carboxy, nitro, cyano, alkyl, aryl, cycloalkyl, cycloalkenyl, heteroaryl or heterocyclyl;

cr) substituted or unsubstituted arylalkyloxy, wherein a substituent of substituted arylalkyloxy is halogen, hydroxy, carboxy, nitro, cyano, alkyl, aryl, cycloalkyl, cycloalkenyl, heteroaryl or heterocyclyl;

cs) substituted or unsubstituted cycloalkylalkyloxy, wherein a substituent of substituted cycloalkylalkyloxy is halogen, hydroxy, carboxy, nitro, cyano, alkyl, aryl, cycloalkyl, cycloalkenyl, heteroaryl or heterocyclyl;

ct) silyloxy;

cu) amino;

cv) alkylamino;

cw) acylamino;

cx) arylamino;

cy) substituted or unsubstituted cycloalkylamino, wherein a substituent of substituted cycloalkylamino is carboxy;

cz) arylalkylamino;

caa) hydroxyamino;

cbb) alkyloxycarbonylamino;

ccc) carbamoylamino;

cdd) alkylsulfonylamino;

cee) arylsulfonylarnino;

cff) cycloalkylsulfonylamino;

cgg) cycloalkenylsulfonylamino;

chh) heteroarylsulfbnylamino;

cii) heterocyclylsulfonylamino;

cjj) substituted or unsubstituted carbamoyl, wherein a substituent of substituted carbamoyl is halogen, hydroxy, carboxy, nitro, cyano, substituted or unsubstituted alkyl (wherein a substituent of substituted alkyl is hydroxy or carboxy), aryl, cycloalkyl, cycloalkenyl, heteroaryl or heterocyclyl;

ckk) substituted or unsubstituted carbamoyloxy, wherein a substituent of substituted carbamoyloxy is halogen, alkyl, aryl, cycloalkyl, cycloalkenyl, heteroaryl or heterocyclyl);

cll) substituted or unsubstituted acyl, wherein a substituent of substituted acyl is halogen, hydroxy, carboxy, nitro, cyano, substituted or unsubstituted alkyl (wherein a substituent of substituted alkyl hydroxy), aryl, cycloalkyl, cycloalkenyl, heteroaryl or heterocyclyl, amino, acylamino or carbamoyl;

cmm) substituted or unsubstituted alkylsulfonyl, wherein a substituent of substituted alkylsulfonyl is halogen, hydroxy, carboxy, nitro, cyano, alkyl, aryl, eycloalkyl, cycloalkenyl, heteroaryl or heterocyclyl;

cnn) substituted or unsubstituted arylsulfonyl, wherein a substituent of substituted arylsulfonyl is halogen, hydroxy, carboxy, nitro, cyano, alkyl, aryl, cycloalkyl, cycloalkenyl, heteroaryl or heterocyclyl;

coo) substituted or unsubstituted cycloalkylsulfonyl, wherein a substituent of substituted cycloalkylsulfonyl is halogen, hydroxy, carboxy, nitro, cyano, alkyl, aryl, cycloalkyl, cycloalkenyl, heteroaryl or heterocyclyl;

cpp) substituted or unsubstituted cycloalkenylsulfonyl, wherein a substituent of substituted cycloalkenylsulfonyl is halogen, hydroxy, carboxy, nitro, cyano, alkyl, aryl, cycloalkyl, cycloalkenyl, heteroaryl or heterocyclyl;
cqq) substituted or unsubstituted heteroarylsulfonyl, wherein a substituent of substituted heteroarylsulfonyl is halogen, hydroxy, carboxy, nitro, cyano, alkyl, aryl, cycloalkyl, cycloalkenyl, heteroaryl or heterocyclyl;
crr) substituted or unsubstituted heterocyclylsulfonyl, wherein a substituent of substituted heterocyclylsulfonyl is halogen, hydroxy, carboxy, nitro, cyano, alkyl, aryl, cycloalkyl, cycloalkenyl, heteroaryl or heterocyclyl;
css) substituted or unsubstituted sulfamoyl, wherein a substituent of substituted sulfamoyl is halogen, alkyl, aryl, cycloalkyl, cycloalkenyl, heteroaryl or heterocyclyl;
ctt) substituted or unsubstituted alkyloxycarbonyl, wherein a substituent of substituted alkyloxycarbonyl is halogen, hydroxy, carboxy, nitro, cyano, alkyl, aryl, cycloalkyl, cycloalkenyl, heteroaryl or heterocyclyl;
cuu) aryloxycarbonyl;
cvv) cycloalkyloxycarbonyl;
cww) cycloalkenyloxycarbonyl;
cxx) heteroaryloxycarbonyl;
cyy) heterocyclyloxycarbonyl;
czz) alkylsulfinyl;
caaa) arylsulfinyl;
cbbb) cycloalkylsulfinyl;
cccc) cycloalkenylsulfinyl;
cddd) heteroarylsulfinyl;
ceee) heterocyclylsulfinyl;
cfff) nitroso;
cggg) substituted or unsubstituted alkylidene, wherein a substituent of substituted alkylidene is halogen, hydroxy, carboxy, nitro, cyano, alkyl, aryl, cycloalkyl, cycloalkenyl, heteroaryl or heterocyclyl;
chhh) azido;
ciii) isocyano;
cjjj) isocyanato;
ckkk) thiocyanato;
clll) isothiocyanato;
cmmm) mercapto;
cnnn) alkylthio;
cooo) $P(=O)(OH)_2$;
cppp) $P(=O)(OCH_2CH_3)_2$;
cqqq) $C(=O)C(=O)OH$;
crrr) $C(CH_3)=N-O-CH_3$;
csss) $C(CH_3)=N-OH$;
cttt) formyloxy;
cuuu) haloformyl;
cvvv) oxalo;
cwww) thioformyl;
cxxx) thiocarboxy;
cyyy) dithiocarboxy;
czzz) thiocarbamoyl;
caaaa) sulfino;
cbbbb) sulfo;
ccccc) sulfoamino;
cdddd) hydrazine;
ceeee) ureido;
cffff) amidino;
cgggg) guanidine;
chhhh) phthalimido;
ciiii) oxo;
cjjjj) morpholino;
ckkkk) piperidino;
cllll) dihydropyranyl; and
cmmmm) pyrrolidyl.

2. The compound according to claim 1 or a pharmaceutically acceptable salt thereof, wherein $R^2$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

3. The compound according to claim 2 or a pharmaceutically acceptable salt thereof, wherein $R^2$ is halogen.

4. The compound according to claim 1 or a pharmaceutically acceptable salt thereof, wherein $R^2$ is hydrogen.

5. The compound according to claim 1 or a pharmaceutically acceptable salt thereof, wherein $R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

6. The compound according to claim 5 or a pharmaceutically acceptable salt thereof, wherein $R^1$ is substituted or unsubstituted aryl.

7. The compound according to claim 1 or a pharmaceutically acceptable salt thereof, wherein Y is substituted or unsubstituted monocyclic heterocyclyl.

8. The compound according to claim 7 or a pharmaceutically acceptable salt thereof, wherein Y is

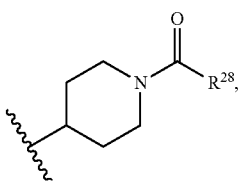

R²⁸ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, or substituted or unsubstituted amino.

9. The compound according to claim 1 or a pharmaceutically acceptable salt thereof, wherein R³ is hydrogen.

10. The compound according to claim 1 or a pharmaceutically acceptable salt thereof, wherein when R¹ is substituted aryl, a substituent of substituted aryl is selected from the group consisting of
- cg) substituted or unsubstituted cycloalkenyl, wherein a substituent of substituted cycloalkenyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, alkyloxycarbonyl, substituted or unsubstituted carbamoyl (wherein a substituent of substituted carbamoyl is substituted or unsubstituted alkyl (wherein a substituent of substituted alkyl is hydroxy)) or alkylsulfonyl;
- ch) substituted or unsubstituted heteroaryl, wherein a substituent of substituted heteroaryl is selected from halogen, hydroxy, carboxy, nitro, cyano, alkyl, aryl, cycloalkyl, cycloalkenyl, or heterocyclyl;
- ci) substituted heterocyclyl, wherein a substituent of substituted heterocyclyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, oxo, substituted or unsubstituted carbamoyl (wherein a substituent of substituted carbamoyl is substituted or unsubstituted alkyl (wherein a substituent of substituted alkyl is hydroxy)) or alkylsulfonyl;
- cl) substituted or unsubstituted aryloxy, wherein a substituent of substituted aryloxy is halogen, hydroxy, carboxy, nitro, cyano, alkyl, aryl, cycloalkyl, cycloalkenyl, heteroaryl or heterocyclyl;
- cm) substituted or unsubstituted cycloalkyloxy, wherein a substituent of substituted cycloalkyloxy is halogen, hydroxy, carboxy, nitro, cyano, alkyl, aryl, cycloalkyl, cycloalkenyl, heteroaryl or heterocyclyl;
- cn) substituted or unsubstituted cycloalkenyloxy, wherein a substituent of substituted cycloalkenyloxy is halogen, hydroxy, carboxy, nitro, cyano, alkyl, aryl, cycloalkyl, cycloalkenyl, heteroaryl or heterocyclyl;
- co) substituted or unsubstituted heteroaryloxy, wherein a substituent of substituted heteroaryloxy is halogen, hydroxy, carboxy, nitro, cyano, alkyl, aryl, cycloalkyl, cycloalkenyl, heteroaryl or heterocyclyl;
- cp) substituted or unsubstituted heterocyclyloxy, wherein a substituent of substituted heterocyclyloxy is halogen, hydroxy, carboxy, nitro, cyano, alkyl, aryl, cycloalkyl, cycloalkenyl, heteroaryl or heterocyclyl;
- cq) substituted or unsubstituted arylalkyl, wherein a substituent of substituted arylalkyl is halogen, hydroxy, carboxy, nitro, cyano, alkyl, aryl, cycloalkyl, cycloalkenyl, heteroaryl or heterocyclyl;
- cr) substituted or unsubstituted arylalkyloxy, wherein a substituent of substituted arylalkyloxy is halogen, hydroxy, carboxy, nitro, cyano, alkyl, aryl, cycloalkyl, cycloalkenyl, heteroaryl or heterocyclyl;
- cs) substituted or unsubstituted cycloalkylalkyloxy, wherein a substituent of substituted cycloalkylalkyloxy is halogen, hydroxy, carboxy, nitro, cyano, alkyl, aryl, cycloalkyl, cycloalkenyl, heteroaryl or heterocyclyl;
- cx) arylamino;
- cy) substituted or unsubstituted cycloalkylamino, wherein a substituent of substituted cycloalkylamino is carboxy;
- cz) arylalkylamino;
- cee) arylsulfonylamino;
- cff) cycloalkylsulfonylamino;
- cgg) cycloalkenylsulfonylamino;
- chh) heteroarylsulfonylamino;
- cii) heterocyclylsulfonylamino;
- cnn) substituted or unsubstituted arylsulfonyl, wherein a substituent of substituted arylsulfonyl is halogen, hydroxy, carboxy, nitro, cyano, alkyl, aryl, cycloalkyl, cycloalkenyl, heteroaryl or heterocyclyl;
- coo) substituted or unsubstituted cycloalkylsulfonyl, wherein a substituent of substituted cycloalkylsulfonyl is halogen, hydroxy, carboxy, nitro, cyano, alkyl, aryl, cycloalkyl, cycloalkenyl, heteroaryl or heterocyclyl;
- cpp) substituted or unsubstituted cycloalkenylsulfonyl, wherein a substituent of substituted cycloalkenylsulfonyl is halogen, hydroxy, carboxy, nitro, cyano, alkyl, aryl, cycloalkyl, cycloalkenyl, heteroaryl or heterocyclyl;
- cqq) substituted or unsubstituted heteroarylsulfonyl, wherein a substituent of substituted heteroarylsulfonyl is halogen, hydroxy, carboxy, nitro, cyano, alkyl, aryl, cycloalkyl, cycloalkenyl, heteroaryl or heterocyclyl;
- crr) substituted or unsubstituted heterocyclylsulfonyl, wherein a substituent of substituted heterocyclylsulfonyl is halogen, hydroxy, carboxy, nitro, cyano, alkyl, aryl, cycloalkyl, cycloalkenyl, heteroaryl or heterocyclyl;
- cuu) aryloxycarbonyl;
- cvv) cycloalkyloxycarbonyl;
- cww) cycloalkenyloxycarbonyl;
- cxx) heteroaryloxycarbonyl;
- cyy) heterocyclyloxycarbonyl;
- caaa) arylsulfinyl;
- cbbb) cycloalkylsulfinyl;
- cccc) cycloalkenylsulfinyl;
- cddd) heteroarylsulfinyl;
- ceee) heterocyclylsulfinyl;
- chhhh) phthalimido;
- cjjjj) morpholino;
- ckkkk) piperidino;
- cllll) dihydropyranyl; and
- cmmmm) pyrrolidyl.

11. The compound according to claim 1 or a pharmaceutically acceptable salt thereof, wherein when R¹ is substituted aryl, a substituent of substituted aryl is selected from the group consisting of
- cg) substituted or unsubstituted cycloalkenyl, wherein a substituent of substituted cycloalkenyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, alkyloxycarbonyl, substituted or unsubstituted carbamoyl (wherein a substituent of substituted carbamoyl is substituted or unsubstituted alkyl (wherein a substituent of substituted alkyl is hydroxy)) or alkylsulfonyl;
ci) substituted heterocyclyl, wherein a substituent of substituted heterocyclyl is halogen, hydroxy, carboxy, nitro, cyano, alkyl, aryl, cycloalkyl, cycloalkenyl, heteroaryl, heterocyclyl, substituted or unsubstituted acyl (wherein a substituent of substituted acyl is hydroxy or alkyloxy), acylamino, oxo, substituted or unsubstituted carbamoyl (wherein a substituent of substituted carbamoyl is substituted or unsubstituted alkyl (wherein a substituent of substituted alkyl is hydroxy)) or alkylsulfonyl;
cjjjj) morpholino;
ckkkk) piperidino;
cllll) dihydropyranyl; and
cmmmm) pyrrolidyl.

12. The compound according to claim 2 or a pharmaceutically acceptable salt thereof, wherein $R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

13. A pharmaceutical composition comprising:
the compound according to claim 1 or a pharmaceutically acceptable salt thereof; and
a pharmaceutically acceptable carrier.

14. A pharmaceutical composition, comprising:
the compound according to claim 1 or a pharmaceutically acceptable salt thereof; and
a pharmaceutically acceptable carrier,
wherein the pharmaceutical composition has an activating effect on adenosine monophosphate-activated protein kinase.

15. A method for treating diabetes, comprising administering the compound according to claim 1 or a pharmaceutically acceptable salt thereof.

* * * * *